US011828707B2

(12) United States Patent
Rajavelu Muralidhar et al.

(10) Patent No.: US 11,828,707 B2
(45) Date of Patent: Nov. 28, 2023

(54) METHOD AND APPARATUS FOR TRANSMITTANCE MEASUREMENTS OF LARGE ARTICLES

(71) Applicant: ASM IP Holding B.V., Almere (NL)

(72) Inventors: Shiva K. T. Rajavelu Muralidhar, Tempe, AZ (US); Youness Alvandi-Tabrizi, Tempe, AZ (US); John DiSanto, Scottsdale, AZ (US); Sam Kim, Chandler, AZ (US)

(73) Assignee: ASM IP Holding B.V., Almere (NL)

( * ) Notice: Subject to any disclaimer, the term of this patent is extended or adjusted under 35 U.S.C. 154(b) by 206 days.

(21) Appl. No.: 17/157,507

(22) Filed: Jan. 25, 2021

(65) Prior Publication Data

US 2021/0239614 A1 Aug. 5, 2021

Related U.S. Application Data

(60) Provisional application No. 62/970,057, filed on Feb. 4, 2020.

(51) Int. Cl.
  *G01N 21/59* (2006.01)
  *G01N 21/958* (2006.01)
  *G01B 11/02* (2006.01)
  *G01N 33/207* (2019.01)

(52) U.S. Cl.
  CPC ........... *G01N 21/59* (2013.01); *G01B 11/028* (2013.01); *G01N 21/958* (2013.01); *G01N 33/207* (2019.01); *G01N 2201/021* (2013.01)

(58) Field of Classification Search
  CPC .... G01N 21/59; G01N 21/958; G01N 33/207; G01N 2021/5976; G01N 2291/267; G01N 2201/021; G01B 11/028
  See application file for complete search history.

(56) References Cited

U.S. PATENT DOCUMENTS

| | | |
|---|---|---|
| D30,036 S | 1/1899 | Rhind |
| D31,889 S | 11/1899 | Gill |
| D56,051 S | 8/1920 | Cohn |
| 2,059,480 A | 11/1936 | Obermaier |
| 2,161,626 A | 6/1939 | Loughner et al. |
| 2,240,163 A | 4/1941 | Pick |
| 2,266,416 A | 12/1941 | Duclos |
| 2,280,778 A | 4/1942 | Andersen |

(Continued)

FOREIGN PATENT DOCUMENTS

| | | |
|---|---|---|
| AT | 520629 | 6/2019 |
| CN | 1186873 | 7/1998 |

(Continued)

OTHER PUBLICATIONS

English Machine Translation of CN-109342375-A (Year: 2019).*

(Continued)

*Primary Examiner* — Dominic J Bologna
(74) *Attorney, Agent, or Firm* — Snell & Wilmer L.L.P.

(57) ABSTRACT

Methods and apparatus for measuring light intensity are disclosed. The methods and apparatus can be used to verify an article, such as a reaction chamber. Exemplary apparatus include a first arm, a light source coupled to the first arm, a second arm, and a sensor coupled to the second arm. The sensor can receive light from the light source that is transmitted through at least a portion of the article.

9 Claims, 5 Drawing Sheets

(56) References Cited

U.S. PATENT DOCUMENTS

| | | |
|---|---|---|
| D142,841 S | 11/1945 | D'Algodt |
| 2,410,420 A | 11/1946 | Bennett |
| 2,441,253 A | 5/1948 | Sarver |
| 2,480,557 A | 8/1949 | Cummins |
| 2,563,931 A | 8/1951 | Harrison |
| 2,660,061 A | 11/1953 | Lewis |
| 2,745,640 A | 5/1956 | Cushman |
| 2,847,320 A | 8/1958 | Bulloff |
| 2,990,045 A | 6/1961 | Root |
| 3,038,951 A | 6/1962 | Mead |
| 3,089,507 A | 5/1963 | Drake et al. |
| 3,094,396 A | 6/1963 | Flugge et al. |
| 3,197,682 A | 7/1965 | Klass et al. |
| 3,232,437 A | 2/1966 | Hultgren |
| 3,263,502 A | 8/1966 | Springfield |
| 3,332,286 A | 7/1967 | Strong |
| 3,410,349 A | 11/1968 | Troutman |
| 3,420,622 A | 1/1969 | Donges et al. |
| 3,588,192 A | 6/1971 | Drutchas et al. |
| 3,634,740 A | 1/1972 | Stevko |
| 3,647,387 A | 3/1972 | Benson |
| 3,647,716 A | 3/1972 | Koches |
| 3,713,899 A | 1/1973 | Sebestyen |
| 3,718,429 A | 2/1973 | Williamson |
| 3,796,182 A | 3/1974 | Rosler |
| 3,814,128 A | 6/1974 | Grantham |
| 3,833,492 A | 9/1974 | Bollyky |
| 3,854,443 A | 12/1974 | Baerg |
| 3,862,397 A | 1/1975 | Anderson et al. |
| 3,867,205 A | 2/1975 | Schley |
| 3,885,504 A | 5/1975 | Baermann |
| 3,887,790 A | 6/1975 | Ferguson |
| 3,904,371 A | 9/1975 | Neti |
| 3,913,058 A | 10/1975 | Nishio et al. |
| 3,913,617 A | 10/1975 | van Laar |
| 3,916,270 A | 10/1975 | Wachtler et al. |
| 3,947,685 A | 3/1976 | Meinel |
| 3,960,559 A | 6/1976 | Suzuki |
| 3,962,004 A | 6/1976 | Sonneborn |
| 3,983,401 A | 9/1976 | Livesay |
| 3,997,638 A | 12/1976 | Manning et al. |
| 4,048,110 A | 9/1977 | Vanderspurt |
| 4,054,071 A | 10/1977 | Patejak |
| 4,058,430 A | 11/1977 | Suntola et al. |
| 4,079,944 A | 3/1978 | Durley et al. |
| 4,093,491 A | 6/1978 | Whelpton et al. |
| 4,099,041 A | 7/1978 | Berkman et al. |
| D249,341 S | 9/1978 | Mertz |
| 4,126,027 A | 11/1978 | Smith et al. |
| 4,134,425 A | 1/1979 | Gussefeld et al. |
| 4,145,699 A | 3/1979 | Hu et al. |
| 4,149,237 A | 4/1979 | Freitas |
| 4,152,760 A | 5/1979 | Freitas et al. |
| 4,157,751 A | 6/1979 | Grundken et al. |
| 4,164,959 A | 8/1979 | Wurzburger |
| 4,176,630 A | 12/1979 | Elmer |
| 4,179,530 A | 12/1979 | Koppl et al. |
| 4,181,330 A | 1/1980 | Kojima |
| 4,184,188 A | 1/1980 | Briglia |
| 4,194,536 A | 3/1980 | Stine et al. |
| 4,195,932 A * | 4/1980 | Popelka ............... G01N 21/314 356/414 |
| 4,217,463 A | 8/1980 | Swearingen |
| 4,229,064 A | 10/1980 | Vetter et al. |
| 4,234,449 A | 11/1980 | Wolson et al. |
| 4,241,000 A | 12/1980 | McCauley et al. |
| 4,314,763 A | 2/1982 | Steigmeier et al. |
| 4,322,592 A | 3/1982 | Martin |
| 4,324,611 A | 4/1982 | Vogel et al. |
| 4,333,735 A | 6/1982 | Hardy |
| 4,355,912 A | 10/1982 | Haak |
| 4,384,918 A | 5/1983 | Abe |
| 4,389,973 A | 6/1983 | Suntola et al. |
| D269,850 S | 7/1983 | Preisler et al. |
| 4,393,013 A | 7/1983 | McMenamin |
| 4,401,507 A | 8/1983 | Engle |
| 4,412,133 A | 10/1983 | Eckes et al. |
| 4,413,022 A | 11/1983 | Suntola et al. |
| 4,414,492 A | 11/1983 | Hanlet |
| 4,436,674 A | 3/1984 | McMenamin |
| 4,444,990 A | 4/1984 | Villar |
| D274,122 S | 6/1984 | Stahel et al. |
| 4,454,370 A | 6/1984 | Voznick |
| 4,455,193 A | 6/1984 | Jeuch et al. |
| 4,465,716 A | 8/1984 | Baber et al. |
| 4,466,766 A | 8/1984 | Geren et al. |
| 4,479,831 A | 10/1984 | Sandow |
| 4,480,284 A | 10/1984 | Tojo et al. |
| 4,481,300 A | 11/1984 | Hartnett et al. |
| 4,484,061 A | 11/1984 | Zelinka et al. |
| 4,488,506 A | 12/1984 | Heinecke et al. |
| 4,495,024 A | 1/1985 | Bok |
| 4,496,828 A | 1/1985 | Kusmierz et al. |
| 4,499,354 A | 2/1985 | Hill et al. |
| 4,502,094 A | 2/1985 | Lewin et al. |
| 4,504,439 A | 3/1985 | Elter et al. |
| 4,512,113 A | 4/1985 | Budinger |
| 4,512,841 A | 4/1985 | Cunningham et al. |
| 4,520,116 A | 5/1985 | Gentilman et al. |
| 4,520,421 A | 5/1985 | Sakitani et al. |
| 4,527,005 A | 7/1985 | McKelvey et al. |
| 4,534,816 A | 8/1985 | Chen et al. |
| 4,535,628 A | 8/1985 | Hope |
| 4,537,001 A | 8/1985 | Uppstrom |
| 4,548,688 A | 10/1985 | Mathews |
| 4,551,192 A | 11/1985 | Di Milia et al. |
| 4,554,611 A | 11/1985 | Lewin |
| 4,560,590 A | 12/1985 | Bok |
| 4,570,328 A | 2/1986 | Price et al. |
| 4,575,408 A | 3/1986 | Bok |
| 4,575,636 A | 3/1986 | Caprari |
| 4,578,560 A | 3/1986 | Tanaka et al. |
| 4,579,080 A | 4/1986 | Martin et al. |
| 4,579,378 A | 4/1986 | Snyders |
| 4,579,623 A | 4/1986 | Suzuki et al. |
| 4,581,520 A | 4/1986 | Vu et al. |
| 4,590,326 A | 5/1986 | Woldy |
| 4,611,966 A | 9/1986 | Johnson |
| 4,620,998 A | 11/1986 | Lalvani |
| 4,622,918 A | 11/1986 | Bok |
| 4,624,728 A | 11/1986 | Bithell et al. |
| D288,556 S | 3/1987 | Wallgren |
| 4,653,541 A | 3/1987 | Oehlschlaeger et al. |
| 4,654,226 A | 3/1987 | Jackson et al. |
| 4,655,592 A | 4/1987 | Allemand |
| 4,662,987 A | 5/1987 | Bok |
| 4,664,769 A | 5/1987 | Cuomo et al. |
| 4,670,126 A | 6/1987 | Messer et al. |
| 4,681,134 A | 7/1987 | Paris |
| 4,693,211 A | 9/1987 | Ogami et al. |
| 4,700,089 A | 10/1987 | Fujii et al. |
| 4,707,815 A | 11/1987 | Yamasaki |
| 4,717,461 A | 1/1988 | Strahl et al. |
| 4,718,637 A | 1/1988 | Contin |
| 4,720,362 A | 1/1988 | Gentilman et al. |
| 4,720,407 A | 1/1988 | Sculke |
| 4,721,533 A | 1/1988 | Phillippi et al. |
| 4,721,534 A | 1/1988 | Phillippi et al. |
| 4,722,298 A | 2/1988 | Rubin et al. |
| 4,724,272 A | 2/1988 | Raniere et al. |
| 4,725,204 A | 2/1988 | Powell |
| 4,735,259 A | 4/1988 | Vincent |
| 4,738,618 A | 4/1988 | Massey et al. |
| 4,738,748 A | 4/1988 | Kisa |
| 4,747,367 A | 5/1988 | Posa |
| 4,749,416 A | 6/1988 | Greenspan |
| 4,750,133 A * | 6/1988 | Eiskamp ............... G01N 21/272 700/266 |
| 4,750,520 A | 6/1988 | Heim et al. |
| 4,753,192 A | 6/1988 | Goldsmith et al. |
| 4,753,856 A | 6/1988 | Haluska et al. |
| 4,756,794 A | 7/1988 | Yoder |
| 4,764,076 A | 8/1988 | Layman et al. |
| 4,770,590 A | 9/1988 | Hugues et al. |

(56) References Cited

U.S. PATENT DOCUMENTS

| | | |
|---|---|---|
| 4,771,015 A | 9/1988 | Kanai |
| 4,775,281 A | 10/1988 | Prentakis |
| 4,776,744 A | 10/1988 | Stonestreet et al. |
| 4,780,169 A | 10/1988 | Stark et al. |
| 4,781,511 A | 11/1988 | Harada et al. |
| 4,789,294 A | 12/1988 | Sato et al. |
| 4,790,258 A | 12/1988 | Drage et al. |
| 4,802,441 A | 2/1989 | Waugh |
| 4,804,086 A | 2/1989 | Grohrock |
| 4,808,387 A | 2/1989 | Datta et al. |
| 4,812,201 A | 3/1989 | Sakai et al. |
| 4,812,217 A | 3/1989 | George et al. |
| 4,821,674 A | 4/1989 | deBoer et al. |
| 4,827,430 A | 5/1989 | Aid et al. |
| 4,828,224 A | 5/1989 | Crabb et al. |
| 4,830,515 A | 5/1989 | Cortes |
| 4,837,113 A | 6/1989 | Luttmer et al. |
| 4,837,185 A | 6/1989 | Yau et al. |
| 4,854,263 A | 8/1989 | Chang et al. |
| 4,854,266 A | 8/1989 | Simson et al. |
| 4,857,137 A | 8/1989 | Tachi et al. |
| 4,857,382 A | 8/1989 | Liu et al. |
| 4,858,557 A | 8/1989 | Pozzetti et al. |
| 4,863,374 A | 9/1989 | Vukovich |
| 4,867,629 A | 9/1989 | Iwasawa et al. |
| 4,871,523 A | 10/1989 | Datta et al. |
| 4,874,273 A | 10/1989 | Tokisue et al. |
| 4,880,982 A | 11/1989 | Hoksaas |
| 4,882,199 A | 11/1989 | Sadoway et al. |
| 4,886,162 A | 12/1989 | Ambrogio |
| 4,916,091 A | 4/1990 | Freeman et al. |
| 4,917,556 A | 4/1990 | Stark et al. |
| 4,920,918 A | 5/1990 | Adams et al. |
| 4,925,388 A | 5/1990 | Iseki et al. |
| 4,931,135 A | 6/1990 | Horiuchi et al. |
| 4,934,831 A | 6/1990 | Volbrecht |
| 4,938,815 A | 7/1990 | McNeilly |
| D309,702 S | 8/1990 | Hall |
| 4,949,671 A | 8/1990 | Davis et al. |
| 4,949,848 A | 8/1990 | Kos |
| 4,950,624 A | 8/1990 | Inuzima et al. |
| 4,956,538 A | 9/1990 | Moslehi |
| 4,958,061 A | 9/1990 | Wakabayashi et al. |
| D311,126 S | 10/1990 | Crowley |
| 4,962,063 A | 10/1990 | Maydan et al. |
| 4,963,506 A | 10/1990 | Liaw et al. |
| 4,976,996 A | 12/1990 | Monkowski et al. |
| 4,978,567 A | 12/1990 | Miller |
| 4,984,904 A | 1/1991 | Nakano et al. |
| 4,985,114 A | 1/1991 | Okudaira |
| 4,986,215 A | 1/1991 | Yamada |
| 4,987,102 A | 1/1991 | Nguyen et al. |
| 4,987,856 A | 1/1991 | Hey |
| 4,989,992 A | 2/1991 | Piai |
| 4,991,614 A | 2/1991 | Hammel |
| 5,002,632 A | 3/1991 | Loewenstein et al. |
| 5,013,691 A | 5/1991 | Lory et al. |
| 5,022,961 A | 6/1991 | Izumi et al. |
| 5,027,746 A | 7/1991 | Frijlink |
| 5,028,366 A | 7/1991 | Harakal et al. |
| D320,148 S | 9/1991 | Andrews |
| 5,049,029 A | 9/1991 | Mitsui et al. |
| 5,053,247 A | 10/1991 | Moore |
| 5,057,436 A | 10/1991 | Ball |
| 5,060,322 A | 10/1991 | Delepine |
| 5,061,083 A | 10/1991 | Grimm et al. |
| 5,062,386 A | 11/1991 | Christensen |
| 5,064,337 A | 11/1991 | Asakawa et al. |
| 5,065,698 A | 11/1991 | Koike |
| 5,067,437 A | 11/1991 | Watanabe et al. |
| 5,069,591 A | 12/1991 | Kinoshita |
| 5,071,258 A | 12/1991 | Usher et al. |
| 5,074,017 A | 12/1991 | Toya et al. |
| 5,082,517 A | 1/1992 | Moslehi |
| 5,084,126 A | 1/1992 | McKee |
| 5,088,444 A | 2/1992 | Ohmine et al. |
| 5,097,890 A | 3/1992 | Nakao |
| 5,098,638 A | 3/1992 | Sawada |
| 5,098,865 A | 3/1992 | Machado |
| 5,104,514 A | 4/1992 | Quartarone |
| 5,107,170 A | 4/1992 | Ishikawa et al. |
| 5,108,192 A | 4/1992 | Mailliet et al. |
| 5,110,407 A | 5/1992 | Ono et al. |
| 5,114,683 A | 5/1992 | Hirase |
| 5,116,018 A | 5/1992 | Friemoth et al. |
| 5,117,121 A | 5/1992 | Watanabe et al. |
| D327,534 S | 6/1992 | Manville |
| 5,119,760 A | 6/1992 | McMillan et al. |
| 5,124,272 A | 6/1992 | Saito et al. |
| 5,125,358 A | 6/1992 | Ueda et al. |
| 5,125,710 A | 6/1992 | Gianelo |
| 5,130,003 A | 7/1992 | Conrad |
| 5,134,965 A | 8/1992 | Tokuda et al. |
| 5,137,286 A | 8/1992 | Whitford |
| 5,151,296 A | 9/1992 | Tokunaga |
| 5,154,301 A | 10/1992 | Kos |
| 5,158,128 A | 10/1992 | Inoue et al. |
| D330,900 S | 11/1992 | Wakegijig |
| 5,167,716 A | 12/1992 | Boitnott et al. |
| 5,167,761 A | 12/1992 | Westendorp et al. |
| 5,174,881 A | 12/1992 | Iwasaki et al. |
| 5,176,451 A | 1/1993 | Sasada |
| 5,178,639 A | 1/1993 | Nishi |
| 5,178,682 A | 1/1993 | Tsukamoto et al. |
| 5,180,273 A | 1/1993 | Sakaya et al. |
| 5,180,435 A | 1/1993 | Markunas et al. |
| 5,181,779 A | 1/1993 | Shia et al. |
| 5,182,232 A | 1/1993 | Chhabra et al. |
| 5,183,511 A | 2/1993 | Yamazaki et al. |
| 5,186,120 A | 2/1993 | Ohnishi et al. |
| D333,606 S | 3/1993 | Kanemitsu et al. |
| 5,192,717 A | 3/1993 | Kawakami |
| 5,193,912 A | 3/1993 | Saunders |
| 5,193,969 A | 3/1993 | Rush et al. |
| 5,194,401 A | 3/1993 | Adams et al. |
| 5,199,603 A | 4/1993 | Prescott |
| 5,208,961 A | 5/1993 | Lajoie |
| 5,213,650 A | 5/1993 | Wang et al. |
| 5,219,226 A | 6/1993 | James |
| 5,221,556 A | 6/1993 | Hawkins et al. |
| 5,225,366 A | 7/1993 | Yoder |
| 5,226,383 A | 7/1993 | Bhat |
| 5,226,713 A | 7/1993 | Matsumura |
| 5,226,967 A | 7/1993 | Chen et al. |
| 5,228,114 A | 7/1993 | Suzuki |
| 5,231,062 A | 7/1993 | Mathers et al. |
| 5,232,508 A | 8/1993 | Arena et al. |
| 5,234,526 A | 8/1993 | Chen et al. |
| 5,242,501 A | 9/1993 | McDiarmid |
| 5,242,539 A | 9/1993 | Kumihashi et al. |
| 5,243,195 A | 9/1993 | Nishi |
| 5,243,202 A | 9/1993 | Mori et al. |
| 5,246,218 A | 9/1993 | Yap et al. |
| 5,246,500 A | 9/1993 | Samata et al. |
| 5,249,960 A | 10/1993 | Monoe |
| 5,250,092 A | 10/1993 | Nakano |
| 5,252,133 A | 10/1993 | Miyazaki et al. |
| 5,252,134 A | 10/1993 | Stauffer |
| 5,259,881 A | 11/1993 | Edwards et al. |
| 5,261,167 A | 11/1993 | Sakata |
| 5,266,526 A | 11/1993 | Aoyama |
| 5,268,989 A | 12/1993 | Moslehi et al. |
| 5,271,967 A | 12/1993 | Kramer et al. |
| 5,273,609 A | 12/1993 | Moslehi |
| 5,277,932 A | 1/1994 | Spencer |
| 5,278,494 A | 1/1994 | Obigane |
| 5,279,886 A | 1/1994 | Kawai et al. |
| 5,279,986 A | 1/1994 | Maloney et al. |
| 5,280,894 A | 1/1994 | Witcraft et al. |
| 5,281,274 A | 1/1994 | Yoder |
| 5,284,519 A | 2/1994 | Gadgil |
| 5,288,684 A | 2/1994 | Yamazaki et al. |
| 5,294,572 A | 3/1994 | Granneman et al. |
| 5,294,778 A | 3/1994 | Carman et al. |

(56) References Cited

U.S. PATENT DOCUMENTS

| | | |
|---|---|---|
| 5,295,777 A | 3/1994 | Hodos |
| 5,298,089 A | 3/1994 | Bowe et al. |
| 5,305,417 A | 4/1994 | Najm et al. |
| 5,306,666 A | 4/1994 | Izumi |
| 5,306,946 A | 4/1994 | Yamamoto |
| 5,308,650 A | 5/1994 | Krummel et al. |
| 5,308,788 A | 5/1994 | Fitch et al. |
| 5,310,410 A | 5/1994 | Begin et al. |
| 5,310,456 A | 5/1994 | Kadomura |
| 5,312,245 A | 5/1994 | Brannen et al. |
| 5,313,061 A | 5/1994 | Drew et al. |
| 5,314,538 A | 5/1994 | Maeda et al. |
| 5,314,570 A | 5/1994 | Ikegaya et al. |
| 5,315,092 A | 5/1994 | Takahashi et al. |
| 5,320,218 A | 6/1994 | Yamashita et al. |
| 5,326,427 A | 7/1994 | Jerbic |
| 5,328,360 A | 7/1994 | Yokokawa |
| 5,328,810 A | 7/1994 | Lowrey et al. |
| 5,335,309 A | 8/1994 | Fujii et al. |
| 5,336,327 A | 8/1994 | Lee |
| 5,338,362 A | 8/1994 | Imahashi |
| 5,340,261 A | 8/1994 | Oosawa et al. |
| 5,346,961 A | 9/1994 | Shaw et al. |
| 5,348,774 A | 9/1994 | Golecki et al. |
| 5,350,480 A | 9/1994 | Gray |
| 5,354,433 A | 10/1994 | Granneman et al. |
| 5,354,580 A | 10/1994 | Goela et al. |
| 5,356,478 A | 10/1994 | Chen et al. |
| 5,356,672 A | 10/1994 | Schmitt et al. |
| 5,360,269 A | 11/1994 | Ogawa et al. |
| 5,362,328 A | 11/1994 | Gardiner et al. |
| 5,364,667 A | 11/1994 | Rhieu |
| D353,452 S | 12/1994 | Groenhoff |
| 5,374,315 A | 12/1994 | Deboer et al. |
| D354,898 S | 1/1995 | Nagy |
| 5,378,501 A | 1/1995 | Foster et al. |
| 5,380,367 A | 1/1995 | Bertone |
| 5,382,311 A | 1/1995 | Ishikawa et al. |
| 5,387,265 A | 2/1995 | Kakizaki et al. |
| 5,388,945 A | 2/1995 | Garric et al. |
| 5,393,577 A | 2/1995 | Uesugi et al. |
| 5,397,395 A | 3/1995 | Sano et al. |
| 5,403,630 A | 4/1995 | Matsui et al. |
| 5,404,082 A | 4/1995 | Hernandez et al. |
| 5,407,449 A | 4/1995 | Zinger |
| 5,407,867 A | 4/1995 | Iwasaki et al. |
| 5,413,813 A | 5/1995 | Cruse et al. |
| 5,414,221 A | 5/1995 | Gardner |
| 5,415,753 A | 5/1995 | Hurwitt et al. |
| 5,418,382 A | 5/1995 | Blackwood et al. |
| 5,421,893 A | 6/1995 | Perlov |
| 5,422,139 A | 6/1995 | Fischer |
| 5,423,942 A | 6/1995 | Robbins et al. |
| 5,426,137 A | 6/1995 | Allen |
| 5,427,824 A | 6/1995 | Inushima et al. |
| 5,430,011 A | 7/1995 | Tanaka et al. |
| 5,431,734 A | 7/1995 | Chapple-Sokol et al. |
| 5,443,646 A | 8/1995 | Yamada et al. |
| 5,443,648 A | 8/1995 | Ohkase |
| 5,443,686 A | 8/1995 | Jones et al. |
| 5,444,217 A | 8/1995 | Moore |
| 5,447,294 A | 9/1995 | Sakata et al. |
| 5,453,124 A | 9/1995 | Moslehi et al. |
| D363,464 S | 10/1995 | Fukasawa |
| 5,456,207 A | 10/1995 | Gedridge et al. |
| 5,456,757 A | 10/1995 | Aruga et al. |
| 5,461,214 A | 10/1995 | Peck et al. |
| 5,462,899 A | 10/1995 | Ikeda |
| 5,463,176 A | 10/1995 | Eckert |
| 5,464,313 A | 11/1995 | Ohsawa |
| 5,474,410 A | 12/1995 | Ozawa et al. |
| 5,474,612 A | 12/1995 | Sato et al. |
| 5,478,429 A | 12/1995 | Komino et al. |
| 5,480,488 A | 1/1996 | Bittner et al. |
| 5,480,818 A | 1/1996 | Matsumoto et al. |
| 5,482,559 A | 1/1996 | Imai et al. |
| 5,484,484 A | 1/1996 | Yamaga et al. |
| 5,494,439 A | 2/1996 | Goldstein et al. |
| 5,494,494 A | 2/1996 | Mizuno et al. |
| 5,496,408 A | 3/1996 | Motoda et al. |
| 5,501,740 A | 3/1996 | Besen et al. |
| 5,503,875 A | 4/1996 | Imai et al. |
| 5,504,042 A | 4/1996 | Cho et al. |
| 5,510,277 A | 4/1996 | Cunningham et al. |
| 5,512,102 A | 4/1996 | Yamazaki |
| 5,514,439 A | 5/1996 | Sibley |
| 5,518,549 A | 5/1996 | Hellwig |
| 5,518,780 A | 5/1996 | Tamor et al. |
| 5,519,234 A | 5/1996 | Paz de Araujo |
| 5,520,743 A | 5/1996 | Takahashi et al. |
| 5,523,616 A | 6/1996 | Yasuhide |
| 5,527,111 A | 6/1996 | Lysen et al. |
| 5,527,417 A | 6/1996 | Iida et al. |
| 5,531,218 A | 7/1996 | Krebs |
| 5,531,835 A | 7/1996 | Fodor et al. |
| 5,537,311 A | 7/1996 | Stevens |
| 5,540,059 A | 7/1996 | Yokokawa |
| 5,540,821 A | 7/1996 | Tepman |
| 5,540,898 A | 7/1996 | Davidson |
| 5,554,557 A | 9/1996 | Koh |
| 5,556,275 A | 9/1996 | Sakata et al. |
| 5,558,717 A | 9/1996 | Zhao et al. |
| 5,559,046 A | 9/1996 | Oishi et al. |
| 5,562,383 A | 10/1996 | Iwai et al. |
| 5,562,947 A | 10/1996 | White et al. |
| 5,562,952 A | 10/1996 | Nakahigashi et al. |
| 5,565,038 A | 10/1996 | Ashley |
| 5,569,402 A | 10/1996 | Meisser et al. |
| 5,574,247 A | 11/1996 | Nishitani et al. |
| 5,576,629 A | 11/1996 | Turner |
| 5,577,331 A | 11/1996 | Suzuki |
| 5,583,736 A | 12/1996 | Anderson et al. |
| 5,584,936 A | 12/1996 | Pickering et al. |
| 5,584,963 A | 12/1996 | Takahashi |
| 5,586,585 A | 12/1996 | Bonora et al. |
| 5,589,002 A | 12/1996 | Su |
| 5,589,110 A | 12/1996 | Motoda et al. |
| 5,595,606 A | 1/1997 | Fujikawa et al. |
| 5,601,641 A | 2/1997 | Stephens |
| 5,602,060 A | 2/1997 | Kobayashi et al. |
| 5,604,410 A | 2/1997 | Vollkommer et al. |
| 5,611,448 A | 3/1997 | Chen |
| 5,616,264 A | 4/1997 | Nishi et al. |
| 5,616,947 A | 4/1997 | Tamura |
| 5,621,982 A | 4/1997 | Yamashita |
| 5,632,919 A | 5/1997 | MacCracken et al. |
| 5,637,153 A | 6/1997 | Niino et al. |
| D380,527 S | 7/1997 | Velez |
| 5,645,646 A | 7/1997 | Beinglass et al. |
| 5,650,013 A | 7/1997 | Yamazaki |
| 5,650,351 A | 7/1997 | Wu |
| 5,653,807 A | 8/1997 | Crumbaker |
| 5,656,093 A | 8/1997 | Burkhart et al. |
| 5,661,263 A | 8/1997 | Salvaggio |
| 5,662,470 A | 9/1997 | Huussen et al. |
| 5,663,899 A | 9/1997 | Zvonar et al. |
| 5,665,608 A | 9/1997 | Chapple-Sokol et al. |
| 5,667,592 A | 9/1997 | Boitnott et al. |
| 5,670,786 A | 9/1997 | Meyer et al. |
| 5,679,215 A | 10/1997 | Barnes et al. |
| 5,681,779 A | 10/1997 | Pasch et al. |
| D386,076 S | 11/1997 | Moore |
| 5,683,517 A | 11/1997 | Shan |
| 5,683,561 A | 11/1997 | Hollars et al. |
| 5,685,912 A | 11/1997 | Nishizaka |
| 5,685,914 A | 11/1997 | Hills et al. |
| 5,690,742 A | 11/1997 | Ogata et al. |
| 5,695,567 A | 12/1997 | Kordina |
| 5,697,706 A | 12/1997 | Ciaravino et al. |
| 5,698,036 A | 12/1997 | Ishii et al. |
| 5,700,729 A | 12/1997 | Lee et al. |
| 5,708,825 A | 1/1998 | Sotomayor |
| 5,709,745 A | 1/1998 | Larkin et al. |
| 5,711,811 A | 1/1998 | Suntola et al. |

(56) References Cited

U.S. PATENT DOCUMENTS

| | | |
|---|---|---|
| 5,716,133 A | 2/1998 | Hosokawa et al. |
| 5,718,574 A | 2/1998 | Shimazu |
| 5,720,927 A | 2/1998 | Cripe et al. |
| D392,855 S | 3/1998 | Pillow |
| 5,724,748 A | 3/1998 | Brooks |
| 5,728,223 A | 3/1998 | Murakarni et al. |
| 5,728,425 A | 3/1998 | Ebe et al. |
| 5,730,801 A | 3/1998 | Tepman et al. |
| 5,730,802 A | 3/1998 | Ishizumi et al. |
| 5,732,597 A | 3/1998 | Devenyi |
| 5,732,744 A | 3/1998 | Barr et al. |
| 5,732,957 A | 3/1998 | Yu |
| 5,736,314 A | 4/1998 | Hayes et al. |
| 5,753,835 A | 5/1998 | Gustin |
| 5,754,390 A | 5/1998 | Sandhu et al. |
| 5,759,281 A | 6/1998 | Gurary et al. |
| 5,761,328 A | 6/1998 | Solberg et al. |
| 5,766,365 A | 6/1998 | Umutoy et al. |
| 5,768,125 A | 6/1998 | Zinger et al. |
| 5,769,952 A | 6/1998 | Komino |
| 5,775,889 A | 7/1998 | Kobayashi et al. |
| 5,777,838 A | 7/1998 | Tamagawa et al. |
| 5,779,203 A | 7/1998 | Edlinger |
| 5,781,693 A | 7/1998 | Ballance et al. |
| 5,782,979 A | 7/1998 | Kaneno |
| 5,790,750 A | 8/1998 | Anderson |
| 5,791,782 A | 8/1998 | Wooten et al. |
| 5,792,272 A | 8/1998 | Van Os et al. |
| 5,796,074 A | 8/1998 | Edelstein et al. |
| 5,801,104 A | 9/1998 | Schuegraf et al. |
| 5,801,945 A | 9/1998 | Comer |
| 5,804,505 A | 9/1998 | Yamada et al. |
| 5,806,980 A | 9/1998 | Berrian |
| 5,813,851 A | 9/1998 | Nakao |
| 5,818,716 A | 10/1998 | Chin et al. |
| 5,819,092 A | 10/1998 | Ferguson et al. |
| 5,819,434 A | 10/1998 | Herchen et al. |
| 5,820,366 A | 10/1998 | Lee |
| 5,820,685 A | 10/1998 | Kurihra et al. |
| 5,820,686 A | 10/1998 | Moore |
| 5,826,129 A | 10/1998 | Hasebe et al. |
| 5,827,420 A | 10/1998 | Shirazi et al. |
| 5,827,435 A | 10/1998 | Samukawa |
| 5,827,757 A | 10/1998 | Robinson et al. |
| 5,836,483 A | 11/1998 | Disel |
| 5,837,058 A | 11/1998 | Chen et al. |
| 5,837,320 A | 11/1998 | Hampden-Smith et al. |
| 5,844,683 A | 12/1998 | Pavloski et al. |
| 5,846,332 A | 12/1998 | Zhao et al. |
| 5,851,293 A | 12/1998 | Lane et al. |
| 5,851,294 A | 12/1998 | Young et al. |
| 5,851,299 A | 12/1998 | Cheng et al. |
| 5,852,445 A | 12/1998 | Yoshikawa et al. |
| 5,852,879 A | 12/1998 | Schumaier |
| 5,853,484 A | 12/1998 | Jeong |
| D403,949 S | 1/1999 | Nakamura |
| D404,370 S | 1/1999 | Kimura |
| D404,372 S | 1/1999 | Ishii |
| 5,855,680 A | 1/1999 | Soininen et al. |
| 5,855,681 A | 1/1999 | Maydan et al. |
| 5,855,687 A | 1/1999 | DuBois et al. |
| 5,855,726 A | 1/1999 | Soraoka et al. |
| 5,857,777 A | 1/1999 | Schuh |
| 5,861,233 A | 1/1999 | Sekine et al. |
| 5,862,302 A | 1/1999 | Okase |
| 5,863,123 A | 1/1999 | Lee et al. |
| 5,865,205 A | 2/1999 | Wilmer |
| 5,866,795 A | 2/1999 | Wang et al. |
| 5,871,586 A | 2/1999 | Crawley et al. |
| 5,872,065 A | 2/1999 | Sivaramakrishnan |
| 5,873,942 A | 2/1999 | Park |
| 5,877,095 A | 3/1999 | Tamura et al. |
| 5,879,128 A | 3/1999 | Tietz et al. |
| 5,879,459 A | 3/1999 | Gadgil et al. |
| 5,880,980 A | 3/1999 | Rothacher et al. |
| 5,882,165 A | 3/1999 | Maydan et al. |
| 5,884,640 A | 3/1999 | Fishkin et al. |
| 5,888,304 A | 3/1999 | Umotoy et al. |
| 5,891,251 A | 4/1999 | MacLeish et al. |
| 5,893,741 A | 4/1999 | Huang |
| 5,897,348 A | 4/1999 | Wu |
| 5,897,378 A | 4/1999 | Eriguchi |
| 5,897,379 A | 4/1999 | Ulrich et al. |
| 5,897,710 A | 4/1999 | Sato et al. |
| D409,894 S | 5/1999 | McClurg |
| 5,904,170 A | 5/1999 | Harvey et al. |
| D411,516 S | 6/1999 | Imafuku et al. |
| 5,908,672 A | 6/1999 | Ryu |
| 5,915,200 A | 6/1999 | Tokumasu et al. |
| 5,915,562 A | 6/1999 | Nyseth et al. |
| 5,916,365 A | 6/1999 | Sherman |
| D412,270 S | 7/1999 | Fredrickson |
| 5,920,798 A | 7/1999 | Higuchi et al. |
| 5,928,426 A | 7/1999 | Aitchison |
| D412,512 S | 8/1999 | Boisvert |
| 5,937,142 A | 8/1999 | Moslehi et al. |
| 5,937,323 A | 8/1999 | Orczyk et al. |
| 5,939,886 A | 8/1999 | Turner et al. |
| 5,947,718 A | 9/1999 | Weaver |
| 5,950,327 A | 9/1999 | Peterson et al. |
| 5,950,925 A | 9/1999 | Fukunaga et al. |
| 5,954,375 A | 9/1999 | Trickle et al. |
| 5,961,775 A | 10/1999 | Fujimura |
| 5,968,275 A | 10/1999 | Lee et al. |
| 5,970,621 A | 10/1999 | Bazydola |
| 5,972,196 A | 10/1999 | Murphy et al. |
| 5,975,492 A | 11/1999 | Brenes |
| 5,976,973 A | 11/1999 | Ohira et al. |
| 5,979,506 A | 11/1999 | Aarseth |
| 5,982,931 A | 11/1999 | Ishimaru |
| 5,984,391 A | 11/1999 | Vanderpot et al. |
| 5,987,480 A | 11/1999 | Donohue et al. |
| 5,989,342 A | 11/1999 | Ikeda et al. |
| 5,992,453 A | 11/1999 | Zimmer |
| 5,997,588 A | 12/1999 | Goodwin |
| 5,997,768 A | 12/1999 | Scully |
| 5,998,870 A | 12/1999 | Lee et al. |
| 6,000,732 A | 12/1999 | Scheler et al. |
| 6,001,183 A | 12/1999 | Gurary et al. |
| 6,001,267 A | 12/1999 | Van Os et al. |
| 6,004,204 A | 12/1999 | Luxton et al. |
| D419,652 S | 1/2000 | Hall et al. |
| 6,013,553 A | 1/2000 | Wallace |
| 6,013,920 A | 1/2000 | Gordon et al. |
| 6,014,677 A | 1/2000 | Hayashi et al. |
| 6,015,459 A | 1/2000 | Jamison et al. |
| 6,015,465 A | 1/2000 | Kholodenko et al. |
| 6,017,779 A | 1/2000 | Miyasaka |
| 6,017,818 A | 1/2000 | Lu |
| 6,022,180 A | 2/2000 | Motoyama et al. |
| 6,022,802 A | 2/2000 | Jang |
| 6,024,799 A | 2/2000 | Chen et al. |
| 6,025,117 A | 2/2000 | Nakano et al. |
| 6,027,163 A | 2/2000 | Longenecker et al. |
| 6,029,602 A | 2/2000 | Bhatnagar |
| 6,030,900 A | 2/2000 | Grassl et al. |
| 6,033,215 A | 3/2000 | Ohsawa |
| 6,035,101 A | 3/2000 | Sajoto et al. |
| 6,035,804 A | 3/2000 | Arami et al. |
| 6,039,809 A | 3/2000 | Toyama et al. |
| 6,042,652 A | 3/2000 | Hyun |
| 6,044,860 A | 4/2000 | Neu |
| 6,045,260 A | 4/2000 | Schwartz et al. |
| 6,048,154 A | 4/2000 | Wytman |
| 6,050,506 A | 4/2000 | Guo et al. |
| 6,053,982 A | 4/2000 | Halpin et al. |
| 6,053,983 A | 4/2000 | Saeki et al. |
| 6,054,013 A | 4/2000 | Collins et al. |
| 6,054,678 A | 4/2000 | Miyazaki |
| 6,060,691 A | 5/2000 | Minami et al. |
| 6,060,721 A | 5/2000 | Huang |
| 6,063,196 A | 5/2000 | Li et al. |
| 6,066,204 A | 5/2000 | Haven |
| 6,068,441 A | 5/2000 | Raaijmakers et al. |

(56) References Cited

U.S. PATENT DOCUMENTS

| | | |
|---|---|---|
| 6,071,572 A | 6/2000 | Mosely et al. |
| 6,072,163 A | 6/2000 | Armstrong et al. |
| 6,073,973 A | 6/2000 | Boscaljon et al. |
| 6,074,154 A | 6/2000 | Ueda et al. |
| 6,074,443 A | 6/2000 | Venkatesh |
| 6,074,514 A | 6/2000 | Bjorkman et al. |
| 6,077,027 A | 6/2000 | Kawamura et al. |
| 6,079,356 A | 6/2000 | Umotoy et al. |
| 6,079,927 A | 6/2000 | Muka |
| 6,083,321 A | 7/2000 | Lei et al. |
| 6,086,677 A | 7/2000 | Umotoy et al. |
| 6,090,212 A | 7/2000 | Mahawili |
| 6,090,442 A | 7/2000 | Klaus et al. |
| 6,090,659 A | 7/2000 | Laibowitz et al. |
| 6,091,062 A | 7/2000 | Pfahnl et al. |
| 6,093,252 A | 7/2000 | Wengert et al. |
| 6,093,253 A | 7/2000 | Lofgren |
| 6,093,611 A | 7/2000 | Gardner et al. |
| 6,095,083 A | 8/2000 | Rice et al. |
| 6,096,133 A | 8/2000 | Yuuki et al. |
| 6,096,267 A | 8/2000 | Kishkovich |
| 6,099,302 A | 8/2000 | Hong et al. |
| 6,099,649 A | 8/2000 | Schmitt et al. |
| 6,099,651 A | 8/2000 | Sajoto et al. |
| 6,102,565 A | 8/2000 | Kita et al. |
| 6,104,002 A | 8/2000 | Hirose et al. |
| 6,104,011 A | 8/2000 | Juliano |
| 6,104,401 A | 8/2000 | Parsons |
| 6,106,625 A | 8/2000 | Koai et al. |
| 6,106,678 A | 8/2000 | Shufflebotham |
| 6,110,531 A | 8/2000 | Paz de Araujo et al. |
| 6,113,703 A | 9/2000 | Anderson et al. |
| 6,119,710 A | 9/2000 | Brown |
| 6,121,061 A | 9/2000 | Van Bilsen et al. |
| 6,121,158 A | 9/2000 | Benchikha et al. |
| 6,122,036 A | 9/2000 | Yamasaki et al. |
| 6,124,600 A | 9/2000 | Moroishi et al. |
| 6,125,789 A | 10/2000 | Gupta et al. |
| 6,126,744 A | 10/2000 | Hawkins et al. |
| 6,126,848 A | 10/2000 | Li et al. |
| 6,127,249 A | 10/2000 | Hu |
| 6,129,044 A | 10/2000 | Zhao et al. |
| 6,129,546 A | 10/2000 | Sada |
| 6,132,207 A | 10/2000 | Stoutjesdijk |
| 6,134,807 A | 10/2000 | Komino |
| 6,135,460 A | 10/2000 | Wise et al. |
| 6,137,240 A | 10/2000 | Bogdan |
| 6,139,239 A | 10/2000 | Snijders |
| 6,139,983 A | 10/2000 | Ohashi et al. |
| 6,140,252 A | 10/2000 | Cho et al. |
| 6,143,079 A | 11/2000 | Halpin |
| 6,143,082 A | 11/2000 | McInerney et al. |
| 6,143,129 A | 11/2000 | Savas et al. |
| 6,146,463 A | 11/2000 | Yudovsky et al. |
| 6,148,761 A | 11/2000 | Majewski et al. |
| 6,151,446 A | 11/2000 | Hunter et al. |
| 6,152,070 A | 11/2000 | Fairbairn et al. |
| 6,152,669 A | 11/2000 | Morita et al. |
| 6,156,151 A | 12/2000 | Komino et al. |
| 6,158,941 A | 12/2000 | Muka et al. |
| 6,159,301 A | 12/2000 | Sato et al. |
| 6,160,244 A | 12/2000 | Ohashi |
| 6,161,500 A | 12/2000 | Kopacz et al. |
| 6,162,323 A | 12/2000 | Koshimizu |
| 6,164,894 A | 12/2000 | Cheng |
| 6,174,809 B1 | 1/2001 | Kang et al. |
| 6,176,929 B1 | 1/2001 | Fukunaga et al. |
| 6,177,688 B1 | 1/2001 | Linthicum et al. |
| 6,178,918 B1 | 1/2001 | Van Os et al. |
| 6,179,955 B1 | 1/2001 | Shin et al. |
| 6,180,979 B1 | 1/2001 | Hofman et al. |
| 6,182,603 B1 | 2/2001 | Shang et al. |
| 6,183,564 B1 | 2/2001 | Reynolds et al. |
| 6,183,565 B1 | 2/2001 | Granneman et al. |
| 6,187,672 B1 | 2/2001 | Zhao et al. |
| 6,187,691 B1 | 2/2001 | Fukuda |
| 6,189,482 B1 | 2/2001 | Zhao et al. |
| 6,190,037 B1 | 2/2001 | Das et al. |
| 6,190,113 B1 | 2/2001 | Bui et al. |
| 6,190,634 B1 | 2/2001 | Lieber et al. |
| 6,191,399 B1 | 2/2001 | Van Bilsen |
| 6,194,037 B1 | 2/2001 | Terasaki et al. |
| 6,200,897 B1 | 3/2001 | Wang et al. |
| 6,201,999 B1 | 3/2001 | Jevtic |
| 6,203,613 B1 | 3/2001 | Gates et al. |
| 6,203,618 B1 | 3/2001 | Hashizume et al. |
| 6,207,932 B1 | 3/2001 | Yoo |
| 6,207,936 B1 | 3/2001 | de Waard |
| 6,209,221 B1 | 4/2001 | Beulens |
| 6,210,485 B1 | 4/2001 | Zhao et al. |
| 6,212,789 B1 | 4/2001 | Kato |
| 6,213,708 B1 | 4/2001 | Allen |
| 6,214,122 B1 | 4/2001 | Thompson |
| 6,214,717 B1 | 4/2001 | Yan et al. |
| 6,217,658 B1 | 4/2001 | Orczyk et al. |
| 6,217,662 B1 | 4/2001 | Kong et al. |
| 6,218,288 B1 | 4/2001 | Li et al. |
| 6,224,679 B1 | 5/2001 | Sasaki et al. |
| 6,225,020 B1 | 5/2001 | Jung et al. |
| 6,225,602 B1 | 5/2001 | Buijze et al. |
| 6,225,745 B1 | 5/2001 | Srivastava |
| 6,230,650 B1 | 5/2001 | Yamazaki |
| 6,231,290 B1 | 5/2001 | Kikuchi et al. |
| 6,235,121 B1 | 5/2001 | Honma et al. |
| 6,235,858 B1 | 5/2001 | Swarup et al. |
| 6,238,734 B1 | 5/2001 | Senzaki et al. |
| 6,239,402 B1 | 5/2001 | Araki et al. |
| 6,239,715 B1 | 5/2001 | Belton |
| 6,240,875 B1 | 6/2001 | Wijck et al. |
| 6,241,822 B1 | 6/2001 | Ide |
| 6,242,359 B1 | 6/2001 | Misra |
| 6,243,654 B1 | 6/2001 | Johnson et al. |
| 6,245,647 B1 | 6/2001 | Akiyama et al. |
| 6,245,665 B1 | 6/2001 | Yokoyama |
| 6,247,245 B1 | 6/2001 | Ishii |
| 6,250,250 B1 | 6/2001 | Maishev et al. |
| 6,255,221 B1 | 7/2001 | Hudson et al. |
| 6,257,758 B1 | 7/2001 | Culbertson |
| 6,261,648 B1 | 7/2001 | Akiba et al. |
| 6,264,467 B1 | 7/2001 | Lue et al. |
| 6,265,113 B1 | 7/2001 | Rosasco et al. |
| 6,265,311 B1 | 7/2001 | Hautala et al. |
| 6,270,572 B1 | 8/2001 | Kim et al. |
| 6,271,148 B1 | 8/2001 | Kao |
| 6,271,320 B1 | 8/2001 | Keller et al. |
| 6,274,496 B1 | 8/2001 | Leusink et al. |
| 6,274,878 B1 | 8/2001 | Li et al. |
| 6,281,098 B1 | 8/2001 | Wang |
| 6,281,141 B1 | 8/2001 | Das et al. |
| 6,283,692 B1 | 9/2001 | Perlov et al. |
| 6,284,050 B1 | 9/2001 | Shi et al. |
| 6,284,149 B1 | 9/2001 | Li et al. |
| 6,287,965 B1 | 9/2001 | Kang et al. |
| 6,287,988 B1 | 9/2001 | Nagamine et al. |
| 6,293,700 B1 | 9/2001 | Lund et al. |
| D449,873 S | 10/2001 | Bronson |
| 6,296,710 B1 | 10/2001 | Allen et al. |
| 6,296,711 B1 | 10/2001 | Loan et al. |
| 6,296,909 B1 | 10/2001 | Spitsberg |
| 6,297,539 B1 | 10/2001 | Ma et al. |
| 6,299,133 B2 | 10/2001 | Waragai et al. |
| 6,302,964 B1 | 10/2001 | Umotoy et al. |
| 6,303,523 B2 | 10/2001 | Cheung |
| 6,305,898 B1 | 10/2001 | Yamagishi et al. |
| 6,311,016 B1 | 10/2001 | Yanagawa et al. |
| 6,312,525 B1 | 11/2001 | Bright et al. |
| 6,315,512 B1 | 11/2001 | Tabrizi et al. |
| 6,316,162 B1 | 11/2001 | Jung et al. |
| 6,316,371 B1 | 11/2001 | Oosterlaken et al. |
| 6,320,320 B1 | 11/2001 | Bailey et al. |
| 6,321,680 B2 | 11/2001 | Cook et al. |
| 6,321,780 B1 | 11/2001 | Iwabuchi |
| D451,893 S | 12/2001 | Robson |
| D452,220 S | 12/2001 | Robson |

(56) References Cited

U.S. PATENT DOCUMENTS

| | | |
|---|---|---|
| 6,325,858 B1 | 12/2001 | Wengert |
| 6,326,322 B1 | 12/2001 | Kim et al. |
| 6,326,597 B1 | 12/2001 | Lubomirsky et al. |
| 6,328,561 B1 | 12/2001 | Hasper et al. |
| 6,328,864 B1 | 12/2001 | Ishizawa et al. |
| 6,329,297 B1 | 12/2001 | Balish |
| 6,333,275 B1 | 12/2001 | Mayer et al. |
| 6,335,049 B1 | 1/2002 | Basceri |
| 6,335,240 B1 | 1/2002 | Kim et al. |
| 6,335,293 B1 | 1/2002 | Luo et al. |
| 6,342,427 B1 | 1/2002 | Choi et al. |
| 6,343,239 B1 | 1/2002 | Toda et al. |
| 6,344,084 B1 | 2/2002 | Koinuma et al. |
| 6,344,232 B1 | 2/2002 | Jones et al. |
| 6,346,419 B1 | 2/2002 | Ryerson et al. |
| 6,347,636 B1 | 2/2002 | Xia |
| 6,350,391 B1 | 2/2002 | Livshits et al. |
| 6,352,049 B1 | 3/2002 | Yin et al. |
| 6,352,945 B1 | 3/2002 | Matsuki |
| 6,357,984 B1 | 3/2002 | Zinger et al. |
| 6,363,294 B1 | 3/2002 | Coronel et al. |
| D455,024 S | 4/2002 | Mimick et al. |
| 6,367,410 B1 | 4/2002 | Leahey et al. |
| 6,368,773 B1 | 4/2002 | Jung et al. |
| 6,368,987 B1 | 4/2002 | Kopacz et al. |
| 6,370,796 B1 | 4/2002 | Zucker |
| 6,372,583 B1 | 4/2002 | Tyagi |
| 6,374,831 B1 | 4/2002 | Chandran |
| 6,375,312 B1 | 4/2002 | Ikeda et al. |
| 6,375,749 B1 | 4/2002 | Boydston et al. |
| 6,375,750 B1 | 4/2002 | Van Os et al. |
| 6,379,466 B1 | 4/2002 | Sahin et al. |
| D457,609 S | 5/2002 | Piano |
| 6,383,300 B1 | 5/2002 | Saito et al. |
| 6,383,566 B1 | 5/2002 | Zagdoun |
| 6,383,955 B1 | 5/2002 | Matsuki |
| 6,387,207 B1 | 5/2002 | Janakiraman |
| 6,387,823 B1 | 5/2002 | Sonderman et al. |
| 6,387,827 B1 | 5/2002 | Mertens et al. |
| 6,390,753 B1 | 5/2002 | de Ridder et al. |
| 6,390,754 B2 | 5/2002 | Yamaga et al. |
| 6,391,803 B1 | 5/2002 | Kim et al. |
| 6,395,650 B1 | 5/2002 | Callegari et al. |
| 6,398,184 B1 | 6/2002 | Sowada et al. |
| 6,399,022 B1 | 6/2002 | Schuler et al. |
| 6,402,806 B1 | 6/2002 | Schmitt et al. |
| 6,410,433 B1 | 6/2002 | Hautala et al. |
| 6,410,459 B2 | 6/2002 | Blalock et al. |
| 6,410,463 B1 | 6/2002 | Matsuki |
| 6,413,321 B1 | 7/2002 | Kim et al. |
| 6,413,583 B1 | 7/2002 | Moghadam et al. |
| 6,420,279 B1 | 7/2002 | Ono et al. |
| 6,423,949 B1 | 7/2002 | Chen et al. |
| D461,233 S | 8/2002 | Whalen |
| D461,882 S | 8/2002 | Piano |
| 6,428,859 B1 | 8/2002 | Chiang et al. |
| 6,429,465 B1 | 8/2002 | Yagi et al. |
| 6,432,206 B1 | 8/2002 | Tolt |
| 6,432,255 B1 | 8/2002 | Sun et al. |
| 6,432,479 B2 | 8/2002 | Chang et al. |
| 6,432,849 B1 | 8/2002 | Endo et al. |
| 6,433,298 B1 | 8/2002 | Ishii |
| 6,435,798 B1 | 8/2002 | Satoh |
| 6,435,865 B1 | 8/2002 | Tseng et al. |
| 6,436,819 B1 | 8/2002 | Zhang |
| 6,437,444 B2 | 8/2002 | Andideh |
| 6,438,502 B1 | 8/2002 | Awtrey |
| 6,439,822 B1 | 8/2002 | Kimura et al. |
| 6,440,261 B1 | 8/2002 | Tepman et al. |
| 6,441,350 B1 | 8/2002 | Stoddard et al. |
| 6,445,574 B1 | 9/2002 | Saw et al. |
| 6,446,573 B2 | 9/2002 | Hirayama et al. |
| 6,447,232 B1 | 9/2002 | Davis et al. |
| 6,447,651 B1 | 9/2002 | Ishikawa et al. |
| 6,447,937 B1 | 9/2002 | Murakawa et al. |
| 6,448,192 B1 | 9/2002 | Kaushik |
| 6,450,117 B1 | 9/2002 | Murugesh et al. |
| 6,450,757 B1 | 9/2002 | Saeki |
| 6,451,713 B1 | 9/2002 | Tay et al. |
| 6,452,017 B1 | 9/2002 | Uhlenbrock et al. |
| 6,454,860 B2 | 9/2002 | Metzner et al. |
| 6,454,909 B1 | 9/2002 | Matsuse et al. |
| 6,455,098 B2 | 9/2002 | Tran et al. |
| 6,455,225 B1 | 9/2002 | Kong et al. |
| 6,455,445 B2 | 9/2002 | Matsuki |
| 6,460,482 B1 | 10/2002 | Kuibira et al. |
| 6,461,435 B1 | 10/2002 | Littau et al. |
| 6,461,436 B1 | 10/2002 | Campbell et al. |
| 6,461,439 B1 | 10/2002 | Granneman et al. |
| 6,462,310 B1 | 10/2002 | Ratliff et al. |
| 6,464,825 B1 | 10/2002 | Shinozaki |
| 6,468,924 B2 | 10/2002 | Lee |
| 6,471,779 B1 | 10/2002 | Nishio et al. |
| 6,472,266 B1 | 10/2002 | Yu et al. |
| 6,474,987 B1 | 11/2002 | Huang et al. |
| 6,475,276 B1 | 11/2002 | Elers et al. |
| 6,475,902 B1 | 11/2002 | Hausmann et al. |
| 6,475,930 B1 | 11/2002 | Junker et al. |
| 6,478,872 B1 | 11/2002 | Chae et al. |
| 6,481,945 B1 | 11/2002 | Hasper et al. |
| 6,482,331 B2 | 11/2002 | Lu et al. |
| 6,482,663 B1 | 11/2002 | Buckland |
| 6,483,989 B1 | 11/2002 | Okada et al. |
| 6,488,774 B1 | 12/2002 | Horie et al. |
| 6,490,493 B1 | 12/2002 | Dharnipragada |
| 6,492,625 B1 | 12/2002 | Boguslavskiy et al. |
| 6,494,065 B2 | 12/2002 | Babbitt |
| 6,494,998 B1 | 12/2002 | Brcka |
| 6,496,819 B1 | 12/2002 | Bello et al. |
| 6,497,734 B1 | 12/2002 | Barber et al. |
| 6,497,767 B1 | 12/2002 | Okase et al. |
| 6,498,091 B1 | 12/2002 | Chen et al. |
| 6,499,533 B2 | 12/2002 | Yamada |
| 6,500,487 B1 | 12/2002 | Holst et al. |
| 6,502,530 B1 | 1/2003 | Turlot et al. |
| 6,503,079 B2 | 1/2003 | Kogano et al. |
| 6,503,330 B1 | 1/2003 | Sneh et al. |
| 6,503,365 B1 | 1/2003 | Kim et al. |
| 6,503,562 B1 | 1/2003 | Saito et al. |
| 6,503,826 B1 | 1/2003 | Oda |
| 6,506,009 B1 | 1/2003 | Nulman et al. |
| 6,506,253 B2 | 1/2003 | Sakuma |
| 6,507,410 B1 | 1/2003 | Robertson et al. |
| 6,511,539 B1 | 1/2003 | Raaijmakers |
| 6,514,313 B1 | 2/2003 | Spiegelman |
| 6,514,666 B1 | 2/2003 | Choi et al. |
| 6,521,295 B1 | 2/2003 | Remington |
| 6,521,547 B1 | 2/2003 | Chang et al. |
| 6,527,884 B1 | 3/2003 | Takakuwa et al. |
| 6,528,171 B1 | 3/2003 | Endler et al. |
| 6,528,430 B2 | 3/2003 | Kwan |
| 6,528,752 B1 | 3/2003 | Ishii et al. |
| 6,528,767 B2 | 3/2003 | Bagley et al. |
| 6,530,994 B1 | 3/2003 | Mahawili |
| 6,531,193 B2 | 3/2003 | Fonash et al. |
| 6,531,412 B2 | 3/2003 | Conti et al. |
| 6,534,133 B1 | 3/2003 | Kaloyeros et al. |
| 6,534,395 B2 | 3/2003 | Werkhoven et al. |
| 6,536,950 B1 | 3/2003 | Green |
| 6,539,891 B1 | 4/2003 | Kang et al. |
| 6,540,469 B2 | 4/2003 | Matsunaga et al. |
| 6,540,838 B2 | 4/2003 | Sneh et al. |
| 6,544,906 B2 | 4/2003 | Rotondaro et al. |
| 6,552,209 B1 | 4/2003 | Lei et al. |
| 6,558,517 B2 | 5/2003 | Basceri |
| 6,558,755 B2 | 5/2003 | Berry et al. |
| 6,559,026 B1 | 5/2003 | Rossman et al. |
| 6,562,094 B2 | 5/2003 | Denker et al. |
| 6,565,763 B1 | 5/2003 | Asakawa et al. |
| 6,566,278 B1 | 5/2003 | Harvey et al. |
| 6,569,239 B2 | 5/2003 | Arai et al. |
| 6,569,971 B2 | 5/2003 | Roh et al. |
| 6,573,030 B1 | 6/2003 | Fairbairn et al. |
| 6,574,644 B2 | 6/2003 | Hsu et al. |

(56) References Cited

U.S. PATENT DOCUMENTS

| | | |
|---|---|---|
| 6,576,062 B2 | 6/2003 | Matsuse |
| 6,576,064 B2 | 6/2003 | Griffiths et al. |
| 6,576,300 B1 | 6/2003 | Berry et al. |
| 6,576,564 B2 | 6/2003 | Agarwal |
| 6,578,589 B1 | 6/2003 | Mayusumi |
| 6,579,833 B1 | 6/2003 | McNallan et al. |
| 6,580,050 B1 | 6/2003 | Miller et al. |
| 6,582,174 B1 | 6/2003 | Hayashi |
| 6,583,048 B2 | 6/2003 | Vincent et al. |
| 6,583,572 B2 | 6/2003 | Veltrop et al. |
| 6,587,108 B1 | 7/2003 | Guerlain et al. |
| 6,589,352 B1 | 7/2003 | Yudovsky et al. |
| 6,589,707 B2 | 7/2003 | Lee et al. |
| 6,589,868 B2 | 7/2003 | Rossman |
| 6,590,251 B2 | 7/2003 | Kang et al. |
| 6,594,550 B1 | 7/2003 | Okrah |
| 6,596,398 B1 | 7/2003 | Russo et al. |
| 6,596,653 B2 | 7/2003 | Tan |
| 6,598,559 B1 | 7/2003 | Vellore et al. |
| 6,602,806 B1 | 8/2003 | Xia et al. |
| 6,607,602 B1 | 8/2003 | Granneman et al. |
| 6,607,868 B2 | 8/2003 | Choi |
| 6,607,948 B1 | 8/2003 | Sugiyama et al. |
| 6,608,745 B2 | 8/2003 | Tsuruta et al. |
| 6,610,375 B2 | 8/2003 | Akiba et al. |
| 6,613,685 B1 | 9/2003 | Granneman et al. |
| 6,616,986 B2 | 9/2003 | Sherman |
| 6,617,253 B1 | 9/2003 | Chu et al. |
| 6,620,251 B2 | 9/2003 | Kitano |
| 6,623,799 B1 | 9/2003 | Lee et al. |
| 6,624,064 B1 | 9/2003 | Sahin |
| 6,627,268 B1 | 9/2003 | Fair et al. |
| 6,627,503 B2 | 9/2003 | Ma et al. |
| 6,630,030 B1 | 10/2003 | Suntola et al. |
| 6,632,478 B2 | 10/2003 | Gaillard et al. |
| 6,633,364 B2 | 10/2003 | Hayashi |
| 6,635,115 B1 | 10/2003 | Fairbairn et al. |
| 6,635,117 B1 | 10/2003 | Kinnard et al. |
| 6,635,578 B1 | 10/2003 | Xu et al. |
| 6,638,839 B2 | 10/2003 | Deng et al. |
| 6,640,145 B2 | 10/2003 | Hoffberg et al. |
| 6,645,304 B2 | 11/2003 | Yamaguchi |
| 6,648,974 B1 | 11/2003 | Ogliari et al. |
| 6,649,921 B1 | 11/2003 | Cekic et al. |
| 6,652,924 B2 | 11/2003 | Sherman |
| 6,656,281 B1 | 12/2003 | Ueda |
| 6,656,282 B2 | 12/2003 | Kim et al. |
| 6,658,933 B2 | 12/2003 | Allegre et al. |
| 6,659,111 B1 | 12/2003 | Mouri et al. |
| 6,660,662 B2 | 12/2003 | Ishikawa et al. |
| 6,662,817 B2 | 12/2003 | Yamagishi |
| 6,663,332 B1 | 12/2003 | Sluijk et al. |
| 6,673,196 B1 | 1/2004 | Oyabu |
| 6,676,290 B1 | 1/2004 | Lu |
| 6,676,759 B1 | 1/2004 | Takagi |
| 6,679,194 B2 | 1/2004 | Ham et al. |
| 6,682,971 B2 | 1/2004 | Tsuneda et al. |
| 6,682,973 B1 | 1/2004 | Paton et al. |
| 6,683,274 B1 | 1/2004 | Kwon et al. |
| D486,891 S | 2/2004 | Cronce |
| 6,684,659 B1 | 2/2004 | Tanaka et al. |
| 6,684,719 B2 | 2/2004 | Gehner et al. |
| 6,686,281 B2 | 2/2004 | Yamazaki et al. |
| 6,688,784 B1 | 2/2004 | Templeton |
| 6,689,220 B1 | 2/2004 | Nguyen |
| 6,692,575 B1 | 2/2004 | Omstead et al. |
| 6,692,576 B2 | 2/2004 | Halpin et al. |
| 6,692,903 B2 | 2/2004 | Chen et al. |
| 6,696,367 B1 | 2/2004 | Aggarwal |
| 6,699,003 B2 | 3/2004 | Saeki |
| 6,699,399 B1 | 3/2004 | Qian et al. |
| 6,700,089 B1 | 3/2004 | Hirooka |
| 6,709,989 B2 | 3/2004 | Ramdani et al. |
| 6,710,364 B2 | 3/2004 | Guldi et al. |
| 6,710,857 B2 | 3/2004 | Kondo |
| 6,712,949 B2 | 3/2004 | Gopal |
| 6,713,824 B1 | 3/2004 | Mikata |
| 6,715,949 B1 | 4/2004 | Fisher et al. |
| 6,716,477 B1 | 4/2004 | Komiyama et al. |
| 6,716,571 B2 | 4/2004 | Gabriel |
| 6,719,499 B1 | 4/2004 | Kuznetsov et al. |
| 6,720,260 B1 | 4/2004 | Fair et al. |
| 6,720,262 B2 | 4/2004 | Koh et al. |
| 6,720,531 B1 | 4/2004 | Jacobson et al. |
| 6,722,837 B2 | 4/2004 | Inui |
| 6,723,642 B1 | 4/2004 | Lim et al. |
| 6,730,614 B1 | 5/2004 | Lim et al. |
| 6,732,006 B2 | 5/2004 | Haanstra et al. |
| 6,734,090 B2 | 5/2004 | Agarwala et al. |
| 6,734,631 B2 | 5/2004 | Juestel et al. |
| 6,737,716 B1 | 5/2004 | Matsuo et al. |
| 6,740,853 B1 | 5/2004 | Johnson et al. |
| 6,743,475 B2 | 6/2004 | Skarp et al. |
| 6,743,738 B2 | 6/2004 | Todd et al. |
| 6,745,095 B1 | 6/2004 | Ben-Dov |
| 6,746,240 B2 | 6/2004 | de Ridder et al. |
| 6,746,308 B1 | 6/2004 | Bode et al. |
| 6,749,671 B2 | 6/2004 | Holst et al. |
| 6,753,507 B2 | 6/2004 | Fure et al. |
| 6,755,221 B2 | 6/2004 | Jeong et al. |
| 6,756,085 B2 | 6/2004 | Waldfried |
| 6,756,293 B2 | 6/2004 | Li et al. |
| 6,756,318 B2 | 6/2004 | Nguyen et al. |
| 6,759,098 B2 | 7/2004 | Han |
| 6,760,981 B2 | 7/2004 | Leap |
| 6,766,545 B2 | 7/2004 | Hodges |
| 6,767,447 B2 | 7/2004 | Uno et al. |
| D494,552 S | 8/2004 | Tezuka et al. |
| 6,776,849 B2 | 8/2004 | Aggarwal et al. |
| 6,780,704 B1 | 8/2004 | Raaijmakers et al. |
| 6,783,875 B2 | 8/2004 | Yamada et al. |
| 6,784,033 B1 | 8/2004 | Yamazaki |
| 6,784,108 B1 | 8/2004 | Donohoe et al. |
| D496,008 S | 9/2004 | Takahashi et al. |
| 6,786,997 B1 | 9/2004 | Yamazaki |
| D497,536 S | 10/2004 | Fujiwara |
| D497,977 S | 11/2004 | Engelbrektsson |
| 6,811,960 B2 | 11/2004 | Lee et al. |
| 6,812,157 B1 | 11/2004 | Gadgil |
| 6,815,350 B2 | 11/2004 | Kim et al. |
| 6,815,352 B1 | 11/2004 | Tamura et al. |
| 6,818,566 B2 | 11/2004 | Leeson et al. |
| 6,818,864 B2 | 11/2004 | Ptak |
| 6,820,570 B2 | 11/2004 | Kilpela et al. |
| 6,821,889 B2 | 11/2004 | Elers et al. |
| 6,821,910 B2 | 11/2004 | Adomaitis et al. |
| 6,824,665 B2 | 11/2004 | Shelnut et al. |
| 6,825,106 B1 | 11/2004 | Gao et al. |
| 6,825,134 B2 | 11/2004 | Law et al. |
| D499,620 S | 12/2004 | Horner-Richardson et al. |
| 6,827,789 B2 | 12/2004 | Lee et al. |
| 6,828,235 B2 | 12/2004 | Takano |
| 6,831,004 B2 | 12/2004 | Byun |
| 6,833,024 B2 | 12/2004 | Holst et al. |
| 6,835,039 B2 | 12/2004 | Van Den Berg |
| 6,838,122 B2 | 1/2005 | Basceri et al. |
| 6,841,201 B2 | 1/2005 | Shanov et al. |
| 6,843,202 B2 | 1/2005 | Kusuda |
| 6,843,858 B2 | 1/2005 | Rossman |
| 6,846,146 B2 | 1/2005 | Inui |
| 6,846,515 B2 | 1/2005 | Vrtis |
| 6,846,742 B2 | 1/2005 | Rossman |
| 6,847,014 B1 | 1/2005 | Benjamin et al. |
| 6,849,241 B2 | 2/2005 | Dauelsberg et al. |
| 6,849,857 B2 | 2/2005 | Ichiki et al. |
| 6,854,580 B2 | 2/2005 | Braford |
| 6,858,524 B2 | 2/2005 | Haukka et al. |
| 6,858,547 B2 | 2/2005 | Metzner |
| 6,861,642 B2 | 3/2005 | Ichiki et al. |
| 6,863,019 B2 | 3/2005 | Shamouilian |
| 6,863,281 B2 | 3/2005 | Endou et al. |
| 6,864,041 B2 | 3/2005 | Brown |
| 6,867,086 B1 | 3/2005 | Chen et al. |
| 6,867,153 B2 | 3/2005 | Tokunaga |

(56)    References Cited

U.S. PATENT DOCUMENTS

| | | |
|---|---|---|
| 6,867,859 B1 | 3/2005 | Powell |
| 6,872,258 B2 | 3/2005 | Park et al. |
| 6,872,259 B2 | 3/2005 | Strang |
| D504,142 S | 4/2005 | Horner-Richardson et al. |
| 6,874,247 B1 | 4/2005 | Hsu |
| 6,874,480 B1 | 4/2005 | Ismailov |
| 6,875,477 B2 | 4/2005 | Trickett et al. |
| 6,875,677 B1 | 4/2005 | Conley, Jr. et al. |
| 6,876,017 B2 | 4/2005 | Goodner |
| 6,876,191 B2 | 4/2005 | de Ridder |
| 6,878,206 B2 | 4/2005 | Tzu et al. |
| 6,878,402 B2 | 4/2005 | Chiang et al. |
| 6,883,733 B1 | 4/2005 | Lind |
| 6,884,066 B2 | 4/2005 | Nguyen et al. |
| 6,884,295 B2 | 4/2005 | Ishi |
| 6,884,319 B2 | 4/2005 | Kim |
| 6,884,475 B2 | 4/2005 | Basceri |
| D505,590 S | 5/2005 | Greiner |
| 6,889,211 B1 | 5/2005 | Yoshiura et al. |
| 6,889,864 B2 | 5/2005 | Lindfors et al. |
| 6,890,596 B2 | 5/2005 | Sarigiannis et al. |
| 6,895,158 B2 | 5/2005 | Alyward et al. |
| 6,899,507 B2 | 5/2005 | Yamagishi et al. |
| 6,902,395 B2 | 6/2005 | Oosterlaken et al. |
| 6,902,647 B2 | 6/2005 | Hasper |
| 6,909,839 B2 | 6/2005 | Wang et al. |
| 6,911,092 B2 | 6/2005 | Sneh |
| 6,913,152 B2 | 7/2005 | Zuk |
| 6,913,796 B2 | 7/2005 | Albano et al. |
| 6,916,398 B2 | 7/2005 | Chen et al. |
| 6,916,559 B2 | 7/2005 | Murakawa et al. |
| 6,917,755 B2 | 7/2005 | Nguyen et al. |
| 6,924,078 B2 | 8/2005 | Lee et al. |
| 6,928,890 B2 | 8/2005 | Gehner et al. |
| 6,929,699 B2 | 8/2005 | Whitesell |
| 6,929,700 B2 | 8/2005 | Tan et al. |
| 6,930,041 B2 | 8/2005 | Agarwal |
| 6,930,059 B2 | 8/2005 | Conley, Jr. et al. |
| 6,935,269 B2 | 8/2005 | Lee et al. |
| 6,939,579 B2 | 9/2005 | Bondestam et al. |
| 6,939,817 B2 | 9/2005 | Sandhu et al. |
| 6,942,753 B2 | 9/2005 | Choi et al. |
| 6,949,204 B1 | 9/2005 | Lenz et al. |
| 6,951,587 B1 | 10/2005 | Narushima |
| 6,952,656 B1 | 10/2005 | Cordova et al. |
| 6,953,609 B2 | 10/2005 | Carollo |
| 6,955,741 B2 | 10/2005 | Yamagishi |
| 6,955,836 B2 | 10/2005 | Kumagai et al. |
| 6,955,928 B1 | 10/2005 | Brennan |
| 6,963,052 B2 | 11/2005 | Kuibira et al. |
| 6,972,055 B2 | 12/2005 | Sferlazzo |
| 6,972,478 B1 | 12/2005 | Waite et al. |
| 6,974,781 B2 | 12/2005 | Timmermans et al. |
| 6,975,921 B2 | 12/2005 | Verhaar |
| 6,976,822 B2 | 12/2005 | Woodruff |
| RE38,937 E | 1/2006 | Nakamura |
| 6,981,832 B2 | 1/2006 | Zinger et al. |
| 6,982,046 B2 | 1/2006 | Srivastava et al. |
| 6,982,103 B2 | 1/2006 | Basceri et al. |
| 6,984,591 B1 | 1/2006 | Buchanan et al. |
| 6,984,595 B1 | 1/2006 | Yamazaki |
| 6,985,788 B2 | 1/2006 | Haanstra et al. |
| 6,986,914 B2 | 1/2006 | Elers et al. |
| 6,987,155 B2 | 1/2006 | Roh et al. |
| 6,990,430 B2 | 1/2006 | Hosek |
| 7,005,227 B2 | 2/2006 | Yueh et al. |
| 7,005,391 B2 | 2/2006 | Min |
| 7,008,879 B2 | 3/2006 | Lee et al. |
| 7,010,580 B1 | 3/2006 | Fu et al. |
| 7,017,514 B1 | 3/2006 | Shepherd et al. |
| 7,018,941 B2 | 3/2006 | Cui et al. |
| 7,021,330 B2 | 4/2006 | Maula et al. |
| 7,021,881 B2 | 4/2006 | Yamagishi |
| 7,036,453 B2 | 5/2006 | Ishikawa et al. |
| 7,041,609 B2 | 5/2006 | Vaartstra |
| 7,045,430 B2 | 5/2006 | Ahn et al. |
| 7,049,226 B2 | 5/2006 | Chung et al. |
| 7,049,247 B2 | 5/2006 | Gates et al. |
| 7,052,584 B2 | 5/2006 | Basceri |
| 7,053,009 B2 | 5/2006 | Conley, Jr. et al. |
| 7,055,263 B2 | 6/2006 | Wu et al. |
| 7,055,875 B2 | 6/2006 | Bonora |
| 7,062,161 B2 | 6/2006 | Kusuda et al. |
| D524,600 S | 7/2006 | Austin et al. |
| D525,127 S | 7/2006 | Cogley et al. |
| 7,070,178 B2 | 7/2006 | Van Der Toorn et al. |
| 7,071,051 B1 | 7/2006 | Jeon et al. |
| 7,073,834 B2 | 7/2006 | Matsumoto et al. |
| 7,074,690 B1 | 7/2006 | Gauri et al. |
| 7,077,614 B1 | 7/2006 | Hasper et al. |
| 7,080,545 B2 | 7/2006 | Dimeo et al. |
| 7,084,060 B1 | 8/2006 | Furukawa |
| 7,084,079 B2 | 8/2006 | Conti et al. |
| 7,085,623 B2 | 8/2006 | Siegers |
| 7,086,347 B2 | 8/2006 | Howald et al. |
| 7,088,003 B2 | 8/2006 | Gates et al. |
| 7,090,394 B2 | 8/2006 | Hashikura et al. |
| 7,092,287 B2 | 8/2006 | Beulens et al. |
| 7,098,149 B2 | 8/2006 | Lukas |
| 7,098,150 B2 | 8/2006 | Misra et al. |
| 7,100,459 B2 | 9/2006 | Gehner et al. |
| 7,101,763 B1 | 9/2006 | Anderson et al. |
| 7,108,753 B2 | 9/2006 | Wood |
| 7,109,098 B1 | 9/2006 | Ramaswamy et al. |
| 7,109,114 B2 | 9/2006 | Chen et al. |
| 7,111,232 B1 | 9/2006 | Bascom |
| 7,115,305 B2 | 10/2006 | Bronikowski et al. |
| 7,115,838 B2 | 10/2006 | Kurara et al. |
| 7,122,085 B2 | 10/2006 | Shero et al. |
| 7,122,222 B2 | 10/2006 | Xiao et al. |
| 7,122,844 B2 | 10/2006 | Nakamura et al. |
| 7,129,165 B2 | 10/2006 | Basol et al. |
| 7,132,360 B2 | 11/2006 | Schaeffer et al. |
| 7,135,421 B2 | 11/2006 | Ahn et al. |
| 7,140,558 B2 | 11/2006 | McCracken et al. |
| 7,141,499 B2 | 11/2006 | Raaijmakers |
| 7,143,897 B1 | 12/2006 | Guzman et al. |
| 7,144,806 B1 | 12/2006 | Fair et al. |
| 7,144,809 B2 | 12/2006 | Elers et al. |
| 7,147,766 B2 | 12/2006 | Uzoh et al. |
| 7,153,542 B2 | 12/2006 | Nguyen et al. |
| D535,673 S | 1/2007 | Conway et al. |
| 7,156,380 B2 | 1/2007 | Soininen |
| 7,163,393 B2 | 1/2007 | Adachi et al. |
| 7,163,721 B2 | 1/2007 | Zhang et al. |
| 7,163,900 B2 | 1/2007 | Weber |
| 7,168,852 B2 | 1/2007 | Linnarsson |
| 7,172,497 B2 | 2/2007 | Basol et al. |
| 7,173,216 B2 | 2/2007 | Ptak |
| 7,183,229 B2 | 2/2007 | Yamanaka |
| 7,186,648 B1 | 3/2007 | Rozbicki |
| 7,192,824 B2 | 3/2007 | Ahn et al. |
| 7,192,892 B2 | 3/2007 | Ahn et al. |
| 7,195,479 B2 | 3/2007 | Beatty et al. |
| 7,195,693 B2 | 3/2007 | Cowans |
| D541,125 S | 4/2007 | Gaudron |
| 7,198,447 B2 | 4/2007 | Morimitsu et al. |
| 7,199,513 B2 | 4/2007 | Huber et al. |
| 7,201,943 B2 | 4/2007 | Park et al. |
| 7,202,148 B2 | 4/2007 | Chen et al. |
| 7,202,512 B2 | 4/2007 | Chen et al. |
| 7,204,886 B2 | 4/2007 | Chen et al. |
| 7,204,887 B2 | 4/2007 | Kawamura et al. |
| 7,205,246 B2 | 4/2007 | MacNeil et al. |
| 7,205,247 B2 | 4/2007 | Lee et al. |
| 7,207,763 B2 | 4/2007 | Lee |
| 7,208,198 B2 | 4/2007 | Basceri et al. |
| 7,208,389 B1 | 4/2007 | Tipton et al. |
| 7,210,925 B2 | 5/2007 | Adachi |
| 7,211,524 B2 | 5/2007 | Ryu et al. |
| 7,211,525 B1 | 5/2007 | Shanker |
| 7,214,630 B1 | 5/2007 | Varadarajan et al. |
| 7,217,617 B2 | 5/2007 | Basceri |
| 7,223,014 B2 | 5/2007 | Lojen |

(56) References Cited

U.S. PATENT DOCUMENTS

| | | | |
|---|---|---|---|
| 7,208,413 B2 | 6/2007 | Byun et al. |
| 7,229,502 B2 | 6/2007 | Wang et al. |
| 7,234,476 B2 | 6/2007 | Arai |
| 7,235,137 B2 | 6/2007 | Kitayama et al. |
| 7,235,482 B2 | 6/2007 | Wu |
| 7,235,501 B2 | 6/2007 | Ahn et al. |
| 7,238,596 B2 | 7/2007 | Kouvetakis et al. |
| 7,238,616 B2 | 7/2007 | Agarwal |
| 7,238,653 B2 | 7/2007 | Lee et al. |
| D549,815 S | 8/2007 | Murphy |
| 7,256,375 B2 | 8/2007 | Oosterlaken |
| 7,265,061 B1 | 9/2007 | Cho et al. |
| 7,274,867 B2 | 9/2007 | Peukert |
| D553,104 S | 10/2007 | Oohashi et al. |
| 7,279,256 B2 | 10/2007 | Son |
| 7,290,813 B2 | 11/2007 | Bonora |
| 7,294,581 B2 | 11/2007 | Haverkort et al. |
| 7,296,460 B2 | 11/2007 | Dimeo et al. |
| 7,297,641 B2 | 11/2007 | Todd et al. |
| 7,298,009 B2 | 11/2007 | Yan et al. |
| 7,301,623 B1 | 11/2007 | Madsen et al. |
| D556,704 S | 12/2007 | Nakamura et al. |
| D557,226 S | 12/2007 | Uchino et al. |
| D558,021 S | 12/2007 | Lawrence |
| 7,307,028 B2 | 12/2007 | Goto et al. |
| 7,307,178 B2 | 12/2007 | Kiyomori et al. |
| 7,311,977 B2 | 12/2007 | Yokota et al. |
| 7,312,148 B2 | 12/2007 | Ramaswamy et al. |
| 7,312,162 B2 | 12/2007 | Ramaswamy et al. |
| 7,312,494 B2 | 12/2007 | Ahn et al. |
| D559,993 S | 1/2008 | Nagakubo et al. |
| D559,994 S | 1/2008 | Nagakubo et al. |
| 7,320,544 B2 | 1/2008 | Hsieh |
| 7,323,401 B2 | 1/2008 | Ramaswamy et al. |
| D562,357 S | 2/2008 | Hardy |
| 7,326,656 B2 | 2/2008 | Brask et al. |
| 7,326,657 B2 | 2/2008 | Xia et al. |
| 7,327,948 B1 | 2/2008 | Shrinivasan |
| 7,329,947 B2 | 2/2008 | Adachi et al. |
| 7,335,611 B2 | 2/2008 | Ramaswamy et al. |
| 7,351,057 B2 | 4/2008 | Berenbak et al. |
| 7,354,482 B2 | 4/2008 | Konishi et al. |
| 7,354,847 B2 | 4/2008 | Chan et al. |
| 7,354,873 B2 | 4/2008 | Fukazawa et al. |
| 7,356,762 B2 | 4/2008 | van Driel |
| 7,357,138 B2 | 4/2008 | Ji et al. |
| 7,361,447 B2 | 4/2008 | Jung |
| 7,375,035 B2 | 5/2008 | Heden et al. |
| 7,376,520 B2 | 5/2008 | Wong |
| 7,378,618 B1 | 5/2008 | Sorabji et al. |
| 7,379,785 B2 | 5/2008 | Higashi et al. |
| D571,383 S | 6/2008 | Ota et al. |
| D571,831 S | 6/2008 | Ota et al. |
| 7,381,644 B1 | 6/2008 | Soubramonium et al. |
| 7,387,685 B2 | 6/2008 | Choi et al. |
| 7,393,207 B2 | 7/2008 | Imai |
| 7,393,418 B2 | 7/2008 | Yokogawa |
| 7,393,736 B2 | 7/2008 | Ahn et al. |
| 7,393,765 B2 | 7/2008 | Hanawa et al. |
| 7,396,491 B2 | 7/2008 | Marking et al. |
| 7,399,388 B2 | 7/2008 | Moghadam et al. |
| 7,399,570 B2 | 7/2008 | Lee et al. |
| 7,402,534 B2 | 7/2008 | Mahajani |
| 7,405,166 B2 | 7/2008 | Liang et al. |
| 7,405,454 B2 | 7/2008 | Ahn et al. |
| D575,713 S | 8/2008 | Ratcliffe |
| 7,408,225 B2 | 8/2008 | Shinriki et al. |
| 7,410,290 B2 | 8/2008 | Tanaka |
| 7,410,666 B2 | 8/2008 | Elers |
| 7,411,352 B2 | 8/2008 | Madocks |
| 7,414,281 B1 | 8/2008 | Fastow |
| D576,001 S | 9/2008 | Brunderman |
| 7,422,635 B2 | 9/2008 | Zheng et al. |
| 7,422,636 B2 | 9/2008 | Ishizaka |
| 7,422,653 B2 | 9/2008 | Blahnik et al. |
| 7,422,775 B2 | 9/2008 | Ramaswamy et al. |
| 7,425,224 B2 | 9/2008 | Nguyen |
| 7,427,571 B2 | 9/2008 | Lindeboom et al. |
| 7,429,532 B2 | 9/2008 | Ramaswamy et al. |
| 7,431,966 B2 | 10/2008 | Derderian et al. |
| 7,432,476 B2 | 10/2008 | Morita et al. |
| 7,437,060 B2 | 10/2008 | Wang et al. |
| 7,442,275 B2 | 10/2008 | Cowans |
| 7,456,429 B2 | 11/2008 | Levy |
| D583,395 S | 12/2008 | Ueda |
| 7,467,632 B2 | 12/2008 | Lee et al. |
| 7,473,655 B2 | 1/2009 | Wang et al. |
| 7,475,588 B2 | 1/2009 | Dimeo et al. |
| 7,476,291 B2 | 1/2009 | Wang et al. |
| 7,479,198 B2 | 1/2009 | Guffrey |
| 7,482,247 B1 | 1/2009 | Papasouliotis |
| 7,482,283 B2 | 1/2009 | Yamasaki et al. |
| D585,968 S | 2/2009 | Elkins et al. |
| 7,489,389 B2 | 2/2009 | Shibazaki et al. |
| 7,494,882 B2 | 2/2009 | Vitale |
| 7,497,614 B2 | 3/2009 | Gaff |
| 7,498,242 B2 | 3/2009 | Kumar et al. |
| 7,501,292 B2 | 3/2009 | Matsushita et al. |
| 7,501,355 B2 | 3/2009 | Bhatia et al. |
| 7,503,980 B2 | 3/2009 | Kida et al. |
| 7,504,344 B2 | 3/2009 | Matsuki et al. |
| D590,933 S | 4/2009 | Vansell |
| 7,514,058 B1 | 4/2009 | Hitzman et al. |
| 7,514,375 B1 | 4/2009 | Shanker et al. |
| D593,585 S | 6/2009 | Ota et al. |
| D593,969 S | 6/2009 | Li |
| 7,541,297 B2 | 6/2009 | Mallick et al. |
| 7,544,398 B1 | 6/2009 | Chang et al. |
| 7,547,363 B2 | 6/2009 | Tomiyasu et al. |
| 7,547,633 B2 | 6/2009 | Ranish et al. |
| 7,550,396 B2 | 6/2009 | Frohberg et al. |
| D596,476 S | 7/2009 | Welch |
| 7,561,982 B2 | 7/2009 | Rund et al. |
| 7,563,715 B2 | 7/2009 | Haukka et al. |
| 7,566,891 B2 | 7/2009 | Rocha-Alvarez et al. |
| 7,569,193 B2 | 8/2009 | Ferron et al. |
| 7,575,968 B2 | 8/2009 | Sadaka et al. |
| 7,579,285 B2 | 8/2009 | Zimmerman et al. |
| 7,579,785 B2 | 8/2009 | Shinmen et al. |
| D600,223 S | 9/2009 | Aggarwal |
| 7,582,555 B1 | 9/2009 | Lang |
| 7,582,575 B2 | 9/2009 | Fukazawa et al. |
| 7,589,003 B2 | 9/2009 | Kouvetakis et al. |
| 7,589,028 B1 | 9/2009 | Cho et al. |
| 7,589,029 B2 | 9/2009 | Derderian et al. |
| 7,591,601 B2 | 9/2009 | Matsuoka et al. |
| 7,591,907 B2 | 9/2009 | Chen et al. |
| D602,575 S | 10/2009 | Breda |
| 7,598,513 B2 | 10/2009 | Kouvetakis et al. |
| 7,601,223 B2 | 10/2009 | Lindfors et al. |
| 7,601,225 B2 | 10/2009 | Tuominen et al. |
| 7,601,652 B2 | 10/2009 | Singh et al. |
| 7,611,640 B1 | 11/2009 | Howald et al. |
| 7,611,751 B2 | 11/2009 | Elers |
| 7,611,980 B2 | 11/2009 | Wells et al. |
| 7,618,226 B2 | 11/2009 | Takizawa |
| 7,621,672 B2 | 11/2009 | Ripley |
| 7,622,369 B1 | 11/2009 | Lee et al. |
| 7,622,378 B2 | 11/2009 | Liu et al. |
| 7,623,940 B2 | 11/2009 | Huskamp et al. |
| D606,952 S | 12/2009 | Lee et al. |
| 7,625,820 B1 | 12/2009 | Papasouliotis |
| 7,629,277 B2 | 12/2009 | Ghatnagar |
| 7,632,549 B2 | 12/2009 | Goundar |
| 7,638,951 B2 | 12/2009 | DeVincentis et al. |
| 7,640,142 B2 | 12/2009 | Tachikawa et al. |
| 7,645,341 B2 | 1/2010 | Kennedy et al. |
| 7,645,484 B2 | 1/2010 | Ishizaka |
| 7,648,895 B2 | 1/2010 | Kurokawa et al. |
| 7,648,927 B2 | 1/2010 | Singh et al. |
| 7,651,269 B2 | 1/2010 | Comendant |
| 7,651,583 B2 | 1/2010 | Kent et al. |
| 7,651,955 B2 | 1/2010 | Ranish et al. |
| 7,651,959 B2 | 1/2010 | Fukazawa et al. |

(56) References Cited

U.S. PATENT DOCUMENTS

| | | |
|---|---|---|
| 7,651,961 B2 | 1/2010 | Clark |
| D609,652 S | 2/2010 | Nagasaka et al. |
| D609,655 S | 2/2010 | Sugimoto |
| 7,661,299 B2 | 2/2010 | Kusunoki |
| 7,662,689 B2 | 2/2010 | Boyanov et al. |
| 7,670,432 B2 | 3/2010 | Li |
| 7,674,726 B2 | 3/2010 | Hasper et al. |
| 7,678,197 B2 | 3/2010 | Maki |
| 7,678,715 B2 | 3/2010 | Mungekar et al. |
| 7,682,454 B2 | 3/2010 | Sneh |
| 7,682,657 B2 | 3/2010 | Sherman |
| D613,829 S | 4/2010 | Griffin et al. |
| D614,153 S | 4/2010 | Fondurulia et al. |
| D614,258 S | 4/2010 | Kojima |
| D614,267 S | 4/2010 | Breda |
| D614,268 S | 4/2010 | Breda |
| D614,593 S | 4/2010 | Lee et al. |
| 7,690,881 B2 | 4/2010 | Yamagishi |
| 7,691,205 B2 | 4/2010 | Ikedo |
| 7,692,171 B2 | 4/2010 | Kaszuba et al. |
| 7,695,808 B2 | 4/2010 | Tuma |
| D616,390 S | 5/2010 | Sato |
| D616,394 S | 5/2010 | Sato |
| 7,712,435 B2 | 5/2010 | Yoshizaki et al. |
| 7,713,874 B2 | 5/2010 | Milligan |
| 7,716,993 B2 | 5/2010 | Ozawa et al. |
| 7,718,930 B2 | 5/2010 | Kawasaki et al. |
| 7,720,560 B2 | 5/2010 | Menser et al. |
| 7,723,648 B2 | 5/2010 | Tsukamoto et al. |
| 7,725,012 B2 | 5/2010 | Aggarwal et al. |
| 7,727,864 B2 | 6/2010 | Elers |
| 7,727,880 B1 | 6/2010 | Chattopadhyay et al. |
| 7,732,343 B2 | 6/2010 | Niroomand et al. |
| 7,736,437 B2 | 6/2010 | Cadwell et al. |
| 7,736,528 B2 | 6/2010 | Okita et al. |
| 7,736,600 B2 | 6/2010 | Clark et al. |
| 7,737,035 B1 | 6/2010 | Lind et al. |
| 7,740,437 B2 | 6/2010 | de Ridder et al. |
| 7,740,705 B2 | 6/2010 | Li |
| 7,745,346 B2 | 6/2010 | Hausmann et al. |
| 7,748,760 B2 | 7/2010 | Kushida |
| 7,749,563 B2 | 7/2010 | Zheng et al. |
| 7,753,584 B2 | 7/2010 | Gambino et al. |
| 7,754,621 B2 | 7/2010 | Putjkonen |
| 7,758,698 B2 | 7/2010 | Bang et al. |
| 7,763,869 B2 | 7/2010 | Matsushita et al. |
| 7,767,262 B2 | 8/2010 | Clark |
| 7,771,796 B2 | 8/2010 | Kohno et al. |
| 7,780,440 B2 | 8/2010 | Shibagaki et al. |
| 7,780,789 B2 | 8/2010 | Wu et al. |
| 7,781,352 B2 | 8/2010 | Fukazawa et al. |
| 7,789,559 B2 | 9/2010 | Waser et al. |
| 7,789,965 B2 | 9/2010 | Matsushita et al. |
| 7,790,633 B1 | 9/2010 | Tarafdar et al. |
| 7,794,546 B2 | 9/2010 | Li |
| 7,798,096 B2 | 9/2010 | Mahajani et al. |
| 7,799,300 B2 | 9/2010 | Lindfors et al. |
| 7,799,706 B2 | 9/2010 | Yeom et al. |
| 7,803,722 B2 | 9/2010 | Liang |
| D625,977 S | 10/2010 | Watson et al. |
| 7,795,160 B2 | 10/2010 | Wang et al. |
| 7,806,587 B2 | 10/2010 | Kobayashi |
| 7,807,566 B2 | 10/2010 | Tsuji et al. |
| 7,807,578 B2 | 10/2010 | Bencher et al. |
| 7,816,278 B2 | 10/2010 | Reed et al. |
| 7,824,492 B2 | 11/2010 | Tois et al. |
| 7,825,040 B1 | 11/2010 | Fukazawa et al. |
| 7,829,460 B2 | 11/2010 | Streck et al. |
| 7,833,348 B2 | 11/2010 | Wada et al. |
| 7,833,353 B2 | 11/2010 | Furukawahara et al. |
| 7,838,084 B2 | 11/2010 | Derderian et al. |
| 7,842,518 B2 | 11/2010 | Miyajima |
| 7,842,622 B1 | 11/2010 | Lee et al. |
| D629,874 S | 12/2010 | Hermans |
| 7,850,449 B2 | 12/2010 | Yang et al. |
| 7,851,019 B2 | 12/2010 | Tuominen et al. |
| 7,851,232 B2 | 12/2010 | van Schravendijk et al. |
| 7,858,519 B2 | 12/2010 | Liu et al. |
| 7,858,533 B2 | 12/2010 | Liu et al. |
| 7,858,898 B2 | 12/2010 | Bailey et al. |
| 7,865,070 B2 | 1/2011 | Nakamura |
| 7,871,198 B2 | 1/2011 | Rempe et al. |
| 7,874,726 B2 | 1/2011 | Jacobs et al. |
| 7,884,918 B2 | 2/2011 | Hattori |
| 7,888,233 B1 | 2/2011 | Gauri |
| 7,894,474 B1 | 2/2011 | Bell |
| D633,452 S | 3/2011 | Namiki et al. |
| D634,329 S | 3/2011 | Wastrom |
| D634,719 S | 3/2011 | Yasuda et al. |
| 7,897,215 B1 | 3/2011 | Fair et al. |
| 7,897,217 B2 | 3/2011 | Faguet |
| 7,902,009 B2 | 3/2011 | Simonelli et al. |
| 7,902,582 B2 | 3/2011 | Forbes et al. |
| 7,906,174 B1 | 3/2011 | Wu et al. |
| 7,910,288 B2 | 3/2011 | Abatchev et al. |
| 7,910,452 B2 | 3/2011 | Roh et al. |
| 7,910,494 B2 | 3/2011 | Dip et al. |
| 7,915,139 B1 | 3/2011 | Lang |
| 7,915,667 B2 | 3/2011 | Knoefler et al. |
| 7,919,142 B2 | 4/2011 | Yeom et al. |
| 7,919,416 B2 | 4/2011 | Lee et al. |
| 7,923,382 B2 | 4/2011 | Huotari et al. |
| 7,925,378 B2 | 4/2011 | Gilchrist et al. |
| 7,935,940 B1 | 5/2011 | Smargiassi |
| 7,939,447 B2 | 5/2011 | Bauer et al. |
| 7,942,969 B2 | 5/2011 | Riker et al. |
| 7,946,762 B2 | 5/2011 | Yednak |
| 7,951,262 B2 | 5/2011 | Koshiishi et al. |
| 7,955,516 B2 | 6/2011 | Chandrachood et al. |
| 7,955,646 B2 | 6/2011 | Cruse et al. |
| 7,955,650 B2 | 6/2011 | Tsuji |
| 7,957,708 B2 | 6/2011 | Karschnia et al. |
| 7,963,736 B2 | 6/2011 | Takizawa et al. |
| 7,967,913 B2 | 6/2011 | Hua et al. |
| 7,972,980 B2 | 7/2011 | Lee et al. |
| 7,977,256 B2 | 7/2011 | Liu et al. |
| 7,981,751 B2 | 7/2011 | Zhu et al. |
| D643,055 S | 8/2011 | Takahashi |
| 7,989,365 B2 | 8/2011 | Park et al. |
| 7,989,736 B2 | 8/2011 | Park et al. |
| 7,992,318 B2 | 8/2011 | Kawaji |
| 7,993,457 B1 | 8/2011 | Krotov et al. |
| 7,994,070 B1 | 8/2011 | Dip et al. |
| 7,994,721 B2 | 8/2011 | Espiau et al. |
| 7,997,795 B2 | 8/2011 | Schwagerman et al. |
| 7,998,875 B2 | 8/2011 | DeYoung |
| 8,003,174 B2 | 8/2011 | Fukazawa |
| 8,003,919 B2 | 8/2011 | Goto et al. |
| 8,004,198 B2 | 8/2011 | Bakre et al. |
| 8,020,315 B2 | 9/2011 | Nishimura |
| 8,030,129 B2 | 10/2011 | Jeong |
| 8,033,771 B1 | 10/2011 | Gage et al. |
| 8,038,835 B2 | 10/2011 | Hayashi et al. |
| 8,041,197 B2 | 10/2011 | Kasai et al. |
| 8,041,450 B2 | 10/2011 | Takizawa et al. |
| 8,043,972 B1 | 10/2011 | Liu et al. |
| 8,046,193 B2 | 10/2011 | Yetter et al. |
| 8,047,711 B2 | 11/2011 | Ploechinger |
| 8,048,783 B2 | 11/2011 | Chung et al. |
| 8,051,799 B2 | 11/2011 | Itagaki et al. |
| 8,052,794 B2 | 11/2011 | Sumakeris et al. |
| 8,055,378 B2 | 11/2011 | Numakura |
| 8,060,252 B2 | 11/2011 | Gage et al. |
| 8,083,853 B2 | 11/2011 | Choi et al. |
| RE43,023 E | 12/2011 | Nakashima et al. |
| D649,986 S | 12/2011 | Fujikata et al. |
| D651,291 S | 12/2011 | Liebson et al. |
| 8,071,451 B2 | 12/2011 | Berry |
| 8,071,452 B2 | 12/2011 | Raisanen |
| 8,072,578 B2 | 12/2011 | Yasuda et al. |
| 8,076,230 B2 | 12/2011 | Wei |
| 8,076,237 B2 | 12/2011 | Uzoh |
| 8,076,250 B1 | 12/2011 | Rajagopalan |
| 8,076,251 B2 | 12/2011 | Akae et al. |

(56) References Cited

U.S. PATENT DOCUMENTS

| | | | |
|---|---|---|---|
| 8,078,310 B2 | 12/2011 | Nishimoto et al. |
| 8,082,946 B2 | 12/2011 | Laverdiere et al. |
| 8,084,104 B2 | 12/2011 | Shinriki et al. |
| 8,084,372 B2 | 12/2011 | You et al. |
| D652,896 S | 1/2012 | Gether |
| 8,092,604 B2 | 1/2012 | Tomiyasu et al. |
| 8,092,606 B2 | 1/2012 | Park et al. |
| 8,100,583 B2 | 1/2012 | Aggarwal |
| D653,734 S | 2/2012 | Sisk |
| D654,882 S | 2/2012 | Honma et al. |
| D654,884 S | 2/2012 | Honma |
| D655,055 S | 2/2012 | Toll |
| 8,110,099 B2 | 2/2012 | Hersey et al. |
| 8,114,734 B2 | 2/2012 | Yang et al. |
| 8,119,466 B2 | 2/2012 | Avouris |
| 8,119,527 B1 | 2/2012 | Chadrashekar et al. |
| D655,260 S | 3/2012 | Honma et al. |
| D655,261 S | 3/2012 | Honma et al. |
| D655,599 S | 3/2012 | Durham |
| 8,128,333 B2 | 3/2012 | Aburatani |
| 8,129,290 B2 | 3/2012 | Balseanu et al. |
| 8,137,462 B2 | 3/2012 | Fondurulia et al. |
| 8,137,465 B1 | 3/2012 | Shrinivasan et al. |
| 8,138,104 B2 | 3/2012 | Balseanu et al. |
| 8,138,676 B2 | 3/2012 | Mills |
| 8,142,862 B2 | 3/2012 | Lee et al. |
| 8,143,174 B2 | 3/2012 | Xia et al. |
| 8,147,242 B2 | 4/2012 | Shibagaki et al. |
| 8,152,922 B2 | 4/2012 | Schmidt et al. |
| 8,158,512 B2 | 4/2012 | Ji et al. |
| 8,172,947 B2 | 5/2012 | Shibata et al. |
| 8,173,554 B2 | 5/2012 | Lee et al. |
| 8,174,400 B2 | 5/2012 | Park et al. |
| 8,178,436 B2 | 5/2012 | King et al. |
| 8,187,679 B2 | 5/2012 | Dickey et al. |
| 8,187,951 B1 | 5/2012 | Wang |
| 8,192,901 B2 | 6/2012 | Kageyama |
| 8,196,234 B2 | 6/2012 | Glunk |
| 8,197,915 B2 | 6/2012 | Oka et al. |
| 8,198,168 B2 | 6/2012 | Tanioku |
| 8,202,575 B2 | 6/2012 | Monsma et al. |
| 8,206,506 B2 | 6/2012 | Kadkhodayan et al. |
| 8,216,380 B2 | 7/2012 | White et al. |
| 8,227,032 B2 | 7/2012 | Dussarrat et al. |
| 8,231,799 B2 | 7/2012 | Bera et al. |
| D665,055 S | 8/2012 | Yanagisawa et al. |
| 8,241,991 B2 | 8/2012 | Hsieh et al. |
| 8,241,992 B2 | 8/2012 | Clevenger et al. |
| 8,242,028 B1 | 8/2012 | van Schravendijk et al. |
| 8,242,031 B2 | 8/2012 | Mallick et al. |
| 8,246,900 B2 | 8/2012 | Kasai et al. |
| 8,252,114 B2 | 8/2012 | Vukovic |
| 8,252,659 B2 | 8/2012 | Huyghabaert et al. |
| 8,252,691 B2 | 8/2012 | Beynet et al. |
| 8,253,204 B2 | 8/2012 | Lee et al. |
| 8,267,633 B2 | 9/2012 | Obikane |
| 8,272,516 B2 | 9/2012 | Salvador |
| 8,278,176 B2 | 10/2012 | Bauer et al. |
| 8,278,224 B1 | 10/2012 | Mui et al. |
| 8,282,769 B2 | 10/2012 | Iizuka |
| 8,282,847 B2 | 10/2012 | Romano |
| 8,282,992 B2 | 10/2012 | Myo et al. |
| 8,287,648 B2 | 10/2012 | Reed et al. |
| 8,291,857 B2 | 10/2012 | Lam et al. |
| 8,293,016 B2 | 10/2012 | Bahng et al. |
| 8,293,642 B2 | 10/2012 | Kim |
| 8,298,336 B2 | 10/2012 | Wang et al. |
| 8,298,951 B1 | 10/2012 | Nakano |
| 8,307,472 B1 | 11/2012 | Saxon et al. |
| 8,309,173 B2 | 11/2012 | Tuominen et al. |
| 8,318,327 B2 | 11/2012 | O'Donnell |
| 8,318,584 B2 | 11/2012 | Li et al. |
| 8,323,413 B2 | 12/2012 | Son |
| 8,324,699 B2 | 12/2012 | Ichijo et al. |
| 8,328,939 B2 | 12/2012 | Choi et al. |
| 8,329,599 B2 | 12/2012 | Fukazawa et al. |
| 8,333,839 B2 | 12/2012 | Oh |
| 8,334,219 B2 | 12/2012 | Lee et al. |
| 8,338,809 B2 | 12/2012 | Yang et al. |
| 8,349,083 B2 | 1/2013 | Takasuka et al. |
| D676,943 S | 2/2013 | Kluss et al. |
| 8,367,528 B2 | 2/2013 | Bauer et al. |
| 8,372,204 B2 | 2/2013 | Nakamura |
| 8,378,464 B2 | 2/2013 | Kato et al. |
| 8,382,370 B2 | 2/2013 | Aggarwal et al. |
| 8,382,939 B2 | 2/2013 | Kutney et al. |
| 8,393,091 B2 | 3/2013 | Kawamoto |
| 8,394,466 B2 | 3/2013 | Hong et al. |
| 8,398,773 B2 | 3/2013 | Jdira et al. |
| 8,402,918 B2 | 3/2013 | Kadkhodayan et al. |
| 8,404,044 B2 | 3/2013 | Arai |
| 8,404,499 B2 | 3/2013 | Moffatt |
| 8,415,258 B2 | 4/2013 | Akae |
| 8,415,259 B2 | 4/2013 | Lee et al. |
| 8,415,587 B2 | 4/2013 | Millman et al. |
| 8,419,959 B2 | 4/2013 | Bettencourt et al. |
| 8,425,682 B2 | 4/2013 | Wang et al. |
| 8,430,620 B1 | 4/2013 | Blank et al. |
| 8,435,894 B2 | 5/2013 | Chandrashekar et al. |
| 8,440,259 B2 | 5/2013 | Chiang et al. |
| 8,443,484 B2 | 5/2013 | Ozaki et al. |
| 8,444,120 B2 | 5/2013 | Gregg et al. |
| 8,445,075 B2 | 5/2013 | Xu et al. |
| 8,450,191 B2 | 5/2013 | Wang |
| 8,454,749 B2 | 6/2013 | Li |
| 8,465,811 B2 | 6/2013 | Ueda |
| 8,465,903 B2 | 6/2013 | Weidman et al. |
| 8,466,411 B2 | 6/2013 | Arai |
| 8,470,187 B2 | 6/2013 | Ha |
| 8,470,718 B2 | 6/2013 | Lee |
| 8,484,846 B2 | 7/2013 | Dhindsa |
| 8,492,170 B2 | 7/2013 | Xie et al. |
| 8,496,377 B2 | 7/2013 | Harr et al. |
| 8,496,756 B2 | 7/2013 | Cruse et al. |
| 8,497,213 B2 | 7/2013 | Yasui et al. |
| 8,501,599 B2 | 8/2013 | Ueno et al. |
| 8,506,162 B2 | 8/2013 | Schick et al. |
| 8,506,713 B2 | 8/2013 | Takagi |
| 8,507,720 B2 | 8/2013 | Shay |
| 8,524,612 B2 | 9/2013 | Li et al. |
| 8,529,701 B2 | 9/2013 | Morita |
| 8,535,767 B1 | 9/2013 | Kimura |
| 8,536,068 B2 | 9/2013 | Weidman et al. |
| D691,974 S | 10/2013 | Osada et al. |
| 8,551,892 B2 | 10/2013 | Nakano |
| 8,557,712 B1 | 10/2013 | Antonelli et al. |
| 8,562,272 B2 | 10/2013 | Lenz |
| 8,563,443 B2 | 10/2013 | Fukazawa |
| 8,569,184 B2 | 10/2013 | Oka |
| D693,200 S | 11/2013 | Saunders |
| D693,782 S | 11/2013 | Mori et al. |
| 8,573,152 B2 | 11/2013 | de la Llera et al. |
| 8,573,154 B2 | 11/2013 | Yorozuya |
| 8,586,484 B2 | 11/2013 | Matsuyama et al. |
| 8,591,659 B1 | 11/2013 | Fang et al. |
| 8,592,005 B2 | 11/2013 | Ueda |
| D694,790 S | 12/2013 | Matsumoto et al. |
| D695,240 S | 12/2013 | Iida et al. |
| 8,608,885 B2 | 12/2013 | Goto et al. |
| 8,614,047 B2 | 12/2013 | Ayothi et al. |
| 8,616,765 B2 | 12/2013 | Darabnia et al. |
| 8,617,411 B2 | 12/2013 | Singh |
| D697,038 S | 1/2014 | Matsumoto et al. |
| 8,623,770 B1 | 1/2014 | Gao et al. |
| 8,633,115 B2 | 1/2014 | Chang et al. |
| 8,637,384 B2 | 1/2014 | Ando et al. |
| D698,904 S | 2/2014 | Milligan et al. |
| 8,642,488 B2 | 2/2014 | Liu et al. |
| 8,647,439 B2 | 2/2014 | Sanchez et al. |
| 8,647,722 B2 | 2/2014 | Kobayashi et al. |
| 8,647,993 B1 | 2/2014 | Lavoie et al. |
| 8,651,788 B1 | 2/2014 | Budde |
| 8,664,627 B1 | 3/2014 | Ishikawa et al. |
| 8,667,654 B2 | 3/2014 | Gros-Jean |

(56) References Cited

U.S. PATENT DOCUMENTS

| | | |
|---|---|---|
| 8,668,957 B2 | 3/2014 | Dussarrat et al. |
| 8,669,185 B2 | 3/2014 | Onizawa |
| 8,679,958 B2 | 3/2014 | Takamure et al. |
| D702,188 S | 4/2014 | Jacobs |
| 8,683,943 B2 | 4/2014 | Onodera et al. |
| 8,697,198 B2 | 4/2014 | Lee |
| 8,703,002 B2 | 4/2014 | Matsudo et al. |
| 8,709,162 B2 | 4/2014 | Leung et al. |
| 8,710,580 B2 | 4/2014 | Sakuma et al. |
| 8,711,338 B2 | 4/2014 | Liu et al. |
| D705,745 S | 5/2014 | Kurs et al. |
| D705,762 S | 5/2014 | Yu |
| 8,664,127 B2 | 5/2014 | Bhatia et al. |
| 8,720,965 B2 | 5/2014 | Hino et al. |
| 8,721,791 B2 | 5/2014 | Choi et al. |
| 8,722,510 B2 | 5/2014 | Watanabe et al. |
| 8,722,546 B2 | 5/2014 | Fukazawa et al. |
| 8,726,837 B2 | 5/2014 | Patalay et al. |
| 8,728,832 B2 | 5/2014 | Raisanen et al. |
| 8,728,956 B2 | 5/2014 | Lavoie et al. |
| 8,741,062 B2 | 6/2014 | Lindfors et al. |
| 8,741,065 B2 | 6/2014 | Odagiri et al. |
| 8,742,668 B2 | 6/2014 | Nakano et al. |
| 8,758,512 B2 | 6/2014 | Lee |
| 8,759,223 B2 | 6/2014 | Sapre et al. |
| D709,536 S | 7/2014 | Yoshimura et al. |
| D709,537 S | 7/2014 | Kuwabara et al. |
| 8,764,085 B2 | 7/2014 | Urabe |
| 8,771,791 B2 | 7/2014 | Lee et al. |
| 8,771,807 B2 | 7/2014 | Xiao et al. |
| 8,779,502 B2 | 7/2014 | Sakuma et al. |
| 8,784,676 B2 | 7/2014 | Guha et al. |
| 8,784,950 B2 | 7/2014 | Fukazawa et al. |
| 8,784,951 B2 | 7/2014 | Fukazawa et al. |
| 8,785,215 B2 | 7/2014 | Kobayashi et al. |
| 8,785,311 B2 | 7/2014 | Miyoshi |
| 8,790,743 B1 | 7/2014 | Omari |
| 8,790,749 B2 | 7/2014 | Omori et al. |
| 8,802,201 B2 | 8/2014 | Raisanen et al. |
| 8,809,170 B2 | 8/2014 | Bauer |
| D712,358 S | 9/2014 | Allen et al. |
| D712,359 S | 9/2014 | Allen et al. |
| 8,820,809 B2 | 9/2014 | Ando et al. |
| 8,821,640 B2 | 9/2014 | Cleary et al. |
| 8,821,985 B2 | 9/2014 | Shao et al. |
| 8,823,672 B2 | 9/2014 | Kim |
| 8,828,886 B2 | 9/2014 | Samukawa et al. |
| 8,841,182 B1 | 9/2014 | Chen et al. |
| 8,845,806 B2 | 9/2014 | Aida et al. |
| 8,846,502 B2 | 9/2014 | Haukka et al. |
| D715,410 S | 10/2014 | Lohmann |
| 8,859,368 B2 | 10/2014 | Deniz |
| 8,860,955 B2 | 10/2014 | Rodnick et al. |
| 8,864,202 B1 | 10/2014 | Schrameyer |
| 8,864,375 B2 | 10/2014 | Abe et al. |
| D716,742 S | 11/2014 | Jang et al. |
| 8,876,974 B2 | 11/2014 | Wan |
| 8,877,300 B2 | 11/2014 | Lee |
| 8,877,655 B2 | 11/2014 | Shero et al. |
| 8,882,923 B2 | 11/2014 | Saido et al. |
| 8,883,270 B2 | 11/2014 | Shero et al. |
| 8,895,108 B2 | 11/2014 | Lee |
| 8,895,395 B1 | 11/2014 | Kerber et al. |
| 8,900,935 B2 | 12/2014 | Guo et al. |
| 8,900,999 B1 | 12/2014 | Wu et al. |
| 8,901,016 B2 | 12/2014 | Jeongseok et al. |
| 8,911,553 B2 | 12/2014 | Baluja et al. |
| 8,911,826 B2 | 12/2014 | Adachi et al. |
| 8,912,101 B2 | 12/2014 | Tsuji et al. |
| D720,838 S | 1/2015 | Yamagishi et al. |
| 8,927,906 B2 | 1/2015 | Tadokoro et al. |
| 8,932,802 B2 | 1/2015 | Wu et al. |
| 8,933,375 B2 | 1/2015 | Dunn et al. |
| 8,937,800 B2 | 1/2015 | Lubomirsky et al. |
| 8,940,646 B1 | 1/2015 | Chandrasekharan |
| D723,153 S | 2/2015 | Borkholder |
| 8,945,305 B2 | 2/2015 | Marsh |
| 8,945,306 B2 | 2/2015 | Tsuda |
| 8,945,339 B2 | 2/2015 | Kakimoto |
| 8,946,830 B2 | 2/2015 | Jung et al. |
| 8,956,971 B2 | 2/2015 | Huakka |
| 8,956,983 B2 | 2/2015 | Swaminathan |
| D723,330 S | 3/2015 | York |
| D724,553 S | 3/2015 | Choi |
| D724,701 S | 3/2015 | Yamagishi et al. |
| D725,168 S | 3/2015 | Yamagishi |
| 8,967,608 B2 | 3/2015 | Mitsumori et al. |
| 8,968,989 B2 | 3/2015 | Ouattara et al. |
| 8,969,934 B1 | 3/2015 | Cheng et al. |
| 8,974,868 B2 | 3/2015 | Ishikawa et al. |
| 8,980,006 B2 | 3/2015 | Huh et al. |
| 8,986,456 B2 | 3/2015 | Fondurulia et al. |
| 8,991,214 B2 | 3/2015 | Hoshino et al. |
| 8,991,887 B2 | 3/2015 | Shin et al. |
| 8,993,054 B2 | 3/2015 | Jung et al. |
| 8,993,072 B2 | 3/2015 | Xiao et al. |
| 8,993,457 B1 | 3/2015 | Ramkumar et al. |
| D726,365 S | 4/2015 | Weigensberg |
| D726,884 S | 4/2015 | Yamagishi et al. |
| 8,999,102 B2 | 4/2015 | Miyoshi et al. |
| 9,004,744 B1 | 4/2015 | Kemp |
| 9,005,539 B2 | 4/2015 | Halpin et al. |
| 9,017,481 B1 | 4/2015 | Pettinger et al. |
| 9,017,933 B2 | 4/2015 | Liu et al. |
| 9,018,093 B2 | 4/2015 | Tsuji et al. |
| 9,018,111 B2 | 4/2015 | Milligan et al. |
| 9,018,567 B2 | 4/2015 | de Ridder et al. |
| 9,021,985 B2 | 5/2015 | Alokozai et al. |
| 9,023,737 B2 | 5/2015 | Beynet et al. |
| 9,023,738 B2 | 5/2015 | Kato et al. |
| 9,029,244 B2 | 5/2015 | Won et al. |
| 9,029,253 B2 | 5/2015 | Milligan et al. |
| 9,029,272 B1 | 5/2015 | Nakano |
| 9,030,664 B2 * | 5/2015 | Park .................... G01N 21/59 356/432 |
| D732,145 S | 6/2015 | Yamagishi |
| D732,644 S | 6/2015 | Yamagishi et al. |
| D733,257 S | 6/2015 | Schoenherr et al. |
| D733,261 S | 6/2015 | Yamagishi et al. |
| D733,262 S | 6/2015 | Kang |
| 9,057,388 B2 | 6/2015 | Comeau et al. |
| 9,064,815 B2 | 6/2015 | Zhang et al. |
| D733,843 S | 7/2015 | Yamagishi |
| D734,377 S | 7/2015 | Hirakida |
| 9,076,635 B2 | 7/2015 | Gross et al. |
| 9,076,726 B2 | 7/2015 | Kauerauf et al. |
| D735,836 S | 8/2015 | Yamagishi et al. |
| D736,348 S | 8/2015 | Tan |
| 9,095,869 B2 | 8/2015 | Kilpi et al. |
| 9,096,931 B2 | 8/2015 | Yednak et al. |
| 9,099,423 B2 | 8/2015 | Weeks et al. |
| 9,099,505 B2 | 8/2015 | Kusakabe et al. |
| 9,111,972 B2 | 8/2015 | Takeshita et al. |
| 9,117,657 B2 | 8/2015 | Nakano et al. |
| 9,117,866 B2 | 8/2015 | Marquardt et al. |
| D739,222 S | 9/2015 | Chadbourne |
| 9,123,510 B2 | 9/2015 | Nakano et al. |
| 9,123,577 B2 | 9/2015 | Fujimoto et al. |
| 9,127,358 B2 | 9/2015 | Inoue et al. |
| 9,127,362 B2 | 9/2015 | Scheible et al. |
| 9,129,897 B2 | 9/2015 | Pore et al. |
| 9,136,108 B2 | 9/2015 | Matsushita et al. |
| 9,136,180 B2 | 9/2015 | Machkaoutsan |
| 9,142,393 B2 | 9/2015 | Okabe et al. |
| 9,142,437 B2 | 9/2015 | Fosnight et al. |
| 9,142,764 B1 | 9/2015 | Wang |
| 9,153,441 B2 | 10/2015 | Takamure et al. |
| 9,163,310 B2 | 10/2015 | Lee |
| 9,166,012 B2 | 10/2015 | Sim et al. |
| 9,169,975 B2 | 10/2015 | Sarin et al. |
| 9,171,714 B2 | 10/2015 | Mori |
| 9,171,715 B2 | 10/2015 | Matero |
| 9,171,716 B2 | 10/2015 | Fukuda |
| D742,202 S | 11/2015 | Cyphers et al. |

(56) References Cited

U.S. PATENT DOCUMENTS

| | | |
|---|---|---|
| D743,357 S | 11/2015 | Vyne |
| D743,513 S | 11/2015 | Yamagishi |
| 9,174,178 B2 | 11/2015 | Berger et al. |
| 9,175,394 B2 | 11/2015 | Yudovsky et al. |
| 9,177,784 B2 | 11/2015 | Raisanen et al. |
| 9,184,047 B2 | 11/2015 | Liu et al. |
| 9,184,054 B1 | 11/2015 | Huang et al. |
| 9,190,263 B2 | 11/2015 | Ishikawa et al. |
| 9,190,264 B2 | 11/2015 | Yuasa et al. |
| 9,196,483 B1 | 11/2015 | Lee et al. |
| D745,641 S | 12/2015 | Blum |
| 9,202,727 B2 | 12/2015 | Dunn et al. |
| 9,214,333 B1 | 12/2015 | Sims et al. |
| 9,214,340 B2 | 12/2015 | Kurita et al. |
| 9,219,006 B2 | 12/2015 | Chatterjee |
| 9,223,203 B2 | 12/2015 | Farm et al. |
| 9,228,259 B2 | 1/2016 | Haukka et al. |
| 9,240,412 B2 | 1/2016 | Xie et al. |
| 9,245,742 B2 | 1/2016 | Haukka |
| 9,252,024 B2 | 2/2016 | Lam et al. |
| 9,252,238 B1 | 2/2016 | Trevino et al. |
| 9,257,274 B2 | 2/2016 | Kang et al. |
| 9,263,298 B2 | 2/2016 | Matsumoto et al. |
| 9,267,204 B2 | 2/2016 | Honma |
| 9,267,850 B2 | 2/2016 | Aggarwal |
| D751,176 S | 3/2016 | Schoenherr et al. |
| 9,275,834 B1 | 3/2016 | Park et al. |
| 9,281,223 B2 | 3/2016 | Hara |
| 9,281,277 B2 | 3/2016 | Baek et al. |
| 9,284,642 B2 | 3/2016 | Nakano |
| 9,287,273 B2 | 3/2016 | Ragnarsson et al. |
| 9,297,705 B2 | 3/2016 | Aggarwal |
| 9,299,557 B2 | 3/2016 | Tolle et al. |
| 9,299,595 B2 | 3/2016 | Dunn et al. |
| D753,269 S | 4/2016 | Yamagishi et al. |
| D753,629 S | 4/2016 | Plattard |
| 9,305,836 B1 | 4/2016 | Gates et al. |
| 9,309,598 B2 | 4/2016 | Wang et al. |
| 9,309,978 B2 | 4/2016 | Hatch et al. |
| 9,310,684 B2 | 4/2016 | Meyers et al. |
| 9,312,155 B2 | 4/2016 | Mori |
| 9,315,897 B2 | 4/2016 | Byun |
| 9,324,811 B2 | 4/2016 | Weeks |
| 9,324,846 B1 | 4/2016 | Camillo |
| D756,929 S | 5/2016 | Harck et al. |
| 9,331,200 B1 | 5/2016 | Wang et al. |
| 9,337,031 B2 | 5/2016 | Kim et al. |
| 9,337,054 B2 | 5/2016 | Hunks et al. |
| 9,337,057 B2 | 5/2016 | Park et al. |
| 9,341,296 B2 | 5/2016 | Yednak |
| 9,343,297 B1 | 5/2016 | Fukazawa et al. |
| 9,343,308 B2 | 5/2016 | Isii |
| 9,343,343 B2 | 5/2016 | Mori |
| 9,343,350 B2 | 5/2016 | Arai |
| 9,349,620 B2 | 5/2016 | Kamata et al. |
| 9,353,440 B2 | 5/2016 | Ge et al. |
| 9,353,441 B2 | 5/2016 | Chung |
| 9,355,876 B2 | 5/2016 | Reuter et al. |
| 9,355,882 B2 | 5/2016 | Wu et al. |
| D759,137 S | 6/2016 | Hassan |
| D759,193 S | 6/2016 | Gutierrez et al. |
| 9,362,107 B2 | 6/2016 | Thadani et al. |
| 9,362,137 B2 | 6/2016 | Kang et al. |
| 9,362,180 B2 | 6/2016 | Lee et al. |
| 9,365,924 B2 | 6/2016 | Nonaka |
| 9,368,352 B2 | 6/2016 | Takamure et al. |
| 9,370,863 B2 | 6/2016 | Tsuji et al. |
| 9,378,969 B2 | 6/2016 | Hsu et al. |
| D761,325 S | 7/2016 | Abed |
| 9,384,987 B2 | 7/2016 | Jung et al. |
| 9,390,909 B2 | 7/2016 | Pasquale et al. |
| 9,394,608 B2 | 7/2016 | Shero et al. |
| 9,396,934 B2 | 7/2016 | Tolle |
| 9,396,956 B1 | 7/2016 | Fukazawa |
| 9,399,228 B2 | 7/2016 | Breiling et al. |
| D764,196 S | 8/2016 | Handler et al. |
| 9,404,587 B2 | 8/2016 | Shugrue |
| 9,412,564 B2 | 8/2016 | Milligan |
| 9,412,581 B2 | 8/2016 | Thadani et al. |
| 9,412,582 B2 | 8/2016 | Sasaki et al. |
| 9,418,885 B2 | 8/2016 | Sung et al. |
| 9,425,078 B2 | 8/2016 | Tang et al. |
| 9,428,833 B1 | 8/2016 | Duvall et al. |
| 9,443,725 B2 | 9/2016 | Liu et al. |
| 9,447,498 B2 | 9/2016 | Shiba et al. |
| 9,449,793 B2 | 9/2016 | Shaji et al. |
| 9,449,795 B2 | 9/2016 | Sabri et al. |
| 9,449,843 B1 | 9/2016 | Korolik et al. |
| 9,449,987 B1 | 9/2016 | Miyata et al. |
| 9,455,138 B1 | 9/2016 | Fukazawa |
| 9,455,177 B1 | 9/2016 | Park et al. |
| 9,460,954 B2 | 10/2016 | De Jong et al. |
| 9,464,352 B2 | 10/2016 | Nakano et al. |
| 9,472,410 B2 | 10/2016 | Sadjadi et al. |
| 9,472,432 B1 | 10/2016 | Blank |
| 9,474,163 B2 | 10/2016 | Tolle et al. |
| 9,478,414 B2 | 10/2016 | Kobayashi et al. |
| 9,478,415 B2 | 10/2016 | Kimura |
| D770,993 S | 11/2016 | Yoshida et al. |
| 9,484,191 B2 | 11/2016 | Winkler |
| 9,496,225 B1 | 11/2016 | Adusumilli et al. |
| 9,514,927 B2 | 12/2016 | Tolle et al. |
| 9,514,932 B2 | 12/2016 | Mallick et al. |
| 9,520,289 B2 | 12/2016 | Park et al. |
| 9,523,148 B1 | 12/2016 | Pore et al. |
| D777,546 S | 1/2017 | Ishii et al. |
| 9,543,180 B2 | 1/2017 | Kamiya |
| 9,556,516 B2 | 1/2017 | Takamure |
| 9,558,931 B2 | 1/2017 | Tang |
| 9,564,312 B2 | 2/2017 | Henri et al. |
| 9,564,314 B2 | 2/2017 | Takamure et al. |
| 9,570,302 B1 | 2/2017 | Chang et al. |
| 9,574,268 B1 | 2/2017 | Dunn et al. |
| 9,576,952 B2 | 2/2017 | Joshi et al. |
| 9,583,333 B2 | 2/2017 | Chatterjee |
| 9,583,345 B2 | 2/2017 | Chen et al. |
| D782,419 S | 3/2017 | Willette |
| 9,589,770 B2 | 3/2017 | Winkler |
| 9,605,342 B2 | 3/2017 | Alokozai et al. |
| 9,605,343 B2 | 3/2017 | Winkler |
| 9,605,736 B1 | 3/2017 | Foshage et al. |
| 9,607,837 B1 | 3/2017 | Namba |
| D783,351 S | 4/2017 | Fujino et al. |
| D784,276 S | 4/2017 | Tiner et al. |
| 9,613,801 B2 | 4/2017 | Carcasi et al. |
| 9,618,846 B2 | 4/2017 | Shamma et al. |
| 9,627,221 B1 | 4/2017 | Zaitsu et al. |
| D785,766 S | 5/2017 | Sato |
| D787,458 S | 5/2017 | Kim et al. |
| 9,640,416 B2 | 5/2017 | Arai |
| 9,640,448 B2 | 5/2017 | Ikegawa et al. |
| 9,640,542 B2 | 5/2017 | Lee et al. |
| 9,644,266 B2 | 5/2017 | Nasu et al. |
| 9,647,114 B2 | 5/2017 | Margetis |
| 9,653,267 B2 | 5/2017 | Carducci et al. |
| 9,657,845 B2 | 5/2017 | Shugrue |
| 9,659,799 B2 | 5/2017 | Lawson |
| 9,663,857 B2 | 5/2017 | Nakano et al. |
| 9,666,528 B1 | 5/2017 | Bergendahl et al. |
| D789,888 S | 6/2017 | Jang et al. |
| D790,041 S | 6/2017 | Jang et al. |
| 9,680,268 B1 | 6/2017 | Finona |
| 9,684,234 B2 | 6/2017 | Darling et al. |
| 9,685,320 B2 | 6/2017 | Kang et al. |
| 9,691,668 B2 | 6/2017 | Chang et al. |
| 9,691,771 B2 | 6/2017 | Lansalot-Matras |
| 9,698,031 B2 | 7/2017 | Kobayashi et al. |
| 9,708,707 B2 | 7/2017 | Ditizio et al. |
| 9,708,708 B2 | 7/2017 | Isobe et al. |
| 9,711,345 B2 | 7/2017 | Shiba et al. |
| D793,352 S | 8/2017 | Hill |
| D793,526 S | 8/2017 | Behdjat |
| D793,572 S | 8/2017 | Kozuka et al. |
| D793,976 S | 8/2017 | Fukushima et al. |

(56) References Cited

U.S. PATENT DOCUMENTS

| | | |
|---|---|---|
| D794,753 S | 8/2017 | Miller |
| D795,208 S | 8/2017 | Sasaki et al. |
| 9,735,024 B2 | 8/2017 | Zaitsu |
| 9,741,546 B2 | 8/2017 | Carducci et al. |
| 9,741,559 B2 | 8/2017 | Shimura et al. |
| 9,745,658 B2 | 8/2017 | Kang et al. |
| 9,748,104 B2 | 8/2017 | Sasaki et al. |
| 9,748,145 B1 | 8/2017 | Kannan et al. |
| D796,458 S | 9/2017 | Jang et al. |
| D796,670 S | 9/2017 | Dolk et al. |
| D797,067 S | 9/2017 | Zhang et al. |
| D798,248 S | 9/2017 | Hanson et al. |
| 9,754,779 B1 | 9/2017 | Ishikawa |
| 9,754,818 B2 | 9/2017 | Shiu et al. |
| 9,759,489 B2 | 9/2017 | Kaneko |
| 9,765,432 B2 | 9/2017 | Ge et al. |
| 9,773,818 B2 | 9/2017 | Kimura |
| D800,782 S | 10/2017 | Bever et al. |
| 9,778,561 B2 | 10/2017 | Marks et al. |
| 9,780,225 B2 | 10/2017 | Venkatasubramanian et al. |
| 9,786,491 B2 | 10/2017 | Suzuki et al. |
| 9,786,570 B2 | 10/2017 | Kang et al. |
| 9,790,595 B2 | 10/2017 | Jung et al. |
| 9,793,115 B2 | 10/2017 | Tolle |
| 9,793,135 B1 | 10/2017 | Zaitsu et al. |
| 9,793,148 B2 | 10/2017 | Yamagishi et al. |
| 9,798,308 B2 | 10/2017 | Mimura |
| 9,799,736 B1 | 10/2017 | Ebrish et al. |
| 9,803,926 B2 | 10/2017 | Kikuchi et al. |
| D801,942 S | 11/2017 | Riker et al. |
| D802,472 S | 11/2017 | Sasaki et al. |
| D802,546 S | 11/2017 | Jang et al. |
| D803,802 S | 11/2017 | Sasaki et al. |
| 9,808,246 B2 | 11/2017 | Shelton et al. |
| 9,812,319 B1 | 11/2017 | Fukazawa et al. |
| 9,812,320 B1 | 11/2017 | Pore et al. |
| 9,812,372 B2 | 11/2017 | Choi et al. |
| 9,820,289 B1 | 11/2017 | Pawar et al. |
| 9,824,881 B2 | 11/2017 | Niskanen et al. |
| 9,824,884 B1 | 11/2017 | Sims et al. |
| 9,824,893 B1 | 11/2017 | Smith et al. |
| 9,837,355 B2 | 12/2017 | Briggs et al. |
| 9,842,835 B1 | 12/2017 | Cheng et al. |
| 9,847,221 B1 | 12/2017 | McLaughlin et al. |
| 9,847,247 B2 | 12/2017 | Huang et al. |
| 9,850,573 B1 | 12/2017 | Sun |
| D807,494 S | 1/2018 | Kim et al. |
| D808,254 S | 1/2018 | Deleu |
| 9,859,151 B1 | 1/2018 | Zhu |
| 9,865,455 B1 | 1/2018 | Sims et al. |
| 9,865,456 B1 | 1/2018 | Pandey et al. |
| 9,865,815 B2 | 1/2018 | Hausmann |
| 9,868,131 B2 | 1/2018 | Kilpi et al. |
| 9,870,964 B1 | 1/2018 | Yoshino et al. |
| 9,875,891 B2 | 1/2018 | Henri et al. |
| 9,875,893 B2 | 1/2018 | Takamure et al. |
| 9,881,788 B2 | 1/2018 | Kim et al. |
| D810,705 S | 2/2018 | Krishnan et al. |
| 9,887,082 B1 | 2/2018 | Pore et al. |
| 9,890,456 B2 | 2/2018 | Tolle et al. |
| 9,891,521 B2 | 2/2018 | Kang et al. |
| 9,892,908 B2 | 2/2018 | Pettinger et al. |
| 9,892,913 B2 | 2/2018 | Margetis et al. |
| 9,895,715 B2 | 2/2018 | Haukka et al. |
| 9,899,291 B2 | 2/2018 | Kato |
| 9,899,405 B2 | 2/2018 | Kim |
| 9,905,420 B2 | 2/2018 | Margetis et al. |
| 9,905,492 B2 | 2/2018 | Tang et al. |
| 9,909,214 B2 | 3/2018 | Suemori |
| 9,909,492 B2 | 3/2018 | Jeswine |
| 9,911,595 B1 | 3/2018 | Smith et al. |
| 9,911,676 B2 | 3/2018 | Tang |
| 9,916,980 B1 | 3/2018 | Knaepen |
| 9,920,451 B2 | 3/2018 | Sivaramakrishnan et al. |
| 9,922,824 B2 | 3/2018 | Okada |
| 9,929,005 B1 | 3/2018 | Shimamoto et al. |
| 9,929,011 B2 | 3/2018 | Hawryluk et al. |
| 9,929,055 B2 | 3/2018 | Dube et al. |
| 9,951,421 B2 | 4/2018 | Lind |
| 9,960,033 B1 | 5/2018 | Nozawa |
| 9,960,072 B2 | 5/2018 | Coomer |
| 9,966,299 B2 | 5/2018 | Tang et al. |
| 9,970,112 B2 | 5/2018 | Koshi et al. |
| 9,984,869 B1 | 5/2018 | Blanquart |
| D819,580 S | 6/2018 | Krishnan et al. |
| 9,987,747 B2 | 6/2018 | Hwang et al. |
| 9,991,138 B2 | 6/2018 | Lin et al. |
| 9,996,004 B2 | 6/2018 | Smith et al. |
| 9,997,357 B2 | 6/2018 | Arghavani et al. |
| 9,997,373 B2 | 6/2018 | Hudson |
| 10,032,628 B2 | 6/2018 | Xie et al. |
| 10,014,212 B2 | 7/2018 | Chen et al. |
| 10,017,856 B1 | 7/2018 | Arnepalli et al. |
| 10,018,920 B2 | 7/2018 | Chang et al. |
| 10,023,960 B2 | 7/2018 | Alokozai |
| 10,032,792 B2 | 7/2018 | Kim et al. |
| D825,505 S | 8/2018 | Hanson et al. |
| D825,614 S | 8/2018 | Bever et al. |
| 10,043,661 B2 | 8/2018 | Kato et al. |
| 10,047,435 B2 | 8/2018 | Haukka et al. |
| 10,053,774 B2 | 8/2018 | Tolle et al. |
| 10,060,473 B2 | 8/2018 | Davey et al. |
| D827,592 S | 9/2018 | Ichino et al. |
| D829,306 S | 9/2018 | Ikedo et al. |
| 10,083,836 B2 | 9/2018 | Milligan |
| D830,981 S | 10/2018 | Jeong et al. |
| 10,087,522 B2 | 10/2018 | Raisanen et al. |
| 10,087,525 B2 | 10/2018 | Schmotzer et al. |
| 10,090,316 B2 | 10/2018 | Ootsuka |
| 10,103,040 B1 | 10/2018 | Oosterlaken et al. |
| 10,106,892 B1 | 10/2018 | Siddiqui et al. |
| RE47,145 E | 11/2018 | Hashimoto |
| D834,686 S | 11/2018 | Yamada et al. |
| 10,121,671 B2 | 11/2018 | Fu et al. |
| 10,134,617 B2 | 11/2018 | Gurary et al. |
| 10,134,757 B2 | 11/2018 | Chun et al. |
| RE47,170 E | 12/2018 | Beynet et al. |
| 10,147,600 B2 | 12/2018 | Takamure et al. |
| 10,167,557 B2 | 1/2019 | Hawkins et al. |
| 10,177,024 B2 | 1/2019 | Gomm et al. |
| 10,177,025 B2 | 1/2019 | Pore |
| 10,179,947 B2 | 1/2019 | Fukazawa |
| 10,186,420 B2 | 1/2019 | Fukazawa |
| 10,190,213 B2 | 1/2019 | Zhu et al. |
| 10,190,214 B2 | 1/2019 | Shon et al. |
| 10,190,701 B2 | 1/2019 | Raj et al. |
| 10,192,734 B2 | 1/2019 | Sanchez et al. |
| 10,193,429 B2 | 1/2019 | Smith et al. |
| D840,364 S | 2/2019 | Ichino et al. |
| 10,204,788 B1 | 2/2019 | Ye et al. |
| 10,211,308 B2 | 2/2019 | Zhu et al. |
| 10,229,833 B2 | 3/2019 | Raisanen et al. |
| 10,229,851 B2 | 3/2019 | Briggs et al. |
| 10,229,985 B1 | 3/2019 | Li et al. |
| 10,236,177 B1 | 3/2019 | Kohen et al. |
| D846,008 S | 4/2019 | Geldenhuys et al. |
| 10,249,524 B2 | 4/2019 | den Hartog Besselink et al. |
| 10,249,577 B2 | 4/2019 | Lee et al. |
| 10,262,859 B2 | 4/2019 | Margetis et al. |
| 10,269,558 B2 | 4/2019 | Blanquart et al. |
| 10,276,355 B2 | 4/2019 | White et al. |
| D849,055 S | 5/2019 | Kneip |
| D849,662 S | 5/2019 | Rike |
| 10,283,353 B2 | 5/2019 | Kobayashi et al. |
| 10,287,684 B2 | 5/2019 | Yanai et al. |
| 10,290,508 B1 | 5/2019 | Kubota et al. |
| 10,297,440 B2 | 5/2019 | Yamazaki et al. |
| RE47,440 E | 6/2019 | Yudovsky et al. |
| 10,312,055 B2 | 6/2019 | Suzuki |
| 10,312,129 B2 | 6/2019 | Coomer |
| 10,319,588 B2 | 6/2019 | Mattinen et al. |
| 10,322,384 B2 | 6/2019 | Stumpf et al. |
| 10,332,747 B1 | 6/2019 | Watanabe et al. |
| 10,332,963 B1 | 6/2019 | Xie |

(56) References Cited

U.S. PATENT DOCUMENTS

| | | |
|---|---|---|
| D855,089 S | 7/2019 | Hopkins |
| 10,340,125 B2 | 7/2019 | Winkler |
| 10,340,135 B2 | 7/2019 | Blanquart |
| 10,343,920 B2 | 7/2019 | Haukka |
| 10,347,547 B2 | 7/2019 | Varadarajan et al. |
| 10,354,873 B2 | 7/2019 | Ko et al. |
| 10,361,201 B2 | 7/2019 | Xie et al. |
| 10,361,366 B2 | 7/2019 | Hakamata et al. |
| 10,367,080 B2 | 7/2019 | Tang et al. |
| 10,388,513 B1 | 8/2019 | Blanquart |
| 10,395,917 B2 | 8/2019 | Niskanen et al. |
| 10,395,919 B2 | 8/2019 | Masaru et al. |
| 10,395,963 B2 | 8/2019 | Cooke |
| D859,136 S | 9/2019 | Tenander et al. |
| 10,400,335 B2 | 9/2019 | Ge et al. |
| 10,410,943 B2 | 9/2019 | Jiang et al. |
| 10,424,476 B2 | 9/2019 | Suzuki et al. |
| 10,424,477 B2 | 9/2019 | Niskanen et al. |
| D864,134 S | 10/2019 | Watarai et al. |
| 10,428,419 B2 | 10/2019 | Huotari et al. |
| 10,435,790 B2 | 10/2019 | Fukazawa et al. |
| D867,867 S | 11/2019 | Tenander et al. |
| 10,468,244 B2 | 11/2019 | Li et al. |
| 10,468,251 B2 | 11/2019 | Ishikawa et al. |
| 10,483,154 B1 | 11/2019 | Smith et al. |
| 10,510,529 B2 | 12/2019 | Suzuki et al. |
| 10,510,871 B1 | 12/2019 | More et al. |
| 10,529,554 B2 | 1/2020 | Ishikawa et al. |
| D876,504 S | 2/2020 | Lee et al. |
| 10,590,531 B1 | 3/2020 | Shirako et al. |
| 10,590,535 B2 | 3/2020 | Huggare |
| 10,600,637 B2 | 3/2020 | Suzuki et al. |
| D880,437 S | 4/2020 | Lee et al. |
| D881,338 S | 4/2020 | Chen |
| 10,622,196 B2 | 4/2020 | Nagayama et al. |
| 10,622,236 B2 | 4/2020 | Kuo et al. |
| 10,648,788 B2 | 5/2020 | Boyd et al. |
| 10,662,525 B2 | 5/2020 | Jang et al. |
| 10,704,143 B1 | 7/2020 | Hisamitsu et al. |
| 10,714,335 B2 | 7/2020 | Kim et al. |
| 10,731,249 B2 | 8/2020 | Hatanpää et al. |
| 10,734,497 B2 | 8/2020 | Zhu et al. |
| 10,741,386 B2 | 8/2020 | Chen et al. |
| 10,763,139 B2 | 9/2020 | Shindo |
| 10,770,336 B2 | 9/2020 | Hill et al. |
| D900,036 S | 10/2020 | Wuester et al. |
| D903,477 S | 12/2020 | Goratela et al. |
| D913,980 S | 3/2021 | Lee et al. |
| D914,620 S | 3/2021 | Rokkam et al. |
| 10,950,477 B2 | 3/2021 | Lin et al. |
| 11,018,003 B2 | 5/2021 | Huang et al. |
| D922,229 S | 6/2021 | Jun et al. |
| 11,053,584 B2 | 7/2021 | Hsieh et al. |
| 2001/0000141 A1 | 4/2001 | Zhou et al. |
| 2001/0001953 A1 | 5/2001 | Griffiths et al. |
| 2001/0002581 A1 | 6/2001 | Nishikawa et al. |
| 2001/0003015 A1 | 6/2001 | Chang et al. |
| 2001/0003191 A1 | 6/2001 | Kovacs et al. |
| 2001/0003271 A1 | 6/2001 | Otsuki |
| 2001/0004880 A1 | 6/2001 | Cho et al. |
| 2001/0006070 A1 | 7/2001 | Shang |
| 2001/0007244 A1 | 7/2001 | Matsuse |
| 2001/0007246 A1 | 7/2001 | Ueda et al. |
| 2001/0007645 A1 | 7/2001 | Honma |
| 2001/0014267 A1 | 8/2001 | Yamaga et al. |
| 2001/0014514 A1 | 8/2001 | Geusic |
| 2001/0015343 A1 | 8/2001 | Sprey et al. |
| 2001/0016273 A1 | 8/2001 | Narasimhan et al. |
| 2001/0017103 A1 | 8/2001 | Takeshita et al. |
| 2001/0018267 A1 | 8/2001 | Shinriki et al. |
| 2001/0019347 A1 | 9/2001 | Hauck |
| 2001/0019777 A1 | 9/2001 | Tanaka et al. |
| 2001/0019900 A1 | 9/2001 | Hasegawa |
| 2001/0020715 A1 | 9/2001 | Yamasaki |
| 2001/0021591 A1 | 9/2001 | Srinivasan et al. |
| 2001/0022215 A1 | 9/2001 | Donohoe |
| 2001/0024387 A1 | 9/2001 | Raaijmakers et al. |
| 2001/0027026 A1 | 10/2001 | Dhindsa et al. |
| 2001/0027585 A1 | 10/2001 | Lee |
| 2001/0028924 A1 | 10/2001 | Sherman |
| 2001/0031535 A1 | 10/2001 | Agnello et al. |
| 2001/0031541 A1 | 10/2001 | Madan et al. |
| 2001/0034097 A1 | 10/2001 | Lim et al. |
| 2001/0038783 A1 | 11/2001 | Nakashima et al. |
| 2001/0039922 A1 | 11/2001 | Nakahara |
| 2001/0039966 A1 | 11/2001 | Walpole et al. |
| 2001/0040511 A1 | 11/2001 | Bushner et al. |
| 2001/0041250 A1 | 11/2001 | Werkhoven et al. |
| 2001/0042511 A1 | 11/2001 | Liu et al. |
| 2001/0042514 A1 | 11/2001 | Mizuno et al. |
| 2001/0042594 A1 | 11/2001 | Shamouilian et al. |
| 2001/0046765 A1 | 11/2001 | Cappellani et al. |
| 2001/0047761 A1 | 12/2001 | Wijck et al. |
| 2001/0048981 A1 | 12/2001 | Suzuki |
| 2001/0049080 A1 | 12/2001 | Asano |
| 2001/0049202 A1 | 12/2001 | Maeda et al. |
| 2001/0052556 A1 | 12/2001 | Ting et al. |
| 2001/0054381 A1 | 12/2001 | Umotoy et al. |
| 2001/0054388 A1 | 12/2001 | Qian |
| 2002/0000195 A1 | 1/2002 | Bang et al. |
| 2002/0000202 A1 | 1/2002 | Yuda et al. |
| 2002/0001971 A1 | 1/2002 | Cho |
| 2002/0001974 A1 | 1/2002 | Chan |
| 2002/0001976 A1 | 1/2002 | Danek |
| 2002/0005400 A1 | 1/2002 | Gat et al. |
| 2002/0005943 A1 | 1/2002 | Voinalovich |
| 2002/0008270 A1 | 1/2002 | Marsh |
| 2002/0009119 A1 | 1/2002 | Matthew et al. |
| 2002/0009213 A1* | 1/2002 | Rowe ............... A61B 5/117 382/128 |
| 2002/0009560 A1 | 1/2002 | Ozono |
| 2002/0009861 A1 | 1/2002 | Narwankar et al. |
| 2002/0011210 A1 | 1/2002 | Satoh et al. |
| 2002/0011211 A1 | 1/2002 | Halpin |
| 2002/0011310 A1 | 1/2002 | Kamarehi et al. |
| 2002/0013792 A1 | 1/2002 | Imielinski et al. |
| 2002/0014204 A1 | 2/2002 | Pyo |
| 2002/0014483 A1 | 2/2002 | Suzuki et al. |
| 2002/0015853 A1 | 2/2002 | Wataya et al. |
| 2002/0016829 A1 | 2/2002 | Defosse |
| 2002/0020429 A1 | 2/2002 | Selbrede et al. |
| 2002/0022347 A1 | 2/2002 | Park et al. |
| 2002/0023677 A1 | 2/2002 | Zheng |
| 2002/0025688 A1 | 2/2002 | Kato |
| 2002/0027945 A1 | 3/2002 | Hirano et al. |
| 2002/0030047 A1 | 3/2002 | Shao et al. |
| 2002/0031644 A1 | 3/2002 | Malofsky et al. |
| 2002/0033183 A1 | 3/2002 | Sun et al. |
| 2002/0036065 A1 | 3/2002 | Yamagishi et al. |
| 2002/0041931 A1 | 4/2002 | Suntola et al. |
| 2002/0043337 A1 | 4/2002 | Goodman et al. |
| 2002/0045336 A1 | 4/2002 | Locati et al. |
| 2002/0047705 A1 | 4/2002 | Tada et al. |
| 2002/0048634 A1 | 4/2002 | Basceri |
| 2002/0050648 A1 | 5/2002 | Kishida et al. |
| 2002/0052119 A1 | 5/2002 | Cleemput |
| 2002/0061716 A1 | 5/2002 | Korovin et al. |
| 2002/0062633 A1 | 5/2002 | Denker et al. |
| 2002/0064592 A1 | 5/2002 | Datta et al. |
| 2002/0064598 A1 | 5/2002 | Wang et al. |
| 2002/0066532 A1 | 6/2002 | Shih et al. |
| 2002/0068458 A1 | 6/2002 | Chiang et al. |
| 2002/0069222 A1 | 6/2002 | McNeely |
| 2002/0073922 A1 | 6/2002 | Frankel et al. |
| 2002/0073923 A1 | 6/2002 | Saito et al. |
| 2002/0076490 A1 | 6/2002 | Chiang et al. |
| 2002/0076507 A1 | 6/2002 | Chiang et al. |
| 2002/0076944 A1 | 6/2002 | Wang et al. |
| 2002/0078893 A1 | 6/2002 | Van Os et al. |
| 2002/0079056 A1 | 6/2002 | Kudo et al. |
| 2002/0079714 A1 | 6/2002 | Soucy et al. |
| 2002/0081826 A1 | 6/2002 | Rotondaro et al. |
| 2002/0086501 A1 | 7/2002 | O'Donnell et al. |
| 2002/0088542 A1 | 7/2002 | Nishikawa et al. |

(56) References Cited

U.S. PATENT DOCUMENTS

| | | |
|---|---|---|
| 2002/0090735 A1 | 7/2002 | Kishkovich et al. |
| 2002/0094378 A1 | 7/2002 | O'Donnell et al. |
| 2002/0094388 A1 | 7/2002 | Fonash et al. |
| 2002/0096211 A1 | 7/2002 | Zheng |
| 2002/0098627 A1 | 7/2002 | Pomarede et al. |
| 2002/0099470 A1 | 7/2002 | Zinger et al. |
| 2002/0100418 A1 | 8/2002 | Sandhu et al. |
| 2002/0104481 A1 | 8/2002 | Chiang et al. |
| 2002/0104751 A1 | 8/2002 | Drewery et al. |
| 2002/0106909 A1 | 8/2002 | Kato et al. |
| 2002/0108570 A1 | 8/2002 | Lindfors |
| 2002/0108670 A1 | 8/2002 | Baker et al. |
| 2002/0108714 A1 | 8/2002 | Doering et al. |
| 2002/0109115 A1 | 8/2002 | Cederstav et al. |
| 2002/0110695 A1 | 8/2002 | Yang et al. |
| 2002/0110991 A1 | 8/2002 | Li |
| 2002/0112114 A1 | 8/2002 | Blair et al. |
| 2002/0114886 A1 | 8/2002 | Chou et al. |
| 2002/0115252 A1 | 8/2002 | Haukka et al. |
| 2002/0117113 A1 | 8/2002 | Tsuruno et al. |
| 2002/0117262 A1 | 8/2002 | Pang et al. |
| 2002/0122885 A1 | 9/2002 | Ahn |
| 2002/0123200 A1 | 9/2002 | Yamamoto et al. |
| 2002/0123230 A1 | 9/2002 | Hubacek |
| 2002/0123237 A1 | 9/2002 | Nguyen et al. |
| 2002/0124883 A1 | 9/2002 | Zheng |
| 2002/0124906 A1 | 9/2002 | Suzuki et al. |
| 2002/0127350 A1 | 9/2002 | Ishikawa et al. |
| 2002/0127956 A1 | 9/2002 | Ashjaee et al. |
| 2002/0129768 A1 | 9/2002 | Carpenter et al. |
| 2002/0132408 A1 | 9/2002 | Ma et al. |
| 2002/0134511 A1 | 9/2002 | Ushioda et al. |
| 2002/0136214 A1 | 9/2002 | Do et al. |
| 2002/0136909 A1 | 9/2002 | Yang |
| 2002/0139775 A1 | 10/2002 | Chang |
| 2002/0146512 A1 | 10/2002 | Rossman |
| 2002/0151327 A1 | 10/2002 | Levitt |
| 2002/0152244 A1 | 10/2002 | Dean et al. |
| 2002/0155219 A1 | 10/2002 | Wang et al. |
| 2002/0155708 A1 | 10/2002 | Lo et al. |
| 2002/0157611 A1 | 10/2002 | Bondestam et al. |
| 2002/0160112 A1 | 10/2002 | Sakai et al. |
| 2002/0164420 A1 | 11/2002 | Derderian et al. |
| 2002/0164423 A1 | 11/2002 | Chiang et al. |
| 2002/0168870 A1 | 11/2002 | Matsuki |
| 2002/0170676 A1 | 11/2002 | Mitrovic et al. |
| 2002/0172768 A1 | 11/2002 | Endo et al. |
| 2002/0174106 A1 | 11/2002 | Martin |
| 2002/0179011 A1 | 12/2002 | Jonnalagadda et al. |
| 2002/0181612 A1 | 12/2002 | Warble et al. |
| 2002/0184111 A1 | 12/2002 | Swanson |
| 2002/0187650 A1 | 12/2002 | Blalock et al. |
| 2002/0187656 A1 | 12/2002 | Tan et al. |
| 2002/0188376 A1 | 12/2002 | Derderian et al. |
| 2002/0192370 A1 | 12/2002 | Metzner et al. |
| 2002/0197402 A1 | 12/2002 | Chiang et al. |
| 2002/0197849 A1 | 12/2002 | Mandal |
| 2003/0000647 A1 | 1/2003 | Yudovsky et al. |
| 2003/0002562 A1 | 1/2003 | Yerlikaya et al. |
| 2003/0003607 A1 | 1/2003 | Kagoshima |
| 2003/0003635 A1 | 1/2003 | Paranjpe et al. |
| 2003/0003696 A1 | 1/2003 | Gelatos et al. |
| 2003/0003719 A1 | 1/2003 | Lim et al. |
| 2003/0008528 A1 | 1/2003 | Xia et al. |
| 2003/0008602 A1 | 1/2003 | Ashjaee et al. |
| 2003/0010355 A1 | 1/2003 | Nowak et al. |
| 2003/0010451 A1 | 1/2003 | Tzu |
| 2003/0010452 A1 | 1/2003 | Park et al. |
| 2003/0012632 A1 | 1/2003 | Saeki |
| 2003/0013314 A1 | 1/2003 | Ying et al. |
| 2003/0015141 A1 | 1/2003 | Takagi |
| 2003/0015294 A1 | 1/2003 | Wang |
| 2003/0015596 A1 | 1/2003 | Evans |
| 2003/0017265 A1 | 1/2003 | Basceri et al. |
| 2003/0017266 A1 | 1/2003 | Basceri et al. |
| 2003/0017268 A1 | 1/2003 | Hu |
| 2003/0019428 A1 | 1/2003 | Ku et al. |
| 2003/0019580 A1 | 1/2003 | Strang |
| 2003/0022468 A1 | 1/2003 | Shioya et al. |
| 2003/0022523 A1 | 1/2003 | Irino et al. |
| 2003/0023338 A1 | 1/2003 | Chin et al. |
| 2003/0024901 A1 | 2/2003 | Ishikawa |
| 2003/0025146 A1 | 2/2003 | Narwankar et al. |
| 2003/0026904 A1 | 2/2003 | Yadav et al. |
| 2003/0027431 A1 | 2/2003 | Sneh et al. |
| 2003/0029303 A1 | 2/2003 | Hasegawa et al. |
| 2003/0029381 A1 | 2/2003 | Nishibayashi |
| 2003/0029475 A1 | 2/2003 | Hua et al. |
| 2003/0029563 A1 | 2/2003 | Kaushal et al. |
| 2003/0032297 A1 | 2/2003 | Lindstrom et al. |
| 2003/0035002 A1 | 2/2003 | Moles |
| 2003/0035705 A1 | 2/2003 | Johnson |
| 2003/0036272 A1 | 2/2003 | Shamouilian et al. |
| 2003/0037800 A1 | 2/2003 | Bailey et al. |
| 2003/0040120 A1 | 2/2003 | Allen et al. |
| 2003/0040158 A1 | 2/2003 | Saitoh |
| 2003/0040196 A1 | 2/2003 | Lim et al. |
| 2003/0040841 A1 | 2/2003 | Nasr et al. |
| 2003/0041971 A1 | 3/2003 | Kido et al. |
| 2003/0042419 A1 | 3/2003 | Katsumata et al. |
| 2003/0045961 A1 | 3/2003 | Nakao |
| 2003/0049372 A1 | 3/2003 | Cook et al. |
| 2003/0049375 A1 | 3/2003 | Nguyen et al. |
| 2003/0049499 A1 | 3/2003 | Murakawa et al. |
| 2003/0049571 A1 | 3/2003 | Hallock et al. |
| 2003/0049580 A1 | 3/2003 | Goodman |
| 2003/0049937 A1 | 3/2003 | Suzuki |
| 2003/0054670 A1 | 3/2003 | Wang et al. |
| 2003/0056726 A1 | 3/2003 | Holst et al. |
| 2003/0057848 A1 | 3/2003 | Yuasa et al. |
| 2003/0059535 A1 | 3/2003 | Luo et al. |
| 2003/0059980 A1 | 3/2003 | Chen et al. |
| 2003/0062359 A1 | 4/2003 | Ho et al. |
| 2003/0065413 A1 | 4/2003 | Liteplo et al. |
| 2003/0066482 A1 | 4/2003 | Pokharna et al. |
| 2003/0066541 A1 | 4/2003 | Sun et al. |
| 2003/0066826 A1 | 4/2003 | Lee et al. |
| 2003/0070617 A1 | 4/2003 | Kim et al. |
| 2003/0071015 A1 | 4/2003 | Chinn et al. |
| 2003/0072882 A1 | 4/2003 | Niinisto et al. |
| 2003/0075107 A1 | 4/2003 | Miyano et al. |
| 2003/0075925 A1 | 4/2003 | Lindfors et al. |
| 2003/0077857 A1 | 4/2003 | Xia et al. |
| 2003/0077883 A1 | 4/2003 | Ohtake |
| 2003/0082296 A1 | 5/2003 | Elers et al. |
| 2003/0082307 A1 | 5/2003 | Chung et al. |
| 2003/0085663 A1 | 5/2003 | Horsky |
| 2003/0091938 A1 | 5/2003 | Fairbairn et al. |
| 2003/0094133 A1 | 5/2003 | Yoshidome et al. |
| 2003/0101938 A1 | 6/2003 | Ronsse et al. |
| 2003/0109107 A1 | 6/2003 | Hsieh et al. |
| 2003/0109951 A1 | 6/2003 | Hsiung et al. |
| 2003/0111012 A1 | 6/2003 | Takeshima |
| 2003/0111013 A1 | 6/2003 | Oosterlaken et al. |
| 2003/0111963 A1 | 6/2003 | Tolmachev et al. |
| 2003/0113995 A1 | 6/2003 | Xia et al. |
| 2003/0116087 A1 | 6/2003 | Nguyen |
| 2003/0121608 A1 | 7/2003 | Chen |
| 2003/0124792 A1 | 7/2003 | Jeon et al. |
| 2003/0124818 A1 | 7/2003 | Luo et al. |
| 2003/0124820 A1 | 7/2003 | Johnsgard et al. |
| 2003/0124842 A1 | 7/2003 | Hytros et al. |
| 2003/0127049 A1 | 7/2003 | Han et al. |
| 2003/0132319 A1 | 7/2003 | Hytros et al. |
| 2003/0133854 A1 | 7/2003 | Tabata et al. |
| 2003/0134038 A1 | 7/2003 | Paranjpe |
| 2003/0140851 A1 | 7/2003 | Janakiraman et al. |
| 2003/0141527 A1 | 7/2003 | Joo et al. |
| 2003/0141820 A1 | 7/2003 | White et al. |
| 2003/0143328 A1 | 7/2003 | Chen |
| 2003/0143846 A1 | 7/2003 | Sekiya et al. |
| 2003/0145789 A1 | 8/2003 | Bauch et al. |
| 2003/0149506 A1 | 8/2003 | Haanstra et al. |
| 2003/0150386 A1 | 8/2003 | Shimada |

(56) References Cited

U.S. PATENT DOCUMENTS

| | | |
|---|---|---|
| 2003/0153177 A1 | 8/2003 | Tepman et al. |
| 2003/0153186 A1 | 8/2003 | Bar-Gadda |
| 2003/0157345 A1 | 8/2003 | Beldi et al. |
| 2003/0157432 A1 | 8/2003 | Rottsegge |
| 2003/0157436 A1 | 8/2003 | Manger et al. |
| 2003/0159653 A1 | 8/2003 | Dando et al. |
| 2003/0159656 A1 | 8/2003 | Tan |
| 2003/0162412 A1 | 8/2003 | Chung |
| 2003/0168001 A1 | 9/2003 | Sneh |
| 2003/0168008 A1 | 9/2003 | Ohmi et al. |
| 2003/0168012 A1 | 9/2003 | Tamura et al. |
| 2003/0168174 A1 | 9/2003 | Foree |
| 2003/0168699 A1 | 9/2003 | Honda |
| 2003/0168750 A1 | 9/2003 | Basceri et al. |
| 2003/0168948 A1 | 9/2003 | Yamagishi et al. |
| 2003/0170153 A1 | 9/2003 | Bar-Gadda |
| 2003/0170583 A1 | 9/2003 | Nakashima |
| 2003/0170945 A1 | 9/2003 | Igeta et al. |
| 2003/0173030 A1 | 9/2003 | Ishii et al. |
| 2003/0173490 A1 | 9/2003 | Lappen |
| 2003/0176074 A1 | 9/2003 | Paterson et al. |
| 2003/0178145 A1 | 9/2003 | Anderson et al. |
| 2003/0180458 A1 | 9/2003 | Sneh |
| 2003/0181065 A1 | 9/2003 | O'Donnell |
| 2003/0183156 A1 | 10/2003 | Dando |
| 2003/0183856 A1 | 10/2003 | Wieczorek et al. |
| 2003/0188682 A1 | 10/2003 | Tois et al. |
| 2003/0188685 A1 | 10/2003 | Wang |
| 2003/0190804 A1 | 10/2003 | Glenn et al. |
| 2003/0192875 A1 | 10/2003 | Bieker et al. |
| 2003/0198587 A1 | 10/2003 | Kaloyeros |
| 2003/0200926 A1 | 10/2003 | Dando et al. |
| 2003/0201541 A1 | 10/2003 | Kim |
| 2003/0205096 A1 | 11/2003 | Gehner et al. |
| 2003/0205202 A1 | 11/2003 | Funaki et al. |
| 2003/0205237 A1 | 11/2003 | Sakuma |
| 2003/0205327 A1 | 11/2003 | Howald et al. |
| 2003/0207032 A1 | 11/2003 | Ahn et al. |
| 2003/0209323 A1 | 11/2003 | Yokogaki |
| 2003/0209326 A1 | 11/2003 | Lee et al. |
| 2003/0209746 A1 | 11/2003 | Horii |
| 2003/0210901 A1 | 11/2003 | Donald et al. |
| 2003/0211735 A1 | 11/2003 | Rossman |
| 2003/0213435 A1 | 11/2003 | Okuda et al. |
| 2003/0213560 A1 | 11/2003 | Wang et al. |
| 2003/0213562 A1 | 11/2003 | Gondhalekar et al. |
| 2003/0215963 A1 | 11/2003 | AmRhein et al. |
| 2003/0217915 A1 | 11/2003 | Ouellet |
| 2003/0219972 A1 | 11/2003 | Green |
| 2003/0221780 A1 | 12/2003 | Lei et al. |
| 2003/0226840 A1 | 12/2003 | Dalton |
| 2003/0228772 A1 | 12/2003 | Cowans |
| 2003/0230986 A1 | 12/2003 | Horsky et al. |
| 2003/0231698 A1 | 12/2003 | Yamaguchi |
| 2003/0232138 A1 | 12/2003 | Tuominen et al. |
| 2003/0232491 A1 | 12/2003 | Yamaguchi |
| 2003/0232497 A1 | 12/2003 | Xi et al. |
| 2003/0232511 A1 | 12/2003 | Metzner et al. |
| 2003/0234371 A1 | 12/2003 | Ziegler |
| 2004/0002224 A1 | 1/2004 | Chono et al. |
| 2004/0005147 A1 | 1/2004 | Wang et al. |
| 2004/0005753 A1 | 1/2004 | Kostamo et al. |
| 2004/0009307 A1 | 1/2004 | Koh et al. |
| 2004/0009679 A1 | 1/2004 | Yeo et al. |
| 2004/0010772 A1 | 1/2004 | McKenna et al. |
| 2004/0011504 A1 | 1/2004 | Ku et al. |
| 2004/0013577 A1 | 1/2004 | Ganguli et al. |
| 2004/0013818 A1 | 1/2004 | Moon et al. |
| 2004/0015300 A1 | 1/2004 | Ganguli et al. |
| 2004/0016637 A1 | 1/2004 | Yang |
| 2004/0018304 A1 | 1/2004 | Chung et al. |
| 2004/0018307 A1 | 1/2004 | Park et al. |
| 2004/0018694 A1 | 1/2004 | Lee et al. |
| 2004/0018723 A1 | 1/2004 | Byun et al. |
| 2004/0018750 A1 | 1/2004 | Sophie et al. |
| 2004/0023125 A1 | 2/2004 | Nozawa et al. |
| 2004/0023516 A1 | 2/2004 | Londergan et al. |
| 2004/0025786 A1 | 2/2004 | Kontani et al. |
| 2004/0025787 A1 | 2/2004 | Selbrede et al. |
| 2004/0026372 A1 | 2/2004 | Takenaka et al. |
| 2004/0029052 A1 | 2/2004 | Park et al. |
| 2004/0031564 A1 | 2/2004 | Gottscho et al. |
| 2004/0035358 A1 | 2/2004 | Basceri et al. |
| 2004/0036129 A1 | 2/2004 | Forbes et al. |
| 2004/0037339 A1 | 2/2004 | Watson et al. |
| 2004/0037675 A1 | 2/2004 | Zinger et al. |
| 2004/0038525 A1 | 2/2004 | Meng et al. |
| 2004/0043149 A1 | 3/2004 | Gordon et al. |
| 2004/0043544 A1 | 3/2004 | Asai et al. |
| 2004/0048439 A1 | 3/2004 | Soman |
| 2004/0048452 A1 | 3/2004 | Sugawara et al. |
| 2004/0048492 A1 | 3/2004 | Ishikawa et al. |
| 2004/0050325 A1 | 3/2004 | Samoilov |
| 2004/0050496 A1 | 3/2004 | Iwai et al. |
| 2004/0052972 A1 | 3/2004 | Schmitt |
| 2004/0056017 A1 | 3/2004 | Renken |
| 2004/0058517 A1 | 3/2004 | Nallan et al. |
| 2004/0062081 A1 | 4/2004 | Drewes |
| 2004/0063289 A1 | 4/2004 | Ohta |
| 2004/0065255 A1 | 4/2004 | Yang et al. |
| 2004/0069226 A1 | 4/2004 | Yoshida et al. |
| 2004/0071897 A1 | 4/2004 | Verplancken et al. |
| 2004/0077182 A1 | 4/2004 | Lim et al. |
| 2004/0079286 A1 | 4/2004 | Lindfors |
| 2004/0079960 A1 | 4/2004 | Shakuda |
| 2004/0080697 A1 | 4/2004 | Song |
| 2004/0082171 A1 | 4/2004 | Shin et al. |
| 2004/0083961 A1 | 5/2004 | Basceri |
| 2004/0083962 A1 | 5/2004 | Bang et al. |
| 2004/0083964 A1 | 5/2004 | Ingle et al. |
| 2004/0083975 A1 | 5/2004 | Tong et al. |
| 2004/0087141 A1 | 5/2004 | Ramanathan et al. |
| 2004/0087168 A1 | 5/2004 | Granneman et al. |
| 2004/0089078 A1 | 5/2004 | Gehner et al. |
| 2004/0089236 A1 | 5/2004 | Yokogawa et al. |
| 2004/0092073 A1 | 5/2004 | Cabral et al. |
| 2004/0092120 A1 | 5/2004 | Wicker |
| 2004/0093963 A1 | 5/2004 | Gehner et al. |
| 2004/0094206 A1 | 5/2004 | Ishida |
| 2004/0094402 A1 | 5/2004 | Gopalraja |
| 2004/0095074 A1 | 5/2004 | Ishii et al. |
| 2004/0099213 A1 | 5/2004 | Adomaitis et al. |
| 2004/0099635 A1 | 5/2004 | Nishikawa |
| 2004/0101622 A1 | 5/2004 | Park et al. |
| 2004/0103914 A1 | 6/2004 | Cheng et al. |
| 2004/0104439 A1 | 6/2004 | Haukka et al. |
| 2004/0105738 A1 | 6/2004 | Ahn et al. |
| 2004/0106249 A1 | 6/2004 | Huotari |
| 2004/0112288 A1 | 6/2004 | Whitesell |
| 2004/0115936 A1 | 6/2004 | DePetrillo et al. |
| 2004/0118342 A1 | 6/2004 | Cheng et al. |
| 2004/0121620 A1 | 6/2004 | Pomarede et al. |
| 2004/0124131 A1 | 7/2004 | Aitchison |
| 2004/0124549 A1 | 7/2004 | Curran |
| 2004/0126213 A1 | 7/2004 | Pelzmann et al. |
| 2004/0126929 A1 | 7/2004 | Tang et al. |
| 2004/0126990 A1 | 7/2004 | Ohta |
| 2004/0127069 A1 | 7/2004 | Yamazaki et al. |
| 2004/0129211 A1 | 7/2004 | Blonigan et al. |
| 2004/0129671 A1 | 7/2004 | Ji et al. |
| 2004/0134429 A1 | 7/2004 | Yamanaka |
| 2004/0137756 A1 | 7/2004 | Li et al. |
| 2004/0142577 A1 | 7/2004 | Sugawara et al. |
| 2004/0144311 A1 | 7/2004 | Chen |
| 2004/0144323 A1 | 7/2004 | Kai |
| 2004/0144980 A1 | 7/2004 | Ahn et al. |
| 2004/0146644 A1 | 7/2004 | Xia et al. |
| 2004/0151844 A1 | 8/2004 | Zhang et al. |
| 2004/0151845 A1 | 8/2004 | Nguyen et al. |
| 2004/0152287 A1 | 8/2004 | Sherrill et al. |
| 2004/0154746 A1 | 8/2004 | Park |
| 2004/0159343 A1 | 8/2004 | Shimbara et al. |
| 2004/0163590 A1 | 8/2004 | Tran et al. |
| 2004/0168627 A1 | 9/2004 | Conley et al. |

(56) References Cited

U.S. PATENT DOCUMENTS

| | | |
|---|---|---|
| 2004/0168742 A1 | 9/2004 | Kim et al. |
| 2004/0168769 A1 | 9/2004 | Matsuoka et al. |
| 2004/0169032 A1 | 9/2004 | Murayama et al. |
| 2004/0185177 A1 | 9/2004 | Basceri et al. |
| 2004/0187304 A1 | 9/2004 | Chen et al. |
| 2004/0187777 A1 | 9/2004 | Okamoto et al. |
| 2004/0187784 A1 | 9/2004 | Sferlazzo |
| 2004/0187790 A1 | 9/2004 | Bader |
| 2004/0187928 A1 | 9/2004 | Ambrosina |
| 2004/0198069 A1 | 10/2004 | Metzner et al. |
| 2004/0200499 A1 | 10/2004 | Harvey et al. |
| 2004/0202786 A1 | 10/2004 | Wongsenakhum et al. |
| 2004/0203251 A1 | 10/2004 | Kawaguchi et al. |
| 2004/0206305 A1 | 10/2004 | Choi et al. |
| 2004/0208228 A1 | 10/2004 | Hashikura et al. |
| 2004/0209477 A1 | 10/2004 | Buxbaum et al. |
| 2004/0211357 A1 | 10/2004 | Gadgil |
| 2004/0212947 A1 | 10/2004 | Nguyen |
| 2004/0213921 A1 | 10/2004 | Leu |
| 2004/0214399 A1 | 10/2004 | Ahn et al. |
| 2004/0214445 A1 | 10/2004 | Shimizu et al. |
| 2004/0217217 A1 | 11/2004 | Han et al. |
| 2004/0219793 A1 | 11/2004 | Hishiya et al. |
| 2004/0220699 A1 | 11/2004 | Heden et al. |
| 2004/0221807 A1 | 11/2004 | Verghese et al. |
| 2004/0221808 A1 | 11/2004 | Kawano |
| 2004/0223893 A1 | 11/2004 | Tabata et al. |
| 2004/0224478 A1 | 11/2004 | Chudzik et al. |
| 2004/0226507 A1 | 11/2004 | Carpenter et al. |
| 2004/0226515 A1 | 11/2004 | Yendler et al. |
| 2004/0228968 A1 | 11/2004 | Basceri |
| 2004/0231600 A1 | 11/2004 | Lee |
| 2004/0231799 A1 | 11/2004 | Lee et al. |
| 2004/0238523 A1 | 12/2004 | Kuibira et al. |
| 2004/0241322 A1 | 12/2004 | Basceri et al. |
| 2004/0241341 A1 | 12/2004 | Lin |
| 2004/0241998 A1 | 12/2004 | Hanson |
| 2004/0245091 A1 | 12/2004 | Karim et al. |
| 2004/0247779 A1 | 12/2004 | Selvamanickam et al. |
| 2004/0250600 A1 | 12/2004 | Bevers et al. |
| 2004/0253790 A1 | 12/2004 | Ootsuka |
| 2004/0253867 A1 | 12/2004 | Matsumoto |
| 2004/0261492 A1 | 12/2004 | Zarkar et al. |
| 2004/0261706 A1 | 12/2004 | Lindfors et al. |
| 2004/0261712 A1 | 12/2004 | Hayashi et al. |
| 2004/0261946 A1 | 12/2004 | Endoh et al. |
| 2004/0266011 A1 | 12/2004 | Lee et al. |
| 2005/0000428 A1 | 1/2005 | Shero et al. |
| 2005/0001062 A1 | 1/2005 | McCracken et al. |
| 2005/0003089 A1 | 1/2005 | Won et al. |
| 2005/0003600 A1 | 1/2005 | Kasai et al. |
| 2005/0003662 A1 | 1/2005 | Jurisch et al. |
| 2005/0006682 A1 | 1/2005 | Bae et al. |
| 2005/0008799 A1 | 1/2005 | Tomiyasu et al. |
| 2005/0009325 A1 | 1/2005 | Chung et al. |
| 2005/0016452 A1 | 1/2005 | Ryu et al. |
| 2005/0016470 A1 | 1/2005 | Kang et al. |
| 2005/0016956 A1 | 1/2005 | Liu et al. |
| 2005/0017272 A1 | 1/2005 | Yamashita et al. |
| 2005/0019026 A1 | 1/2005 | Wang et al. |
| 2005/0019494 A1 | 1/2005 | Moghadam et al. |
| 2005/0019960 A1 | 1/2005 | Lee et al. |
| 2005/0020071 A1 | 1/2005 | Sonobe et al. |
| 2005/0023231 A1 | 2/2005 | Huang et al. |
| 2005/0023624 A1 | 2/2005 | Ahn et al. |
| 2005/0026402 A1 | 2/2005 | Jurgensen |
| 2005/0033075 A1 | 2/2005 | Chi et al. |
| 2005/0034664 A1 | 2/2005 | Koh et al. |
| 2005/0034674 A1 | 2/2005 | Ono |
| 2005/0037154 A1 | 2/2005 | Koh et al. |
| 2005/0037578 A1 | 2/2005 | Chen et al. |
| 2005/0037610 A1 | 2/2005 | Cha |
| 2005/0037619 A1 | 2/2005 | Granneman et al. |
| 2005/0040144 A1 | 2/2005 | Sellers |
| 2005/0042778 A1 | 2/2005 | Peukert |
| 2005/0046825 A1 | 3/2005 | Powell et al. |
| 2005/0048797 A1 | 3/2005 | Fukazawa |
| 2005/0051093 A1 | 3/2005 | Makino et al. |
| 2005/0051100 A1 | 3/2005 | Chiang et al. |
| 2005/0051854 A1 | 3/2005 | Cabral et al. |
| 2005/0054175 A1 | 3/2005 | Bauer |
| 2005/0054198 A1 | 3/2005 | Um |
| 2005/0054228 A1 | 3/2005 | March |
| 2005/0056218 A1 | 3/2005 | Sun et al. |
| 2005/0056780 A1 | 3/2005 | Miller et al. |
| 2005/0059261 A1 | 3/2005 | Basceri et al. |
| 2005/0059262 A1 | 3/2005 | Yin et al. |
| 2005/0059264 A1 | 3/2005 | Cheung |
| 2005/0061964 A1 | 3/2005 | Nagano et al. |
| 2005/0062773 A1 | 3/2005 | Fouet |
| 2005/0063451 A1 | 3/2005 | Abe et al. |
| 2005/0064207 A1 | 3/2005 | Senzaki et al. |
| 2005/0064719 A1 | 3/2005 | Liu |
| 2005/0066893 A1 | 3/2005 | Soininen |
| 2005/0069651 A1 | 3/2005 | Miyoshi |
| 2005/0070123 A1 | 3/2005 | Hirano |
| 2005/0070128 A1 | 3/2005 | Xia et al. |
| 2005/0070729 A1 | 3/2005 | Kiyomori et al. |
| 2005/0072357 A1 | 4/2005 | Shero et al. |
| 2005/0074576 A1 | 4/2005 | Chaiken et al. |
| 2005/0074983 A1 | 4/2005 | Shinriki et al. |
| 2005/0079124 A1 | 4/2005 | Sanderson |
| 2005/0079691 A1 | 4/2005 | Kim et al. |
| 2005/0081786 A1 | 4/2005 | Kubista et al. |
| 2005/0085090 A1 | 4/2005 | Mui et al. |
| 2005/0090123 A1 | 4/2005 | Nishimura et al. |
| 2005/0092247 A1 | 5/2005 | Schmidt |
| 2005/0092249 A1 | 5/2005 | Kilpela et al. |
| 2005/0092439 A1 | 5/2005 | Keeton et al. |
| 2005/0092733 A1 | 5/2005 | Ito et al. |
| 2005/0095770 A1 | 5/2005 | Kumagai et al. |
| 2005/0095779 A1 | 5/2005 | Park et al. |
| 2005/0095859 A1 | 5/2005 | Chen et al. |
| 2005/0098107 A1 | 5/2005 | Du Bois et al. |
| 2005/0100669 A1 | 5/2005 | Kools et al. |
| 2005/0101154 A1 | 5/2005 | Huang |
| 2005/0101843 A1 | 5/2005 | Quinn et al. |
| 2005/0104112 A1 | 5/2005 | Haukka et al. |
| 2005/0106762 A1 | 5/2005 | Chakrapani et al. |
| 2005/0106893 A1 | 5/2005 | Wilk |
| 2005/0107627 A1 | 5/2005 | Dussarrat et al. |
| 2005/0109461 A1 | 5/2005 | Sun |
| 2005/0110069 A1 | 5/2005 | Kil et al. |
| 2005/0112282 A1 | 5/2005 | Gordon et al. |
| 2005/0115946 A1 | 6/2005 | Shim et al. |
| 2005/0118804 A1 | 6/2005 | Byun et al. |
| 2005/0118837 A1 | 6/2005 | Todd |
| 2005/0120805 A1 | 6/2005 | Lane |
| 2005/0120962 A1 | 6/2005 | Ushioda et al. |
| 2005/0121145 A1 | 6/2005 | Du Bois et al. |
| 2005/0123690 A1 | 6/2005 | Derderian et al. |
| 2005/0130427 A1 | 6/2005 | Seok-Jun |
| 2005/0132957 A1 | 6/2005 | El-Raghy |
| 2005/0133160 A1 | 6/2005 | Kennedy et al. |
| 2005/0133161 A1 | 6/2005 | Carpenter et al. |
| 2005/0133166 A1 | 6/2005 | Satitpunwaycha et al. |
| 2005/0136188 A1 | 6/2005 | Chang |
| 2005/0136657 A1 | 6/2005 | Yokoi et al. |
| 2005/0139160 A1 | 6/2005 | Lei et al. |
| 2005/0141591 A1 | 6/2005 | Sakano |
| 2005/0142361 A1 | 6/2005 | Nakanishi |
| 2005/0145338 A1 | 7/2005 | Park et al. |
| 2005/0148162 A1 | 7/2005 | Chen et al. |
| 2005/0150601 A1 | 7/2005 | Srivastava |
| 2005/0151184 A1 | 7/2005 | Lee et al. |
| 2005/0153571 A1 | 7/2005 | Senzaki |
| 2005/0153573 A1 | 7/2005 | Okudaira et al. |
| 2005/0160987 A1 | 7/2005 | Kasai et al. |
| 2005/0161434 A1 | 7/2005 | Sugawara et al. |
| 2005/0164469 A1 | 7/2005 | Haupt |
| 2005/0170306 A1 | 8/2005 | Oosterlaken et al. |
| 2005/0172895 A1 | 8/2005 | Kijima et al. |
| 2005/0173003 A1 | 8/2005 | Laverdiere et al. |
| 2005/0175789 A1 | 8/2005 | Helms |

(56) References Cited

U.S. PATENT DOCUMENTS

| | | |
|---|---|---|
| 2005/0178333 A1 | 8/2005 | Loke et al. |
| 2005/0181535 A1 | 8/2005 | Yun et al. |
| 2005/0181555 A1 | 8/2005 | Haukka et al. |
| 2005/0183827 A1 | 8/2005 | White et al. |
| 2005/0186688 A1 | 8/2005 | Basceri |
| 2005/0187647 A1 | 8/2005 | Wang et al. |
| 2005/0191828 A1 | 9/2005 | Al-Bayati et al. |
| 2005/0193948 A1 | 9/2005 | Oohirabaru et al. |
| 2005/0193952 A1 | 9/2005 | Goodman et al. |
| 2005/0199013 A1 | 9/2005 | Vandroux et al. |
| 2005/0199342 A1 | 9/2005 | Shajii et al. |
| 2005/0201908 A1 | 9/2005 | Nakamura et al. |
| 2005/0208217 A1 | 9/2005 | Shinriki et al. |
| 2005/0208219 A1 | 9/2005 | Basceri |
| 2005/0208718 A1 | 9/2005 | Lim et al. |
| 2005/0211167 A1 | 9/2005 | Gunji |
| 2005/0211384 A1 | 9/2005 | Hayashi |
| 2005/0212119 A1 | 9/2005 | Shero |
| 2005/0214457 A1 | 9/2005 | Schmitt et al. |
| 2005/0214458 A1 | 9/2005 | Meiere |
| 2005/0208778 A1 | 10/2005 | Li |
| 2005/0218462 A1 | 10/2005 | Ahn et al. |
| 2005/0221021 A1 | 10/2005 | Strang |
| 2005/0221618 A1 | 10/2005 | AmRhein et al. |
| 2005/0223982 A1 | 10/2005 | Park et al. |
| 2005/0223994 A1 | 10/2005 | Blomiley et al. |
| 2005/0227502 A1 | 10/2005 | Schmitt et al. |
| 2005/0229848 A1 | 10/2005 | Shinriki |
| 2005/0229849 A1 | 10/2005 | Silvetti et al. |
| 2005/0229972 A1 | 10/2005 | Hoshi et al. |
| 2005/0233477 A1 | 10/2005 | Yamazaki et al. |
| 2005/0238807 A1 | 10/2005 | Lin et al. |
| 2005/0241176 A1 | 11/2005 | Shero et al. |
| 2005/0241763 A1 | 11/2005 | Huang et al. |
| 2005/0241765 A1 | 11/2005 | Dhindsa et al. |
| 2005/0245058 A1 | 11/2005 | Lee et al. |
| 2005/0249876 A1 | 11/2005 | Kawahara et al. |
| 2005/0250340 A1 | 11/2005 | Chen et al. |
| 2005/0251990 A1 | 11/2005 | Choi |
| 2005/0252447 A1 | 11/2005 | Zhao et al. |
| 2005/0252449 A1 | 11/2005 | Nguyen et al. |
| 2005/0252455 A1 | 11/2005 | Moriya et al. |
| 2005/0253061 A1 | 11/2005 | Cameron et al. |
| 2005/0255257 A1 | 11/2005 | Choi et al. |
| 2005/0255327 A1 | 11/2005 | Chaney et al. |
| 2005/0258280 A1 | 11/2005 | Goto et al. |
| 2005/0260347 A1 | 11/2005 | Narwankar et al. |
| 2005/0260837 A1 | 11/2005 | Walther et al. |
| 2005/0260850 A1 | 11/2005 | Loke |
| 2005/0263072 A1 | 12/2005 | Balasubramanian et al. |
| 2005/0263075 A1 | 12/2005 | Wang et al. |
| 2005/0263719 A1 | 12/2005 | Ohdaira et al. |
| 2005/0263932 A1 | 12/2005 | Heugel |
| 2005/0268856 A1 | 12/2005 | Miller et al. |
| 2005/0271812 A1 | 12/2005 | Myo et al. |
| 2005/0271813 A1 | 12/2005 | Kher et al. |
| 2005/0272247 A1 | 12/2005 | Ikeda et al. |
| 2005/0274323 A1 | 12/2005 | Seidel et al. |
| 2005/0276928 A1 | 12/2005 | Okumura et al. |
| 2005/0277271 A1 | 12/2005 | Beintner |
| 2005/0282101 A1 | 12/2005 | Adachi |
| 2005/0282350 A1 | 12/2005 | Chou et al. |
| 2005/0284573 A1 | 12/2005 | Egley et al. |
| 2005/0284991 A1 | 12/2005 | Saez |
| 2005/0285097 A1 | 12/2005 | Shang et al. |
| 2005/0285208 A1 | 12/2005 | Ren et al. |
| 2005/0287725 A1 | 12/2005 | Kitagawa |
| 2005/0287771 A1 | 12/2005 | Seamons et al. |
| 2006/0000411 A1 | 1/2006 | Seo |
| 2006/0006538 A1 | 1/2006 | Allman et al. |
| 2006/0008997 A1 | 1/2006 | Jang et al. |
| 2006/0009044 A1 | 1/2006 | Igeta et al. |
| 2006/0013674 A1 | 1/2006 | Elliott et al. |
| 2006/0013946 A1 | 1/2006 | Park et al. |
| 2006/0014384 A1 | 1/2006 | Lee et al. |
| 2006/0014397 A1 | 1/2006 | Seamons et al. |
| 2006/0016783 A1 | 1/2006 | Wu et al. |
| 2006/0019033 A1 | 1/2006 | Muthukrishnan et al. |
| 2006/0019495 A1 | 1/2006 | Marcadal et al. |
| 2006/0019502 A1 | 1/2006 | Park et al. |
| 2006/0021572 A1 | 2/2006 | Wolden |
| 2006/0021573 A1 | 2/2006 | Monsma et al. |
| 2006/0021703 A1 | 2/2006 | Umotoy et al. |
| 2006/0024439 A2 | 2/2006 | Tuominen et al. |
| 2006/0026314 A1 | 2/2006 | Franchuk et al. |
| 2006/0032443 A1 | 2/2006 | Hasebe et al. |
| 2006/0040054 A1 | 2/2006 | Pearlstein et al. |
| 2006/0040508 A1 | 2/2006 | Ji |
| 2006/0046518 A1 | 3/2006 | Hill et al. |
| 2006/0048710 A1 | 3/2006 | Horiguchi et al. |
| 2006/0051505 A1 | 3/2006 | Kortshagen et al. |
| 2006/0051520 A1 | 3/2006 | Behle et al. |
| 2006/0051925 A1 | 3/2006 | Ahn et al. |
| 2006/0057799 A1 | 3/2006 | Horiguchi et al. |
| 2006/0057828 A1 | 3/2006 | Omura |
| 2006/0057858 A1 | 3/2006 | Chung et al. |
| 2006/0060930 A1 | 3/2006 | Metz et al. |
| 2006/0062910 A1 | 3/2006 | Meiere |
| 2006/0063346 A1 | 3/2006 | Lee et al. |
| 2006/0068097 A1 | 3/2006 | Yamasaki et al. |
| 2006/0068104 A1 | 3/2006 | Ishizaka |
| 2006/0068121 A1 | 3/2006 | Lee et al. |
| 2006/0068125 A1 | 3/2006 | Radhakrishnan |
| 2006/0081558 A1 | 4/2006 | Collins et al. |
| 2006/0087638 A1 | 4/2006 | Hirayanagi |
| 2006/0090702 A1 | 5/2006 | Koo et al. |
| 2006/0093756 A1 | 5/2006 | Rajagopalan et al. |
| 2006/0094236 A1 | 5/2006 | Elkins et al. |
| 2006/0096540 A1 | 5/2006 | Choi |
| 2006/0097220 A1 | 5/2006 | Kim et al. |
| 2006/0097305 A1 | 5/2006 | Lee |
| 2006/0099782 A1 | 5/2006 | Ritenour |
| 2006/0102968 A1 | 5/2006 | Bojarczuk et al. |
| 2006/0105566 A1 | 5/2006 | Waldfried et al. |
| 2006/0107898 A1 | 5/2006 | Blomberg |
| 2006/0108221 A1 | 5/2006 | Goodwin et al. |
| 2006/0108331 A1 | 5/2006 | Nozawa et al. |
| 2006/0110930 A1 | 5/2006 | Senzaki |
| 2006/0110934 A1 | 5/2006 | Fukuchi |
| 2006/0113038 A1 | 6/2006 | Gondhalekar et al. |
| 2006/0113675 A1 | 6/2006 | Chang et al. |
| 2006/0113806 A1 | 6/2006 | Tsuji et al. |
| 2006/0115589 A1 | 6/2006 | Vukovic |
| 2006/0118240 A1 | 6/2006 | Holber et al. |
| 2006/0118241 A1 | 6/2006 | Ohmi et al. |
| 2006/0125099 A1 | 6/2006 | Gordon et al. |
| 2006/0127067 A1 | 6/2006 | Wintenberger et al. |
| 2006/0128142 A1 | 6/2006 | Whelan et al. |
| 2006/0128168 A1 | 6/2006 | Ahn et al. |
| 2006/0130751 A1 | 6/2006 | Volfovski et al. |
| 2006/0130767 A1 | 6/2006 | Herchen |
| 2006/0133955 A1 | 6/2006 | Peters |
| 2006/0137608 A1 | 6/2006 | Choi et al. |
| 2006/0137609 A1 | 6/2006 | Puchacz et al. |
| 2006/0141155 A1 | 6/2006 | Gordon et al. |
| 2006/0141758 A1 | 6/2006 | Naumann et al. |
| 2006/0144820 A1 | 7/2006 | Sawin et al. |
| 2006/0147626 A1 | 7/2006 | Blomberg |
| 2006/0148151 A1 | 7/2006 | Murthy et al. |
| 2006/0148180 A1 | 7/2006 | Ahn et al. |
| 2006/0151117 A1 | 7/2006 | Kasanami et al. |
| 2006/0154424 A1 | 7/2006 | Yang et al. |
| 2006/0156979 A1 | 7/2006 | Thakur et al. |
| 2006/0156981 A1 | 7/2006 | Fondurulia |
| 2006/0162658 A1 | 7/2006 | Weidman |
| 2006/0162661 A1 | 7/2006 | Jung et al. |
| 2006/0162863 A1 | 7/2006 | Kim et al. |
| 2006/0163612 A1 | 7/2006 | Kouvetakis et al. |
| 2006/0163683 A1 | 7/2006 | Roth et al. |
| 2006/0165892 A1 | 7/2006 | Weidman |
| 2006/0166428 A1 | 7/2006 | Kamioka |
| 2006/0172531 A1 | 8/2006 | Lin et al. |
| 2006/0175669 A1 | 8/2006 | Kim et al. |
| 2006/0176928 A1 | 8/2006 | Nakamura et al. |

(56) References Cited

U.S. PATENT DOCUMENTS

| | | |
|---|---|---|
| 2006/0177855 A1 | 8/2006 | Utermohlen |
| 2006/0182885 A1 | 8/2006 | Lei et al. |
| 2006/0185589 A1 | 8/2006 | Zehavi et al. |
| 2006/0188360 A1 | 8/2006 | Bonora et al. |
| 2006/0191555 A1 | 8/2006 | Yoshida et al. |
| 2006/0193979 A1 | 8/2006 | Meiere et al. |
| 2006/0193980 A1 | 8/2006 | Hasegawa |
| 2006/0196418 A1 | 9/2006 | Lindfors et al. |
| 2006/0196420 A1 | 9/2006 | Ushakov et al. |
| 2006/0196421 A1 | 9/2006 | Ronsse et al. |
| 2006/0199357 A1 | 9/2006 | Wan et al. |
| 2006/0205194 A1 | 9/2006 | Bauer |
| 2006/0205223 A1 | 9/2006 | Smayling |
| 2006/0205231 A1 | 9/2006 | Chou et al. |
| 2006/0208215 A1 | 9/2006 | Metzner et al. |
| 2006/0211224 A1 | 9/2006 | Matsuda |
| 2006/0211243 A1 | 9/2006 | Ishizaka et al. |
| 2006/0211259 A1 | 9/2006 | Maes |
| 2006/0213437 A1 | 9/2006 | Ishizaka et al. |
| 2006/0213439 A1 | 9/2006 | Ishizaka |
| 2006/0213441 A1 | 9/2006 | Kobrin et al. |
| 2006/0216942 A1 | 9/2006 | Kim et al. |
| 2006/0219169 A1 | 10/2006 | Chen et al. |
| 2006/0219361 A1 | 10/2006 | Wang et al. |
| 2006/0219363 A1 | 10/2006 | Matsumoto et al. |
| 2006/0223301 A1 | 10/2006 | Vanhaelemeersch et al. |
| 2006/0223337 A1 | 10/2006 | Ahn et al. |
| 2006/0226117 A1 | 10/2006 | Bertram et al. |
| 2006/0228496 A1 | 10/2006 | Choi |
| 2006/0228863 A1 | 10/2006 | Zhang et al. |
| 2006/0228888 A1 | 10/2006 | Lee et al. |
| 2006/0228898 A1 | 10/2006 | Wajda et al. |
| 2006/0236934 A1 | 10/2006 | Choi et al. |
| 2006/0240187 A1 | 10/2006 | Weidman |
| 2006/0240574 A1 | 10/2006 | Yoshie |
| 2006/0240662 A1 | 10/2006 | Conley et al. |
| 2006/0247404 A1 | 11/2006 | Todd |
| 2006/0249175 A1 | 11/2006 | Nowak et al. |
| 2006/0249253 A1 | 11/2006 | Dando |
| 2006/0251827 A1 | 11/2006 | Nowak |
| 2006/0252228 A1 | 11/2006 | Jeng |
| 2006/0252244 A1 | 11/2006 | Vaartstra et al. |
| 2006/0252351 A1 | 11/2006 | Kundracik |
| 2006/0254514 A1 | 11/2006 | Kang et al. |
| 2006/0257563 A1 | 11/2006 | Doh et al. |
| 2006/0257584 A1 | 11/2006 | Derderian et al. |
| 2006/0258078 A1 | 11/2006 | Lee et al. |
| 2006/0258173 A1 | 11/2006 | Xiao et al. |
| 2006/0260545 A1 | 11/2006 | Ramaswamy et al. |
| 2006/0263522 A1 | 11/2006 | Byun |
| 2006/0263540 A1 | 11/2006 | Ramaswamy et al. |
| 2006/0264060 A1 | 11/2006 | Ramaswamy et al. |
| 2006/0264066 A1 | 11/2006 | Bartholomew |
| 2006/0266289 A1 | 11/2006 | Verghese et al. |
| 2006/0269690 A1 | 11/2006 | Watanabe et al. |
| 2006/0269692 A1 | 11/2006 | Balseanu |
| 2006/0275710 A1 | 12/2006 | Yamazaki et al. |
| 2006/0275933 A1 | 12/2006 | Du Bois et al. |
| 2006/0278524 A1 | 12/2006 | Stowell |
| 2006/0283629 A1 | 12/2006 | Kikuchi et al. |
| 2006/0286774 A1 | 12/2006 | Singh et al. |
| 2006/0286775 A1 | 12/2006 | Singh et al. |
| 2006/0286817 A1 | 12/2006 | Kato et al. |
| 2006/0286818 A1 | 12/2006 | Wang et al. |
| 2006/0286819 A1 | 12/2006 | Seutter |
| 2006/0291982 A1 | 12/2006 | Tanaka |
| 2006/0292310 A1 | 12/2006 | Le et al. |
| 2006/0292845 A1 | 12/2006 | Chiang et al. |
| 2007/0004204 A1 | 1/2007 | Fukazawa et al. |
| 2007/0006806 A1 | 1/2007 | Imai |
| 2007/0010072 A1 | 1/2007 | Bailey et al. |
| 2007/0012402 A1 | 1/2007 | Sneh |
| 2007/0014919 A1 | 1/2007 | Hamalainen et al. |
| 2007/0020160 A1 | 1/2007 | Berkman et al. |
| 2007/0020167 A1 | 1/2007 | Han et al. |
| 2007/0020830 A1 | 1/2007 | Speranza |
| 2007/0020953 A1 | 1/2007 | Tsai et al. |
| 2007/0022954 A1 | 2/2007 | Iizuka et al. |
| 2007/0026148 A1 | 2/2007 | Arai et al. |
| 2007/0026162 A1 | 2/2007 | Wei et al. |
| 2007/0026540 A1 | 2/2007 | Nooten et al. |
| 2007/0026654 A1 | 2/2007 | Huotari et al. |
| 2007/0028842 A1 | 2/2007 | Inagawa et al. |
| 2007/0031598 A1 | 2/2007 | Okuyama et al. |
| 2007/0031599 A1 | 2/2007 | Gschwandtner et al. |
| 2007/0032004 A1 | 2/2007 | Ramaswamy et al. |
| 2007/0032045 A1 | 2/2007 | Kasahara et al. |
| 2007/0032054 A1 | 2/2007 | Ramaswamy et al. |
| 2007/0032082 A1 | 2/2007 | Ramaswamy et al. |
| 2007/0032095 A1 | 2/2007 | Ramaswamy et al. |
| 2007/0034477 A1 | 2/2007 | Inui |
| 2007/0037343 A1 | 2/2007 | Colombo et al. |
| 2007/0037412 A1 | 2/2007 | Dip et al. |
| 2007/0042117 A1 | 2/2007 | Kupurao et al. |
| 2007/0042581 A1 | 2/2007 | Sano et al. |
| 2007/0044716 A1 | 3/2007 | Tetsuka et al. |
| 2007/0045244 A1 | 3/2007 | Lee et al. |
| 2007/0047384 A1 | 3/2007 | McLaughlin et al. |
| 2007/0048953 A1 | 3/2007 | Gealy et al. |
| 2007/0049053 A1 | 3/2007 | Mahajani |
| 2007/0051299 A1 | 3/2007 | Ong et al. |
| 2007/0051312 A1 | 3/2007 | Sneh |
| 2007/0051471 A1 | 3/2007 | Kawaguchi et al. |
| 2007/0054049 A1 | 3/2007 | Lindfors et al. |
| 2007/0054499 A1 | 3/2007 | Jang |
| 2007/0056843 A1 | 3/2007 | Ye et al. |
| 2007/0056850 A1 | 3/2007 | Ye et al. |
| 2007/0059948 A1 | 3/2007 | Metzner et al. |
| 2007/0062439 A1 | 3/2007 | Wada et al. |
| 2007/0062453 A1 | 3/2007 | Ishikawa |
| 2007/0062646 A1 | 3/2007 | Ogawa et al. |
| 2007/0065578 A1 | 3/2007 | McDougall |
| 2007/0065597 A1 | 3/2007 | Kaido et al. |
| 2007/0066010 A1 | 3/2007 | Ando |
| 2007/0066038 A1 | 3/2007 | Sadjadi et al. |
| 2007/0066079 A1 | 3/2007 | Kolster et al. |
| 2007/0066084 A1 | 3/2007 | Wajda et al. |
| 2007/0074665 A1 | 4/2007 | Chacin et al. |
| 2007/0077355 A1 | 4/2007 | Chacin et al. |
| 2007/0082132 A1 | 4/2007 | Shinriki |
| 2007/0082500 A1 | 4/2007 | Norman et al. |
| 2007/0082508 A1 | 4/2007 | Chiang et al. |
| 2007/0084405 A1 | 4/2007 | Kim |
| 2007/0087296 A1 | 4/2007 | Kim et al. |
| 2007/0087515 A1 | 4/2007 | Yieh et al. |
| 2007/0087579 A1 | 4/2007 | Kitayama et al. |
| 2007/0089670 A1 | 4/2007 | Ikedo |
| 2007/0092696 A1 | 4/2007 | Tsukatani et al. |
| 2007/0095283 A1 | 5/2007 | Galewski |
| 2007/0095286 A1 | 5/2007 | Baek et al. |
| 2007/0096194 A1 | 5/2007 | Streck et al. |
| 2007/0098527 A1 | 5/2007 | Hall et al. |
| 2007/0107845 A1 | 5/2007 | Ishizawa et al. |
| 2007/0111030 A1 | 5/2007 | Nakano et al. |
| 2007/0111470 A1 | 5/2007 | Smythe |
| 2007/0111545 A1 | 5/2007 | Lee et al. |
| 2007/0113788 A1 | 5/2007 | Nozawa et al. |
| 2007/0116872 A1 | 5/2007 | Li et al. |
| 2007/0116873 A1 | 5/2007 | Li et al. |
| 2007/0116887 A1 | 5/2007 | Faguet |
| 2007/0116888 A1 | 5/2007 | Faguet |
| 2007/0119370 A1 | 5/2007 | Ma et al. |
| 2007/0120275 A1 | 5/2007 | Liu |
| 2007/0123037 A1 | 5/2007 | Lee et al. |
| 2007/0123060 A1 | 5/2007 | Rahtu |
| 2007/0123189 A1 | 5/2007 | Saito et al. |
| 2007/0125762 A1 | 6/2007 | Cui et al. |
| 2007/0128538 A1 | 6/2007 | Fairbairn et al. |
| 2007/0128570 A1 | 6/2007 | Goto et al. |
| 2007/0128858 A1 | 6/2007 | Haukka et al. |
| 2007/0128876 A1 | 6/2007 | Fukiage |
| 2007/0128888 A1 | 6/2007 | Goto et al. |
| 2007/0129621 A1 | 6/2007 | Kellogg et al. |
| 2007/0131168 A1 | 6/2007 | Gomi et al. |

(56) References Cited

U.S. PATENT DOCUMENTS

| | | |
|---|---|---|
| 2007/0134821 A1 | 6/2007 | Thakur et al. |
| 2007/0134919 A1 | 6/2007 | Gunji et al. |
| 2007/0134942 A1 | 6/2007 | Ahn et al. |
| 2007/0137794 A1 | 6/2007 | Qiu et al. |
| 2007/0144442 A1 | 6/2007 | Migita |
| 2007/0146621 A1 | 6/2007 | Yeom |
| 2007/0148347 A1 | 6/2007 | Hatanpaa et al. |
| 2007/0148350 A1 | 6/2007 | Rahtu |
| 2007/0148990 A1 | 6/2007 | Deboer et al. |
| 2007/0153625 A1 | 6/2007 | Lundgren et al. |
| 2007/0155138 A1 | 7/2007 | Tomasini et al. |
| 2007/0157466 A1 | 7/2007 | Kida et al. |
| 2007/0157683 A1 | 7/2007 | Li |
| 2007/0158026 A1 | 7/2007 | Amikura |
| 2007/0163440 A1 | 7/2007 | Kim et al. |
| 2007/0163490 A1 | 7/2007 | Habel et al. |
| 2007/0163625 A1 | 7/2007 | Lee |
| 2007/0163996 A1 | 7/2007 | Horiguchi |
| 2007/0166457 A1 | 7/2007 | Yamoto et al. |
| 2007/0166459 A1 | 7/2007 | Chang et al. |
| 2007/0166966 A1 | 7/2007 | Todd et al. |
| 2007/0166999 A1 | 7/2007 | Vaarstra |
| 2007/0170372 A1 | 7/2007 | Horsky |
| 2007/0173071 A1 | 7/2007 | Afzali-Ardakani et al. |
| 2007/0175393 A1 | 8/2007 | Nishimura et al. |
| 2007/0175397 A1 | 8/2007 | Tomiyasu et al. |
| 2007/0178235 A1 | 8/2007 | Yamada et al. |
| 2007/0181066 A1 | 8/2007 | Cadwell et al. |
| 2007/0184179 A1 | 8/2007 | Waghray et al. |
| 2007/0186849 A1 | 8/2007 | Furuya |
| 2007/0186952 A1 | 8/2007 | Honda et al. |
| 2007/0187362 A1 | 8/2007 | Nakagawa et al. |
| 2007/0187363 A1 | 8/2007 | Oka et al. |
| 2007/0190266 A1 | 8/2007 | Fu et al. |
| 2007/0190362 A1 | 8/2007 | Weidman |
| 2007/0190744 A1 | 8/2007 | Hiraiwa et al. |
| 2007/0190782 A1 | 8/2007 | Park |
| 2007/0199510 A1 | 8/2007 | Weiner et al. |
| 2007/0202678 A1 | 8/2007 | Plombon et al. |
| 2007/0205788 A1 | 9/2007 | Natsuhara et al. |
| 2007/0207275 A1 | 9/2007 | Nowak et al. |
| 2007/0209588 A1 | 9/2007 | Li et al. |
| 2007/0209590 A1 | 9/2007 | Li |
| 2007/0210890 A1 | 9/2007 | Hsu et al. |
| 2007/0212484 A1 | 9/2007 | Li |
| 2007/0212811 A1 | 9/2007 | Hanawa et al. |
| 2007/0212827 A1 | 9/2007 | Girotra et al. |
| 2007/0215048 A1 | 9/2007 | Suzuki et al. |
| 2007/0215278 A1 | 9/2007 | Furuse et al. |
| 2007/0215580 A1 | 9/2007 | Koshiishi et al. |
| 2007/0218200 A1 | 9/2007 | Suzuki et al. |
| 2007/0218705 A1 | 9/2007 | Matsuki et al. |
| 2007/0222131 A1 | 9/2007 | Fukumoto et al. |
| 2007/0224777 A1 | 9/2007 | Hamelin |
| 2007/0224833 A1 | 9/2007 | Morisada et al. |
| 2007/0227665 A1 | 10/2007 | Matsumoto et al. |
| 2007/0231488 A1 | 10/2007 | Von Kaenel |
| 2007/0232031 A1 | 10/2007 | Singh et al. |
| 2007/0232071 A1 | 10/2007 | Balseanu et al. |
| 2007/0232501 A1 | 10/2007 | Tonomura |
| 2007/0234955 A1 | 10/2007 | Suzuki et al. |
| 2007/0237697 A1 | 10/2007 | Clark |
| 2007/0237698 A1 | 10/2007 | Clark |
| 2007/0237699 A1 | 10/2007 | Clark |
| 2007/0238305 A1 | 10/2007 | Delgadino et al. |
| 2007/0241688 A1 | 10/2007 | DeVancentis et al. |
| 2007/0243317 A1 | 10/2007 | Du Bois et al. |
| 2007/0247075 A1 | 10/2007 | Kim et al. |
| 2007/0248767 A1 | 10/2007 | Okura |
| 2007/0248832 A1 | 10/2007 | Maeda et al. |
| 2007/0249131 A1 | 10/2007 | Allen et al. |
| 2007/0251444 A1 | 11/2007 | Gros-Jean et al. |
| 2007/0251456 A1 | 11/2007 | Herchen et al. |
| 2007/0252233 A1 | 11/2007 | Yamazaki et al. |
| 2007/0252244 A1 | 11/2007 | Srividya et al. |
| 2007/0252532 A1 | 11/2007 | DeVancentis et al. |
| 2007/0254414 A1 | 11/2007 | Miyanami |
| 2007/0258506 A1 | 11/2007 | Schwagerman et al. |
| 2007/0258855 A1 | 11/2007 | Turcot et al. |
| 2007/0259778 A1 | 11/2007 | Spencer et al. |
| 2007/0261868 A1 | 11/2007 | Gross |
| 2007/0264427 A1 | 11/2007 | Shinriki et al. |
| 2007/0264793 A1 | 11/2007 | Oh et al. |
| 2007/0264807 A1 | 11/2007 | Leone et al. |
| 2007/0266932 A1 | 11/2007 | Hiramatsu |
| 2007/0266945 A1 | 11/2007 | Shuto et al. |
| 2007/0269983 A1 | 11/2007 | Sneh |
| 2007/0275166 A1 | 11/2007 | Thridandam et al. |
| 2007/0277735 A1 | 12/2007 | Mokhesi et al. |
| 2007/0281082 A1 | 12/2007 | Mokhesi et al. |
| 2007/0281105 A1 | 12/2007 | Mokhesi et al. |
| 2007/0281106 A1 | 12/2007 | Lubomirsky et al. |
| 2007/0281496 A1 | 12/2007 | Ingle et al. |
| 2007/0286957 A1 | 12/2007 | Suzuki et al. |
| 2007/0289534 A1 | 12/2007 | Lubomirsky et al. |
| 2007/0292974 A1 | 12/2007 | Mizuno et al. |
| 2007/0295602 A1 | 12/2007 | Tiller et al. |
| 2007/0298362 A1 | 12/2007 | Rocha-Alvarez et al. |
| 2007/0298565 A1 | 12/2007 | Nieh et al. |
| 2008/0003425 A1 | 1/2008 | Spencer et al. |
| 2008/0003824 A1 | 1/2008 | Padhi et al. |
| 2008/0003838 A1 | 1/2008 | Haukka et al. |
| 2008/0006208 A1 | 1/2008 | Ueno et al. |
| 2008/0018004 A1 | 1/2008 | Steidl |
| 2008/0020591 A1 | 1/2008 | Balseanu et al. |
| 2008/0020593 A1 | 1/2008 | Wang et al. |
| 2008/0023436 A1 | 1/2008 | Gros-Jean et al. |
| 2008/0026162 A1 | 1/2008 | Dickey et al. |
| 2008/0026574 A1 | 1/2008 | Brcka |
| 2008/0026597 A1 | 1/2008 | Munro et al. |
| 2008/0029790 A1 | 2/2008 | Ahn et al. |
| 2008/0031708 A1 | 2/2008 | Bonora et al. |
| 2008/0032514 A1 | 2/2008 | Sano et al. |
| 2008/0035055 A1 | 2/2008 | Dip et al. |
| 2008/0035306 A1 | 2/2008 | White et al. |
| 2008/0035607 A1 | 2/2008 | O'Hara et al. |
| 2008/0036354 A1 | 2/2008 | Letz et al. |
| 2008/0038485 A1 | 2/2008 | Fukazawa et al. |
| 2008/0038934 A1 | 2/2008 | Vrtis et al. |
| 2008/0042165 A1 | 2/2008 | Sugizaki |
| 2008/0042192 A1 | 2/2008 | Park et al. |
| 2008/0043803 A1 | 2/2008 | Bandoh |
| 2008/0044932 A1 | 2/2008 | Samoilov et al. |
| 2008/0044938 A1 | 2/2008 | England et al. |
| 2008/0050536 A1 | 2/2008 | Aing et al. |
| 2008/0050538 A1 | 2/2008 | Hirata |
| 2008/0054332 A1 | 3/2008 | Kim et al. |
| 2008/0054813 A1 | 3/2008 | Espiau et al. |
| 2008/0056860 A1 | 3/2008 | Natume |
| 2008/0057659 A1 | 3/2008 | Forbes et al. |
| 2008/0061667 A1 | 3/2008 | Gaertner et al. |
| 2008/0063798 A1 | 3/2008 | Kher et al. |
| 2008/0066778 A1 | 3/2008 | Matsushita et al. |
| 2008/0067146 A1 | 3/2008 | Onishi et al. |
| 2008/0069951 A1 | 3/2008 | Chacin et al. |
| 2008/0069955 A1 | 3/2008 | Hong et al. |
| 2008/0072821 A1 | 3/2008 | Dalton et al. |
| 2008/0075562 A1 | 3/2008 | Maria et al. |
| 2008/0075838 A1 | 3/2008 | Inoue et al. |
| 2008/0075881 A1 | 3/2008 | Won et al. |
| 2008/0076070 A1 | 3/2008 | Koh et al. |
| 2008/0076266 A1 | 3/2008 | Fukazawa et al. |
| 2008/0076281 A1 | 3/2008 | Ciancanelli et al. |
| 2008/0081104 A1 | 4/2008 | Hasebe et al. |
| 2008/0081113 A1 | 4/2008 | Clark |
| 2008/0081121 A1 | 4/2008 | Morita et al. |
| 2008/0083710 A1 | 4/2008 | Chen et al. |
| 2008/0083948 A1 | 4/2008 | Lin et al. |
| 2008/0085226 A1 | 4/2008 | Fondurulia et al. |
| 2008/0085610 A1 | 4/2008 | Wang et al. |
| 2008/0087218 A1 | 4/2008 | Shimada et al. |
| 2008/0087642 A1 | 4/2008 | Sawin et al. |
| 2008/0087890 A1 | 4/2008 | Ahn et al. |
| 2008/0092815 A1 | 4/2008 | Chen et al. |

(56) References Cited

U.S. PATENT DOCUMENTS

| | | |
|---|---|---|
| 2008/0092821 A1 | 4/2008 | Otsuka et al. |
| 2008/0099147 A1 | 5/2008 | Myo et al. |
| 2008/0102203 A1 | 5/2008 | Wu |
| 2008/0102205 A1 | 5/2008 | Barry et al. |
| 2008/0102208 A1 | 5/2008 | Wu et al. |
| 2008/0102603 A1 | 5/2008 | Kobayashi et al. |
| 2008/0102630 A1 | 5/2008 | Saito |
| 2008/0105276 A1 | 5/2008 | Yeh et al. |
| 2008/0110401 A1 | 5/2008 | Fujikawa et al. |
| 2008/0110568 A1 | 5/2008 | Son et al. |
| 2008/0113094 A1 | 5/2008 | Casper |
| 2008/0113096 A1 | 5/2008 | Mahajani |
| 2008/0113097 A1 | 5/2008 | Mahajani et al. |
| 2008/0118334 A1 | 5/2008 | Bonora |
| 2008/0121177 A1 | 5/2008 | Bang et al. |
| 2008/0121626 A1 | 5/2008 | Thomas et al. |
| 2008/0121962 A1 | 5/2008 | Forbes et al. |
| 2008/0124197 A1 | 5/2008 | van der Meulen et al. |
| 2008/0124908 A1 | 5/2008 | Forbes et al. |
| 2008/0124945 A1 | 5/2008 | Miya et al. |
| 2008/0124946 A1 | 5/2008 | Xiao et al. |
| 2008/0128726 A1 | 6/2008 | Sakata et al. |
| 2008/0129209 A1 | 6/2008 | Deakins et al. |
| 2008/0132046 A1 | 6/2008 | Walther |
| 2008/0133154 A1 | 6/2008 | Krauss et al. |
| 2008/0134887 A1 | 6/2008 | Sherer |
| 2008/0135516 A1 | 6/2008 | Yokogawa et al. |
| 2008/0135936 A1 | 6/2008 | Nakajima |
| 2008/0142046 A1 | 6/2008 | Johnson et al. |
| 2008/0142483 A1 | 6/2008 | Hua |
| 2008/0146033 A1 | 6/2008 | Park |
| 2008/0149031 A1 | 6/2008 | Chu et al. |
| 2008/0149593 A1 | 6/2008 | Bai et al. |
| 2008/0152463 A1 | 6/2008 | Chidambaram et al. |
| 2008/0153308 A1 | 6/2008 | Ogawa et al. |
| 2008/0153311 A1 | 6/2008 | Padhi et al. |
| 2008/0156769 A1 | 7/2008 | Weiner et al. |
| 2008/0157157 A1 | 7/2008 | Tonomura |
| 2008/0157212 A1 | 7/2008 | Lavoie et al. |
| 2008/0157365 A1 | 7/2008 | Ott et al. |
| 2008/0173237 A1 | 7/2008 | Collins |
| 2008/0173238 A1 | 7/2008 | Nakashima et al. |
| 2008/0173240 A1 | 7/2008 | Furukawahara |
| 2008/0173326 A1 | 7/2008 | Gu et al. |
| 2008/0176335 A1 | 7/2008 | Alberti et al. |
| 2008/0176375 A1 | 7/2008 | Erben et al. |
| 2008/0176412 A1 | 7/2008 | Komeda |
| 2008/0178608 A1 | 7/2008 | Tandou et al. |
| 2008/0178805 A1 | 7/2008 | Paterson et al. |
| 2008/0179104 A1 | 7/2008 | Zhang |
| 2008/0179291 A1 | 7/2008 | Collins et al. |
| 2008/0179715 A1 | 7/2008 | Coppa |
| 2008/0182075 A1 | 7/2008 | Chopra |
| 2008/0182390 A1 | 7/2008 | Lemmi et al. |
| 2008/0182411 A1 | 7/2008 | Elers |
| 2008/0191193 A1 | 8/2008 | Li et al. |
| 2008/0193643 A1 | 8/2008 | Dip |
| 2008/0194088 A1 | 8/2008 | Srinivasan et al. |
| 2008/0194105 A1 | 8/2008 | Dominguez et al. |
| 2008/0194113 A1 | 8/2008 | Kim et al. |
| 2008/0194169 A1 | 8/2008 | Sterling et al. |
| 2008/0199977 A1 | 8/2008 | Weigel et al. |
| 2008/0202416 A1 | 8/2008 | Provencher |
| 2008/0202689 A1 | 8/2008 | Kim |
| 2008/0203487 A1 | 8/2008 | Hohage et al. |
| 2008/0205483 A1 | 8/2008 | Rempe et al. |
| 2008/0210162 A1 | 9/2008 | Yonebayashi |
| 2008/0210278 A1 | 9/2008 | Orii et al. |
| 2008/0211423 A1 | 9/2008 | Shinmen et al. |
| 2008/0211526 A1 | 9/2008 | Shinma |
| 2008/0213696 A1 | 9/2008 | Meeus et al. |
| 2008/0214003 A1 | 9/2008 | Xia et al. |
| 2008/0216077 A1 | 9/2008 | Emani et al. |
| 2008/0216742 A1 | 9/2008 | Takebayashi |
| 2008/0216958 A1 | 9/2008 | Goto et al. |
| 2008/0220619 A1 | 9/2008 | Matsushita et al. |
| 2008/0223130 A1 | 9/2008 | Snell et al. |
| 2008/0223725 A1 | 9/2008 | Han et al. |
| 2008/0224240 A1 | 9/2008 | Ahn et al. |
| 2008/0228306 A1 | 9/2008 | Yetter et al. |
| 2008/0229811 A1 | 9/2008 | Zhao et al. |
| 2008/0230352 A1 | 9/2008 | Hirata |
| 2008/0230371 A1 | 9/2008 | McHugh |
| 2008/0233288 A1 | 9/2008 | Clark |
| 2008/0237572 A1 | 10/2008 | Chui et al. |
| 2008/0237604 A1 | 10/2008 | Alshareef et al. |
| 2008/0241052 A1 | 10/2008 | Hooper et al. |
| 2008/0241384 A1 | 10/2008 | Jeong |
| 2008/0241387 A1 | 10/2008 | Keto |
| 2008/0242116 A1 | 10/2008 | Clark |
| 2008/0246101 A1 | 10/2008 | Li et al. |
| 2008/0248310 A1 | 10/2008 | Kim et al. |
| 2008/0248597 A1 | 10/2008 | Qin et al. |
| 2008/0257102 A1 | 10/2008 | Packer |
| 2008/0257494 A1 | 10/2008 | Hayashi et al. |
| 2008/0260345 A1 | 10/2008 | Mertesdorf et al. |
| 2008/0260963 A1 | 10/2008 | Yoon et al. |
| 2008/0261405 A1 | 10/2008 | Yang et al. |
| 2008/0261413 A1 | 10/2008 | Mahajani |
| 2008/0264337 A1 | 10/2008 | Sano et al. |
| 2008/0264443 A1 | 10/2008 | Shrinivasan et al. |
| 2008/0267598 A1 | 10/2008 | Nakamura |
| 2008/0268171 A1 | 10/2008 | Ma et al. |
| 2008/0268635 A1 | 10/2008 | Yu et al. |
| 2008/0272424 A1 | 11/2008 | Kim et al. |
| 2008/0274369 A1 | 11/2008 | Lee et al. |
| 2008/0276864 A1 | 11/2008 | Koelmel et al. |
| 2008/0277647 A1 | 11/2008 | Kouvetakis et al. |
| 2008/0277656 A1 | 11/2008 | Park et al. |
| 2008/0277715 A1 | 11/2008 | Ohmi et al. |
| 2008/0282970 A1 | 11/2008 | Heys et al. |
| 2008/0283962 A1 | 11/2008 | Dyer |
| 2008/0286463 A1 | 11/2008 | Tiner et al. |
| 2008/0289574 A1 | 11/2008 | Jacobs et al. |
| 2008/0289650 A1 | 11/2008 | Arena |
| 2008/0289767 A1 | 11/2008 | Tandou et al. |
| 2008/0291964 A1 | 11/2008 | Shrimpling |
| 2008/0293198 A1 | 11/2008 | Kojima et al. |
| 2008/0295872 A1 | 12/2008 | Riker et al. |
| 2008/0298945 A1 | 12/2008 | Cox |
| 2008/0299326 A1 | 12/2008 | Fukazawa |
| 2008/0299758 A1 | 12/2008 | Harada et al. |
| 2008/0302303 A1 | 12/2008 | Choi et al. |
| 2008/0303744 A1 | 12/2008 | Hirayama et al. |
| 2008/0305014 A1 | 12/2008 | Honda |
| 2008/0305246 A1 | 12/2008 | Choi et al. |
| 2008/0305443 A1 | 12/2008 | Nakamura |
| 2008/0314319 A1 | 12/2008 | Hamano et al. |
| 2008/0314892 A1 | 12/2008 | Graham |
| 2008/0315292 A1 | 12/2008 | Ji et al. |
| 2008/0317972 A1 | 12/2008 | Hendriks |
| 2009/0000550 A1 | 1/2009 | Tran et al. |
| 2009/0000551 A1 | 1/2009 | Choi et al. |
| 2009/0000769 A1 | 1/2009 | Lin et al. |
| 2009/0004875 A1 | 1/2009 | Shen et al. |
| 2009/0011145 A1 | 1/2009 | Yun |
| 2009/0011150 A1 | 1/2009 | Jeon et al. |
| 2009/0011608 A1 | 1/2009 | Nabatame |
| 2009/0014879 A1 | 1/2009 | Park et al. |
| 2009/0017227 A1 | 1/2009 | Fu et al. |
| 2009/0017631 A1 | 1/2009 | Bencher |
| 2009/0017733 A1 | 1/2009 | Takahashi et al. |
| 2009/0020072 A1 | 1/2009 | Mizunaga et al. |
| 2009/0023229 A1 | 1/2009 | Matsushita |
| 2009/0029503 A1 | 1/2009 | Arai |
| 2009/0029528 A1 | 1/2009 | Sanchez et al. |
| 2009/0029564 A1 | 1/2009 | Yamashita et al. |
| 2009/0031954 A1 | 2/2009 | Nishikido et al. |
| 2009/0033907 A1 | 2/2009 | Watson |
| 2009/0035463 A1 | 2/2009 | Dip |
| 2009/0035584 A1 | 2/2009 | Tran et al. |
| 2009/0035927 A1 | 2/2009 | Olsen et al. |
| 2009/0035946 A1 | 2/2009 | Pierreux et al. |
| 2009/0035947 A1 | 2/2009 | Horii |

(56) References Cited

U.S. PATENT DOCUMENTS

| | | |
|---|---|---|
| 2009/0036292 A1 | 2/2009 | Sun et al. |
| 2009/0039475 A1 | 2/2009 | Shioya |
| 2009/0041952 A1 | 2/2009 | Yoon et al. |
| 2009/0041984 A1 | 2/2009 | Mayers et al. |
| 2009/0042344 A1 | 2/2009 | Ye et al. |
| 2009/0042408 A1 | 2/2009 | Maeda |
| 2009/0045749 A1 | 2/2009 | Ganachev et al. |
| 2009/0045829 A1 | 2/2009 | Awazu |
| 2009/0047426 A1 | 2/2009 | Park et al. |
| 2009/0047433 A1 | 2/2009 | Kim et al. |
| 2009/0047447 A1 | 2/2009 | Sawin et al. |
| 2009/0050621 A1 | 2/2009 | Awazu |
| 2009/0052498 A1 | 2/2009 | Halpin et al. |
| 2009/0053023 A1 | 2/2009 | Wakabayashi |
| 2009/0053900 A1 | 2/2009 | Nozawa et al. |
| 2009/0053906 A1 | 2/2009 | Miya et al. |
| 2009/0056112 A1 | 3/2009 | Kobayashi |
| 2009/0056629 A1 | 3/2009 | Katz et al. |
| 2009/0057269 A1 | 3/2009 | Katz et al. |
| 2009/0060480 A1 | 3/2009 | Herchen |
| 2009/0061083 A1 | 3/2009 | Chiang et al. |
| 2009/0061644 A1 | 3/2009 | Chiang et al. |
| 2009/0061647 A1 | 3/2009 | Mallick et al. |
| 2009/0075490 A1 | 3/2009 | Dussarrat |
| 2009/0075491 A1 | 3/2009 | Liu et al. |
| 2009/0080136 A1 | 3/2009 | Nagayama et al. |
| 2009/0081879 A1 | 3/2009 | Sukekawa et al. |
| 2009/0084317 A1 | 4/2009 | Wu |
| 2009/0085156 A1 | 4/2009 | Dewey et al. |
| 2009/0087585 A1 | 4/2009 | Lee et al. |
| 2009/0087964 A1 | 4/2009 | Maeda et al. |
| 2009/0087967 A1 | 4/2009 | Todd |
| 2009/0090382 A1 | 4/2009 | Morisada |
| 2009/0093080 A1 | 4/2009 | Choi et al. |
| 2009/0093094 A1 | 4/2009 | Ye et al. |
| 2009/0093100 A1 | 4/2009 | Xia et al. |
| 2009/0095221 A1 | 4/2009 | Tam et al. |
| 2009/0104351 A1 | 4/2009 | Kakegawa |
| 2009/0104594 A1 | 4/2009 | Webb |
| 2009/0104789 A1 | 4/2009 | Mallick et al. |
| 2009/0107404 A1 | 4/2009 | Ogliari et al. |
| 2009/0108308 A1 | 4/2009 | Yang et al. |
| 2009/0112458 A1 | 4/2009 | Nakai |
| 2009/0115064 A1 | 5/2009 | Sandhu et al. |
| 2009/0116936 A1 | 5/2009 | Marubayashi et al. |
| 2009/0117717 A1 | 5/2009 | Tomasini et al. |
| 2009/0117723 A1 | 5/2009 | Kim et al. |
| 2009/0117746 A1 | 5/2009 | Masuda |
| 2009/0120580 A1 | 5/2009 | Kagoshima et al. |
| 2009/0122293 A1 | 5/2009 | Shibazaki |
| 2009/0122458 A1 | 5/2009 | Lischer et al. |
| 2009/0124131 A1 | 5/2009 | Breunsbach et al. |
| 2009/0130331 A1 | 5/2009 | Asai |
| 2009/0130859 A1 | 5/2009 | Itatani et al. |
| 2009/0136665 A1 | 5/2009 | Choi et al. |
| 2009/0136668 A1 | 5/2009 | Gregg et al. |
| 2009/0136683 A1 | 5/2009 | Fukasawa et al. |
| 2009/0137055 A1 | 5/2009 | Bognar |
| 2009/0139657 A1 | 6/2009 | Lee et al. |
| 2009/0142905 A1 | 6/2009 | Yamazaki |
| 2009/0142933 A1 | 6/2009 | Yajima et al. |
| 2009/0142935 A1 | 6/2009 | Fukazawa et al. |
| 2009/0146322 A1 | 6/2009 | Weling et al. |
| 2009/0147819 A1 | 6/2009 | Goodman et al. |
| 2009/0155488 A1 | 6/2009 | Nakano et al. |
| 2009/0156015 A1 | 6/2009 | Park et al. |
| 2009/0156017 A1 | 6/2009 | Fukazawa et al. |
| 2009/0159000 A1 | 6/2009 | Aggarwal et al. |
| 2009/0159002 A1 | 6/2009 | Bera et al. |
| 2009/0159424 A1 | 6/2009 | Liu et al. |
| 2009/0162647 A1 | 6/2009 | Sun et al. |
| 2009/0162996 A1 | 6/2009 | Ramaswamy et al. |
| 2009/0163038 A1 | 6/2009 | Miyoshi |
| 2009/0165715 A1 | 7/2009 | Oh |
| 2009/0165721 A1 | 7/2009 | Pitney et al. |
| 2009/0165722 A1 | 7/2009 | Ha |
| 2009/0166616 A1 | 7/2009 | Uchiyama |
| 2009/0176018 A1 | 7/2009 | Zou et al. |
| 2009/0179365 A1 | 7/2009 | Lerner et al. |
| 2009/0183520 A1 | 7/2009 | Yukimoto |
| 2009/0186479 A1 | 7/2009 | Okabe et al. |
| 2009/0186571 A1 | 7/2009 | Haro |
| 2009/0194233 A1 | 8/2009 | Tamura et al. |
| 2009/0197015 A1 | 8/2009 | Kudela et al. |
| 2009/0197411 A1 | 8/2009 | Dussarrat et al. |
| 2009/0200494 A1 | 8/2009 | Hatem |
| 2009/0200547 A1 | 8/2009 | Griffin et al. |
| 2009/0204403 A1 | 8/2009 | Hollander et al. |
| 2009/0206056 A1 | 8/2009 | Xu |
| 2009/0209081 A1 | 8/2009 | Matero |
| 2009/0211523 A1 | 8/2009 | Kuppurao et al. |
| 2009/0211525 A1 | 8/2009 | Sarigiannis et al. |
| 2009/0214825 A1 | 8/2009 | Sun et al. |
| 2009/0217871 A1 | 9/2009 | Kim et al. |
| 2009/0221149 A1 | 9/2009 | Hammond et al. |
| 2009/0221151 A1 | 9/2009 | Honda et al. |
| 2009/0223441 A1 | 9/2009 | Arena et al. |
| 2009/0227094 A1 | 9/2009 | Bateman |
| 2009/0230211 A1 | 9/2009 | Kobayashi et al. |
| 2009/0232985 A1 | 9/2009 | Dussarrat et al. |
| 2009/0236014 A1 | 9/2009 | Wilson |
| 2009/0236276 A1 | 9/2009 | Kurth et al. |
| 2009/0236315 A1 | 9/2009 | Willwerth et al. |
| 2009/0239386 A1 | 9/2009 | Suzaki et al. |
| 2009/0242130 A1 | 10/2009 | Tian et al. |
| 2009/0242957 A1 | 10/2009 | Ma et al. |
| 2009/0246374 A1 | 10/2009 | Vukovic |
| 2009/0246399 A1 | 10/2009 | Goundar |
| 2009/0246971 A1 | 10/2009 | Reid et al. |
| 2009/0250004 A1 | 10/2009 | Yamada et al. |
| 2009/0250955 A1 | 10/2009 | Aoki |
| 2009/0255901 A1 | 10/2009 | Okita |
| 2009/0256127 A1 | 10/2009 | Feist et al. |
| 2009/0261331 A1 | 10/2009 | Yang et al. |
| 2009/0266296 A1 | 10/2009 | Tachibana et al. |
| 2009/0267135 A1 | 10/2009 | Tanaka et al. |
| 2009/0267225 A1 | 10/2009 | Eguchi |
| 2009/0269506 A1 | 10/2009 | Okura et al. |
| 2009/0269507 A1 | 10/2009 | Yu et al. |
| 2009/0269941 A1 | 10/2009 | Raisanen |
| 2009/0275205 A1 | 11/2009 | Kiehlbauch et al. |
| 2009/0275210 A1 | 11/2009 | Shanker et al. |
| 2009/0277510 A1 | 11/2009 | Shikata |
| 2009/0277874 A1 | 11/2009 | Rui et al. |
| 2009/0280248 A1 | 11/2009 | Goodman et al. |
| 2009/0283041 A1 | 11/2009 | Tomiyasu et al. |
| 2009/0283217 A1 | 11/2009 | Lubomirsky et al. |
| 2009/0284156 A1 | 11/2009 | Banna et al. |
| 2009/0286400 A1 | 11/2009 | Heo et al. |
| 2009/0286402 A1 | 11/2009 | Xia et al. |
| 2009/0286405 A1 | 11/2009 | Okesaku et al. |
| 2009/0289300 A1 | 11/2009 | Sasaki et al. |
| 2009/0291208 A1 | 11/2009 | Gordon et al. |
| 2009/0291566 A1 | 11/2009 | Ueno et al. |
| 2009/0297696 A1 | 12/2009 | Pore et al. |
| 2009/0297710 A1 | 12/2009 | Lindfors |
| 2009/0297731 A1 | 12/2009 | Goundar |
| 2009/0298257 A1 | 12/2009 | Lee et al. |
| 2009/0302002 A1 | 12/2009 | Collins et al. |
| 2009/0302434 A1 | 12/2009 | Pallem et al. |
| 2009/0304558 A1 | 12/2009 | Patton |
| 2009/0308315 A1 | 12/2009 | de Ridder |
| 2009/0308425 A1 | 12/2009 | Yednak |
| 2009/0311857 A1 | 12/2009 | Todd et al. |
| 2009/0314208 A1 | 12/2009 | Zhou et al. |
| 2009/0314309 A1 | 12/2009 | Sankarakrishnan et al. |
| 2009/0315093 A1 | 12/2009 | Li et al. |
| 2009/0317214 A1 | 12/2009 | Hsiao et al. |
| 2009/0320754 A1 | 12/2009 | Oya |
| 2009/0320881 A1 | 12/2009 | Aitchison |
| 2009/0324971 A1 | 12/2009 | De Vries et al. |
| 2009/0324989 A1 | 12/2009 | Witz et al. |
| 2009/0325391 A1 | 12/2009 | De Vusser et al. |
| 2009/0325469 A1 | 12/2009 | Koo et al. |

(56) References Cited

U.S. PATENT DOCUMENTS

| | | |
|---|---|---|
| 2010/0000608 A1 | 1/2010 | Goto et al. |
| 2010/0001409 A1 | 1/2010 | Humbert et al. |
| 2010/0003406 A1 | 1/2010 | Lam et al. |
| 2010/0006031 A1 | 1/2010 | Choi et al. |
| 2010/0006923 A1 | 1/2010 | Fujitsuka |
| 2010/0008656 A1 | 1/2010 | Sorabji et al. |
| 2010/0012036 A1 | 1/2010 | Silva et al. |
| 2010/0012153 A1 | 1/2010 | Shigemoto et al. |
| 2010/0014479 A1 | 1/2010 | Kim |
| 2010/0015813 A1 | 1/2010 | McGinnis et al. |
| 2010/0018460 A1 | 1/2010 | Singh et al. |
| 2010/0018913 A1 | 1/2010 | Blum |
| 2010/0022097 A1 | 1/2010 | Yamoto et al. |
| 2010/0024727 A1 | 2/2010 | Kim et al. |
| 2010/0024872 A1 | 2/2010 | Kishimoto |
| 2010/0025766 A1 | 2/2010 | Nuttinck et al. |
| 2010/0025796 A1 | 2/2010 | Dabiran |
| 2010/0031884 A1 | 2/2010 | Aggarwal et al. |
| 2010/0032587 A1 | 2/2010 | Hosch et al. |
| 2010/0032842 A1 | 2/2010 | Herdt et al. |
| 2010/0034719 A1 | 2/2010 | Dussarrat et al. |
| 2010/0038687 A1 | 2/2010 | Klaus et al. |
| 2010/0040441 A1 | 2/2010 | Obikane |
| 2010/0041179 A1 | 2/2010 | Lee |
| 2010/0041243 A1 | 2/2010 | Cheng et al. |
| 2010/0046321 A1 | 2/2010 | McLaughlin et al. |
| 2010/0050943 A1 | 3/2010 | Kato et al. |
| 2010/0051584 A1 | 3/2010 | Okita et al. |
| 2010/0051597 A1 | 3/2010 | Morita et al. |
| 2010/0055312 A1 | 3/2010 | Kato et al. |
| 2010/0055316 A1 | 3/2010 | Honma |
| 2010/0055318 A1 | 3/2010 | Volf et al. |
| 2010/0055442 A1 | 3/2010 | Kellock |
| 2010/0055898 A1 | 3/2010 | Chang et al. |
| 2010/0058984 A1 | 3/2010 | Marubayashi |
| 2010/0065758 A1 | 3/2010 | Liu et al. |
| 2010/0068009 A1 | 3/2010 | Kimura |
| 2010/0068383 A1 | 3/2010 | Kato et al. |
| 2010/0068414 A1 | 3/2010 | Takahashi et al. |
| 2010/0068891 A1 | 3/2010 | Hatanaka et al. |
| 2010/0075037 A1 | 3/2010 | Marsh et al. |
| 2010/0075488 A1 | 3/2010 | Collins et al. |
| 2010/0075507 A1 | 3/2010 | Chang et al. |
| 2010/0078601 A1 | 4/2010 | Pallem et al. |
| 2010/0078746 A1 | 4/2010 | Jung |
| 2010/0081094 A1 | 4/2010 | Hasebe et al. |
| 2010/0081293 A1 | 4/2010 | Mallick et al. |
| 2010/0086703 A1 | 4/2010 | Mangum et al. |
| 2010/0087069 A1 | 4/2010 | Miya et al. |
| 2010/0089320 A1 | 4/2010 | Kim |
| 2010/0089870 A1 | 4/2010 | Hiroshima et al. |
| 2010/0090149 A1 | 4/2010 | Thompson et al. |
| 2010/0092679 A1 | 4/2010 | Lee et al. |
| 2010/0092696 A1 | 4/2010 | Shinriki |
| 2010/0093187 A1 | 4/2010 | Lee et al. |
| 2010/0094430 A1 | 4/2010 | Krumdieck |
| 2010/0098862 A1 | 4/2010 | Xu et al. |
| 2010/0101728 A1 | 4/2010 | Iwasaki |
| 2010/0102417 A1 | 4/2010 | Ganguli et al. |
| 2010/0105936 A1 | 4/2010 | Tada et al. |
| 2010/0111648 A1 | 5/2010 | Tamura et al. |
| 2010/0112496 A1 | 5/2010 | Nakajima et al. |
| 2010/0116207 A1 | 5/2010 | Givens |
| 2010/0116208 A1 | 5/2010 | Sangam |
| 2010/0116209 A1 | 5/2010 | Kato |
| 2010/0119439 A1 | 5/2010 | Shindou |
| 2010/0119727 A1 | 5/2010 | Takagi |
| 2010/0119844 A1 | 5/2010 | Sun et al. |
| 2010/0120261 A1 | 5/2010 | Kim et al. |
| 2010/0121100 A1 | 5/2010 | Shay |
| 2010/0124610 A1 | 5/2010 | Aikawa et al. |
| 2010/0124618 A1 | 5/2010 | Kobayashi et al. |
| 2010/0124621 A1 | 5/2010 | Kobayashi et al. |
| 2010/0126415 A1 | 5/2010 | Ishino et al. |
| 2010/0126539 A1 | 5/2010 | Lee et al. |
| 2010/0126605 A1 | 5/2010 | Stones |
| 2010/0126666 A1 | 5/2010 | Tandou et al. |
| 2010/0129548 A1 | 5/2010 | Sneh |
| 2010/0129670 A1 | 5/2010 | Sun et al. |
| 2010/0129990 A1 | 5/2010 | Nishizawa et al. |
| 2010/0130015 A1 | 5/2010 | Nakajima et al. |
| 2010/0130017 A1 | 5/2010 | Luo et al. |
| 2010/0130105 A1 | 5/2010 | Lee |
| 2010/0133255 A1 | 6/2010 | Bahng et al. |
| 2010/0134023 A1 | 6/2010 | Mills |
| 2010/0136216 A1 | 6/2010 | Tsuei et al. |
| 2010/0140221 A1 | 6/2010 | Kikuchi et al. |
| 2010/0140684 A1 | 6/2010 | Ozawa |
| 2010/0143609 A1 | 6/2010 | Fukazawa et al. |
| 2010/0144150 A1 | 6/2010 | Sills et al. |
| 2010/0144162 A1 | 6/2010 | Lee et al. |
| 2010/0144968 A1 | 6/2010 | Lee et al. |
| 2010/0145547 A1 | 6/2010 | Darabnia et al. |
| 2010/0147396 A1 | 6/2010 | Yamagishi et al. |
| 2010/0151206 A1 | 6/2010 | Wu et al. |
| 2010/0159638 A1 | 6/2010 | Jeong |
| 2010/0159707 A1 | 6/2010 | Huang et al. |
| 2010/0162752 A1 | 7/2010 | Tabata et al. |
| 2010/0162956 A1 | 7/2010 | Murakami et al. |
| 2010/0163187 A1 | 7/2010 | Yokogawa et al. |
| 2010/0163524 A1 | 7/2010 | Arai |
| 2010/0163937 A1 | 7/2010 | Clendenning |
| 2010/0166630 A1 | 7/2010 | Gu et al. |
| 2010/0168404 A1 | 7/2010 | Girolami et al. |
| 2010/0170441 A1 | 7/2010 | Won et al. |
| 2010/0170868 A1 | 7/2010 | Lin et al. |
| 2010/0173432 A1 | 7/2010 | White et al. |
| 2010/0178137 A1 | 7/2010 | Chintalapati et al. |
| 2010/0178423 A1 | 7/2010 | Shimizu et al. |
| 2010/0180819 A1 | 7/2010 | Hatanaka et al. |
| 2010/0183825 A1 | 7/2010 | Becker et al. |
| 2010/0184302 A1 | 7/2010 | Lee et al. |
| 2010/0186669 A1 | 7/2010 | Shin et al. |
| 2010/0189923 A1 | 7/2010 | Goundar et al. |
| 2010/0193501 A1 | 8/2010 | Zucker et al. |
| 2010/0193955 A1 | 8/2010 | Milligan et al. |
| 2010/0195392 A1 | 8/2010 | Freeman |
| 2010/0195690 A1 | 8/2010 | Moench et al. |
| 2010/0197107 A1 | 8/2010 | Matsuzaki |
| 2010/0202860 A1 | 8/2010 | Reed |
| 2010/0203242 A1 | 8/2010 | Borden |
| 2010/0206767 A1 | 8/2010 | Odashima et al. |
| 2010/0209598 A1 | 8/2010 | Xu et al. |
| 2010/0210108 A1 | 8/2010 | Ishizaka et al. |
| 2010/0219757 A1 | 9/2010 | Benzerrouk et al. |
| 2010/0221452 A1 | 9/2010 | Kang |
| 2010/0224130 A1 | 9/2010 | Smith et al. |
| 2010/0227458 A1 | 9/2010 | Chung et al. |
| 2010/0229795 A1 | 9/2010 | Tanabe |
| 2010/0229965 A1 | 9/2010 | Kashima et al. |
| 2010/0230051 A1 | 9/2010 | Iizuka |
| 2010/0230863 A1 | 9/2010 | Moench et al. |
| 2010/0233885 A1 | 9/2010 | Kushibiki et al. |
| 2010/0233886 A1 | 9/2010 | Yang et al. |
| 2010/0236691 A1 | 9/2010 | Yamazaki |
| 2010/0243166 A1 | 9/2010 | Hayashi et al. |
| 2010/0244688 A1 | 9/2010 | Braun et al. |
| 2010/0248465 A1 | 9/2010 | Yi et al. |
| 2010/0252434 A1 | 10/2010 | Roy |
| 2010/0255196 A1 | 10/2010 | Geisler et al. |
| 2010/0255198 A1 | 10/2010 | Cleary et al. |
| 2010/0255218 A1 | 10/2010 | Oka et al. |
| 2010/0255625 A1 | 10/2010 | De Vries |
| 2010/0255658 A1 | 10/2010 | Aggarwal |
| 2010/0258809 A1 | 10/2010 | Muller |
| 2010/0259152 A1 | 10/2010 | Yasuda et al. |
| 2010/0266765 A1 | 10/2010 | White et al. |
| 2010/0267224 A1 | 10/2010 | Choi et al. |
| 2010/0267248 A1 | 10/2010 | Ma |
| 2010/0270675 A1 | 10/2010 | Harada |
| 2010/0246630 A1 | 11/2010 | Kaszynski et al. |
| 2010/0275846 A1 | 11/2010 | Kitagawa |
| 2010/0279008 A1 | 11/2010 | Takagi |
| 2010/0279512 A1 | 11/2010 | Udea et al. |

(56) References Cited

U.S. PATENT DOCUMENTS

| | | |
|---|---|---|
| 2010/0282163 A1 | 11/2010 | Aggarwal et al. |
| 2010/0282170 A1 | 11/2010 | Nishizawa |
| 2010/0282645 A1 | 11/2010 | Wang |
| 2010/0285237 A1 | 11/2010 | Ditizio et al. |
| 2010/0285319 A1 | 11/2010 | Kwak et al. |
| 2010/0294199 A1 | 11/2010 | Tran et al. |
| 2010/0297391 A1 | 11/2010 | Kley |
| 2010/0301752 A1 | 12/2010 | Bakre et al. |
| 2010/0304047 A1 | 12/2010 | Yang et al. |
| 2010/0307415 A1 | 12/2010 | Shero et al. |
| 2010/0317177 A1 | 12/2010 | Huang et al. |
| 2010/0317198 A1 | 12/2010 | Antonelli |
| 2010/0322604 A1 | 12/2010 | Fondurulia et al. |
| 2010/0322822 A1 | 12/2010 | Fritchie et al. |
| 2010/0326358 A1 | 12/2010 | Choi |
| 2011/0000619 A1 | 1/2011 | Suh |
| 2011/0003087 A1 | 1/2011 | Soininen et al. |
| 2011/0003450 A1 | 1/2011 | Lee et al. |
| 2011/0005684 A1 | 1/2011 | Hayami et al. |
| 2011/0006402 A1 | 1/2011 | Zhou |
| 2011/0006406 A1 | 1/2011 | Urbanowicz et al. |
| 2011/0008950 A1 | 1/2011 | Xu |
| 2011/0014359 A1 | 1/2011 | Hashim |
| 2011/0014795 A1 | 1/2011 | Lee |
| 2011/0017139 A1 | 1/2011 | Chiang et al. |
| 2011/0021033 A1 | 1/2011 | Ikeuchi et al. |
| 2011/0027725 A1 | 2/2011 | Tsutsumi et al. |
| 2011/0027999 A1 | 2/2011 | Sparks et al. |
| 2011/0031562 A1 | 2/2011 | Lin et al. |
| 2011/0034039 A1 | 2/2011 | Liang et al. |
| 2011/0039419 A1 | 2/2011 | Date et al. |
| 2011/0041764 A1 | 2/2011 | Webb et al. |
| 2011/0042200 A1 | 2/2011 | Wilby |
| 2011/0045610 A1 | 2/2011 | van Schravendijk et al. |
| 2011/0045676 A1 | 2/2011 | Park et al. |
| 2011/0046314 A1 | 2/2011 | Klipp et al. |
| 2011/0048642 A1 | 3/2011 | Mihara et al. |
| 2011/0048769 A1 | 3/2011 | Fujiwara |
| 2011/0049100 A1 | 3/2011 | Han et al. |
| 2011/0052833 A1 | 3/2011 | Hanawa et al. |
| 2011/0053383 A1 | 3/2011 | Shero et al. |
| 2011/0056513 A1 | 3/2011 | Hombach et al. |
| 2011/0056626 A1 | 3/2011 | Brown et al. |
| 2011/0057248 A1 | 3/2011 | Ma et al. |
| 2011/0061810 A1 | 3/2011 | Ganguly et al. |
| 2011/0065289 A1 | 3/2011 | Asai |
| 2011/0067522 A1 | 3/2011 | Lai |
| 2011/0070380 A1 | 3/2011 | Shero et al. |
| 2011/0070740 A1 | 3/2011 | Bettencourt et al. |
| 2011/0076401 A1 | 3/2011 | Chao et al. |
| 2011/0081519 A1 | 4/2011 | Dillingh |
| 2011/0083496 A1 | 4/2011 | Lin et al. |
| 2011/0086516 A1 | 4/2011 | Lee et al. |
| 2011/0089166 A1 | 4/2011 | Hunter et al. |
| 2011/0089419 A1 | 4/2011 | Yamazaki et al. |
| 2011/0089469 A1 | 4/2011 | Merckling |
| 2011/0091650 A1 | 4/2011 | Noguchi et al. |
| 2011/0092077 A1 | 4/2011 | Xu et al. |
| 2011/0097901 A1 | 4/2011 | Banna et al. |
| 2011/0098841 A1 | 4/2011 | Tsuda |
| 2011/0100489 A1 | 5/2011 | Orito et al. |
| 2011/0104395 A1 | 5/2011 | Kumagai et al. |
| 2011/0107512 A1 | 5/2011 | Gilbert |
| 2011/0108194 A1 | 5/2011 | Yoshioka et al. |
| 2011/0108424 A1 | 5/2011 | Puget et al. |
| 2011/0108741 A1 | 5/2011 | Ingram |
| 2011/0108929 A1 | 5/2011 | Meng |
| 2011/0114261 A1 | 5/2011 | Matsumoto et al. |
| 2011/0114601 A1 | 5/2011 | Lubomirsky et al. |
| 2011/0115378 A1 | 5/2011 | Lubomirsky et al. |
| 2011/0117490 A1 | 5/2011 | Bae et al. |
| 2011/0117492 A1 | 5/2011 | Yamada et al. |
| 2011/0117728 A1 | 5/2011 | Su et al. |
| 2011/0117732 A1 | 5/2011 | Bauer et al. |
| 2011/0117737 A1 | 5/2011 | Agarwala et al. |
| 2011/0117749 A1 | 5/2011 | Sheu |
| 2011/0121503 A1 | 5/2011 | Burrows et al. |
| 2011/0121736 A1 | 5/2011 | Hirayama et al. |
| 2011/0124196 A1 | 5/2011 | Lee |
| 2011/0127702 A1 | 6/2011 | Gautam et al. |
| 2011/0132542 A1 | 6/2011 | Ilzuka |
| 2011/0135842 A1 | 6/2011 | Faguet et al. |
| 2011/0139272 A1 | 6/2011 | Matsumoto et al. |
| 2011/0139748 A1 | 6/2011 | Donnelly et al. |
| 2011/0140172 A1 | 6/2011 | Chu |
| 2011/0140173 A1 | 6/2011 | Ramdani |
| 2011/0143032 A1 | 6/2011 | Vrtis et al. |
| 2011/0143461 A1 | 6/2011 | Fish et al. |
| 2011/0155264 A1 | 6/2011 | Minami et al. |
| 2011/0155322 A1 | 6/2011 | Himori et al. |
| 2011/0159200 A1 | 6/2011 | Kogure |
| 2011/0159202 A1 | 6/2011 | Matsushita |
| 2011/0159673 A1 | 6/2011 | Hanawa et al. |
| 2011/0159680 A1 | 6/2011 | Yoo |
| 2011/0168330 A1 | 7/2011 | Sakaue et al. |
| 2011/0171380 A1 | 7/2011 | Higashi et al. |
| 2011/0171775 A1 | 7/2011 | Yamamoto et al. |
| 2011/0175011 A1 | 7/2011 | Ehrne et al. |
| 2011/0177648 A1 | 7/2011 | Tanner et al. |
| 2011/0180233 A1 | 7/2011 | Bera et al. |
| 2011/0183079 A1 | 7/2011 | Jackson et al. |
| 2011/0183269 A1 | 7/2011 | Zhu |
| 2011/0183527 A1 | 7/2011 | Cho |
| 2011/0185969 A1 | 8/2011 | Yang |
| 2011/0186984 A1 | 8/2011 | Saito et al. |
| 2011/0192820 A1 | 8/2011 | Yeom et al. |
| 2011/0195574 A1 | 8/2011 | Blasco et al. |
| 2011/0198034 A1 | 8/2011 | Sun et al. |
| 2011/0198417 A1 | 8/2011 | Detmar et al. |
| 2011/0198736 A1 | 8/2011 | Shero et al. |
| 2011/0204025 A1 | 8/2011 | Tahara |
| 2011/0207332 A1 | 8/2011 | Liu et al. |
| 2011/0210468 A1 | 9/2011 | Shannon et al. |
| 2011/0212625 A1 | 9/2011 | Toyoda et al. |
| 2011/0217838 A1 | 9/2011 | Hsieh et al. |
| 2011/0220874 A1 | 9/2011 | Hanrath |
| 2011/0223334 A1 | 9/2011 | Yudovsky et al. |
| 2011/0226421 A1 | 9/2011 | Hayashi |
| 2011/0232678 A1 | 9/2011 | Shih et al. |
| 2011/0236201 A1 | 9/2011 | Shende |
| 2011/0236594 A1 | 9/2011 | Haverkamp et al. |
| 2011/0236600 A1 | 9/2011 | Fox et al. |
| 2011/0237040 A1 | 9/2011 | Ng et al. |
| 2011/0237082 A1 | 9/2011 | Nakajima et al. |
| 2011/0239936 A1 | 10/2011 | Suzaki et al. |
| 2011/0239940 A1 | 10/2011 | Benvenuti et al. |
| 2011/0244673 A1 | 10/2011 | Cho et al. |
| 2011/0253044 A1 | 10/2011 | Tam et al. |
| 2011/0254052 A1 | 10/2011 | Kouvetakis |
| 2011/0256675 A1 | 10/2011 | Avouris |
| 2011/0256692 A1 | 10/2011 | Tam et al. |
| 2011/0256724 A1 | 10/2011 | Chandrasekharan et al. |
| 2011/0256726 A1 | 10/2011 | Lavoie et al. |
| 2011/0256727 A1 | 10/2011 | Beynet et al. |
| 2011/0256734 A1 | 10/2011 | Hausmann et al. |
| 2011/0259519 A1 | 10/2011 | Kenworthy et al. |
| 2011/0262642 A1 | 10/2011 | Xiao et al. |
| 2011/0263107 A1 | 10/2011 | Chung et al. |
| 2011/0263115 A1 | 10/2011 | Ganguli et al. |
| 2011/0264250 A1 | 10/2011 | Nishimura et al. |
| 2011/0265549 A1 | 11/2011 | Cruse et al. |
| 2011/0265715 A1 | 11/2011 | Keller |
| 2011/0265725 A1 | 11/2011 | Tsuji |
| 2011/0265951 A1 | 11/2011 | Xu et al. |
| 2011/0266611 A1 | 11/2011 | Kim et al. |
| 2011/0269314 A1 | 11/2011 | Lee et al. |
| 2011/0275018 A1 | 11/2011 | Matteo et al. |
| 2011/0275166 A1 | 11/2011 | Shero et al. |
| 2011/0277690 A1 | 11/2011 | Rozenzon et al. |
| 2011/0281417 A1 | 11/2011 | Gordon et al. |
| 2011/0283933 A1 | 11/2011 | Makarov et al. |
| 2011/0286819 A1 | 11/2011 | Shibata et al. |
| 2011/0291243 A1 | 12/2011 | Seamons |
| 2011/0294075 A1 | 12/2011 | Chen et al. |

(56) References Cited

U.S. PATENT DOCUMENTS

| | | |
|---|---|---|
| 2011/0294288 A1 | 12/2011 | Lee et al. |
| 2011/0297088 A1 | 12/2011 | Song et al. |
| 2011/0298062 A1 | 12/2011 | Ganguli et al. |
| 2011/0300720 A1 | 12/2011 | Fu |
| 2011/0305102 A1 | 12/2011 | Berger et al. |
| 2011/0305856 A1 | 12/2011 | Bonn |
| 2011/0308453 A1 | 12/2011 | Su et al. |
| 2011/0308460 A1 | 12/2011 | Hong et al. |
| 2011/0312191 A1 | 12/2011 | Ohkura et al. |
| 2011/0318142 A1 | 12/2011 | Gage et al. |
| 2011/0318888 A1 | 12/2011 | Komatsu et al. |
| 2011/0318935 A1 | 12/2011 | Oyabu et al. |
| 2012/0001172 A1 | 1/2012 | Shang et al. |
| 2012/0003500 A1 | 1/2012 | Yoshida et al. |
| 2012/0003599 A1 | 1/2012 | Patalay et al. |
| 2012/0003726 A1 | 1/2012 | Jones et al. |
| 2012/0003831 A1 | 1/2012 | Kang et al. |
| 2012/0006489 A1 | 1/2012 | Okita |
| 2012/0009802 A1 | 1/2012 | Lavoie |
| 2012/0012556 A1 | 1/2012 | Matsumoto et al. |
| 2012/0021252 A1 | 1/2012 | Lee |
| 2012/0024223 A1 | 2/2012 | Torres et al. |
| 2012/0024227 A1 | 2/2012 | Takasuka et al. |
| 2012/0024231 A1 | 2/2012 | Horino |
| 2012/0024478 A1 | 2/2012 | Huang et al. |
| 2012/0024479 A1 | 2/2012 | Palagashvili et al. |
| 2012/0027547 A1 | 2/2012 | Jager et al. |
| 2012/0028454 A1 | 2/2012 | Swaminathan et al. |
| 2012/0028469 A1 | 2/2012 | Onizawa et al. |
| 2012/0031333 A1 | 2/2012 | Kurita et al. |
| 2012/0031500 A1 | 2/2012 | Hirose et al. |
| 2012/0032311 A1 | 2/2012 | Gates |
| 2012/0033695 A1 | 2/2012 | Hayashi et al. |
| 2012/0034793 A1 | 2/2012 | Narushima et al. |
| 2012/0036732 A1 | 2/2012 | Varadarajan |
| 2012/0040097 A1 | 2/2012 | Volf et al. |
| 2012/0040528 A1 | 2/2012 | Kim et al. |
| 2012/0043556 A1 | 2/2012 | Dube et al. |
| 2012/0043617 A1 | 2/2012 | Nakagawa et al. |
| 2012/0046421 A1 | 2/2012 | Darling et al. |
| 2012/0052681 A1 | 3/2012 | Marsh |
| 2012/0055401 A1 | 3/2012 | Tozawa |
| 2012/0058270 A1 | 3/2012 | Winter et al. |
| 2012/0058630 A1 | 3/2012 | Quinn |
| 2012/0064690 A1 | 3/2012 | Hirota et al. |
| 2012/0064726 A1 | 3/2012 | Nozawa et al. |
| 2012/0064764 A1 | 3/2012 | Islam |
| 2012/0068242 A1 | 3/2012 | Shin et al. |
| 2012/0070136 A1 | 3/2012 | Koelmel et al. |
| 2012/0070997 A1 | 3/2012 | Larson |
| 2012/0073400 A1 | 3/2012 | Wang |
| 2012/0074533 A1 | 3/2012 | Aoyama |
| 2012/0077349 A1 | 3/2012 | Li et al. |
| 2012/0077350 A1 | 3/2012 | Miya et al. |
| 2012/0080756 A1 | 4/2012 | Suzuki |
| 2012/0083134 A1 | 4/2012 | Wu et al. |
| 2012/0088031 A1 | 4/2012 | Neel |
| 2012/0088369 A1 | 4/2012 | Weidman et al. |
| 2012/0090704 A1 | 4/2012 | Laverdiere et al. |
| 2012/0091522 A1 | 4/2012 | Ozaki et al. |
| 2012/0094010 A1 | 4/2012 | Sugiura et al. |
| 2012/0094468 A1 | 4/2012 | Bhatia et al. |
| 2012/0098107 A1 | 4/2012 | Raisanen et al. |
| 2012/0100464 A1 | 4/2012 | Kageyama |
| 2012/0103264 A1 | 5/2012 | Choi et al. |
| 2012/0103522 A1 | 5/2012 | Hohenwarter |
| 2012/0103939 A1 | 5/2012 | Wu et al. |
| 2012/0104514 A1 | 5/2012 | Park et al. |
| 2012/0107607 A1 | 5/2012 | Takaki et al. |
| 2012/0108039 A1 | 5/2012 | Zajaji |
| 2012/0108048 A1 | 5/2012 | Lim et al. |
| 2012/0111271 A1 | 5/2012 | Begarney et al. |
| 2012/0114877 A1 | 5/2012 | Lee |
| 2012/0115250 A1 | 5/2012 | Ariga et al. |
| 2012/0115257 A1 | 5/2012 | Matsuyam et al. |
| 2012/0119337 A1 | 5/2012 | Sasaki et al. |
| 2012/0121823 A1 | 5/2012 | Chhabra |
| 2012/0122275 A1 | 5/2012 | Koo et al. |
| 2012/0122302 A1 | 5/2012 | Weisman et al. |
| 2012/0122319 A1 | 5/2012 | Shimizu |
| 2012/0125258 A1 | 5/2012 | Lee |
| 2012/0126300 A1 | 5/2012 | Park et al. |
| 2012/0128897 A1 | 5/2012 | Xiao et al. |
| 2012/0135145 A1 | 5/2012 | Je et al. |
| 2012/0139009 A1 | 6/2012 | Ning et al. |
| 2012/0145078 A1 | 6/2012 | Huang et al. |
| 2012/0146113 A1 | 6/2012 | Suzuki et al. |
| 2012/0149207 A1 | 6/2012 | Graff |
| 2012/0149213 A1 | 6/2012 | Nittala |
| 2012/0156108 A1 | 6/2012 | Fondurulia et al. |
| 2012/0156890 A1 | 6/2012 | Yim et al. |
| 2012/0160172 A1 | 6/2012 | Wamura et al. |
| 2012/0160809 A1 | 6/2012 | Ishibashi et al. |
| 2012/0161126 A1 | 6/2012 | Yamazaki |
| 2012/0161405 A1 | 6/2012 | Mohn |
| 2012/0162651 A1* | 6/2012 | Glover ............... G01N 33/1893 356/434 |
| 2012/0164327 A1 | 6/2012 | Sato |
| 2012/0164837 A1 | 6/2012 | Tan et al. |
| 2012/0164842 A1 | 6/2012 | Watanabe |
| 2012/0164846 A1 | 6/2012 | Ha et al. |
| 2012/0170040 A1* | 7/2012 | Park ....................... G01N 21/59 356/432 |
| 2012/0170170 A1 | 7/2012 | Gros-Jean |
| 2012/0171391 A1 | 7/2012 | Won |
| 2012/0171874 A1 | 7/2012 | Thridandam et al. |
| 2012/0175518 A1 | 7/2012 | Godet et al. |
| 2012/0175751 A1 | 7/2012 | Gatineau et al. |
| 2012/0177845 A1 | 7/2012 | Odedra et al. |
| 2012/0180719 A1 | 7/2012 | Inoue et al. |
| 2012/0180954 A1 | 7/2012 | Yang et al. |
| 2012/0183689 A1 | 7/2012 | Suzuki et al. |
| 2012/0186521 A1 | 7/2012 | Iwasaki et al. |
| 2012/0186573 A1 | 7/2012 | Jdira et al. |
| 2012/0187083 A1 | 7/2012 | Hashizume |
| 2012/0187305 A1 | 7/2012 | Elam et al. |
| 2012/0187375 A1 | 7/2012 | Guo et al. |
| 2012/0190178 A1 | 7/2012 | Wang et al. |
| 2012/0190185 A1 | 7/2012 | Rogers |
| 2012/0190208 A1 | 7/2012 | Ozu et al. |
| 2012/0196048 A1 | 8/2012 | Ueda |
| 2012/0196242 A1 | 8/2012 | Volfovski et al. |
| 2012/0196450 A1 | 8/2012 | Balseanu et al. |
| 2012/0202358 A1 | 8/2012 | Gealy et al. |
| 2012/0206033 A1 | 8/2012 | Matsuyama |
| 2012/0207456 A1 | 8/2012 | Kim et al. |
| 2012/0212121 A1 | 8/2012 | Lin |
| 2012/0213947 A1 | 8/2012 | Lee |
| 2012/0214318 A1 | 8/2012 | Fukazawa et al. |
| 2012/0216743 A1 | 8/2012 | Itoh et al. |
| 2012/0219735 A1 | 8/2012 | Bakker et al. |
| 2012/0219824 A1 | 8/2012 | Prolier |
| 2012/0220139 A1 | 8/2012 | Lee et al. |
| 2012/0222813 A1 | 9/2012 | Pal et al. |
| 2012/0222815 A1 | 9/2012 | Sabri et al. |
| 2012/0225192 A1 | 9/2012 | Yudovsky et al. |
| 2012/0225561 A1 | 9/2012 | Watanabe |
| 2012/0231611 A1 | 9/2012 | Gatineau et al. |
| 2012/0231771 A1 | 9/2012 | Marcus |
| 2012/0232340 A1 | 9/2012 | Levy et al. |
| 2012/0238074 A1 | 9/2012 | Santhanam et al. |
| 2012/0240858 A1 | 9/2012 | Taniyama et al. |
| 2012/0241089 A1 | 9/2012 | Dielmann et al. |
| 2012/0241411 A1 | 9/2012 | Darling et al. |
| 2012/0244703 A1 | 9/2012 | Nakayama et al. |
| 2012/0247386 A1 | 10/2012 | Sanchez et al. |
| 2012/0252229 A1 | 10/2012 | Timans et al. |
| 2012/0258257 A1 | 10/2012 | Nguyen et al. |
| 2012/0263875 A1 | 10/2012 | Brenninger et al. |
| 2012/0263876 A1 | 10/2012 | Haukka et al. |
| 2012/0263887 A1 | 10/2012 | Papasouliotis et al. |
| 2012/0264051 A1 | 10/2012 | Angelov et al. |
| 2012/0264305 A1 | 10/2012 | Nakano |
| 2012/0267048 A1 | 10/2012 | Moyama et al. |

(56) References Cited

U.S. PATENT DOCUMENTS

| | | |
|---|---|---|
| 2012/0269962 A1 | 10/2012 | Blomberg et al. |
| 2012/0269967 A1 | 10/2012 | Yudovsky et al. |
| 2012/0270339 A1 | 10/2012 | Xie et al. |
| 2012/0270384 A1 | 10/2012 | Sanchez et al. |
| 2012/0270393 A1 | 10/2012 | Pore et al. |
| 2012/0270407 A1 | 10/2012 | Werner et al. |
| 2012/0273052 A1 | 11/2012 | Ye et al. |
| 2012/0273162 A1 | 11/2012 | Mahadeswaraswamy |
| 2012/0276306 A1 | 11/2012 | Ueda |
| 2012/0288625 A1 | 11/2012 | Furuya et al. |
| 2012/0289053 A1 | 11/2012 | Holland et al. |
| 2012/0289056 A1 | 11/2012 | Bergman et al. |
| 2012/0289057 A1 | 11/2012 | DeDontney |
| 2012/0295427 A1 | 11/2012 | Bauer |
| 2012/0295449 A1 | 11/2012 | Fukazawa |
| 2012/0302055 A1 | 11/2012 | Pore et al. |
| 2012/0303313 A1 | 11/2012 | Moroi et al. |
| 2012/0304935 A1 | 12/2012 | Oosterlaken et al. |
| 2012/0305026 A1 | 12/2012 | Nomura et al. |
| 2012/0305196 A1 | 12/2012 | Mori et al. |
| 2012/0305987 A1 | 12/2012 | Hirler et al. |
| 2012/0307588 A1 | 12/2012 | Hanada et al. |
| 2012/0309181 A1 | 12/2012 | Machkaoutsan et al. |
| 2012/0310440 A1 | 12/2012 | Darabnia et al. |
| 2012/0315113 A1 | 12/2012 | Hiroki |
| 2012/0315404 A1 | 12/2012 | Li et al. |
| 2012/0318334 A1 | 12/2012 | Bedell et al. |
| 2012/0318457 A1 | 12/2012 | Nguyen et al. |
| 2012/0318773 A1 | 12/2012 | Wu et al. |
| 2012/0319279 A1 | 12/2012 | Isobayashi |
| 2012/0320491 A1 | 12/2012 | Doh et al. |
| 2012/0321786 A1 | 12/2012 | Satitpunwaycha et al. |
| 2012/0322252 A1 | 12/2012 | Son et al. |
| 2012/0325148 A1 | 12/2012 | Yamagishi et al. |
| 2012/0328780 A1 | 12/2012 | Yamagishi et al. |
| 2012/0329208 A1 | 12/2012 | Pore et al. |
| 2013/0002121 A1 | 1/2013 | Ma |
| 2013/0005122 A1 | 1/2013 | Schwarzenbach et al. |
| 2013/0005147 A1 | 1/2013 | Angyal et al. |
| 2013/0008607 A1 | 1/2013 | Matsumoto et al. |
| 2013/0011630 A1 | 1/2013 | Sullivan et al. |
| 2013/0011983 A1 | 1/2013 | Tsai |
| 2013/0011984 A1 | 1/2013 | Wang et al. |
| 2013/0012003 A1 | 1/2013 | Haukka et al. |
| 2013/0012034 A1 | 1/2013 | Ahn et al. |
| 2013/0014697 A1 | 1/2013 | Kanayama |
| 2013/0014896 A1 | 1/2013 | Shoji et al. |
| 2013/0017503 A1 | 1/2013 | de Ridder et al. |
| 2013/0019944 A1 | 1/2013 | Hekmatshoar-Tabai et al. |
| 2013/0019945 A1 | 1/2013 | Hekmatshoar-Tabai et al. |
| 2013/0019960 A1 | 1/2013 | Choi et al. |
| 2013/0020246 A1 | 1/2013 | Hoots et al. |
| 2013/0023120 A1 | 1/2013 | Yaehashi et al. |
| 2013/0023124 A1 | 1/2013 | Nemani et al. |
| 2013/0023129 A1 | 1/2013 | Reed |
| 2013/0025538 A1 | 1/2013 | Collins et al. |
| 2013/0025786 A1 | 1/2013 | Davidkovich et al. |
| 2013/0026451 A1 | 1/2013 | Bangsaruntip et al. |
| 2013/0032085 A1 | 2/2013 | Hanawa et al. |
| 2013/0037532 A1 | 2/2013 | Volfovski et al. |
| 2013/0037858 A1 | 2/2013 | Hong et al. |
| 2013/0037886 A1 | 2/2013 | Tsai et al. |
| 2013/0040447 A1 | 2/2013 | Swaminathan et al. |
| 2013/0040481 A1 | 2/2013 | Vallely et al. |
| 2013/0042811 A1 | 2/2013 | Shanker et al. |
| 2013/0048606 A1 | 2/2013 | Mao et al. |
| 2013/0052585 A1 | 2/2013 | Ayothi et al. |
| 2013/0052836 A1 | 2/2013 | Hirose et al. |
| 2013/0059078 A1 | 3/2013 | Gatineau et al. |
| 2013/0059415 A1 | 3/2013 | Kato et al. |
| 2013/0061755 A1 | 3/2013 | Frederick |
| 2013/0062753 A1 | 3/2013 | Nguyen et al. |
| 2013/0062839 A1 | 3/2013 | Tschinderle et al. |
| 2013/0064973 A1 | 3/2013 | Chen et al. |
| 2013/0065189 A1 | 3/2013 | Yoshii et al. |
| 2013/0068391 A1 | 3/2013 | Mazzocco et al. |
| 2013/0068727 A1 | 3/2013 | Okita |
| 2013/0068970 A1 | 3/2013 | Matsushita |
| 2013/0069052 A1 | 3/2013 | Sandhu |
| 2013/0070456 A1 | 3/2013 | Jang et al. |
| 2013/0075746 A1 | 3/2013 | Mallikarjunaswamy et al. |
| 2013/0075788 A1 | 3/2013 | Tomabechi |
| 2013/0078376 A1 | 3/2013 | Higashino et al. |
| 2013/0078392 A1 | 3/2013 | Xiao et al. |
| 2013/0081702 A1 | 4/2013 | Mohammed et al. |
| 2013/0082274 A1 | 4/2013 | Yang |
| 2013/0084156 A1 | 4/2013 | Shimamoto |
| 2013/0084408 A1 | 4/2013 | Nakao et al. |
| 2013/0084711 A1 | 4/2013 | Liang et al. |
| 2013/0084714 A1 | 4/2013 | Oka et al. |
| 2013/0085618 A1 | 4/2013 | Ding |
| 2013/0089667 A1 | 4/2013 | Lai et al. |
| 2013/0089716 A1 | 4/2013 | Krishnamurthy et al. |
| 2013/0089988 A1 | 4/2013 | Wang et al. |
| 2013/0092085 A1 | 4/2013 | Lee |
| 2013/0093048 A1 | 4/2013 | Chang et al. |
| 2013/0093321 A1 | 4/2013 | Yoshikawa et al. |
| 2013/0095664 A1 | 4/2013 | Matero et al. |
| 2013/0095973 A1 | 4/2013 | Kroneberger et al. |
| 2013/0099318 A1 | 4/2013 | Adam et al. |
| 2013/0104988 A1 | 5/2013 | Yednak et al. |
| 2013/0104992 A1 | 5/2013 | Yednak et al. |
| 2013/0107415 A1 | 5/2013 | Banna et al. |
| 2013/0109172 A1 | 5/2013 | Collins et al. |
| 2013/0109192 A1 | 5/2013 | Hawkins et al. |
| 2013/0112251 A1 | 5/2013 | Hang et al. |
| 2013/0113085 A1 | 5/2013 | Michaelson et al. |
| 2013/0115383 A1 | 5/2013 | Lu et al. |
| 2013/0115763 A1 | 5/2013 | Takamure et al. |
| 2013/0115768 A1 | 5/2013 | Pore et al. |
| 2013/0118405 A1 | 5/2013 | Ho et al. |
| 2013/0118895 A1 | 5/2013 | Roozeboom et al. |
| 2013/0119018 A1 | 5/2013 | Kanarik et al. |
| 2013/0122712 A1 | 5/2013 | Kim et al. |
| 2013/0122722 A1 | 5/2013 | Cissell et al. |
| 2013/0126515 A1 | 5/2013 | Shero et al. |
| 2013/0129577 A1 | 5/2013 | Halpin et al. |
| 2013/0130490 A1 | 5/2013 | Lee et al. |
| 2013/0134148 A1 | 5/2013 | Tachikawa |
| 2013/0137279 A1 | 5/2013 | Yamamoto et al. |
| 2013/0143401 A1 | 6/2013 | Yu et al. |
| 2013/0143415 A1 | 6/2013 | Yudovsky et al. |
| 2013/0145587 A1 | 6/2013 | Adhiprakasha |
| 2013/0145984 A1 | 6/2013 | Zhang et al. |
| 2013/0147050 A1 | 6/2013 | Bonner, III et al. |
| 2013/0149874 A1 | 6/2013 | Hirose et al. |
| 2013/0152933 A1 | 6/2013 | Lischer et al. |
| 2013/0157409 A1 | 6/2013 | Vaidya |
| 2013/0157521 A1 | 6/2013 | Aldrich et al. |
| 2013/0160709 A1 | 6/2013 | White et al. |
| 2013/0161629 A1 | 6/2013 | Han et al. |
| 2013/0162142 A1 | 6/2013 | Nishino et al. |
| 2013/0164458 A1 | 6/2013 | Soininen et al. |
| 2013/0168353 A1 | 7/2013 | Okita et al. |
| 2013/0168354 A1 | 7/2013 | Kanarik |
| 2013/0171818 A1 | 7/2013 | Kim et al. |
| 2013/0175596 A1 | 7/2013 | Cheng et al. |
| 2013/0177706 A1 | 7/2013 | Baluja et al. |
| 2013/0180448 A1 | 7/2013 | Sakaue et al. |
| 2013/0183814 A1 | 7/2013 | Huang et al. |
| 2013/0186340 A1 | 7/2013 | Omori et al. |
| 2013/0189635 A1 | 7/2013 | Lim et al. |
| 2013/0189854 A1 | 7/2013 | Hausmann et al. |
| 2013/0196502 A1 | 8/2013 | Haukka et al. |
| 2013/0196507 A1 | 8/2013 | Ma et al. |
| 2013/0200518 A1 | 8/2013 | Ahmed et al. |
| 2013/0202387 A1 | 8/2013 | Hiroki |
| 2013/0203258 A1 | 8/2013 | Chen et al. |
| 2013/0203266 A1 | 8/2013 | Hintze |
| 2013/0203267 A1 | 8/2013 | Pomarede et al. |
| 2013/0206066 A1 | 8/2013 | Han et al. |
| 2013/0209940 A1 | 8/2013 | Sakamoto et al. |
| 2013/0210241 A1 | 8/2013 | Lavoie et al. |
| 2013/0213300 A1 | 8/2013 | Sung et al. |

(56) References Cited

U.S. PATENT DOCUMENTS

| | | |
|---|---|---|
| 2013/0214232 A1 | 8/2013 | Tendulkar et al. |
| 2013/0216710 A1 | 8/2013 | Masuda et al. |
| 2013/0217239 A1 | 8/2013 | Mallick et al. |
| 2013/0217240 A1 | 8/2013 | Mallick et al. |
| 2013/0217241 A1 | 8/2013 | Underwood et al. |
| 2013/0217243 A1 | 8/2013 | Underwood et al. |
| 2013/0219853 A1 | 8/2013 | Little et al. |
| 2013/0220550 A1 | 8/2013 | Koo et al. |
| 2013/0224964 A1 | 8/2013 | Fukazawa |
| 2013/0228225 A1 | 9/2013 | Leeser |
| 2013/0228902 A1 | 9/2013 | Tomizawa et al. |
| 2013/0230814 A1 | 9/2013 | Dunn et al. |
| 2013/0230987 A1 | 9/2013 | Draeger et al. |
| 2013/0234203 A1 | 9/2013 | Tsai et al. |
| 2013/0242287 A1 | 9/2013 | Schlezinger |
| 2013/0247937 A1 | 9/2013 | Nunomura et al. |
| 2013/0256265 A1 | 10/2013 | Darling et al. |
| 2013/0256838 A1 | 10/2013 | Sanchez et al. |
| 2013/0256962 A1 | 10/2013 | Ranish |
| 2013/0260371 A1 | 10/2013 | Holt |
| 2013/0264659 A1 | 10/2013 | Jung |
| 2013/0267045 A1 | 10/2013 | Lee et al. |
| 2013/0269609 A1 | 10/2013 | Leeser |
| 2013/0269612 A1 | 10/2013 | Cheng et al. |
| 2013/0270600 A1 | 10/2013 | Helander et al. |
| 2013/0270676 A1 | 10/2013 | Lindert et al. |
| 2013/0273330 A1 | 10/2013 | Wang et al. |
| 2013/0276978 A1 | 10/2013 | Bluck et al. |
| 2013/0280891 A1 | 10/2013 | Kim et al. |
| 2013/0285155 A1 | 10/2013 | Glass |
| 2013/0287526 A1 | 10/2013 | Bluck et al. |
| 2013/0288427 A1 | 10/2013 | Hung et al. |
| 2013/0288471 A1 | 10/2013 | Chi |
| 2013/0288480 A1 | 10/2013 | Sanchez et al. |
| 2013/0288485 A1 | 10/2013 | Liang et al. |
| 2013/0292047 A1 | 11/2013 | Tian et al. |
| 2013/0292676 A1 | 11/2013 | Milligan et al. |
| 2013/0292807 A1 | 11/2013 | Raisanen et al. |
| 2013/0295779 A1 | 11/2013 | Chandra et al. |
| 2013/0299944 A1 | 11/2013 | Lai et al. |
| 2013/0302520 A1 | 11/2013 | Wang et al. |
| 2013/0302999 A1 | 11/2013 | Won et al. |
| 2013/0303803 A1 | 11/2013 | Doerr et al. |
| 2013/0306615 A1* | 11/2013 | Rozbicki ............... G02B 7/32 248/205.5 |
| 2013/0309876 A1 | 11/2013 | Ogawa |
| 2013/0312663 A1 | 11/2013 | Khosla et al. |
| 2013/0313656 A1 | 11/2013 | Tong |
| 2013/0319290 A1 | 12/2013 | Xiao et al. |
| 2013/0320429 A1 | 12/2013 | Thomas |
| 2013/0323435 A1 | 12/2013 | Xiao et al. |
| 2013/0323859 A1 | 12/2013 | Chen et al. |
| 2013/0323935 A1 | 12/2013 | Suzuki et al. |
| 2013/0330165 A1 | 12/2013 | Wimplinger |
| 2013/0330911 A1 | 12/2013 | Huang et al. |
| 2013/0330933 A1 | 12/2013 | Fukazawa et al. |
| 2013/0333619 A1 | 12/2013 | Omari |
| 2013/0337172 A1 | 12/2013 | Lee |
| 2013/0337583 A1 | 12/2013 | Kobayashi et al. |
| 2013/0337639 A1 | 12/2013 | Ivanstov et al. |
| 2013/0337653 A1 | 12/2013 | Kovalgin et al. |
| 2013/0340619 A1 | 12/2013 | Tammera |
| 2013/0340678 A1 | 12/2013 | Wamura et al. |
| 2013/0344248 A1 | 12/2013 | Clark |
| 2014/0000843 A1 | 1/2014 | Dunn et al. |
| 2014/0001520 A1 | 1/2014 | Glass |
| 2014/0004274 A1 | 1/2014 | Thompson |
| 2014/0007808 A1 | 1/2014 | Okabe et al. |
| 2014/0014642 A1 | 1/2014 | Elliot et al. |
| 2014/0014644 A1 | 1/2014 | Akiba et al. |
| 2014/0015108 A1 | 1/2014 | Kim et al. |
| 2014/0015186 A1 | 1/2014 | Wessel et al. |
| 2014/0017408 A1 | 1/2014 | Gandikota et al. |
| 2014/0017414 A1 | 1/2014 | Fukazawa et al. |
| 2014/0017908 A1 | 1/2014 | Beynet et al. |
| 2014/0020619 A1 | 1/2014 | Vincent et al. |
| 2014/0020764 A1 | 1/2014 | Woelk et al. |
| 2014/0020839 A1 | 1/2014 | Kenney et al. |
| 2014/0023794 A1 | 1/2014 | Mahajani et al. |
| 2014/0024223 A1 | 1/2014 | Kilpi et al. |
| 2014/0027884 A1 | 1/2014 | Tang et al. |
| 2014/0030447 A1 | 1/2014 | Lee |
| 2014/0033978 A1 | 2/2014 | Adachi et al. |
| 2014/0034240 A1 | 2/2014 | Kim et al. |
| 2014/0034632 A1 | 2/2014 | Pan et al. |
| 2014/0036274 A1 | 2/2014 | Marquardt et al. |
| 2014/0045324 A1 | 2/2014 | Brabant et al. |
| 2014/0045342 A1 | 2/2014 | Mallick et al. |
| 2014/0047705 A1 | 2/2014 | Singh |
| 2014/0048765 A1 | 2/2014 | Ma et al. |
| 2014/0053866 A1 | 2/2014 | Baluja et al. |
| 2014/0056679 A1 | 2/2014 | Yamabe et al. |
| 2014/0056770 A1 | 2/2014 | Bedard et al. |
| 2014/0057187 A1 | 2/2014 | Suzuki et al. |
| 2014/0057454 A1 | 2/2014 | Subramonium |
| 2014/0058179 A1 | 2/2014 | Stevens et al. |
| 2014/0060147 A1 | 3/2014 | Sarin et al. |
| 2014/0060572 A1 | 3/2014 | Yasumuro et al. |
| 2014/0061770 A1 | 3/2014 | Lee |
| 2014/0062304 A1 | 3/2014 | Nakano et al. |
| 2014/0065841 A1 | 3/2014 | Matero |
| 2014/0067110 A1 | 3/2014 | Lawson et al. |
| 2014/0072710 A1 | 3/2014 | Valle |
| 2014/0072726 A1 | 3/2014 | Kim |
| 2014/0072925 A1 | 3/2014 | Kaneko |
| 2014/0073082 A1 | 3/2014 | Song |
| 2014/0073143 A1 | 3/2014 | Alokozai et al. |
| 2014/0076861 A1 | 3/2014 | Cornelius et al. |
| 2014/0077240 A1 | 3/2014 | Roucka et al. |
| 2014/0080314 A1 | 3/2014 | Sasajima et al. |
| 2014/0084341 A1 | 3/2014 | Weeks |
| 2014/0087490 A1 | 3/2014 | Kahlon |
| 2014/0087544 A1 | 3/2014 | Tolle |
| 2014/0087564 A1 | 3/2014 | Shimizu et al. |
| 2014/0094027 A1 | 4/2014 | Azumo et al. |
| 2014/0096716 A1 | 4/2014 | Chung et al. |
| 2014/0097468 A1 | 4/2014 | Okita |
| 2014/0099794 A1 | 4/2014 | Ingle et al. |
| 2014/0099798 A1 | 4/2014 | Tsuji |
| 2014/0103145 A1 | 4/2014 | White et al. |
| 2014/0106574 A1 | 4/2014 | Kang et al. |
| 2014/0110798 A1 | 4/2014 | Cai |
| 2014/0113457 A1 | 4/2014 | Sims |
| 2014/0116335 A1 | 5/2014 | Tsuji et al. |
| 2014/0117380 A1 | 5/2014 | Loboda et al. |
| 2014/0120312 A1 | 5/2014 | He et al. |
| 2014/0120487 A1 | 5/2014 | Kaneko |
| 2014/0120678 A1 | 5/2014 | Shinriki et al. |
| 2014/0120723 A1 | 5/2014 | Fu et al. |
| 2014/0120738 A1 | 5/2014 | Jung |
| 2014/0120750 A1 | 5/2014 | Johnson |
| 2014/0127422 A1 | 5/2014 | Shao et al. |
| 2014/0127907 A1 | 5/2014 | Yang |
| 2014/0130687 A1 | 5/2014 | Shibusawa et al. |
| 2014/0138779 A1 | 5/2014 | Xie et al. |
| 2014/0141165 A1 | 5/2014 | Sato et al. |
| 2014/0141625 A1 | 5/2014 | Fukazawa et al. |
| 2014/0141674 A1 | 5/2014 | Galbreath et al. |
| 2014/0144375 A1 | 5/2014 | Kim et al. |
| 2014/0144500 A1 | 5/2014 | Cao et al. |
| 2014/0145332 A1 | 5/2014 | Ryan et al. |
| 2014/0147587 A1 | 5/2014 | Endo et al. |
| 2014/0148924 A1 | 5/2014 | Brak et al. |
| 2014/0158154 A1 | 6/2014 | Kondo et al. |
| 2014/0158786 A1 | 6/2014 | Santo |
| 2014/0159170 A1 | 6/2014 | Raisanen et al. |
| 2014/0162401 A1 | 6/2014 | Kawano et al. |
| 2014/0167187 A1 | 6/2014 | Kuo et al. |
| 2014/0170320 A1 | 6/2014 | Yamamoto et al. |
| 2014/0170335 A1 | 6/2014 | Shao et al. |
| 2014/0174354 A1 | 6/2014 | Arai |
| 2014/0174357 A1 | 6/2014 | Kim et al. |
| 2014/0174927 A1 | 6/2014 | Bashir et al. |
| 2014/0175054 A1 | 6/2014 | Carlson et al. |

(56) References Cited

U.S. PATENT DOCUMENTS

| | | |
|---|---|---|
| 2014/0179091 A1 | 6/2014 | Clark |
| 2014/0179092 A1 | 6/2014 | Kim |
| 2014/0182053 A1 | 7/2014 | Huang |
| 2014/0182689 A1 | 7/2014 | Shareef et al. |
| 2014/0187022 A1 | 7/2014 | Falster et al. |
| 2014/0187045 A1 | 7/2014 | Hua et al. |
| 2014/0190581 A1 | 7/2014 | Nagase et al. |
| 2014/0191389 A1 | 7/2014 | Lee et al. |
| 2014/0193983 A1 | 7/2014 | Lavoie |
| 2014/0202382 A1 | 7/2014 | Kim et al. |
| 2014/0202386 A1 | 7/2014 | Taga |
| 2014/0202388 A1 | 7/2014 | Um et al. |
| 2014/0209976 A1 | 7/2014 | Yang et al. |
| 2014/0213061 A1 | 7/2014 | Huang et al. |
| 2014/0217065 A1 | 8/2014 | Winkler et al. |
| 2014/0220247 A1 | 8/2014 | Haukka et al. |
| 2014/0225065 A1 | 8/2014 | Rachmady et al. |
| 2014/0227072 A1 | 8/2014 | Lee et al. |
| 2014/0227444 A1 | 8/2014 | Winter et al. |
| 2014/0227861 A1 | 8/2014 | Wu et al. |
| 2014/0227881 A1 | 8/2014 | Lubomirsky et al. |
| 2014/0231922 A1 | 8/2014 | Kim et al. |
| 2014/0234466 A1 | 8/2014 | Gao et al. |
| 2014/0234550 A1 | 8/2014 | Winter et al. |
| 2014/0234992 A1 | 8/2014 | Kubota et al. |
| 2014/0238607 A1 | 8/2014 | Nozawa et al. |
| 2014/0238608 A1 | 8/2014 | Sabri et al. |
| 2014/0242298 A1 | 8/2014 | Lansalot-Matras et al. |
| 2014/0242806 A1 | 8/2014 | Knapp et al. |
| 2014/0242808 A1 | 8/2014 | Akiyama et al. |
| 2014/0245948 A1 | 9/2014 | Nguyen et al. |
| 2014/0251788 A1 | 9/2014 | Ge et al. |
| 2014/0251953 A1 | 9/2014 | Winkler et al. |
| 2014/0251954 A1 | 9/2014 | Winkler et al. |
| 2014/0252134 A1 | 9/2014 | Chen |
| 2014/0252479 A1 | 9/2014 | Utomo et al. |
| 2014/0252710 A1 | 9/2014 | Cuvalci et al. |
| 2014/0256160 A1 | 9/2014 | Wada et al. |
| 2014/0260684 A1 | 9/2014 | Christmann |
| 2014/0262028 A1 | 9/2014 | Kelekar |
| 2014/0262034 A1 | 9/2014 | Ishibashi et al. |
| 2014/0262193 A1 | 9/2014 | Im et al. |
| 2014/0263172 A1 | 9/2014 | Xie et al. |
| 2014/0263272 A1 | 9/2014 | Duan et al. |
| 2014/0264297 A1 | 9/2014 | Kumar et al. |
| 2014/0264444 A1 | 9/2014 | Guo et al. |
| 2014/0264902 A1 | 9/2014 | Ting et al. |
| 2014/0265090 A1 | 9/2014 | Hou |
| 2014/0265832 A1 | 9/2014 | Kenney et al. |
| 2014/0271081 A1 | 9/2014 | Lavitsky et al. |
| 2014/0272194 A1 | 9/2014 | Xiao et al. |
| 2014/0272341 A1 | 9/2014 | Duan et al. |
| 2014/0273428 A1 | 9/2014 | Shero |
| 2014/0273477 A1 | 9/2014 | Niskanen |
| 2014/0273497 A1 | 9/2014 | Payne et al. |
| 2014/0273510 A1 | 9/2014 | Chen et al. |
| 2014/0273528 A1 | 9/2014 | Niskanen |
| 2014/0273530 A1 | 9/2014 | Nguyen |
| 2014/0273531 A1 | 9/2014 | Niskanen |
| 2014/0283747 A1 | 9/2014 | Kasai et al. |
| 2014/0287164 A1 | 9/2014 | Xiao et al. |
| 2014/0287595 A1 | 9/2014 | Shimamoto et al. |
| 2014/0290573 A1 | 10/2014 | Okabe et al. |
| 2014/0290578 A1 | 10/2014 | Wamura et al. |
| 2014/0306250 A1 | 10/2014 | Gardner et al. |
| 2014/0308108 A1 | 10/2014 | Fosnight et al. |
| 2014/0312767 A1 | 10/2014 | Tian et al. |
| 2014/0322862 A1 | 10/2014 | Xie et al. |
| 2014/0322885 A1 | 10/2014 | Xie et al. |
| 2014/0327117 A1 | 11/2014 | Bencher et al. |
| 2014/0339981 A1 | 11/2014 | Komatsu et al. |
| 2014/0346142 A1 | 11/2014 | Chapuis et al. |
| 2014/0346600 A1 | 11/2014 | Cheng et al. |
| 2014/0346650 A1 | 11/2014 | Raisanen et al. |
| 2014/0349033 A1 | 11/2014 | Nonaka et al. |
| 2014/0349068 A1 | 11/2014 | Inglis et al. |
| 2014/0357090 A1 | 12/2014 | Knaepen et al. |
| 2014/0360430 A1 | 12/2014 | Armour et al. |
| 2014/0363980 A1 | 12/2014 | Kawamata et al. |
| 2014/0363983 A1 | 12/2014 | Nakano et al. |
| 2014/0363985 A1 | 12/2014 | Jang et al. |
| 2014/0366804 A1 | 12/2014 | Pak et al. |
| 2014/0367043 A1 | 12/2014 | Bishara et al. |
| 2014/0367642 A1 | 12/2014 | Guo |
| 2014/0377960 A1 | 12/2014 | Koiwa |
| 2015/0004316 A1 | 1/2015 | Thompson et al. |
| 2015/0004317 A1 | 1/2015 | Dussarrat et al. |
| 2015/0004318 A1 | 1/2015 | Alasaarela et al. |
| 2015/0004798 A1 | 1/2015 | Chandrasekharan et al. |
| 2015/0004806 A1 | 1/2015 | Ndiege et al. |
| 2015/0007770 A1 | 1/2015 | Chandrasekharan et al. |
| 2015/0010381 A1 | 1/2015 | Cai |
| 2015/0011095 A1 | 1/2015 | Chandrasekharan et al. |
| 2015/0014632 A1 | 1/2015 | Kim et al. |
| 2015/0014823 A1 | 1/2015 | Mallikarjunan et al. |
| 2015/0017794 A1 | 1/2015 | Takamure |
| 2015/0021599 A1 | 1/2015 | Ridgeway |
| 2015/0024567 A1 | 1/2015 | Tsai et al. |
| 2015/0024609 A1 | 1/2015 | Milligan et al. |
| 2015/0030766 A1 | 1/2015 | Lind et al. |
| 2015/0030782 A1 | 1/2015 | Ivanov et al. |
| 2015/0031218 A1 | 1/2015 | Karakawa |
| 2015/0041431 A1 | 2/2015 | Zafiropoulo et al. |
| 2015/0048485 A1 | 2/2015 | Tolle |
| 2015/0056815 A1 | 2/2015 | Fernandez |
| 2015/0056821 A1 | 2/2015 | Ishikawa et al. |
| 2015/0061078 A1 | 3/2015 | Abel et al. |
| 2015/0064923 A1 | 3/2015 | Matsumoto et al. |
| 2015/0069354 A1 | 3/2015 | Helander et al. |
| 2015/0072509 A1 | 3/2015 | Chi et al. |
| 2015/0077742 A1* | 3/2015 | Wootton ............ G01N 21/8806 356/239.3 |
| 2015/0078874 A1 | 3/2015 | Sansoni |
| 2015/0079311 A1 | 3/2015 | Nakano |
| 2015/0086316 A1 | 3/2015 | Greenberg |
| 2015/0086716 A1 | 3/2015 | Park et al. |
| 2015/0087139 A1 | 3/2015 | O'Neill et al. |
| 2015/0087154 A1 | 3/2015 | Guha et al. |
| 2015/0091057 A1 | 4/2015 | Xie et al. |
| 2015/0091134 A1 | 4/2015 | Amaratunga et al. |
| 2015/0094470 A1 | 4/2015 | Sanchez et al. |
| 2015/0096973 A1 | 4/2015 | Dunn et al. |
| 2015/0099065 A1 | 4/2015 | Canizares et al. |
| 2015/0099072 A1 | 4/2015 | Takamure et al. |
| 2015/0099123 A1 | 4/2015 | Barbee et al. |
| 2015/0099342 A1 | 4/2015 | Tsai |
| 2015/0099374 A1 | 4/2015 | Kakimoto et al. |
| 2015/0099375 A1 | 4/2015 | Haripin et al. |
| 2015/0102466 A1 | 4/2015 | Colinge |
| 2015/0104574 A1 | 4/2015 | Lee et al. |
| 2015/0104575 A1 | 4/2015 | Takoudis et al. |
| 2015/0110147 A1 | 4/2015 | Mizuno |
| 2015/0110968 A1 | 4/2015 | Lavoie et al. |
| 2015/0111374 A1 | 4/2015 | Bao |
| 2015/0111395 A1 | 4/2015 | Hashimoto et al. |
| 2015/0114295 A1 | 4/2015 | Kim et al. |
| 2015/0118009 A1 | 4/2015 | Hsieh et al. |
| 2015/0118846 A1 | 4/2015 | Isii et al. |
| 2015/0118863 A1 | 4/2015 | Rathod et al. |
| 2015/0122180 A1 | 5/2015 | Chang et al. |
| 2015/0125628 A1 | 5/2015 | Kim et al. |
| 2015/0126036 A1 | 5/2015 | Zhao |
| 2015/0132212 A1 | 5/2015 | Winkler et al. |
| 2015/0132953 A1 | 5/2015 | Nowling et al. |
| 2015/0137315 A1 | 5/2015 | Chen et al. |
| 2015/0140210 A1 | 5/2015 | Jung et al. |
| 2015/0144060 A1 | 5/2015 | Park |
| 2015/0147482 A1 | 5/2015 | Kang et al. |
| 2015/0147483 A1 | 5/2015 | Fukazawa |
| 2015/0147488 A1 | 5/2015 | Choi et al. |
| 2015/0147875 A1 | 5/2015 | Takamure et al. |
| 2015/0147877 A1 | 5/2015 | Jung |
| 2015/0152547 A1 | 6/2015 | Nakamura et al. |
| 2015/0152553 A1 | 6/2015 | Popp et al. |

(56) References Cited

U.S. PATENT DOCUMENTS

| | | |
|---|---|---|
| 2015/0155140 A1 | 6/2015 | Lee et al. |
| 2015/0155177 A1 | 6/2015 | Zhang et al. |
| 2015/0155370 A1 | 6/2015 | Tsai et al. |
| 2015/0162168 A1 | 6/2015 | Oehrlien |
| 2015/0162185 A1 | 6/2015 | Pore |
| 2015/0162214 A1 | 6/2015 | Thompson |
| 2015/0167159 A1 | 6/2015 | Halpin et al. |
| 2015/0167161 A1 | 6/2015 | Canizares et al. |
| 2015/0167162 A1 | 6/2015 | Barik et al. |
| 2015/0167165 A1 | 6/2015 | Lindfors |
| 2015/0167705 A1 | 6/2015 | Lee et al. |
| 2015/0170907 A1 | 6/2015 | Haukka et al. |
| 2015/0170914 A1 | 6/2015 | Haukka et al. |
| 2015/0170945 A1 | 6/2015 | Segawa et al. |
| 2015/0170947 A1 | 6/2015 | Bluck |
| 2015/0170954 A1 | 6/2015 | Agarwal |
| 2015/0170975 A1 | 6/2015 | Blatchford et al. |
| 2015/0171177 A1 | 6/2015 | Cheng et al. |
| 2015/0174768 A1 | 6/2015 | Rodnick |
| 2015/0175467 A1 | 6/2015 | Denifl et al. |
| 2015/0176124 A1 | 6/2015 | Greer et al. |
| 2015/0176126 A1 | 6/2015 | Ge et al. |
| 2015/0179415 A1 | 6/2015 | Sasaki et al. |
| 2015/0179501 A1 | 6/2015 | Jhaveri et al. |
| 2015/0179564 A1 | 6/2015 | Lee et al. |
| 2015/0179640 A1 | 6/2015 | Kim et al. |
| 2015/0184287 A1 | 7/2015 | Tsung et al. |
| 2015/0184291 A1 | 7/2015 | Alokozai et al. |
| 2015/0187559 A1 | 7/2015 | Sano |
| 2015/0187568 A1 | 7/2015 | Pettinger et al. |
| 2015/0187611 A1 | 7/2015 | Sato |
| 2015/0187908 A1 | 7/2015 | Zhang et al. |
| 2015/0203961 A1 | 7/2015 | Ha et al. |
| 2015/0203967 A1 | 7/2015 | Dhas et al. |
| 2015/0211124 A1 | 7/2015 | Nozawa et al. |
| 2015/0211125 A1 | 7/2015 | Yoshikawa et al. |
| 2015/0217330 A1 | 8/2015 | Haukka |
| 2015/0217456 A1 | 8/2015 | Tsuji et al. |
| 2015/0218695 A1 | 8/2015 | Odedra |
| 2015/0218698 A1 | 8/2015 | Yoon et al. |
| 2015/0218700 A1 | 8/2015 | Nguyen et al. |
| 2015/0221479 A1 | 8/2015 | Chen et al. |
| 2015/0221480 A1 | 8/2015 | Duan et al. |
| 2015/0221519 A1 | 8/2015 | Marks et al. |
| 2015/0225850 A1 | 8/2015 | Arora et al. |
| 2015/0228513 A1 | 8/2015 | Parkhe et al. |
| 2015/0228572 A1 | 8/2015 | Yang et al. |
| 2015/0228645 A1 | 8/2015 | Chuang et al. |
| 2015/0228749 A1 | 8/2015 | Ando et al. |
| 2015/0240357 A1 | 8/2015 | Tachibana et al. |
| 2015/0240359 A1 | 8/2015 | Jdira et al. |
| 2015/0240360 A1 | 8/2015 | Leeser |
| 2015/0241787 A1 | 8/2015 | Yaegashi |
| 2015/0243522 A1 | 8/2015 | Kitagaito et al. |
| 2015/0243542 A1 | 8/2015 | Yoshihara et al. |
| 2015/0243545 A1 | 8/2015 | Tang |
| 2015/0243563 A1 | 8/2015 | Lee et al. |
| 2015/0243658 A1 | 8/2015 | Joshi et al. |
| 2015/0247259 A1 | 9/2015 | Hekmatshoar-Tabari et al. |
| 2015/0249013 A1 | 9/2015 | Arghavani et al. |
| 2015/0255319 A1 | 9/2015 | Kikuchi et al. |
| 2015/0255324 A1 | 9/2015 | Li et al. |
| 2015/0255385 A1 | 9/2015 | Lee et al. |
| 2015/0259790 A1 | 9/2015 | Newman |
| 2015/0259801 A1 | 9/2015 | Matsumoto et al. |
| 2015/0262828 A1 | 9/2015 | Brand et al. |
| 2015/0263033 A1 | 9/2015 | Aoyama |
| 2015/0267294 A1 | 9/2015 | Itatani |
| 2015/0267295 A1 | 9/2015 | Hill et al. |
| 2015/0267297 A1 | 9/2015 | Shiba |
| 2015/0267298 A1 | 9/2015 | Saitou et al. |
| 2015/0267299 A1 | 9/2015 | Hawkins |
| 2015/0267301 A1 | 9/2015 | Hill et al. |
| 2015/0270140 A1 | 9/2015 | Gupta et al. |
| 2015/0270146 A1 | 9/2015 | Yoshihara et al. |
| 2015/0275355 A1 | 10/2015 | Mallikarjunan et al. |
| 2015/0275357 A1 | 10/2015 | Kamakura et al. |
| 2015/0279665 A1 | 10/2015 | Zafiropoulo |
| 2015/0279681 A1 | 10/2015 | Knoops |
| 2015/0279682 A1 | 10/2015 | Nakatani et al. |
| 2015/0279708 A1 | 10/2015 | Kobayashi et al. |
| 2015/0279956 A1 | 10/2015 | Ozaki et al. |
| 2015/0280051 A1 | 10/2015 | Xu |
| 2015/0284848 A1 | 10/2015 | Nakano et al. |
| 2015/0287591 A1 | 10/2015 | Pore et al. |
| 2015/0287612 A1 | 10/2015 | Luere et al. |
| 2015/0287626 A1 | 10/2015 | Arai |
| 2015/0287710 A1 | 10/2015 | Yun et al. |
| 2015/0291830 A1 | 10/2015 | Galbreath et al. |
| 2015/0292088 A1 | 10/2015 | Canizares |
| 2015/0299848 A1 | 10/2015 | Haukka et al. |
| 2015/0307982 A1 | 10/2015 | Firouzdor et al. |
| 2015/0307989 A1 | 10/2015 | Lindfors |
| 2015/0308586 A1 | 10/2015 | Shugrue et al. |
| 2015/0311043 A1 | 10/2015 | Sun et al. |
| 2015/0311151 A1 | 10/2015 | Chi et al. |
| 2015/0303056 A1 | 11/2015 | Varadarajan et al. |
| 2015/0315704 A1 | 11/2015 | Nakano et al. |
| 2015/0322569 A1 | 11/2015 | Kilpi et al. |
| 2015/0325432 A1 | 11/2015 | Ishizaka |
| 2015/0332921 A1 | 11/2015 | Lee et al. |
| 2015/0340247 A1 | 11/2015 | Balakrishnan et al. |
| 2015/0340266 A1 | 11/2015 | Ngo et al. |
| 2015/0340500 A1 | 11/2015 | Brunco |
| 2015/0340609 A1 | 11/2015 | Banno et al. |
| 2015/0343559 A1 | 12/2015 | Morikazu et al. |
| 2015/0343741 A1 | 12/2015 | Shibata et al. |
| 2015/0345018 A1 | 12/2015 | Detavernier et al. |
| 2015/0345022 A1 | 12/2015 | Yudovsky et al. |
| 2015/0348755 A1 | 12/2015 | Han et al. |
| 2015/0349073 A1 | 12/2015 | Kang |
| 2015/0353478 A1 | 12/2015 | Hoshino et al. |
| 2015/0354060 A1 | 12/2015 | Yabe et al. |
| 2015/0361550 A1 | 12/2015 | Yabe et al. |
| 2015/0361553 A1 | 12/2015 | Murakawa |
| 2015/0364347 A1 | 12/2015 | Nguyen et al. |
| 2015/0364371 A1 | 12/2015 | Yen |
| 2015/0364747 A1 | 12/2015 | Elam et al. |
| 2015/0367253 A1 | 12/2015 | Kanyal et al. |
| 2015/0368798 A1 | 12/2015 | Kwong |
| 2015/0371864 A1 | 12/2015 | Hsu et al. |
| 2015/0372056 A1 | 12/2015 | Seong et al. |
| 2015/0376211 A1 | 12/2015 | Girard |
| 2015/0376785 A1 | 12/2015 | Knaapen et al. |
| 2015/0380296 A1 | 12/2015 | Antonelli et al. |
| 2016/0002776 A1 | 1/2016 | Nal et al. |
| 2016/0002786 A1 | 1/2016 | Gatineau et al. |
| 2016/0005571 A1 | 1/2016 | Della Rosa et al. |
| 2016/0005595 A1 | 1/2016 | Liu et al. |
| 2016/0005596 A1 | 1/2016 | Behera et al. |
| 2016/0005839 A1 | 1/2016 | Yieh et al. |
| 2016/0010208 A1 | 1/2016 | Huang et al. |
| 2016/0013022 A1 | 1/2016 | Ayoub |
| 2016/0013024 A1 | 1/2016 | Milligan et al. |
| 2016/0013086 A1 | 1/2016 | Yang et al. |
| 2016/0017493 A1 | 1/2016 | Dhas |
| 2016/0020071 A1 | 1/2016 | Khaja et al. |
| 2016/0020092 A1 | 1/2016 | Kang et al. |
| 2016/0024655 A1 | 1/2016 | Yudovsky et al. |
| 2016/0024656 A1 | 1/2016 | White et al. |
| 2016/0032453 A1 | 2/2016 | Qian et al. |
| 2016/0035542 A1 | 2/2016 | Hausmann |
| 2016/0035566 A1 | 2/2016 | LaVoie |
| 2016/0035596 A1 | 2/2016 | Kamiya |
| 2016/0042954 A1 | 2/2016 | Sung et al. |
| 2016/0051964 A1 | 2/2016 | Tolle et al. |
| 2016/0056074 A1 | 2/2016 | Na |
| 2016/0056156 A1 | 2/2016 | Ghani et al. |
| 2016/0060752 A1 | 3/2016 | Jacques et al. |
| 2016/0063790 A1* | 3/2016 | Stewart ............... G07D 7/1205 356/365 |
| 2016/0064208 A1 | 3/2016 | Zafiropoulo et al. |
| 2016/0064231 A1 | 3/2016 | Agarwal et al. |
| 2016/0069613 A1 | 3/2016 | Colgan et al. |

(56) References Cited

U.S. PATENT DOCUMENTS

| | | |
|---|---|---|
| 2016/0071750 A1 | 3/2016 | de Ridder et al. |
| 2016/0076949 A1 | 3/2016 | Sabah et al. |
| 2016/0079054 A1 | 3/2016 | Chen et al. |
| 2016/0085003 A1 | 3/2016 | Jaiswal |
| 2016/0086811 A1 | 3/2016 | Mackedanz et al. |
| 2016/0087028 A1 | 3/2016 | Hirota et al. |
| 2016/0097123 A1 | 4/2016 | Shugrue et al. |
| 2016/0099150 A1 | 4/2016 | Tsai |
| 2016/0099166 A1 | 4/2016 | Yudovsky |
| 2016/0099250 A1 | 4/2016 | Rabkin et al. |
| 2016/0102214 A1 | 4/2016 | Dietz et al. |
| 2016/0111272 A1 | 4/2016 | Girard |
| 2016/0111304 A1 | 4/2016 | Takahashi et al. |
| 2016/0111438 A1 | 4/2016 | Tsutsumi et al. |
| 2016/0115590 A1 | 4/2016 | Haukka et al. |
| 2016/0118224 A1 | 4/2016 | Kohno et al. |
| 2016/0133307 A1 | 5/2016 | Lee et al. |
| 2016/0133504 A1 | 5/2016 | Chu et al. |
| 2016/0133628 A1 | 5/2016 | Xie |
| 2016/0141172 A1 | 5/2016 | Kang |
| 2016/0145738 A1 | 5/2016 | Liu et al. |
| 2016/0148800 A1 | 5/2016 | Henri et al. |
| 2016/0148801 A1 | 5/2016 | Yabe et al. |
| 2016/0148806 A1 | 5/2016 | Henri et al. |
| 2016/0148811 A1 | 5/2016 | Nakatani et al. |
| 2016/0148821 A1 | 5/2016 | Singh |
| 2016/0152649 A1 | 6/2016 | Gordon |
| 2016/0153088 A1 | 6/2016 | Tsuji et al. |
| 2016/0155629 A1 | 6/2016 | Hawryluk et al. |
| 2016/0163556 A1 | 6/2016 | Briggs et al. |
| 2016/0163558 A1 | 6/2016 | Hudson et al. |
| 2016/0163561 A1 | 6/2016 | Hudson et al. |
| 2016/0163711 A1 | 6/2016 | Arndt et al. |
| 2016/0163972 A1 | 6/2016 | Swaminathan et al. |
| 2016/0168699 A1 | 6/2016 | Fukazawa et al. |
| 2016/0168704 A1 | 6/2016 | Choi et al. |
| 2016/0169766 A1 | 6/2016 | Ishibashi et al. |
| 2016/0172189 A1 | 6/2016 | Tapily |
| 2016/0172296 A1 | 6/2016 | Lim et al. |
| 2016/0175805 A1 | 6/2016 | Catchpole et al. |
| 2016/0177448 A1 | 6/2016 | Ikeda |
| 2016/0181117 A1 | 6/2016 | Arghavani et al. |
| 2016/0181128 A1 | 6/2016 | Mori |
| 2016/0181368 A1 | 6/2016 | Weeks |
| 2016/0190137 A1 | 6/2016 | Tsai et al. |
| 2016/0195331 A1 | 7/2016 | Hyon et al. |
| 2016/0196969 A1 | 7/2016 | Berry et al. |
| 2016/0196970 A1 | 7/2016 | Takamure et al. |
| 2016/0203995 A1 | 7/2016 | Kanarik et al. |
| 2016/0204005 A1 | 7/2016 | Oki et al. |
| 2016/0204436 A1 | 7/2016 | Barker et al. |
| 2016/0211135 A1 | 7/2016 | Noda et al. |
| 2016/0211147 A1 | 7/2016 | Fukazawa |
| 2016/0211166 A1 | 7/2016 | Yan et al. |
| 2016/0215387 A1 | 7/2016 | Liu et al. |
| 2016/0217857 A1 | 7/2016 | Paudel |
| 2016/0218028 A1 | 7/2016 | Schaller et al. |
| 2016/0222504 A1 | 8/2016 | Haukka et al. |
| 2016/0222509 A1 | 8/2016 | Honma |
| 2016/0222516 A1 | 8/2016 | Ikeda et al. |
| 2016/0225588 A1 | 8/2016 | Shaikh et al. |
| 2016/0225607 A1 | 8/2016 | Yamamoto et al. |
| 2016/0225632 A1 | 8/2016 | Shaikh et al. |
| 2016/0237559 A1 | 8/2016 | Tsuji |
| 2016/0245704 A1 | 8/2016 | Osaka et al. |
| 2016/0256187 A1 | 9/2016 | Shelton et al. |
| 2016/0268102 A1 | 9/2016 | White |
| 2016/0268107 A1 | 9/2016 | White |
| 2016/0273095 A1 | 9/2016 | Lin et al. |
| 2016/0273101 A1 | 9/2016 | Komori et al. |
| 2016/0273106 A1 | 9/2016 | Kanjolia et al. |
| 2016/0273128 A1 | 9/2016 | Kang |
| 2016/0276148 A1 | 9/2016 | Qian et al. |
| 2016/0276212 A1 | 9/2016 | Horikoshi |
| 2016/0279629 A1 | 9/2016 | Michishita et al. |
| 2016/0281223 A1 | 9/2016 | Sowa et al. |
| 2016/0281230 A1 | 9/2016 | Varadarajan et al. |
| 2016/0284517 A1 | 9/2016 | Saido |
| 2016/0284542 A1 | 9/2016 | Noda et al. |
| 2016/0289828 A1 | 10/2016 | Shero et al. |
| 2016/0293398 A1 | 10/2016 | Danek et al. |
| 2016/0293609 A1 | 10/2016 | Jha et al. |
| 2016/0305015 A1 | 10/2016 | Nakamura et al. |
| 2016/0307739 A1 | 10/2016 | Lee et al. |
| 2016/0307740 A1 | 10/2016 | Kim et al. |
| 2016/0307766 A1 | 10/2016 | Jongbloed et al. |
| 2016/0312360 A1 | 10/2016 | Rasheed et al. |
| 2016/0314960 A1 | 10/2016 | Cheng et al. |
| 2016/0314962 A1 | 10/2016 | Higashino et al. |
| 2016/0314964 A1 | 10/2016 | Tang et al. |
| 2016/0314967 A1 | 10/2016 | Tolle |
| 2016/0315168 A1 | 10/2016 | Dussarrat et al. |
| 2016/0334709 A1 | 11/2016 | Huli et al. |
| 2016/0336178 A1 | 11/2016 | Swaminathan et al. |
| 2016/0336392 A1 | 11/2016 | Tominaga et al. |
| 2016/0343612 A1 | 11/2016 | Wang et al. |
| 2016/0345384 A1 | 11/2016 | Zhang et al. |
| 2016/0351413 A1 | 12/2016 | Schmidt et al. |
| 2016/0351747 A1 | 12/2016 | Forrest et al. |
| 2016/0358772 A1 | 12/2016 | Xie |
| 2016/0362783 A1 | 12/2016 | Tolle et al. |
| 2016/0362813 A1 | 12/2016 | Bao et al. |
| 2016/0365280 A1 | 12/2016 | Brink et al. |
| 2016/0365414 A1 | 12/2016 | Peng et al. |
| 2016/0372321 A1 | 12/2016 | Krishnan et al. |
| 2016/0372365 A1 | 12/2016 | Tang et al. |
| 2016/0372744 A1 | 12/2016 | Essaki et al. |
| 2016/0376700 A1 | 12/2016 | Haukka |
| 2016/0376701 A1 | 12/2016 | Takewaki et al. |
| 2016/0376704 A1 | 12/2016 | Raisanen |
| 2016/0379826 A9 | 12/2016 | Arghavani et al. |
| 2016/0379851 A1 | 12/2016 | Swaminathan et al. |
| 2016/0381732 A1 | 12/2016 | Moench et al. |
| 2017/0009347 A1 | 1/2017 | Jang et al. |
| 2017/0009367 A1 | 1/2017 | Harris et al. |
| 2017/0011889 A1 | 1/2017 | Winkler et al. |
| 2017/0011926 A1 | 1/2017 | Harada et al. |
| 2017/0011950 A1 | 1/2017 | Schmotzer |
| 2017/0018477 A1 | 1/2017 | Kato |
| 2017/0018570 A1 | 1/2017 | Lue et al. |
| 2017/0022612 A1 | 1/2017 | Lei et al. |
| 2017/0025280 A1 | 1/2017 | Milligan |
| 2017/0025291 A1 | 1/2017 | Lin |
| 2017/0029945 A1 | 2/2017 | Kamakura |
| 2017/0032942 A1 | 2/2017 | Walfried |
| 2017/0032943 A1 | 2/2017 | Spaulding et al. |
| 2017/0032992 A1 | 2/2017 | Hoechbauer |
| 2017/0033004 A1 | 2/2017 | Siew et al. |
| 2017/0037513 A1 | 2/2017 | Haukka |
| 2017/0040146 A1 | 2/2017 | Huang et al. |
| 2017/0040164 A1 | 2/2017 | Wang et al. |
| 2017/0040198 A1 | 2/2017 | Lin et al. |
| 2017/0040206 A1 | 2/2017 | Schmotzer et al. |
| 2017/0044664 A1 | 2/2017 | Dussarrat et al. |
| 2017/0044665 A1 | 2/2017 | Shon et al. |
| 2017/0044666 A1 | 2/2017 | Jang et al. |
| 2017/0047446 A1 | 2/2017 | Margetis et al. |
| 2017/0051402 A1 | 2/2017 | Mori |
| 2017/0051405 A1 | 2/2017 | Fukazawa et al. |
| 2017/0051406 A1 | 2/2017 | Mori et al. |
| 2017/0051408 A1 | 2/2017 | Kosuke et al. |
| 2017/0053811 A1 | 2/2017 | Fung et al. |
| 2017/0058402 A1 | 3/2017 | Wenxu et al. |
| 2017/0062204 A1 | 3/2017 | Suzuki et al. |
| 2017/0062209 A1 | 3/2017 | Shiba |
| 2017/0062210 A1 | 3/2017 | Visser et al. |
| 2017/0062218 A1 | 3/2017 | Duan et al. |
| 2017/0062224 A1 | 3/2017 | Fu et al. |
| 2017/0062258 A1 | 3/2017 | Bluck |
| 2017/0069725 A1 | 3/2017 | Bhimarasetti et al. |
| 2017/0091320 A1 | 3/2017 | Psota et al. |
| 2017/0092469 A1 | 3/2017 | Kurita et al. |
| 2017/0092531 A1 | 3/2017 | Coomer |
| 2017/0092535 A1 | 3/2017 | Kimihiko et al. |

(56) References Cited

U.S. PATENT DOCUMENTS

| | | |
|---|---|---|
| 2017/0092847 A1 | 3/2017 | Kim et al. |
| 2017/0100742 A1 | 4/2017 | Pore et al. |
| 2017/0102612 A1 | 4/2017 | Meyers et al. |
| 2017/0103907 A1 | 4/2017 | Chu et al. |
| 2017/0104061 A1 | 4/2017 | Peng et al. |
| 2017/0107621 A1 | 4/2017 | Suemori |
| 2017/0110313 A1 | 4/2017 | Tang et al. |
| 2017/0110601 A1 | 4/2017 | Blomberg et al. |
| 2017/0114460 A1 | 4/2017 | Kim et al. |
| 2017/0114464 A1 | 4/2017 | Iriuda et al. |
| 2017/0114465 A1 | 4/2017 | Kalutarage et al. |
| 2017/0117141 A1 | 4/2017 | Zhu et al. |
| 2017/0117202 A1 | 4/2017 | Tang et al. |
| 2017/0117203 A1 | 4/2017 | Tang et al. |
| 2017/0117222 A1 | 4/2017 | Kim et al. |
| 2017/0121845 A1 | 5/2017 | Grutzmacher et al. |
| 2017/0130332 A1 | 5/2017 | Stumpf |
| 2017/0136578 A1 | 5/2017 | Yoshimura |
| 2017/0140924 A1 | 5/2017 | Suzuki et al. |
| 2017/0140925 A1 | 5/2017 | Suzuki et al. |
| 2017/0145564 A1 | 5/2017 | Bertuch et al. |
| 2017/0146909 A1 | 5/2017 | Smith et al. |
| 2017/0148918 A1 | 5/2017 | Ye et al. |
| 2017/0152968 A1 | 6/2017 | Raj et al. |
| 2017/0154757 A1 | 6/2017 | Winkler et al. |
| 2017/0154770 A1 | 6/2017 | Margetis et al. |
| 2017/0154895 A1 | 6/2017 | Huo |
| 2017/0159177 A1 | 6/2017 | Monsma et al. |
| 2017/0165624 A1 | 6/2017 | Ravoin et al. |
| 2017/0167023 A1 | 6/2017 | Proia et al. |
| 2017/0170033 A1 | 6/2017 | Okabe et al. |
| 2017/0173696 A1 | 6/2017 | Sheinman |
| 2017/0175290 A1 | 6/2017 | Chen et al. |
| 2017/0178899 A1 | 6/2017 | Kabansky et al. |
| 2017/0178939 A1 | 6/2017 | Omori |
| 2017/0178942 A1 | 6/2017 | Sakata et al. |
| 2017/0179036 A1 | 6/2017 | Chen et al. |
| 2017/0186621 A1 | 6/2017 | Zaitsu |
| 2017/0186754 A1 | 6/2017 | Blomberg et al. |
| 2017/0191159 A1 | 7/2017 | Polyak et al. |
| 2017/0191164 A1 | 7/2017 | Alokozai et al. |
| 2017/0191685 A1 | 7/2017 | Ronne et al. |
| 2017/0191861 A1 | 7/2017 | Rondano et al. |
| 2017/0196562 A1 | 7/2017 | Shelton |
| 2017/0200622 A1 | 7/2017 | Shiokawa et al. |
| 2017/0204516 A1 | 7/2017 | Nguyen et al. |
| 2017/0213960 A1 | 7/2017 | de Araujo et al. |
| 2017/0216762 A1 | 8/2017 | Shugrue et al. |
| 2017/0218515 A1 | 8/2017 | Shin et al. |
| 2017/0222008 A1 | 8/2017 | Hsu et al. |
| 2017/0226636 A1 | 8/2017 | Xiao |
| 2017/0232457 A1 | 8/2017 | Toshiki et al. |
| 2017/0233868 A1 | 8/2017 | Donoso et al. |
| 2017/0243734 A1 | 8/2017 | Ishikawa et al. |
| 2017/0250068 A1 | 8/2017 | Ishikawa et al. |
| 2017/0250075 A1 | 8/2017 | Caymax et al. |
| 2017/0253968 A1 | 9/2017 | Yahata |
| 2017/0256393 A1 | 9/2017 | Kim et al. |
| 2017/0256417 A1 | 9/2017 | Chou |
| 2017/0256429 A1 | 9/2017 | Lawson et al. |
| 2017/0260649 A1 | 9/2017 | Coomer |
| 2017/0263437 A1 | 9/2017 | Li et al. |
| 2017/0263438 A1 | 9/2017 | Li et al. |
| 2017/0267527 A1 | 9/2017 | Kim et al. |
| 2017/0267531 A1 | 9/2017 | Huakka |
| 2017/0271143 A1 | 9/2017 | Fukiage et al. |
| 2017/0271191 A1 | 9/2017 | Yoo et al. |
| 2017/0271256 A1 | 9/2017 | Inatsuka |
| 2017/0271501 A1 | 9/2017 | Avci et al. |
| 2017/0278705 A1 | 9/2017 | Murakami et al. |
| 2017/0278707 A1 | 9/2017 | Margetis et al. |
| 2017/0283312 A1 | 10/2017 | Lee et al. |
| 2017/0283313 A1 | 10/2017 | Lee et al. |
| 2017/0287681 A1 | 10/2017 | Nitadori et al. |
| 2017/0287744 A1 | 10/2017 | Kobayashi et al. |
| 2017/0294318 A1 | 10/2017 | Yoshida et al. |
| 2017/0294339 A1 | 10/2017 | Tapily |
| 2017/0294499 A1 | 10/2017 | Lu et al. |
| 2017/0301519 A1 | 10/2017 | Naim et al. |
| 2017/0301542 A1 | 10/2017 | Maes et al. |
| 2017/0303382 A1 | 10/2017 | Smith et al. |
| 2017/0306478 A1 | 10/2017 | Raisanen et al. |
| 2017/0306479 A1 | 10/2017 | Raisanen et al. |
| 2017/0306480 A1 | 10/2017 | Zhu et al. |
| 2017/0306494 A1 | 10/2017 | Lin et al. |
| 2017/0309490 A1 | 10/2017 | Ogawa |
| 2017/0309528 A1 | 10/2017 | Bansal et al. |
| 2017/0314125 A1 | 11/2017 | Fenwick et al. |
| 2017/0316933 A1 | 11/2017 | Xie et al. |
| 2017/0316940 A1 | 11/2017 | Ishikawa et al. |
| 2017/0317194 A1 | 11/2017 | Tang et al. |
| 2017/0323783 A1 | 11/2017 | Sanchez et al. |
| 2017/0323784 A1 | 11/2017 | Faguet et al. |
| 2017/0338111 A1 | 11/2017 | Takamure et al. |
| 2017/0338133 A1 | 11/2017 | Tan et al. |
| 2017/0338134 A1 | 11/2017 | Tan et al. |
| 2017/0338192 A1 | 11/2017 | Lee et al. |
| 2017/0342559 A1 | 11/2017 | Fukazawa et al. |
| 2017/0343896 A1 | 11/2017 | Darling et al. |
| 2017/0345674 A1 | 11/2017 | Ranjan et al. |
| 2017/0350688 A1 | 12/2017 | Boyd et al. |
| 2017/0358445 A1 | 12/2017 | O'Shaugnessy et al. |
| 2017/0358482 A1 | 12/2017 | Chen et al. |
| 2017/0358670 A1 | 12/2017 | Kub et al. |
| 2017/0362710 A1 | 12/2017 | Ge et al. |
| 2017/0365467 A1 | 12/2017 | Shimamoto et al. |
| 2017/0369993 A1 | 12/2017 | Sun |
| 2017/0372884 A1 | 12/2017 | Margetis et al. |
| 2017/0372919 A1 | 12/2017 | Manna et al. |
| 2017/0373188 A1 | 12/2017 | Mochizuki et al. |
| 2018/0005814 A1 | 1/2018 | Kumar et al. |
| 2018/0010243 A1 | 1/2018 | Lee et al. |
| 2018/0010247 A1 | 1/2018 | Niskanen |
| 2018/0011052 A1 | 1/2018 | Andersson et al. |
| 2018/0012792 A1 | 1/2018 | Zhu |
| 2018/0019165 A1 | 1/2018 | Baum et al. |
| 2018/0025890 A1 | 1/2018 | Choi et al. |
| 2018/0025907 A1 | 1/2018 | Kalutarage et al. |
| 2018/0025939 A1 | 1/2018 | Kovalgin et al. |
| 2018/0033614 A1 | 2/2018 | Chandra et al. |
| 2018/0033616 A1 | 2/2018 | Masaru |
| 2018/0033625 A1 | 2/2018 | Yoo |
| 2018/0033645 A1 | 2/2018 | Saido et al. |
| 2018/0033674 A1 | 2/2018 | Jeong |
| 2018/0033679 A1 | 2/2018 | Pore |
| 2018/0040746 A1 | 2/2018 | Johnson et al. |
| 2018/0044800 A1 | 2/2018 | Hendrix et al. |
| 2018/0047591 A1 | 2/2018 | Ogo |
| 2018/0047621 A1 | 2/2018 | Armini |
| 2018/0047749 A1 | 2/2018 | Kim |
| 2018/0053660 A1 | 2/2018 | Jandl et al. |
| 2018/0053769 A1 | 2/2018 | Kim et al. |
| 2018/0057931 A1 | 3/2018 | Cha et al. |
| 2018/0057934 A1 | 3/2018 | Cooper et al. |
| 2018/0057937 A1 | 3/2018 | Lee et al. |
| 2018/0061628 A1 | 3/2018 | Ou et al. |
| 2018/0061851 A1 | 3/2018 | Ootsuka |
| 2018/0068844 A1 | 3/2018 | Chen et al. |
| 2018/0068862 A1 | 3/2018 | Terakura et al. |
| 2018/0068950 A1 | 3/2018 | Bruley et al. |
| 2018/0069019 A1 | 3/2018 | Kim et al. |
| 2018/0076021 A1 | 3/2018 | Fukushima et al. |
| 2018/0083435 A1 | 3/2018 | Redler |
| 2018/0087152 A1 | 3/2018 | Yoshida |
| 2018/0087154 A1 | 3/2018 | Pore et al. |
| 2018/0087156 A1 | 3/2018 | Kohei et al. |
| 2018/0090583 A1 | 3/2018 | Choi et al. |
| 2018/0094350 A1 | 4/2018 | Verghese et al. |
| 2018/0094351 A1 | 4/2018 | Verghese et al. |
| 2018/0096821 A1 | 4/2018 | Lubomirsky |
| 2018/0096844 A1 | 4/2018 | Dutartre et al. |
| 2018/0097076 A1 | 4/2018 | Cheng et al. |
| 2018/0102276 A1 | 4/2018 | Zhu et al. |
| 2018/0105701 A1 | 4/2018 | Larsson et al. |

(56) References Cited

U.S. PATENT DOCUMENTS

| | | |
|---|---|---|
| 2018/0105930 A1 | 4/2018 | Kang et al. |
| 2018/0108587 A1 | 4/2018 | Jiang |
| 2018/0114680 A1 | 4/2018 | Kim et al. |
| 2018/0119283 A1 | 5/2018 | Fukazawa |
| 2018/0122642 A1 | 5/2018 | Raisanen |
| 2018/0122709 A1 | 5/2018 | Xie |
| 2018/0122959 A1 | 5/2018 | Calka et al. |
| 2018/0126379 A1 | 5/2018 | Ramsey et al. |
| 2018/0127876 A1 | 5/2018 | Tolle et al. |
| 2018/0130652 A1 | 5/2018 | Pettinger et al. |
| 2018/0130701 A1 | 5/2018 | Chun |
| 2018/0135172 A1 | 5/2018 | Nogami et al. |
| 2018/0135173 A1 | 5/2018 | Kim et al. |
| 2018/0135179 A1 | 5/2018 | Toshiyuki et al. |
| 2018/0138036 A1 | 5/2018 | Baldesseroni et al. |
| 2018/0142353 A1 | 5/2018 | Tetsuya et al. |
| 2018/0142357 A1 | 5/2018 | Yoshikazu |
| 2018/0148832 A1 | 5/2018 | Chatterjee et al. |
| 2018/0151346 A1 | 5/2018 | Blanquart |
| 2018/0151358 A1 | 5/2018 | Margetis et al. |
| 2018/0151588 A1 | 5/2018 | Tsutsumi et al. |
| 2018/0155832 A1 | 6/2018 | Hamalainen et al. |
| 2018/0155836 A1 | 6/2018 | Arai et al. |
| 2018/0158688 A1 | 6/2018 | Chen |
| 2018/0158716 A1 | 6/2018 | Konkola et al. |
| 2018/0163305 A1 | 6/2018 | Batzer et al. |
| 2018/0166258 A1 | 6/2018 | Kim et al. |
| 2018/0166315 A1 | 6/2018 | Coomer |
| 2018/0171472 A1 | 6/2018 | Yamada et al. |
| 2018/0171475 A1 | 6/2018 | Maes et al. |
| 2018/0171477 A1 | 6/2018 | Kim et al. |
| 2018/0172172 A1 | 6/2018 | Oehler et al. |
| 2018/0173109 A1 | 6/2018 | Gronheid et al. |
| 2018/0174801 A1 | 6/2018 | Chen et al. |
| 2018/0174826 A1 | 6/2018 | Raaijmakers et al. |
| 2018/0179625 A1 | 6/2018 | Takagi et al. |
| 2018/0180509 A1 | 6/2018 | Sawachi et al. |
| 2018/0182613 A1 | 6/2018 | Blanquart et al. |
| 2018/0182618 A1 | 6/2018 | Blanquart et al. |
| 2018/0187303 A1 | 7/2018 | Gatineau et al. |
| 2018/0189923 A1 | 7/2018 | Zhong et al. |
| 2018/0190496 A1 | 7/2018 | Ashihara et al. |
| 2018/0195174 A1 | 7/2018 | Kim et al. |
| 2018/0204733 A1 | 7/2018 | Sherpa et al. |
| 2018/0209042 A1 | 7/2018 | Wu et al. |
| 2018/0211834 A1 | 7/2018 | Takamure et al. |
| 2018/0223047 A1 | 8/2018 | Xiao et al. |
| 2018/0223429 A1 | 8/2018 | Fukazawa et al. |
| 2018/0230595 A1 | 8/2018 | Suda et al. |
| 2018/0233372 A1 | 8/2018 | Vayrynen et al. |
| 2018/0245215 A1 | 8/2018 | Lei et al. |
| 2018/0246101 A1 | 8/2018 | Sasisekharan et al. |
| 2018/0254211 A1 | 9/2018 | Kosakai et al. |
| 2018/0258532 A1 | 9/2018 | Kato et al. |
| 2018/0265294 A1 | 9/2018 | Hayashi |
| 2018/0265972 A1 | 9/2018 | Firouzdor et al. |
| 2018/0265973 A1 | 9/2018 | Firouzdor et al. |
| 2018/0269057 A1 | 9/2018 | Lei et al. |
| 2018/0274098 A1 | 9/2018 | Takagi et al. |
| 2018/0277338 A1 | 9/2018 | Fukada et al. |
| 2018/0277423 A1 | 9/2018 | Lottes |
| 2018/0286638 A1 | 10/2018 | Susa |
| 2018/0286663 A1 | 10/2018 | Kobayashi et al. |
| 2018/0286668 A1 | 10/2018 | Baum et al. |
| 2018/0286672 A1 | 10/2018 | Van Aerde et al. |
| 2018/0286675 A1 | 10/2018 | Blomberg et al. |
| 2018/0286711 A1 | 10/2018 | Oosterlaken et al. |
| 2018/0294187 A1 | 10/2018 | Thombare et al. |
| 2018/0305247 A1 | 10/2018 | Feng et al. |
| 2018/0308686 A1 | 10/2018 | Xie et al. |
| 2018/0308701 A1 | 10/2018 | Na et al. |
| 2018/0312966 A1 | 11/2018 | Chan et al. |
| 2018/0315597 A1 | 11/2018 | Varadarajan et al. |
| 2018/0315838 A1 | 11/2018 | Morrow et al. |
| 2018/0323055 A1 | 11/2018 | Woodruff et al. |
| 2018/0323056 A1 | 11/2018 | Woodruff et al. |
| 2018/0323059 A1 | 11/2018 | Bhargava et al. |
| 2018/0325414 A1 | 11/2018 | Marashdeh et al. |
| 2018/0327892 A1 | 11/2018 | Wu et al. |
| 2018/0327898 A1 | 11/2018 | Wu et al. |
| 2018/0327899 A1 | 11/2018 | Wu et al. |
| 2018/0331117 A1 | 11/2018 | Titus et al. |
| 2018/0337087 A1 | 11/2018 | Sandhu et al. |
| 2018/0350587 A1 | 12/2018 | Jia et al. |
| 2018/0350588 A1 | 12/2018 | Raisanen et al. |
| 2018/0350620 A1 | 12/2018 | Zaitsu et al. |
| 2018/0350653 A1 | 12/2018 | Jeong et al. |
| 2018/0355480 A1 | 12/2018 | Kondo |
| 2018/0355484 A1 | 12/2018 | Lansalot-Matras et al. |
| 2018/0358222 A1 | 12/2018 | Venkatasubramanian et al. |
| 2018/0363131 A1 | 12/2018 | Lee et al. |
| 2018/0363139 A1 | 12/2018 | Rajavelu et al. |
| 2018/0366314 A1 | 12/2018 | Niskanen et al. |
| 2018/0371610 A1 | 12/2018 | Banerjee et al. |
| 2019/0003050 A1 | 1/2019 | Dezelah et al. |
| 2019/0003052 A1 | 1/2019 | Shero et al. |
| 2019/0006797 A1 | 1/2019 | Paynter et al. |
| 2019/0013199 A1 | 1/2019 | Bhargava et al. |
| 2019/0019670 A1 | 1/2019 | Lin et al. |
| 2019/0019714 A1 | 1/2019 | Kosakai et al. |
| 2019/0027573 A1 | 1/2019 | Zhu et al. |
| 2019/0027583 A1 | 1/2019 | Margetis et al. |
| 2019/0027584 A1 | 1/2019 | Margetis et al. |
| 2019/0027605 A1 | 1/2019 | Tolle et al. |
| 2019/0032209 A1 | 1/2019 | Huggare |
| 2019/0032998 A1 | 1/2019 | Jdira et al. |
| 2019/0035605 A1 | 1/2019 | Suzuki |
| 2019/0035647 A1 | 1/2019 | Lee et al. |
| 2019/0035698 A1 | 1/2019 | Tanaka |
| 2019/0035810 A1 | 1/2019 | Chun et al. |
| 2019/0040529 A1 | 2/2019 | Verbaas et al. |
| 2019/0046947 A1 | 2/2019 | Strohm et al. |
| 2019/0051544 A1 | 2/2019 | Verbaas |
| 2019/0051548 A1 | 2/2019 | den Hartog Besselink et al. |
| 2019/0051555 A1 | 2/2019 | Hill et al. |
| 2019/0057857 A1 | 2/2019 | Ishikawa et al. |
| 2019/0057858 A1 | 2/2019 | Hausmann et al. |
| 2019/0058043 A1 | 2/2019 | Dewey et al. |
| 2019/0062907 A1 | 2/2019 | Kim et al. |
| 2019/0062917 A1 | 2/2019 | Sung et al. |
| 2019/0066978 A1 | 2/2019 | Um et al. |
| 2019/0066997 A1 | 2/2019 | Klaver et al. |
| 2019/0067003 A1 | 2/2019 | Zope et al. |
| 2019/0067004 A1 | 2/2019 | Kohen et al. |
| 2019/0067014 A1 | 2/2019 | Shrestha et al. |
| 2019/0067016 A1 | 2/2019 | Zhu et al. |
| 2019/0067085 A1 | 2/2019 | Kweskin |
| 2019/0067094 A1 | 2/2019 | Zope et al. |
| 2019/0067095 A1 | 2/2019 | Zhu et al. |
| 2019/0078206 A1 | 3/2019 | Wu et al. |
| 2019/0080903 A1 | 3/2019 | Abel et al. |
| 2019/0081072 A1 | 3/2019 | Chun et al. |
| 2019/0085451 A1 | 3/2019 | Lei et al. |
| 2019/0086807 A1 | 3/2019 | Kachel et al. |
| 2019/0088555 A1 | 3/2019 | Xie et al. |
| 2019/0089143 A1 | 3/2019 | Malone et al. |
| 2019/0093117 A1 | 3/2019 | Jdira et al. |
| 2019/0096708 A1 | 3/2019 | Sharma |
| 2019/0106788 A1 | 4/2019 | Hawkins et al. |
| 2019/0109002 A1 | 4/2019 | Mattinen et al. |
| 2019/0109009 A1 | 4/2019 | Longrie et al. |
| 2019/0109043 A1 | 4/2019 | Wang et al. |
| 2019/0112711 A1 | 4/2019 | Lyons et al. |
| 2019/0115206 A1 | 4/2019 | Kim et al. |
| 2019/0115237 A1 | 4/2019 | den Hartog Besselink et al. |
| 2019/0115451 A1 | 4/2019 | Lee et al. |
| 2019/0131124 A1 | 5/2019 | Kohen et al. |
| 2019/0140067 A1 | 5/2019 | Zhu et al. |
| 2019/0148177 A1 | 5/2019 | Yin et al. |
| 2019/0148224 A1 | 5/2019 | Kuroda et al. |
| 2019/0148398 A1 | 5/2019 | Kim |
| 2019/0148556 A1 | 5/2019 | Wang et al. |
| 2019/0153593 A1 | 5/2019 | Zhu et al. |
| 2019/0157054 A1 | 5/2019 | White et al. |

(56) References Cited

U.S. PATENT DOCUMENTS

| | | |
|---|---|---|
| 2019/0157067 A1 | 5/2019 | Bhuyan et al. |
| 2019/0163056 A1 | 5/2019 | Maes et al. |
| 2019/0164763 A1 | 5/2019 | Raisanen et al. |
| 2019/0172701 A1 | 6/2019 | Jia et al. |
| 2019/0172714 A1 | 6/2019 | Bobek et al. |
| 2019/0176435 A1 | 6/2019 | Bellman et al. |
| 2019/0181002 A1 | 6/2019 | Iijima et al. |
| 2019/0185999 A1 | 6/2019 | Shanbhag et al. |
| 2019/0189447 A1 | 6/2019 | Kamp et al. |
| 2019/0198297 A1 | 6/2019 | Aramaki et al. |
| 2019/0198359 A1 | 6/2019 | Kamimura et al. |
| 2019/0198571 A1 | 6/2019 | Xu et al. |
| 2019/0204029 A1 | 7/2019 | Tanabe |
| 2019/0211450 A1 | 7/2019 | Adachi et al. |
| 2019/0217277 A1 | 7/2019 | Jeon et al. |
| 2019/0221433 A1 | 7/2019 | Raisanen et al. |
| 2019/0229008 A1 | 7/2019 | Rokkam et al. |
| 2019/0233446 A1 | 8/2019 | MacDonald et al. |
| 2019/0233940 A1 | 8/2019 | Guo et al. |
| 2019/0237325 A1 | 8/2019 | Wang et al. |
| 2019/0237327 A1 | 8/2019 | Kohen et al. |
| 2019/0244803 A1 | 8/2019 | Suzuki |
| 2019/0249300 A1 | 8/2019 | Hatanpaa et al. |
| 2019/0249303 A1 | 8/2019 | Kuroda et al. |
| 2019/0252195 A1 | 8/2019 | Haukka |
| 2019/0252196 A1 | 8/2019 | Vayrynen et al. |
| 2019/0259611 A1 | 8/2019 | Nakano et al. |
| 2019/0259612 A1 | 8/2019 | Nozawa et al. |
| 2019/0264324 A1 | 8/2019 | Shugrue et al. |
| 2019/0271078 A1 | 9/2019 | Raisanen et al. |
| 2019/0272981 A1 | 9/2019 | Xu et al. |
| 2019/0272993 A1 | 9/2019 | Mattinen et al. |
| 2019/0273133 A1 | 9/2019 | Agrawal et al. |
| 2019/0276934 A1 | 9/2019 | Verghese et al. |
| 2019/0287769 A1 | 9/2019 | Blomberg et al. |
| 2019/0295837 A1 | 9/2019 | Pore et al. |
| 2019/0301014 A1 | 10/2019 | Pierreux et al. |
| 2019/0304776 A1 | 10/2019 | Choi |
| 2019/0304780 A1 | 10/2019 | Kohen et al. |
| 2019/0304790 A1 | 10/2019 | Mousa et al. |
| 2019/0304821 A1 | 10/2019 | Pierreux et al. |
| 2019/0311894 A1 | 10/2019 | Girard et al. |
| 2019/0311897 A1 | 10/2019 | Kang et al. |
| 2019/0311940 A1 | 10/2019 | Choi et al. |
| 2019/0318910 A1 | 10/2019 | Mori |
| 2019/0318923 A1 | 10/2019 | Blanquart et al. |
| 2019/0319100 A1 | 10/2019 | Chen et al. |
| 2019/0322812 A1 | 10/2019 | Wojtecki et al. |
| 2019/0330740 A1 | 10/2019 | Klaver |
| 2019/0333753 A1 | 10/2019 | Ueda et al. |
| 2019/0333761 A1 | 10/2019 | Tois et al. |
| 2019/0338418 A1 | 11/2019 | Goradia et al. |
| 2019/0346300 A1 | 11/2019 | Kim et al. |
| 2019/0348261 A1 | 11/2019 | Lin et al. |
| 2019/0348273 A1 | 11/2019 | Tang et al. |
| 2019/0348515 A1 | 11/2019 | Li et al. |
| 2019/0362970 A1 | 11/2019 | Wang et al. |
| 2019/0362989 A1 | 11/2019 | Reuter et al. |
| 2019/0363006 A1 | 11/2019 | Min |
| 2019/0363015 A1 | 11/2019 | Cheng et al. |
| 2019/0368040 A1 | 12/2019 | Kachel et al. |
| 2019/0368041 A1 | 12/2019 | Sreeram et al. |
| 2019/0371594 A1 | 12/2019 | Niskanen et al. |
| 2019/0371640 A1 | 12/2019 | Raisanen et al. |
| 2019/0375638 A1 | 12/2019 | Haukka |
| 2019/0376180 A1 | 12/2019 | Niskanen |
| 2019/0378711 A1 | 12/2019 | Suzuki et al. |
| 2019/0378916 A1 | 12/2019 | Tang et al. |
| 2019/0385907 A1 | 12/2019 | Gottheim et al. |
| 2019/0390338 A1 | 12/2019 | Raisanen et al. |
| 2019/0390343 A1 | 12/2019 | Min et al. |
| 2019/0393304 A1 | 12/2019 | Guillorn et al. |
| 2019/0393308 A1 | 12/2019 | Lo et al. |
| 2020/0002811 A1 | 1/2020 | Sreeram et al. |
| 2020/0002812 A1 | 1/2020 | Lee et al. |
| 2020/0012081 A1 | 1/2020 | Komai |
| 2020/0013612 A1 | 1/2020 | Blanquart et al. |
| 2020/0013613 A1 | 1/2020 | Blanquart |
| 2020/0013626 A1 | 1/2020 | Longrie et al. |
| 2020/0013629 A1 | 1/2020 | de Roest et al. |
| 2020/0018421 A1 | 1/2020 | Shugrue |
| 2020/0035489 A1 | 1/2020 | Huang et al. |
| 2020/0040458 A1 | 2/2020 | Ma et al. |
| 2020/0048768 A1 | 2/2020 | Wiegers et al. |
| 2020/0052056 A1 | 2/2020 | Park et al. |
| 2020/0052089 A1 | 2/2020 | Yu et al. |
| 2020/0056282 A1 | 2/2020 | Raisanen et al. |
| 2020/0056286 A1 | 2/2020 | Shero et al. |
| 2020/0058469 A1 | 2/2020 | Ranjan et al. |
| 2020/0063262 A1 | 2/2020 | Katou et al. |
| 2020/0064737 A1 | 2/2020 | de Roest |
| 2020/0066512 A1 | 2/2020 | Tois et al. |
| 2020/0066552 A1 | 2/2020 | Susa |
| 2020/0080200 A1 | 3/2020 | Um et al. |
| 2020/0083054 A1 | 3/2020 | Väyrynen et al. |
| 2020/0083375 A1 | 3/2020 | Tolle et al. |
| 2020/0083469 A1 | 3/2020 | Lhullier |
| 2020/0102649 A1 | 4/2020 | Reed |
| 2020/0102653 A1 | 4/2020 | Muralidhar et al. |
| 2020/0105579 A1 | 4/2020 | Zhu |
| 2020/0105594 A1 | 4/2020 | Cheng et al. |
| 2020/0105895 A1 | 4/2020 | Tang et al. |
| 2020/0109472 A1 | 4/2020 | Um et al. |
| 2020/0111669 A1 | 4/2020 | Zaitsu et al. |
| 2020/0111690 A1 | 4/2020 | Oosterlaken |
| 2020/0118811 A1 | 4/2020 | Utsuno et al. |
| 2020/0118815 A1 | 4/2020 | Fukazawa et al. |
| 2020/0118817 A1 | 4/2020 | Blomberg et al. |
| 2020/0119038 A1 | 4/2020 | Hopkins et al. |
| 2020/0126771 A1 | 4/2020 | Roh et al. |
| 2020/0126840 A1 | 4/2020 | Roh et al. |
| 2020/0131634 A1 | 4/2020 | Gao et al. |
| 2020/0135512 A1 | 4/2020 | Oosterlaken et al. |
| 2020/0135915 A1 | 4/2020 | Savant et al. |
| 2020/0140995 A1 | 5/2020 | Blanquart et al. |
| 2020/0141003 A1 | 5/2020 | Lee et al. |
| 2020/0144058 A1 | 5/2020 | Kohen |
| 2020/0152473 A1 | 5/2020 | Tapily et al. |
| 2020/0152750 A1 | 5/2020 | Morrow et al. |
| 2020/0161129 A1 | 5/2020 | Mattinen et al. |
| 2020/0161438 A1 | 5/2020 | Tang et al. |
| 2020/0168485 A1 | 5/2020 | Fluit |
| 2020/0279758 A1 | 5/2020 | Sharma |
| 2020/0173020 A1 | 6/2020 | Huggare |
| 2020/0176244 A1 | 6/2020 | Lee et al. |
| 2020/0176246 A1 | 6/2020 | Huotari et al. |
| 2020/0181770 A1 | 6/2020 | Longrie et al. |
| 2020/0185249 A1 | 6/2020 | Rice et al. |
| 2020/0185257 A1 | 6/2020 | Nishiwaki |
| 2020/0194253 A1 | 6/2020 | Banerjee et al. |
| 2020/0194268 A1 | 6/2020 | Sharma |
| 2020/0203157 A1 | 6/2020 | Su |
| 2020/0224309 A1 | 7/2020 | Sreeram et al. |
| 2020/0224311 A1 | 7/2020 | Niskanen et al. |
| 2020/0227243 A1 | 7/2020 | Kim et al. |
| 2020/0227250 A1 | 7/2020 | Pore et al. |
| 2020/0227325 A1 | 7/2020 | Xie et al. |
| 2020/0232096 A1 | 7/2020 | Hatanpää et al. |
| 2020/0234989 A1 | 7/2020 | Jeong |
| 2020/0251328 A1 | 8/2020 | Zaitsu et al. |
| 2020/0258766 A1 | 8/2020 | Garssen et al. |
| 2020/0266057 A1 | 8/2020 | Lee et al. |
| 2020/0266097 A1 | 8/2020 | Liu et al. |
| 2020/0266098 A1 | 8/2020 | Pore et al. |
| 2020/0266208 A1 | 8/2020 | Kim et al. |
| 2020/0270749 A1 | 8/2020 | Li et al. |
| 2020/0270752 A1 | 8/2020 | Pierreux et al. |
| 2020/0273728 A1 | 8/2020 | Benjaminson et al. |
| 2020/0273729 A1 | 8/2020 | Verbaas et al. |
| 2020/0279721 A1 | 9/2020 | White et al. |
| 2020/0283893 A1 | 9/2020 | Byun et al. |
| 2020/0283894 A1 | 9/2020 | Lehn et al. |
| 2020/0284467 A1 | 9/2020 | Lindeboom et al. |
| 2020/0286725 A1 | 9/2020 | Sharma et al. |

(56) References Cited

U.S. PATENT DOCUMENTS

| | | | |
|---|---|---|---|
| 2020/0286726 A1 | 9/2020 | Shero et al. | |
| 2020/0294789 A1 | 9/2020 | Woodruff et al. | |
| 2020/0303180 A1 | 9/2020 | Kim et al. | |
| 2020/0303196 A1 | 9/2020 | Chen et al. | |
| 2020/0309455 A1 | 10/2020 | Fluit | |
| 2020/0312652 A1 | 10/2020 | Kang et al. | |
| 2020/0312681 A1 | 10/2020 | Tanaka et al. | |
| 2020/0318237 A1 | 10/2020 | Fukazawa | |
| 2020/0321209 A1 | 10/2020 | Ishikawa et al. | |
| 2020/0332416 A1 | 10/2020 | Fluit | |
| 2020/0333248 A1* | 10/2020 | Onoda | B01L 3/50273 |
| 2020/0340113 A1 | 10/2020 | Hatanpää et al. | |
| 2020/0340138 A1 | 10/2020 | Tolle et al. | |
| 2020/0343134 A1 | 10/2020 | Kovalgin et al. | |
| 2020/0343358 A1 | 10/2020 | Zhu et al. | |
| 2020/0350193 A1 | 11/2020 | Garssen | |
| 2020/0354836 A1 | 11/2020 | Yednak et al. | |
| 2020/0355296 A1 | 11/2020 | Shugrue et al. | |
| 2020/0357631 A1 | 11/2020 | Ueda | |
| 2020/0365391 A1 | 11/2020 | Blanquart et al. | |
| 2020/0365433 A1 | 11/2020 | de Ridder et al. | |
| 2020/0365434 A1 | 11/2020 | de Ridder | |
| 2020/0365444 A1 | 11/2020 | Hill et al. | |
| 2020/0373152 A1 | 11/2020 | Blanquart | |
| 2020/0385861 A1 | 12/2020 | Deye et al. | |
| 2020/0385867 A1 | 12/2020 | Kim et al. | |
| 2020/0385868 A1 | 12/2020 | Kim et al. | |
| 2020/0395199 A1 | 12/2020 | Miyama | |
| 2020/0395209 A1 | 12/2020 | Yoshimoto et al. | |
| 2020/0395444 A1 | 12/2020 | Lo et al. | |
| 2020/0402846 A1 | 12/2020 | Collins et al. | |
| 2021/0002762 A1 | 1/2021 | Jun et al. | |
| 2021/0005449 A1 | 1/2021 | Blanquart et al. | |
| 2021/0005450 A1 | 1/2021 | Mattinen et al. | |
| 2021/0005723 A1 | 1/2021 | Tang et al. | |
| 2021/0013010 A1 | 1/2021 | Yoshikawa et al. | |
| 2021/0013034 A1 | 1/2021 | Wu et al. | |
| 2021/0013037 A1 | 1/2021 | Sun et al. | |
| 2021/0013042 A1 | 1/2021 | Väyrynen et al. | |
| 2021/0013085 A1 | 1/2021 | Roh et al. | |
| 2021/0020429 A1 | 1/2021 | Khazaka et al. | |
| 2021/0020431 A1 | 1/2021 | Blanquart et al. | |
| 2021/0020432 A1 | 1/2021 | Blanquart | |
| 2021/0020467 A1 | 1/2021 | Sekiguchi | |
| 2021/0020470 A1 | 1/2021 | Lee | |
| 2021/0028021 A1 | 1/2021 | Mousa et al. | |
| 2021/0017648 A1 | 2/2021 | Kubota et al. | |
| 2021/0032754 A1 | 2/2021 | White et al. | |
| 2021/0033977 A1 | 2/2021 | Raaijmakers et al. | |
| 2021/0035785 A1 | 2/2021 | Jeong et al. | |
| 2021/0035786 A1 | 2/2021 | Jeong et al. | |
| 2021/0035802 A1 | 2/2021 | Tolle et al. | |
| 2021/0035824 A1 | 2/2021 | de Ridder | |
| 2021/0035839 A1 | 2/2021 | de Ridder | |
| 2021/0035840 A1 | 2/2021 | de Ridder et al. | |
| 2021/0035841 A1 | 2/2021 | Fluit | |
| 2021/0035842 A1 | 2/2021 | de Ridder | |
| 2021/0035854 A1 | 2/2021 | Yoo et al. | |
| 2021/0040613 A1 | 2/2021 | White et al. | |
| 2021/0040615 A1 | 2/2021 | White et al. | |
| 2021/0043444 A1 | 2/2021 | Blanquart | |
| 2021/0050231 A1 | 2/2021 | Oosterlaken | |
| 2021/0054500 A1 | 2/2021 | Zope et al. | |
| 2021/0054504 A1 | 2/2021 | Wang et al. | |
| 2021/0057214 A1 | 2/2021 | Kengoyama et al. | |
| 2021/0057223 A1 | 2/2021 | Stevens et al. | |
| 2021/0057275 A1 | 2/2021 | Pierreux et al. | |
| 2021/0057570 A1 | 2/2021 | Lin et al. | |
| 2021/0066075 A1 | 3/2021 | Zhang et al. | |
| 2021/0066079 A1 | 3/2021 | Lima et al. | |
| 2021/0066080 A1 | 3/2021 | Mattinen et al. | |
| 2021/0066083 A1 | 3/2021 | Haukka | |
| 2021/0066084 A1 | 3/2021 | Raisanen et al. | |
| 2021/0070783 A1 | 3/2021 | Odedra et al. | |
| 2021/0071296 A1 | 3/2021 | Watarai et al. | |
| 2021/0071298 A1 | 3/2021 | Maes et al. | |
| 2021/0074527 A1 | 3/2021 | Lee et al. | |
| 2021/0082692 A1 | 3/2021 | Kikuchi | |
| 2021/0090878 A1 | 3/2021 | Kang et al. | |
| 2021/0095372 A1 | 4/2021 | Minjauw et al. | |
| 2021/0102289 A1 | 4/2021 | Tsuji et al. | |
| 2021/0102290 A1 | 4/2021 | Acosta et al. | |
| 2021/0102292 A1 | 4/2021 | Lin et al. | |
| 2021/0104384 A1 | 4/2021 | Parkhe | |
| 2021/0104399 A1 | 4/2021 | Kuroda et al. | |
| 2021/0108328 A1 | 4/2021 | Yanagisawa | |
| 2021/0111025 A1 | 4/2021 | Zyulkov et al. | |
| 2021/0111053 A1 | 4/2021 | De Ridder | |
| 2021/0118667 A1 | 4/2021 | Fukazawa et al. | |
| 2021/0118679 A1 | 4/2021 | Lima et al. | |
| 2021/0118687 A1 | 4/2021 | Wang et al. | |
| 2021/0125827 A1 | 4/2021 | Khazaka et al. | |
| 2021/0125832 A1 | 4/2021 | Bhatnagar | |
| 2021/0134588 A1 | 5/2021 | Kohen et al. | |
| 2021/0134959 A1 | 5/2021 | Lima et al. | |
| 2021/0140043 A1 | 5/2021 | Thombare et al. | |
| 2021/0143003 A1 | 5/2021 | Fukuda et al. | |
| 2021/0151315 A1 | 5/2021 | Pierreux et al. | |
| 2021/0151348 A1 | 5/2021 | Utsuno et al. | |
| 2021/0151352 A1 | 5/2021 | Zope et al. | |
| 2021/0156024 A1 | 5/2021 | Roh et al. | |
| 2021/0156030 A1 | 5/2021 | Shugrue | |
| 2021/0159077 A1 | 5/2021 | Longrie et al. | |
| 2021/0166910 A1 | 6/2021 | Kim et al. | |
| 2021/0166924 A1 | 6/2021 | Moon et al. | |
| 2021/0166925 A1 | 6/2021 | Moon et al. | |
| 2021/0166940 A1 | 6/2021 | Nozawa | |
| 2021/0172064 A1 | 6/2021 | Moon | |
| 2021/0175052 A1 | 6/2021 | Takahashi et al. | |
| 2021/0180184 A1 | 6/2021 | Verni et al. | |
| 2021/0180188 A1 | 6/2021 | Kim et al. | |
| 2021/0180189 A1 | 6/2021 | Shugrue et al. | |
| 2021/0181106 A1* | 6/2021 | Shimizu | G01N 21/49 |
| 2021/0193458 A1 | 6/2021 | Salmi et al. | |
| 2021/0199569 A1* | 7/2021 | Hamilton | B29C 66/41 |
| 2021/0205758 A1 | 7/2021 | Kimtee et al. | |
| 2021/0207269 A1 | 7/2021 | Huang et al. | |
| 2021/0207270 A1 | 7/2021 | de Ridder et al. | |
| 2021/0210373 A1 | 7/2021 | Singu et al. | |
| 2021/0214842 A1 | 7/2021 | Yoon et al. | |
| 2021/0225615 A1 | 7/2021 | Yoshida | |
| 2021/0225622 A1 | 7/2021 | Shoji | |
| 2021/0225642 A1 | 7/2021 | Utsuno et al. | |
| 2021/0225643 A1 | 7/2021 | Kuroda et al. | |
| 2021/0230744 A1 | 7/2021 | Kimtee et al. | |
| 2021/0230746 A1 | 7/2021 | Shiba | |
| 2021/0233772 A1 | 7/2021 | Zhu et al. | |
| 2021/0238736 A1 | 8/2021 | Butail et al. | |
| 2021/0238742 A1 | 8/2021 | Susa et al. | |
| 2021/0239614 A1 | 8/2021 | Muralidhar et al. | |
| 2021/0242011 A1 | 8/2021 | Shero et al. | |
| 2021/0246556 A1 | 8/2021 | Mori | |
| 2021/0247693 A1 | 8/2021 | Maes et al. | |
| 2021/0249303 A1 | 8/2021 | Blanquart | |
| 2021/0254216 A1 | 8/2021 | Mori et al. | |
| 2021/0254238 A1 | 8/2021 | Khazaka et al. | |
| 2021/0257213 A1 | 8/2021 | Kikuchi et al. | |
| 2021/0257509 A1 | 8/2021 | Nishiwaki | |
| 2021/0265134 A1 | 8/2021 | Singh et al. | |
| 2021/0265158 A1 | 8/2021 | Kaneko | |
| 2021/0268554 A1 | 9/2021 | Mori | |
| 2021/0269914 A1 | 9/2021 | Väyrynen et al. | |
| 2021/0272821 A1 | 9/2021 | Oosterlaken | |
| 2021/0273109 A1 | 9/2021 | Yamazaki et al. | |
| 2021/0280448 A1 | 9/2021 | Ganguli et al. | |
| 2021/0285102 A1 | 9/2021 | Yoon et al. | |
| 2021/0287878 A1 | 9/2021 | Um et al. | |
| 2021/0287912 A1 | 9/2021 | Shiba et al. | |
| 2021/0287928 A1 | 9/2021 | Kim et al. | |
| 2021/0288476 A1 | 9/2021 | Wei | |
| 2021/0292902 A1 | 9/2021 | Kajbafvala et al. | |
| 2021/0296130 A1 | 9/2021 | Longrie et al. | |
| 2021/0296144 A1 | 9/2021 | Lin et al. | |
| 2021/0310125 A1 | 10/2021 | Ma et al. | |

(56) References Cited

U.S. PATENT DOCUMENTS

| | | | |
|---|---|---|---|
| 2021/0313150 A1 | 10/2021 | Kang et al. | |
| 2021/0313167 A1 | 10/2021 | Pore et al. | |
| 2021/0313170 A1 | 10/2021 | Suzuki | |
| 2021/0313178 A1 | 10/2021 | Nakano | |
| 2021/0313182 A1 | 10/2021 | Zhu et al. | |
| 2021/0317576 A1 | 10/2021 | Väyrynen et al. | |
| 2021/0319982 A1 | 10/2021 | Kim et al. | |
| 2021/0320003 A1 | 10/2021 | Sugiura et al. | |
| 2021/0320010 A1 | 10/2021 | Wang et al. | |
| 2021/0320020 A1 | 10/2021 | Oosterlaken et al. | |
| 2021/0324510 A1 | 10/2021 | Kuwano et al. | |
| 2021/0324518 A1 | 10/2021 | de Ridder | |
| 2021/0327704 A1 | 10/2021 | Kajbafvala et al. | |
| 2021/0327714 A1 | 10/2021 | Lee et al. | |
| 2021/0327715 A1 | 10/2021 | Xie et al. | |
| 2021/0328036 A1 | 10/2021 | Li et al. | |
| 2021/0041284 A1 | 11/2021 | Yednak | |

FOREIGN PATENT DOCUMENTS

| | | | |
|---|---|---|---|
| CN | 2588350 | 11/2003 | |
| CN | 1563483 | 1/2005 | |
| CN | 1655362 | 8/2005 | |
| CN | 1664987 | 9/2005 | |
| CN | 1825535 | 8/2006 | |
| CN | 101047143 | 10/2007 | |
| CN | 101142012 | 3/2008 | |
| CN | 101609858 | 12/2009 | |
| CN | 101681873 | 3/2010 | |
| CN | 101308794 | 9/2010 | |
| CN | 102094183 | 6/2011 | |
| CN | 102383106 | 3/2012 | |
| CN | 103014846 | 4/2013 | |
| CN | 102539019 | 9/2013 | |
| CN | 103515222 | 1/2014 | |
| CN | 102373440 | 7/2014 | |
| CN | 203721699 | 7/2014 | |
| CN | 104244620 | 12/2014 | |
| CN | 104307264 | 1/2015 | |
| CN | 104498895 | 4/2015 | |
| CN | 104517892 | 4/2015 | |
| CN | 204629865 | 9/2015 | |
| CN | 105253917 | 1/2016 | |
| CN | 205448240 | 8/2016 | |
| CN | 104342637 | 2/2017 | |
| CN | 206145834 | 5/2017 | |
| CN | 104233226 | 6/2017 | |
| CN | 106895521 | 6/2017 | |
| CN | 104201108 | 11/2017 | |
| CN | 104630735 | 12/2017 | |
| CN | 107675144 | 2/2018 | |
| CN | 108389798 | 8/2018 | |
| CN | 106011785 | 10/2018 | |
| CN | 108910843 | 11/2018 | |
| CN | 109000352 | 12/2018 | |
| CN | 109342375 A * | 2/2019 | ............. G01N 21/59 |
| DE | 8902307 | 8/1989 | |
| DE | 3836696 | 12/1989 | |
| DE | 3626724 | 6/1994 | |
| DE | 10133013 | 1/2003 | |
| DE | 102008052750 | 6/2009 | |
| EP | 0058571 | 8/1982 | |
| EP | 0499004 | 8/1992 | |
| EP | 0634785 | 1/1995 | |
| EP | 0550058 | 11/1998 | |
| EP | 0887632 | 12/1998 | |
| EP | 678909 | 7/1999 | |
| EP | 1061567 | 12/2000 | |
| EP | 1889817 | 2/2008 | |
| EP | 2036600 | 3/2009 | |
| EP | 2426233 | 7/2012 | |
| FR | 686869 | 7/1930 | |
| FR | 1408266 | 8/1965 | |
| FR | 2233614 | 1/1975 | |
| FR | 2517790 | 6/1983 | |
| FR | 2610007 | 8/1990 | |
| FR | 2708624 | 2/1995 | |
| GB | 400010 | 10/1933 | |
| GB | 752-277 | 7/1956 | |
| GB | 1186889 | 6/1966 | |
| GB | 1514921 | 6/1978 | |
| GB | 2051875 | 1/1981 | |
| JP | 58-19462 | 4/1983 | |
| JP | S5979545 | 5/1984 | |
| JP | S59127847 | 7/1984 | |
| JP | 59-211779 | 11/1984 | |
| JP | S60110133 | 6/1985 | |
| JP | 61038863 | 2/1986 | |
| JP | S62237236 | 10/1987 | |
| JP | S63136532 | 6/1988 | |
| JP | H0165766 | 6/1989 | |
| JP | H01185176 | 7/1989 | |
| JP | H01-296613 | 11/1989 | |
| JP | H01-307229 | 12/1989 | |
| JP | H01313954 | 12/1989 | |
| JP | H02-93071 | 4/1990 | |
| JP | H02-185038 | 7/1990 | |
| JP | H02-217469 | 8/1990 | |
| JP | H03-044472 | 2/1991 | |
| JP | H03-155625 | 7/1991 | |
| JP | H03211753 | 9/1991 | |
| JP | H03-248427 | 11/1991 | |
| JP | H04-29313 | 1/1992 | |
| JP | H04-115531 | 4/1992 | |
| JP | H05-6880 | 1/1993 | |
| JP | H05-23079 | 3/1993 | |
| JP | H05-118928 | 5/1993 | |
| JP | H05-171446 | 7/1993 | |
| JP | H05-291142 | 11/1993 | |
| JP | H06-053210 | 2/1994 | |
| JP | H06-84888 | 3/1994 | |
| JP | H06-140399 | 5/1994 | |
| JP | H0616433 | 6/1994 | |
| JP | 6204231 | 7/1994 | |
| JP | H06-319177 | 11/1994 | |
| JP | H06-338497 | 12/1994 | |
| JP | H07-29836 | 1/1995 | |
| JP | H07-297271 | 1/1995 | |
| JP | H07-066267 | 3/1995 | |
| JP | H07-74162 | 3/1995 | |
| JP | H07-109576 | 4/1995 | |
| JP | H07-034936 | 8/1995 | |
| JP | H07-225214 | 8/1995 | |
| JP | 7-272694 | 10/1995 | |
| JP | H07-283149 | 10/1995 | |
| JP | H07-209093 | 11/1995 | |
| JP | H08-181135 | 7/1996 | |
| JP | H08-335558 | 12/1996 | |
| JP | H09-064149 | 3/1997 | |
| JP | 9-89676 | 4/1997 | |
| JP | H09-148322 | 6/1997 | |
| JP | H10-41096 | 2/1998 | |
| JP | H10-50635 | 2/1998 | |
| JP | H10-50800 | 2/1998 | |
| JP | H10-064696 | 3/1998 | |
| JP | H10-153494 | 6/1998 | |
| JP | H10-227703 | 8/1998 | |
| JP | H10-0261620 | 9/1998 | |
| JP | H11-097163 | 4/1999 | |
| JP | H11-118615 | 4/1999 | |
| JP | H11-183264 | 7/1999 | |
| JP | H11-183265 | 7/1999 | |
| JP | H11-195688 | 7/1999 | |
| JP | H11-287715 | 10/1999 | |
| JP | 2000068355 | 3/2000 | |
| JP | 2000182949 | 6/2000 | |
| JP | 2000269163 | 9/2000 | |
| JP | 2001015698 | 1/2001 | |
| JP | 2001023872 | 1/2001 | |
| JP | 2001207265 | 7/2001 | |
| JP | 2001207268 | 7/2001 | |
| JP | 2001210602 | 8/2001 | |
| JP | 2001220677 | 8/2001 | |
| JP | 2001257199 | 9/2001 | |

(56) References Cited

FOREIGN PATENT DOCUMENTS

| | | |
|---|---|---|
| JP | 2001287180 | 10/2001 |
| JP | 2002118066 | 4/2002 |
| JP | 2002164342 | 6/2002 |
| JP | 2002170781 | 6/2002 |
| JP | 2002237375 | 8/2002 |
| JP | 2003035574 | 2/2003 |
| JP | 2003053688 | 2/2003 |
| JP | 2003133300 | 5/2003 |
| JP | 2003153706 | 5/2003 |
| JP | 2003303814 | 10/2003 |
| JP | 2004014952 | 1/2004 |
| JP | 2004023043 | 1/2004 |
| JP | 2004088077 | 3/2004 |
| JP | 2004091848 | 3/2004 |
| JP | 2004113270 | 4/2004 |
| JP | 2004128019 | 4/2004 |
| JP | 2004134553 | 4/2004 |
| JP | 2004163293 | 6/2004 |
| JP | 2004244298 | 9/2004 |
| JP | 2004244661 | 9/2004 |
| JP | 2005033221 | 9/2004 |
| JP | 2004294638 | 10/2004 |
| JP | 3589954 | 11/2004 |
| JP | 2004310019 | 11/2004 |
| JP | 2005033221 | 2/2005 |
| JP | 2005079254 | 3/2005 |
| JP | 2005507030 | 3/2005 |
| JP | 2005172489 | 6/2005 |
| JP | 3725100 | 12/2005 |
| JP | 2006028572 | 2/2006 |
| JP | 2006049352 | 2/2006 |
| JP | 2006059931 | 3/2006 |
| JP | 2006090762 | 4/2006 |
| JP | 2006124831 | 5/2006 |
| JP | 2006124832 | 5/2006 |
| JP | 2006153706 | 6/2006 |
| JP | 2006186271 | 7/2006 |
| JP | 2006188729 | 7/2006 |
| JP | 2006278058 | 10/2006 |
| JP | 2006319261 | 11/2006 |
| JP | 2007027777 | 2/2007 |
| JP | 2007287902 | 11/2007 |
| JP | 3140111 | 3/2008 |
| JP | 2008060304 | 3/2008 |
| JP | 2008066159 | 3/2008 |
| JP | 2008085129 | 4/2008 |
| JP | 2008089320 | 4/2008 |
| JP | 2008172083 | 7/2008 |
| JP | 2008198629 | 8/2008 |
| JP | 2008202107 | 9/2008 |
| JP | 2009016815 | 1/2009 |
| JP | 2009088421 | 4/2009 |
| JP | 2009099938 | 5/2009 |
| JP | 2009194248 | 8/2009 |
| JP | 2009239082 | 10/2009 |
| JP | 2009251216 | 10/2009 |
| JP | 2009252851 | 10/2009 |
| JP | 2010067940 | 3/2010 |
| JP | 2010097834 | 4/2010 |
| JP | 2010205967 | 9/2010 |
| JP | 2010251444 | 10/2010 |
| JP | 2010255218 | 11/2010 |
| JP | 2011049592 | 3/2011 |
| JP | 2011162830 | 8/2011 |
| JP | 2011181681 | 9/2011 |
| JP | 2009010412 | 2/2012 |
| JP | 2012146939 | 8/2012 |
| JP | 2012164736 | 8/2012 |
| JP | 2012195513 | 10/2012 |
| JP | 2013026479 | 2/2013 |
| JP | 2013196822 | 9/2013 |
| JP | 2013235912 | 11/2013 |
| JP | D1422467 | 8/2014 |
| JP | 2014222693 | 11/2014 |
| JP | 2015021175 | 2/2015 |
| JP | 2015115461 | 6/2015 |
| JP | 2016098406 | 5/2016 |
| JP | 2010123843 | 6/2016 |
| JP | 2016174158 | 9/2016 |
| JP | 2017183242 | 10/2017 |
| JP | 2017220011 | 12/2017 |
| JP | 6519897 | 5/2019 |
| KR | 1998-0026850 | 7/1998 |
| KR | 20000000946 | 1/2000 |
| KR | 10-0253664 | 4/2000 |
| KR | 10-2000-0031098 | 6/2000 |
| KR | 10-2000-0045257 | 7/2000 |
| KR | 100273261 | 12/2000 |
| KR | 10-0295043 | 4/2001 |
| KR | 10-2002-0027695 | 4/2002 |
| KR | 10-2002-0064028 | 8/2002 |
| KR | 2002-0086763 | 11/2002 |
| KR | 10-0377095 | 3/2003 |
| KR | 2003-0092305 | 12/2003 |
| KR | 10-2005-0054122 | 6/2005 |
| KR | 10-0547248 | 1/2006 |
| KR | 10-0593960 | 6/2006 |
| KR | 10-2006-0129566 | 12/2006 |
| KR | 10-0688484 | 2/2007 |
| KR | 20070041701 | 4/2007 |
| KR | 10-2007-0079797 | 8/2007 |
| KR | 10-2007-0084683 | 8/2007 |
| KR | 10-2007-0117817 | 12/2007 |
| KR | 2008-0058620 | 6/2008 |
| KR | 10-2009-0039936 | 4/2009 |
| KR | 10-2009-0055443 | 6/2009 |
| KR | 10-2009-0056475 | 6/2009 |
| KR | 10-2009-0086790 | 8/2009 |
| KR | 10-2009-0105977 | 10/2009 |
| KR | 10-0936694 | 1/2010 |
| KR | 10-2010-0015073 | 2/2010 |
| KR | 10-2010-0020834 | 2/2010 |
| KR | 10-2010-0032812 | 3/2010 |
| KR | 10-2010-0077442 | 7/2010 |
| KR | 10-2010-0079920 | 7/2010 |
| KR | 10-2010-0122701 | 11/2010 |
| KR | 10-2010-0132779 | 12/2010 |
| KR | 10-2011-0058534 | 6/2011 |
| KR | 10-1114219 | 3/2012 |
| KR | 10-2012-0111060 | 10/2012 |
| KR | 10-2013-0007806 | 1/2013 |
| KR | 10-2013-0067600 | 6/2013 |
| KR | 10-2013-0129149 | 11/2013 |
| KR | 10-1347962 | 1/2014 |
| KR | 10-1491726 | 2/2015 |
| KR | 10-1535573 | 7/2015 |
| KR | 101758892 | 7/2017 |
| KR | 10-2019-0032077 | 3/2019 |
| NL | 8600255 | 9/1987 |
| NL | 8701549 | 2/1989 |
| RU | 1786406 | 1/1993 |
| SU | 494614 | 2/1976 |
| SU | 1408319 | 7/1988 |
| TW | 538327 | 6/2003 |
| TW | 540093 | 7/2003 |
| TW | M292692 | 6/2006 |
| TW | 200731357 | 8/2007 |
| TW | 200903625 | 1/2009 |
| TW | 201213596 | 4/2012 |
| TW | 201234453 | 8/2012 |
| TW | 201247690 | 12/2012 |
| TW | M446412 | 2/2013 |
| TW | 201330086 | 7/2013 |
| TW | D162593 | 8/2014 |
| TW | D164568 | 12/2014 |
| TW | 201531587 | 8/2015 |
| TW | M512254 | 11/2015 |
| TW | I514509 | 12/2015 |
| TW | 201613231 | 4/2016 |
| TW | M553518 | 12/2017 |
| TW | D196097 | 2/2019 |
| WO | 1987001508 | 3/1987 |
| WO | 1990004045 | 4/1990 |
| WO | 1991004522 | 4/1991 |

(56) References Cited

FOREIGN PATENT DOCUMENTS

| | | |
|---|---|---|
| WO | 1991006975 | 5/1991 |
| WO | 1992000477 | 1/1992 |
| WO | 1994027315 | 11/1994 |
| WO | 1996017107 | 6/1996 |
| WO | 1997003223 | 1/1997 |
| WO | 1998032893 | 7/1998 |
| WO | 1999023690 | 5/1999 |
| WO | DM/048579 | 7/1999 |
| WO | 2004008491 | 7/2002 |
| WO | 2004007800 | 1/2004 |
| WO | 2004008827 | 1/2004 |
| WO | 2004010467 | 1/2004 |
| WO | 2004106584 | 12/2004 |
| WO | 2005112082 | 11/2005 |
| WO | 2006035281 | 4/2006 |
| WO | 2006054854 | 5/2006 |
| WO | 2006056091 | 6/2006 |
| WO | 2006078666 | 7/2006 |
| WO | 2006080782 | 8/2006 |
| WO | 2006097525 | 9/2006 |
| WO | 2006101857 | 9/2006 |
| WO | 2006114781 | 11/2006 |
| WO | 2007024720 | 3/2007 |
| WO | 2007027165 | 3/2007 |
| WO | 2007076195 | 7/2007 |
| WO | 2007088940 | 8/2007 |
| WO | 2007117718 | 10/2007 |
| WO | 2007131051 | 11/2007 |
| WO | 2007140376 | 12/2007 |
| WO | 2008045972 | 4/2008 |
| WO | 2008091900 | 7/2008 |
| WO | 2008121463 | 10/2008 |
| WO | 2008147731 | 12/2008 |
| WO | 2009028619 | 3/2009 |
| WO | 2009029532 | 3/2009 |
| WO | 2009039251 | 3/2009 |
| WO | 2009099776 | 8/2009 |
| WO | 2009154889 | 12/2009 |
| WO | 2009154896 | 12/2009 |
| WO | 2010039363 | 4/2010 |
| WO | 2010077533 | 7/2010 |
| WO | 2010100702 | 9/2010 |
| WO | 2010110558 | 9/2010 |
| WO | 2010118051 | 10/2010 |
| WO | 2010129428 | 11/2010 |
| WO | 2010129430 | 11/2010 |
| WO | 2010129431 | 11/2010 |
| WO | 2011019950 | 2/2011 |
| WO | 2011149640 | 12/2011 |
| WO | 2012056592 | 5/2012 |
| WO | 2012077590 | 6/2012 |
| WO | 2013043330 | 3/2013 |
| WO | 2013078065 | 5/2013 |
| WO | 2013078066 | 5/2013 |
| WO | 2013177269 | 11/2013 |
| WO | 2014107290 | 7/2014 |
| WO | 2015026230 | 2/2015 |
| WO | 2015107009 | 7/2015 |
| WO | 2015112728 | 7/2015 |
| WO | 2015127614 | 9/2015 |
| WO | 2016019795 | 2/2016 |
| WO | 2018109553 | 6/2016 |
| WO | 2018109554 | 6/2016 |
| WO | 2017108713 | 6/2017 |
| WO | 2017108714 | 6/2017 |
| WO | 2017125401 | 7/2017 |
| WO | 2017212546 | 12/2017 |
| WO | 2018003072 | 1/2018 |
| WO | 2018008088 | 1/2018 |
| WO | 2018013778 | 1/2018 |
| WO | 2018020316 | 2/2018 |
| WO | 2018020318 | 2/2018 |
| WO | 2018020320 | 2/2018 |
| WO | 2018020327 | 2/2018 |
| WO | 2018105349 | 6/2018 |
| WO | 2018109551 | 6/2018 |
| WO | 2018109552 | 6/2018 |
| WO | 2018178771 | 10/2018 |
| WO | 2019030565 | 2/2019 |
| WO | 2019103610 | 5/2019 |
| WO | 2019103613 | 5/2019 |
| WO | 2019142055 | 7/2019 |
| WO | 2019158960 | 8/2019 |
| WO | 2019214578 | 11/2019 |
| WO | 2019217749 | 11/2019 |
| WO | WO-2019221191 A1 * 11/2019 ............. C30B 15/10 |
| WO | 2019229537 | 12/2019 |
| WO | 2020002995 | 1/2020 |
| WO | 2020003000 | 1/2020 |
| WO | 2020118100 | 6/2020 |
| WO | 2021072042 | 4/2021 |

OTHER PUBLICATIONS

CNIPA; Office Action dated Jan. 10, 2013 in Application No. 201080015699.9.
CNIPA; Office Action dated Aug. 1, 2013 in Application No. 201080015699.9.
CNIPA; Office Action dated Jan. 21, 2014 in Application No. 201080015699.9.
CNIPA; Office Action dated Jul. 25, 2014 in Application No. 201080015699.9.
CNIPA; Office Action dated Jan. 12, 2015 in Application No. 201080015699.9.
CNIPA; Notice of Allowance dated May 8, 2015 in Application No. 201080015699.9.
CNIPA; Office Action dated Dec. 10, 2013 in Application No. 201080020267.7.
CNIPA; Notice of Allowance dated Aug. 22, 2014 in Application No. 201080020267.7.
CNIPA; Office Action dated Jan. 21, 2013 in Application No. 201080020268.1.
CNIPA; Office Action dated Sep. 26, 2013 in Application No. 201080020268.1.
CNIPA; Office Action dated Apr. 3, 2014 in Application No. 201080020268.1.
CNIPA; Office Action dated Sep. 23, 2014 in Application No. 201080020268.1.
CNIPA; Office Action dated Apr. 7, 2015 in Application No. 201080020268.1.
CNIPA; Notice of Allowance dated Oct. 16, 2015 in Application No. 201080020268.1.
CNIPA; Office Action dated May 24, 2013 in Application No. 201080036764.6.
CNIPA; Office Action dated Jan. 2, 2014 in Application No. 201080036764.6.
CNIPA; Office Action dated Jul. 1, 2014 in Application No. 201080036764.6.
CNIPA; Notice of Allowance dated Oct. 24, 2014 in Application No. 201080036764.6.
CNIPA; Office Action dated Feb. 8, 2014 in Application No. 201110155056.0.
CNIPA; Office Action dated Sep. 16, 2014 in Application No. 201110155056.0.
CNIPA; Office Action dated Feb. 9, 2015 in Application No. 201110155056.0.
CNIPA; Notice of Allowance dated Aug. 26, 2015 in Application No. 201110155056.0.
CNIPA; Office Action dated Dec. 4, 2015 in Application No. 201210201995.9.
CNIPA; Office Action dated Jul. 14, 2016 in Application No. 201210201995.9.
CNIPA; Office Action dated Jan. 20, 2017 in Application No. 201210201995.9.
CNIPA; Notice of Allowance dated Apr. 13, 2017 in Application No. 201210201995.9.
CNIPA; Office Action dated Dec. 24, 2015 in Application No. 201280057466.4.

(56) References Cited

OTHER PUBLICATIONS

CNIPA; Notice of Allowance dated Jun. 16, 2016 in Application No. 201280057466.4.
CNIPA; Office Action dated Dec. 4, 2015 in Application No. 201280057542.1.
CNIPA; Office Action dated May 16, 2016 in Application No. 201280057542.1.
CNIPA; Office Action dated Sep. 9, 2016 in Application No. 201280057542.1.
CNIPA; Notice of Allowance dated Jan. 3, 2017 in Application No. 201280057542.1.
CNIPA; Office Action dated Dec. 5, 2016 in Application No. 201310412808.6.
CNIPA; Notice of Allowance dated Jul. 20, 2017 in Application No. 201310412808.6.
CNIPA; Office Action dated Feb. 5, 2018 in Application No. 201410331047.6.
CNIPA; Office Action dated Dec. 14, 2018 in Application No. 201410331047.6.
CNIPA; Notice of Allowance dated Jun. 14, 2019 in Application No. 201410331047.6.
CNIPA; Office Action dated Oct. 19, 2018 in Application No. 201510765170.3.
CNIPA; Office Action dated Jun. 28, 2019 in Application No. 201510765170.3.
CNIPA; Notice of Allowance dated Sep. 30, 2019 in Application No. 201510765170.3.
CNIPA; Office Action dated Oct. 31, 2018 in Application No. 201510765406.3.
CNIPA; Office Action dated Jun. 28, 2019 in Application No. 201510765406.3.
CNIPA; Notice of Allowance dated Dec. 27, 2019 in Application No. 201510765406.3.
CNIPA; Office Action dated Jan. 21, 2020 in Application No. 201610028064.1.
CNIPA; Notice of Allowance dated May 22, 2020 in Application No. 201610028064.1.
CNIPA; Office Action dated Mar. 26, 2020 in Application No. 201610131743.1.
CNIPA; Office Action dated Oct. 16, 2020 in Application No. 201610131743.1.
CNIPA; Office Action dated Mar. 14, 2019 in Application No. 201610141027.1.
CNIPA; Notice of Allowance dated Sep. 3, 2019 in Application No. 201610141027.1.
CNIPA; Office Action dated Jul. 23, 2019 in Application No. 201610897958.4.
CNIPA; Office Action dated Feb. 28, 2020 in Application No. 201610897958.4.
CNIPA; Office Action dated Jun. 16, 2020 in Application No. 201610897958.4.
CNIPA; Office Action dated Nov. 4, 2019 in Application No. 201610898822.5.
CNIPA; Office Action dated Jul. 3, 2020 in Application No. 201610898822.5.
CNIPA; Notice of Allowance dated Oct. 9, 2020 in Application No. 201610898822.5.
CNIPA; Office Action dated May 18, 2020 in Application No. 201610982040.X.
CNIPA; Office Action dated May 29, 2020 in Application No. 201710131319.1.
CNIPA; Office Action dated Jun. 1, 2020 in Application No. 201710173292.2.
CNIPA; Notice of Allowance dated Nov. 4, 2020 in Application No. 201710173292.2.
CNIPA; Office Action dated Dec. 20, 2018 in Application No. 201710738549.4.
CNIPA; Office Action dated Jun. 20, 2019 in Application No. 201711120632.1.
CNIPA; Notice of Allowance dated May 25, 2017 in Application No. 201730010308.9.
CNIPA; Office Action dated Aug. 31, 2020 in Application No. 201780044761.9.
CNIPA; Office Action dated Nov. 11, 2019 in Application No. 201810379112.0.
CNIPA; Office Action dated Apr. 27, 2020 in Application No. 201810379112.0.
CNIPA; Office Action dated Apr. 27, 2020 in Application No. 201810836604.8.
CNIPA; Office Action dated Jul. 30, 2020 in Application No. 201810836604.8.
CNIPA; Office Action dated Apr. 22, 2020 in Application No. 201810994464.7.
CNIPA; Notice of Allowance dated Oct. 24, 2018 in Application No. 201830060972.9.
CNIPA; Notice of Allowance dated Nov. 1, 2018 in Application No. 201830397219.9.
CNIPA; Notice of Allowance dated May 14, 2020 in Application No. 201930615780.4.
CNIPA; Notice of Allowance dated Apr. 27, 2020 in Application No. 201930660355.7.
CNIPA; Notice of Allowance dated Jun. 2, 2020 in Application No. 202030048819.1.
CNIPA; Notice of Allowance dated May 15, 2020 in Application No. 202030048854.3.
CNIPA; Notice of Allowance dated May 15, 2020 in Application No. 202030053560.X.
CNIPA; Notice of Allowance dated Aug. 7, 2020 in Application No. 202030053609.1.
CNIPA; Notice of Allowance dated May 20, 2020 in Application No. 202030053634.X.
EPO; Office Action dated Jul. 29, 2008 in Application No. 00902194.0.
EPO; Supplementary European Search Report and Opinion dated Nov. 9, 2012 in Application No. 08798519.8.
EPO; Office Action dated Jul. 18, 2016 in Application No. 08798519.8.
EPO; Extended European Search Report dated Dec. 9, 2016 in Application No. 09767208.3.
EPO; Office Action dated Aug. 10, 2018 in Application No. 09767208.3.
EPO; Notice of Allowance dated Aug. 1, 2019 in Application No. 09767208.3.
EPO; Office Action dated Jun. 27, 2003 in Application No. 97929595.3.
EPO; Office Action dated Feb. 18, 2004 in Application No. 97929595.3.
EPO; Notice of Allowance dated Apr. 29, 2004 in Application No. 97929595.3.
EPO; Supplementary European Search Report and Opinion dated Jan. 5, 2017 in Application No. 09836647.9.
EPO; Office Action dated Feb. 28, 2018 in Application No. 09836647.9.
EPO; Office Action dated Jan. 11, 2019 in Application No. 09836647.9.
EPO; Notice of Allowance dated Oct. 16, 2019 in Application No. 09836647.9.
EPO; Notice of Allowance dated Jan. 10, 2001 in Application No. 98911263.6.
EPO; Office Action dated Jun. 6, 2001 in Application No. 98911277.6.
EPO; Office Action dated Jun. 27, 2003 in Application No. 98967122.7.
EPO; Notice of Allowance dated Feb. 23, 2004 in Application No. 98967122.7.
EPO; Office Action dated Sep. 22, 2003 in Application No. 99946447.2.
EPO; Office Action dated Nov. 25, 2003 in Application No. 99946447.2.
EPO; Office Action dated Mar. 30, 2004 in Application No. 99946447.2.

(56) References Cited

OTHER PUBLICATIONS

EPO; Office Action dated Jul. 19, 2004 in Application No. 99946447.2.
EPO; Notice of Allowance dated Sep. 22, 2004 in Application No. 99946447.2.
EPO; Supplementary European Search Report dated May 27, 2002 in Application No. 99973123.
EPO; Notice of Allowance dated Jun. 11, 2004 in Application No. 99973123.
EPO; Extended European Search Report dated Apr. 28, 2014 in Application No. 11162225.4.
EPO; Notice of Allowance dated Feb. 3, 2015 in Application No. 11162225.4.
EPO; Extended European Search Report dated Nov. 29, 2019 in Application No. 19188826.2.
EPO; Extended European Search Report dated Mar. 3, 2020 in Application No. 19205558.0.
IPOS; Notice of Allowance dated Aug. 14, 2017 in Application No. 10201401237.
JPO; Office Action dated Aug. 10, 2009 in Application No. 2003029767.
JPO; Office Action dated Apr. 13, 2010 in Application No. 2003029767.
JPO; Notice of Allowance dated Jun. 24, 2010 in Application No. 2003029767.
JPO; Office Action dated Oct. 30, 2008 in Application No. 2004558313.
JPO; Office Action dated Feb. 19, 2009 in Application No. 2004558313.
JPO; Notice of Allowance dated Jun. 30, 2009 in Application No. 2004558313.
JPO; Office Action dated Mar. 16, 2012 in Application No. 2009-532567.
JPO; Notice of Allowance dated Jul. 23, 2012 in Application No. 2009-532567.
JPO; Notice of Allowance dated Mar. 29, 2013 in Application No. 2010-509478.
JPO; Office Action dated Dec. 20, 2011 in Application No. 2010-522075.
JPO; Office Action dated Apr. 11, 2012 in Application No. 2010-522075.
JPO; Office Action dated May 15, 2013 in Application No. 2010058415.
JPO; Office Action dated Oct. 30, 2013 in Application No. 2010058415.
JPO; Office Action dated Aug. 7, 2014 in Application No. 2010058415.
JPO; Notice of Allowance dated Dec. 18, 2014 in Application No. 2010058415.
JPO; Office Action dated Aug. 22, 2013 in Application No. 2010-153754.
JPO; Office Action dated Oct. 30, 2013 in Application No. 2010-193285.
JPO; Office Action dated Aug. 26, 2015 in Application No. 2011-284831.
JPO; Notice of Allowance dated Mar. 3, 2016 in Application No. 2011-284831.
JPO; Office Action dated May 31, 2012 in Application No. 2011-514650.
JPO; Office Action dated Sep. 11, 2012 in Application No. 2011-514650.
JPO; Notice of Allowance dated Dec. 10, 2012 in Application No. 2011-514650.
JPO; Office Action dated Dec. 10, 2014 in Application No. 2011090067.
JPO; Notice of Allowance dated Apr. 28, 2015 in Application No. 2011090067.
JPO; Office Action dated Jul. 14, 2016 in Application No. 2012-153698.
JPO; Notice of Allowance dated Oct. 21, 2016 in Application No. 2012-153698.
JPO; Office Action dated Dec. 20, 2013 in Application No. 2012-504786.
JPO; Office Action dated Jan. 25, 2014 in Application No. 2012-504786.
JPO; Office Action dated Dec. 1, 2014 in Application No. 2012-504786.
JPO; Notice of Allowance dated Jun. 12, 2015 in Application No. 2012504786.
JPO; Office Action dated Mar. 11, 2013 in Application No. 2012-509857.
JPO; Notice of Allowance dated Jun. 29, 2013 in Application No. 2012-509857.
JPO; Office Action dated May 19, 2017 in Application No. 2013-160173.
JPO; Notice of Allowance dated Aug. 23, 2017 in Application No. 2013-160173.
JPO; Office Action dated Aug. 14, 2017 in Application No. 2013-178344.
JPO; Office Action dated Jan. 23, 2018 in Application No. 2013-178344.
JPO; Notice of Allowance dated Jul. 24, 2018 in Application No. 2013-178344.
JPO; Office Action dated Apr. 3, 2018 in Application No. 2014-120675.
JPO; Notice of Allowance dated Jun. 6, 2018 in Application No. 2014-120675.
JPO; Office Action dated Mar. 28, 2018 in Application No. 2014-188835.
JPO; Notice of Allowance dated Jun. 6, 2018 in Application No. 2014-188835.
JPO; Office Action dated Apr. 12, 2018 in Application No. 2014-205548.
JPO; Notice of Allowance dated Dec. 19, 2019 in Application No. 2014205548.
JPO; Notice of Allowance dated May 14, 2018 in Application No. 2014-216540.
JPO; Office Action dated Jul. 20, 2018 in Application No. 2015-034774.
JPO; Office Action dated Jun. 27, 2019 in Application No. 2015034774.
JPO; Notice of Allowance dated Nov. 20, 2019 in Application No. 2015034774.
JPO; Office Action dated Jan. 30, 19 in Application No. 2015052198.
JPO; Notice of Allowance dated Apr. 5, 19 in Application No. 2015052198.
JPO; Office Action dated Aug. 29, 2019 in Application No. 2016001928.
JPO; Notice of Allowance dated Dec. 17, 2019 in Application No. 2016001928.
JPO; Office Action dated Jun. 1, 2020 in Application No. 2016-206625.
JPO; Office Action dated Aug. 28, 2020 in Application No. 2017-139817.
JPO; Notice of Allowance dated Jul. 1, 2020 in Application No. 2019-025168.
JPO; Office Action dated Aug. 24, 2020 in Application No. 2019-119908.
JPO; Office Action dated Jun. 29, 2020 in Application No. 2020-502653.
KIPO; Office Action dated Dec. 10, 2015 in Application No. 10-2010-0028336.
KIPO; Office Action dated Jun. 29, 2016 in Application No. 10-2010-0028336.
KIPO; Notice of Allowance dated Sep. 29, 2016 in Application No. 10-2010-0028336.
KIPO; Office Action dated Mar. 3, 2016 in Application No. 10-2010-0067768.
KIPO; Office Action dated Aug. 1, 2016 in Application No. 10-2010-0067768.
KIPO; Notice of Allowance dated Dec. 1, 2016 in Application No. 10-2010-0067768.
KIPO; Office Action dated May 2, 2016 in Application No. 10-2010-0082446.
KIPO; Office Action dated Sep. 19, 2016 in Application No. 10-2010-0082446.
KIPO; Notice of Allowance dated Mar. 7, 2017 in Application No. 10-2010-0082446.
KIPO; Office Action dated Mar. 13, 2017 in Application No. 20110034612.
KIPO; Office Action dated Jul. 20, 2017 in Application No. 20110034612.

(56) References Cited

OTHER PUBLICATIONS

KIPO; Notice of Allowance dated Sep. 1, 2017 in Application No. 20110034612.
KIPO; Office Action dated Nov. 24, 2017 in Application No. 10-2011-0036449.
KIPO; Office Action dated May 23, 2017 in Application No. 10-2011-0036449.
KIPO; Office Action dated Apr. 2, 2018 in Application No. 10-2011-0036449.
KIPO; Notice of Allowance dated Oct. 24, 2018 in Application No. 10-2011-0036449.
KIPO; Office Action dated Sep. 4, 2017 in Application No. 10-2011-0087600.
KIPO; Notice of Allowance dated Jan. 11, 2018 in Application No. 10-2011-0087600.
KIPO; Office Action dated Oct. 23, 2017 in Application No. 10-2011-0142924.
KIPO; Notice of Allowance dated Mar. 14, 2018 in Application No. 10-2011-0142924.
KIPO; Office Action dated Dec. 11, 2015 in Application No. 10-2011-7023416.
KIPO; Office Action dated Mar. 13, 2016 in Application No. 10-2011-7023416.
KIPO; Notice of Allowance dated 6/2/0216 in Application No. 10-2011-7023416.
KIPO; Office Action dated Oct. 30, 2017 in Application No. 10-2012-0041878.
KIPO; Notice of Allowance dated Feb. 28, 2018 in Application No. 10-2012-0041878.
KIPO; Office Action dated Mar. 21, 2018 in Application No. 10-2012-0042518.
KIPO; Notice of Allowance dated May 30, 2018 in Application No. 10-2012-0042518.
KIPO; Office Action dated Mar. 21, 2018 in Application No. 10-2012-0064526.
KIPO; Office Action dated Sep. 18, 2018 in Application No. 10-2012-0064526.
KIPO; Office Action dated Dec. 13, 2018 in Application No. 10-2012-0064526.
KIPO; Office Action dated Jan. 12, 2019 in Application No. 10-2012-0064526.
KIPO; Notice of Allowance dated Jul. 5, 2019 in Application No. 10-2012-0064526.
KIPO; Office Action dated Mar. 30, 2018 in Application No. 10-2012-0076564.
KIPO; Office Action dated Sep. 27, 2018 in Application No. 10-2012-0076564.
KIPO; Office Action dated Mar. 27, 2019 in Application No. 10-2012-0076564.
KIPO; Decision of Intellectual Property Trial and Appeal Board dated Jun. 23, 2020 in Application No. 10-2012-0076564.
KIPO; Office Action dated Apr. 30, 2018 in Application No. 10-2012-0103114.
KIPO; Notice of Allowance dated Nov. 22, 2018 in Application No. 10-2012-0103114.
KIPO; Office Action dated Oct. 24, 2016 in Application No. 10-2012-7004062.
KIPO; Office Action dated Jul. 24, 2017 in Application No. 10-2012-7004062.
KIPO; Decision of Intellectual Property Trial and Appeal Board dated May 13, 2019 in Application No. 10-2012-7004062.
KIPO; Office Action dated May 30, 2019 in Application No. 10-2012-7004062.
KIPO; Notice of Allowance dated Sep. 27, 2019 in Application No. 10-2012-7004062.
KIPO; Office Action dated Apr. 24, 2019 in Application No. 10-2013-0036823.
KIPO; Notice of Allowance dated Aug. 29, 2019 in Application No. 10-2013-0036823.
KIPO; Office Action dated Aug. 27, 2019 in Application No. 10-2013-0049598.
KIPO; Office Action dated Feb. 28, 2020 in Application No. 10-2013-0049598.
KIPO; Notice of Allowance dated Sep. 25, 2020 in Application No. 10-2013-0049598.
KIPO; Office Action dated May 31, 2019 in Application No. 10-2013-0050740.
KIPO; Office Action dated Nov. 27, 2019 in Application No. 10-2013-0050740.
KIPO; Notice of Allowance dated Apr. 23, 2020 in Application No. 10-2013-0050740.
KIPO; Office Action dated Mar. 27, 2019 in Application No. 10-2013-0084459.
KIPO; Notice of Allowance dated Oct. 30, 2019 in Application No. 10-2013-0084459.
KIPO; Office Action dated Apr. 30, 2019 in Application No. 10-2013-0088450.
KIPO; Office Action dated Nov. 29, 2019 in Application No. 10-2013-0088450.
KIPO; Notice of Allowance dated Jan. 13, 2020 in Application No. 10-2013-0088450.
KIPO; Office Action dated Aug. 27, 2019 in Application No. 10-2013-0089998.
KIPO; Notice of Allowance dated Feb. 27, 2020 in Application No. 10-2013-0089998.
KIPO; Office Action dated Dec. 4, 2019 in Application No. 10-2013-0098575.
KIPO; Office Action dated Jun. 19, 2020 in Application No. 10-2013-0098575.
KIPO; Notice of Allowance dated Aug. 13, 2020 in Application No. 10-2013-0098575.
KIPO; Office Action dated Apr. 19, 2019 in Application No. 10-2013-0101944.
KIPO; Notice of Allowance dated Oct. 8, 2019 in Application No. 10-2013-0101944.
KIPO; Office Action dated Nov. 12, 2019 in Application No. 10-2013-0102026.
KIPO; Notice of Allowance dated May 14, 2020 in Application No. 10-2013-0102026.
KIPO; Office Action dated Aug. 15, 2019 in Application No. 10-2013-0109390.
KIPO; Notice of Allowance dated Oct. 21, 2019 in Application No. 10-2013-0109390.
KIPO; Office Action dated Oct. 7, 2019 in Application No. 10-2013-0114079.
KIPO; Notice of Allowance dated Mar. 4, 2020 in Application No. 10-2013-0114079.
KIPO; Office Action dated May 21, 2019 in Application No. 10-2013-0121554.
KIPO; Notice of Allowance dated Oct. 28, 2019 in Application No. 10-2013-0121554.
KIPO; Office Action dated Mar. 30, 2020 in Application No. 10-2014-0011764.
KIPO; Notice of Allowance dated Oct. 27, 2020 in Application No. 10-2014-0011764.
KIPO; Office Action dated Jul. 21, 2020 in Application No. 10-2014-0011765.
KIPO; Office Action dated Feb. 3, 2020 in Application No. 10-2014-0021615.
KIPO; Notice of Allowance dated Sep. 8, 2020 in Application No. 10-2014-0021615.
KIPO; Office Action dated Oct. 26, 2020 in Application No. 10-2014-0027217.
KIPO; Office Action dated Feb. 15, 2020 in Application No. 10-2014-0027305.
KIPO; Notice of Allowance dated Oct. 12, 2020 in Application No. 10-2014-0027305.
KIPO; Office Action dated Jul. 9, 2020 in Application No. 10-2014-0060120.
KIPO; Office Action dated Aug. 18, 2020 in Application No. 10-2014-0071653.

(56) References Cited

OTHER PUBLICATIONS

KIPO; Office Action dated May 21, 2020 in Application No. 10-2014-0086902.
KIPO; Notice of Allowance dated Oct. 19, 2020 in Application No. 10-2014-0086902.
KIPO; Office Action dated May 21, 2020 in Application No. 10-2014-0091092.
KIPO; Notice of Allowance dated Sep. 27, 2020 in Application No. 10-2014-0091092.
KIPO; Office Action dated Mar. 11, 2020 in Application No. 10-2014-0103853.
KIPO; Office Action dated Oct. 5, 2020 in Application No. 10-2014-0103853.
KIPO; Office Action dated Oct. 7, 2020 in Application No. 10-2014-0128626.
KIPO; Office Action dated Jan. 22, 2019 in Application No. 10-2014-7017110.
KIPO; Notice of Allowance dated Aug. 26, 2019 in Application No. 10-2014-7017110.
KIPO; Office Action dated Sep. 28, 2017 in Application No. 10-2014-7017112.
KIPO; Notice of Allowance dated Feb. 23, 2018 in Application No. 10-2014-7017112.
KIPO; Office Action dated Nov. 9, 2016 in Application No. 10-2016-7023913.
KIPO; Notice of Allowance dated May 30, 2017 in Application No. 10-2016-7023913.
KIPO; Office Action dated Jul. 21, 2020 in Application No. 10-2017-0087308.
KIPO; Notice of Allowance dated Oct. 26, 2020 in Application No. 10-2017-0087308.
KIPO; Notice of Allowance dated Feb. 27, 2018 in Application No. 10-2017-0175442.
KIPO; Office Action dated Sep. 28, 2017 in Application No. 10-2017-7023740.
KIPO; Final Office Action dated Jun. 17, 2019 in Application No. 10-2017-7023740.
KIPO; Notice of Allowance dated Jul. 19, 2018 in Application No. 20187013945.
KIPO; Office Action dated Jun. 30, 2020 in Application No. 10-2019-0044213.
KIPO; Notice of Allowance dated Nov. 29, 2019 in Application No. 10-2019-0127773.
KIPO; Offie Action dated Apr. 22, 2020 in Application No. 10-2020-0009462.
KIPO; Notice of Allowance dated Oct. 28, 2020 in Application No. 10-2020-0009462.
KIPO; Office Action dated Feb. 12, 2020 in Application No. 10-2020-7000992.
KIPO; Notice of Allowance dated Jul. 20, 2020 in Application No. 10-2020-7000992.
KIPO; Office Action dated Sep. 15, 2017 in Application No. 30-2017-0001320.
KIPO; Notice of Allowance dated Jan. 19, 2018 in Application No. 30-2017-0001320.
KIPO; Notice of Allowance dated Jul. 10, 2018 in Application No. 30-2017-0052872.
KIPO; Office Action dated Jul. 11, 2018 in Application No. 30-2018-0006016.
KIPO; Notice of Allowance dated Oct. 16, 2018 in Application No. 30-2018-0006016.
KIPO; Office Action dated Jan. 30, 2019 in Application No. 30-2018-0033442.
KIPO; Notice of Allowance dated Apr. 1, 2019 in Application No. 30-2018-0033442.
KIPO; Notice of Allowance dated Oct. 20, 2020 in Application No. 30-2019-0054013 M001.
KIPO; Notice of Allowance dated Oct. 20, 2020 in Application No. 30-2019-0054013 M002.
KIPO; Notice of Allowance dated Oct. 22, 2020 in Application No. 30-2019-0058076.
TIPO; Office Action dated Aug. 30, 2013 in Application No. 97132391.
TIPO; Office Action dated Dec. 20, 2013 in Application No. 98117513.
TIPO; Notice of Allowance dated Jun. 12, 2014 in Application No. 98117513.
TIPO; Office Action dated Jul. 4, 2014 in Application No. 99110511.
TIPO; Notice of Allowance dated Feb. 24, 2016 in Application No. 99110511.
TIPO; Office Action dated Aug. 27, 2014 in Application No. 99114329.
TIPO; Notice of Allowance dated Jan. 28, 2015 in Application No. 99114329.
TIPO; Office Action dated Dec. 26, 2014 in Application 99114330.
TIPO; Notice of Allowance dated Apr. 28, 2015 in Application No. 99114330.
TIPO; Office Action dated Aug. 14, 2014 in Application No. 99114331.
TIPO; Notice of Allowance dated Oct. 16, 2015 in Application No. 99114331.
TIPO; Office Action dated Dec. 19, 2014 in Application No. 99127063.
TIPO; Notice of Allowance dated Mar. 14, 2016 in Application No. 99127063.
TIPO; Notice of Allowance dated Oct. 2, 2015 in Application No. 100130472.
TIPO; Office Action dated Feb. 19, 2016 in Application No. 100113130.
TIPO; Notice of Allowance dated Jun. 29, 2016 in Applicaton No. 100113130.
TIPO; Notice of Allowance dated Nov. 2, 2016 in Application No. 101142581.
TIPO; Office Action dated Apr. 28, 2016 in Application No. 101142582.
TIPO; Notice of Allowance dated Aug. 19, 2016 in Application No. 101142582.
TIPO; Office Action dated Aug. 1, 2016 in Application No. 101124745.
TIPO; Notice of Allowance dated Oct. 19, 2016 in Application No. 101124745.
TIPO; Office Action dated Sep. 19, 2016 in Application No. 102113028.
TIPO; Notice of Allowance dated Feb. 13, 2017 in Application No. 102113028.
TIPO; Office Action dated Aug. 2016 in Application No. 102115605.
TIPO; Office Action dated Feb. 24, 2017 in Application No. 102115605.
TIPO; Notice of Allowance dated Dec. 26, 2017 in Application No. 102115605.
TIPO; Office Action dated Nov. 15, 2016 in Application No. 102125191.
TIPO; Office Action dated Jun. 20, 2017 in Application No. 102125191.
TIPO; Notice of Allowance dated Feb. 20, 2020 in Application No. 102125191.
TIPO; Office Action dated Dec. 6, 2016 in Application No. 102126071.
TIPO; Office Action dated May 17, 2018 in Application No. 102126071.
TIPO; Notice of Allowance dated Aug. 24, 2018 in Application No. 102126071.
TIPO; Office Action dated Feb. 10, 2017 in Application No. 102127065.
TIPO; Notice of Allowance dated Jul. 18, 2017 in Application No. 102127065.
TIPO; Office Action dated Nov. 3, 2016 in Application No. 102129262.
TIPO; Notice of Allowance dated Mar. 3, 2017 in Application No. 102129262.
TIPO; Office Action dated Dec. 29, 2016 in Application No. 102129397.
TIPO; Notice of Allowance dated Aug. 29, 2017 in Application No. 102129397.
TIPO; Office Action dated Nov. 3, 2016 in Application No. 102131839.

(56) References Cited

OTHER PUBLICATIONS

TIPO; Notice of Allowance dated Jan. 26, 2017 in Application No. 102131839.
TIPO; Office Action dated Dec. 2, 2016 in Application No. 102136496.
TIPO; Office Action dated Jan. 10, 2018 in Application No. 102136496.
TIPO; Office Action dated Aug. 16, 2019 in Application No. 102136496.
TIPO; Notice of Allowance dated Jan. 7, 2020 in Application No. 102136496.
TIPO; Office Action dated Nov. 11, 2016 in Application No. 102132952.
TIPO; Notice of Allowance dated Apr. 19, 2017 in Application No. 102132952.
TIPO; Office Action dated Jul. 17, 2017 in Application No. 103101400.
TIPO; Notice of Allowance dated Jan. 24, 2018 in Application No. 103101400.
TIPO; Office Action dated Feb. 23, 2017 in Application No. 103102563.
TIPO; Notice of Allowance dated Nov. 30, 2017 in Application No. 103102563.
TIPO; Office Action dated Mar. 3, 2017 in Application No. 103105251.
TIPO; Notice of Allowance dated Oct. 20, 2017 in Application No. 103105251.
TIPO; Office Action dated Nov. 1, 2017 in Application No. 103106021.
TIPO; Notice of Allowance dated Apr. 10, 2018 in Application No. 103106021.
TIPO; Office Action dated Oct. 31, 2017 in Application No. 103106022.
TIPO; Notice of Allowance dated Apr. 10, 2018 in Application No. 103106022.
TIPO; Office Action dated Jul. 5, 2017 in Application No. 103117477.
TIPO; Notice of Allowance dated Jan. 22, 2018 in Application No. 103117477.
TIPO; Office Action dated Nov. 22, 2017 in Application No. 103117478.
TIPO; Notice of Allowance dated Mar. 13, 2018 in Application No. 103117478.
TIPO; Office Action dated May 19, 2017 in Application No. 103120478.
TIPO; Notice of Allowance dated Sep. 25, 2017 in Application No. 103120478.
TIPO; Office Action dated Sep. 20, 2018 in Application No. 103123439.
TIPO; Notice of Allowance dated Jul. 10, 2019 in Application No. 103123439.
TIPO; Office Action dated Nov. 8, 2017 in Application No. 103124509.
TIPO; Notice of Allowance dated Apr. 25, 2018 in Application No. 103124509.
TIPO; Office Action dated Nov. 20, 2017 in Application No. 103127588.
TIPO; Notice of Allowance dated Jun. 19, 2018 in Application No. 103127588.
TIPO; Office Action dated Sep. 19, 2017 in Application No. 103127734.
TIPO; Notice of Allowance dated Dec. 11, 2017 in Application No. 103127734.
TIPO; Office Action dated Sep. 26, 2018 in Application No. 103132230.
TIPO; Notice of Allowance dated Jan. 29, 2019 in Application No. 103132230.
TIPO; Office Action dated Nov. 22, 2017 in Application No. 103134537.
TIPO; Notice of Allowance dated Apr. 19, 2018 in Application No. 103134537.
TIPO; Office Action dated Aug. 24, 2017 in Application No. 103136251.
TIPO; Notice of Allowance dated Oct. 17, 2017 in Application No. 103136251.
TIPO; Office Action dated Feb. 26, 2018 in Application No. 103138510.
TIPO; Notice of Allowance dated Jun. 13, 2018 in Application No. 103138510.
TIPO; Office Action dated May 21, 2018 in Application No. 103139014.
TIPO; Notice of Allowance dated Sep. 11, 2018 in Application No. 103139014.
TIPO; Office Action dated Jun. 22, 2018 in Application No. 104105533.
TIPO; Office Action dated Feb. 22, 2019 in Application No. 104105533.
TIPO; Notice of Allowance dated Sep. 27, 2019 in Application No. 104105533.
TIPO; Office Action dated Nov. 19, 2018 in Application No. 104105965.
TIPO; Notice of Allowance dated Sep. 23, 2019 in Application No. 104105965.
TIPO; Office Action dated Jul. 9, 2018 in Application No. 104107876.
TIPO; Notice of Allowance dated May 9, 2019 in Application No. 104107876.
TIPO; Office Action dated Aug. 7, 2018 Application No. 104107888.
TIPO; Notice of Allowance dated Apr. 26, 2019 in Application No. 104107888.
TIPO; Office Action dated May 6, 2019 in Application No. 104108277.
TIPO; Office Action dated Jan. 17, 2020 in Application No. 104108277.
TIPO; Office Action dated Jul. 9, 2018 in Application No. 104110326.
TIPO; Notice of Allowance dated May 8, 2019 in Application No. 104110326.
TIPO; Office Action dated Jun. 13, 2018 in Application No. 104111910.
TIPO; Notice of Allowance dated Sep. 18, 2018 in Application No. 104111910.
TIPO; Office Action dated Apr. 29, 2019 in Application No. 104122889.
TIPO; Notice of Allowance dated Oct. 4, 2019 in Application No. 104122889.
TIPO; Office Action dated Jan. 30, 2019 in Application No. 104122890.
TIPO; Notice of Allowance dated Jul. 19, 2019 in Application No. 104122890.
TIPO; Office Action dated Jul. 11, 2018 in Application No. 104124377.
TIPO; Notice of Allowance dated Jun. 19, 2019 in Application No. 104124377.
TIPO; Office Action dated Jan. 7, 2019 in Application No. 104132991.
TIPO; Notice of Allowance dated Apr. 12, 2019 in Application No. 104132991.
TIPO; Office Action dated Apr. 25, 2019 in Application No. 104141679.
TIPO; Notice of Allowance dated Nov. 27, 2019 in Application No. 104141679.
TIPO; Office Action dated Apr. 25, 2019 in Application No. 105101536.
TIPO; Office Action dated Dec. 13, 2019 in Application No. 105101536.
TIPO; Notice of Allowance dated May 4, 2020 in Application No. 105101536.
TIPO; Office Action dated Nov. 6, 2019 in Application No. 105101537.
TIPO; Notice of Allowance dated Jul. 1, 2020 in Application No. 105101537.
TIPO; Notice of Allowance dated May 7, 2019 in Application No. 105104453.
TIPO; Office Action dated Dec. 13, 2019 in Application No. 105111990.
TIPO; Notice of Allowance dated Sep. 4, 2020 in Application No. 105111990.
TIPO; Office Action dated Jul. 5, 2019 in Application No. 105112363.
TIPO; Notice of Allowance dated Dec. 10, 2019 in Application No. 105112363.
TIPO; Office Action dated Oct. 1, 2019 in Application No. 105114105.
TIPO; Notice of Allowance dated Jan. 15, 2020 in Application No. 105114105.
TIPO; Office Action dated Sep. 9, 2019 in Application No. 105115513.
TIPO; Notice of Allowance dated Feb. 10, 2020 in Application No. 105115513.
TIPO; Office Action dated Oct. 3, 2019 in Application No. 105119533.
TIPO; Notice of Allowance dated Mar. 13, 2020 in Application No. 105119533.

(56) References Cited

OTHER PUBLICATIONS

TIPO; Office Action dated Jan. 20, 2020 in Application No. 105122394.
TIPO; Office Action dated Sep. 7, 2020 in Application No. 105122394.
TIPO; Office Action dated Jan. 17, 2020 in Application No. 105122586.
TIPO; Notice of Allowance dated Aug. 31, 2020 in Application No. 105122586.
TIPO; Office Action dated Oct. 28, 2019 in Application No. 105122715.
TIPO; Notice of Allowance dated Feb. 13, 2020 in Application No. 105122715.
TIPO; Office Action dated Apr. 14, 2020 in Application No. 105129977.
TIPO; Office Action dated Sep. 18, 2020 in Application No. 105129977.
TIPO; Office Action dated Mar. 17, 2020 in Application No. 105130130.
TIPO; Notice of Allowance dated Sep. 25, 2020 in Application No. 105130130.
TIPO; Office Action Received Aug. 25, 2020 in Application No. 105131284.
TIPO; Office Action dated Aug. 25, 2020 in Application No. 105131896.
TIPO; Office Action dated Sep. 30, 2020 in Application No. 105142668.
TIPO; Notice of Allowance dated Dec. 5, 2017 in Application No. 105308015.
TIPO; Notice of Allowance dated Apr. 11, 2018 in Application No. 105308015D01.
TIPO; Office Action dated Aug. 11, 2020 in Application No. 106100823.
TIPO; Office Action dated Jun. 17, 2020 in Application No. 106108152.
TIPO; Office Action dated Oct. 7, 2020 in Application No. 106108522.
TIPO; Office Action dated Aug. 21, 2020 in Application No. 106111548.
TIPO; Office Action dated Oct. 8, 2020 in Application No. 106111693.
TIPO; Office Action dated Sep. 30, 2020 in Application No. 106113604.
TIPO; Office Action dated 11/6//2017 in Application No. 106117181.
TIPO; Notice of Allowance dated Jun. 5, 2018 in Application No. 106117181.
TIPO; Office Action dated Sep. 28, 2018 in Application No. 106119537.
TIPO; Office Action dated Jul. 15, 2020 in Application No. 106120365.
TIPO; Office Action dated Nov. 12, 2020 in Application No. 106120365.
TIPO; Office Action dated Nov. 18, 2020 in Application No. 106120902.
TIPO; Office Action dated Oct. 8, 2020 in Application No. 106123203.
TIPO; Office Action dated Dec. 26, 2018 in Application No. 106127690.
TIPO; Office Action dated Aug. 31, 2018 in Application No. 106138119.
TIPO; Office Action dated Jun. 25, 2018 in Application No. 106138800.
TIPO; Office Action dated Jan. 7, 2019 in Application No. 106138800.
TIPO; Notice of Allowance dated Sep. 20, 2019 in Application No. 106138800.
TIPO; Office Action dated Oct. 3, 2018 in Application No. 106142731.
TIPO; Office Action dated Sep. 28, 2018 in Application No. 107112951.
TIPO; Office Action dated Aug. 27, 2019 in Application No. 107116804.
TIPO; Notice of Allowance dated Jan. 16, 2020 in Application No. 107116804.
TIPO; Office Action dated Nov. 20, 2018 in Application No. 107118271.
TIPO; Office Action dated Jun. 4, 2019 in Application No. 107123992.
TIPO; Office Action dated May 28, 2019 in Application No. 107125586.
TIPO; Office Action dated Jan. 17, 2020 in Application No. 107127688.
TIPO; Notice of Allowance dated Aug. 29, 2018 in Application No. 107300633.
TIPO; Notice of Allowance dated Feb. 21, 19 in Application No. 107303723.
TIPO; Office Action dated Jun. 28, 2019 in Application No. 108102948.
TIPO; Office Action dated Dec. 24, 2019 in Application No. 108105002.
TIPO; Office Action dated Feb. 3, 2020 in Application No. 108114221.
TIPO; Office Action dated Nov. 13, 2019 in Application No. 108115406.
TIPO; Office Action dated Feb. 21, 2020 in Application No. 108120947.
TIPO; Notice of Allowance dated Mar. 12, 2020 in Application No. 108129100.
TIPO; Office Action dated Jun. 24, 2020 in Application No. 108135004.
TIPO; Office Action dated Jun. 29, 2020 in Application No. 108137226.
TIPO; Office Action dated Jul. 9, 2020 in Application No. 108137227.
TIPO; Office Action dated Aug. 17, 2020 in Application No. 108139018.
TIPO; Notice of Allowance dated Oct. 19, 2020 in Application No. 108306935.
TIPO; Notice of Allowance dated Oct. 19, 2020 in Application No. 108306935D01.
TIPO; Notice of Allowance dated Jul. 15, 2020 in Application No. 108307027.
TIPO; Notice of Allowance dated Oct. 19, 2020 in Application No. 108307027D01.
TIPO; Notice of Allowance dated Sep. 15, 2020 in Application No. 108307301.
TIPO; Notice of Allowance dated Sep. 25, 2020 in Application No. 108307759.
USPTO; Non-Final Office Action dated Mar. 28, 2001 in U.S. Appl. No. 09/452,844.
USPTO; Final Office Action dated Sep. 11, 2001 in U.S. Appl. No. 09/452,844.
USPTO; Advisory Action dated Jan. 24, 2002 in U.S. Appl. No. 09/452,844.
USPTO; Non-Final Office Action dated Apr. 9, 2002 in U.S. Appl. No. 09/452,844.
USPTO; Final Office Action dated Sep. 27, 2002 in U.S. Appl. No. 09/452,844.
USPTO; Notice of Allowance dated Jun. 17, 2003 in U.S. Appl. No. 09/452,844.
USPTO; Non-Final Office Action dated Oct. 31, 2003 in U.S. Appl. No. 09/452,844.
USPTO; Notice of Allowance dated Mar. 26, 2004 in U.S. Appl. No. 09/452,844.
USPTO; Non-Final Office Action dated Dec. 10, 2002 in U.S. Appl. No. 09/771,673.
USPTO; Final Office Action dated May 29, 2003 in U.S. Appl. No. 09/771,673.
USPTO; Final Office Action dated Feb. 6, 2004 in U.S. Appl. No. 09/771,673.
USPTO; Advisory Action dated Apr. 20, 2004 in U.S. Appl. No. 09/771,673.
USPTO; Notice of Allowance dated Jul. 29, 2004 in U.S. Appl. No. 09/771,673.
USPTO; Non-Final Office Action dated Jan. 3, 2002 in U.S. Appl. No. 09/807,580.
USPTO; Final Office Action dated Jun. 21, 2002 in U.S. Appl. No. 09/807,580.
USPTO; Advisory Action dated Aug. 27, 2002 in U.S. Appl. No. 09/807,580.
USPTO; Non-Final Action dated Nov. 27, 2002 in U.S. Appl. No. 09/807,580.
USPTO; Final Office Action dated May 27, 2003 in U.S. Appl. No. 09/807,580.
USPTO; Advisory Action dated Oct. 22, 2003 in U.S. Appl. No. 09/807,580.
USPTO; Examiner's Answer to Appeal Brief dated May 6, 2004 in U.S. Appl. No. 09/807,580.
USPTO; Decision on Appeal dated Feb. 16, 2005 in U.S. Appl. No. 09/807,580.

(56) References Cited

OTHER PUBLICATIONS

USPTO; Non-Final Action dated May 19, 2005 in U.S. Appl. No. 09/807,580.
USPTO; Final Action dated Nov. 21, 2005 in U.S. Appl. No. 09/807,580.
USPTO; Notice of Allowance dated Feb. 23, 2006 in U.S. Appl. No. 09/807,580.
USPTO; Notice of Allowance dated Jul. 26, 2005 in U.S. Appl. No. 10/033,058.
USPTO; Non-Final Office Action dated Aug. 25, 2005 in U.S. Appl. No. 10/191,635.
USPTO; Final Office Action dated Apr. 25, 2006 in U.S. Appl. No. 10/191,635.
USPTO; Non-Final Office Action dated Nov. 20, 2006 in U.S. Appl. No. 10/191,635.
USPTO; Notice of Allowance dated May 21, 2007 in U.S. Appl. No. 10/191,635.
USPTO; Notice of Allowance dated Feb. 20, 2008 in U.S. Appl. No. 10/191,635.
USPTO; Non-Final Office Action dated May 13, 2003 in U.S. Appl. No. 10/222,229.
USPTO; Non-Final Office Action dated Oct. 22, 2003 in U.S. Appl. No. 10/222,229.
USPTO; Final Office Action dated Mar. 22, 2004 in U.S. Appl. No. 10/222,229.
USPTO; Advisory Action dated Oct. 7, 2004 in U.S. Appl. No. 10/222,229.
USPTO; Non-Final Office Action dated Dec. 22, 2004 in U.S. Appl. No. 10/222,229.
USPTO; Final Office Action dated Jun. 20, 2005 in U.S. Appl. No. 10/222,229.
USPTO; Advisory Action dated Nov. 16, 2005 in U.S. Appl. No. 10/222,229.
USPTO; Notice of Allowance dated Mar. 8, 2006 in U.S. Appl. No. 10/222,229.
USPTO; Non-Final Office Action dated Feb. 9, 2004 in U.S. Appl. No. 10/603,515.
USPTO; Notice of Allowance dated Jun. 18, 2004 in U.S. Appl. No. 10/603,515.
USPTO; Non-Final Office Action dated Jan. 26, 2005 in U.S. Appl. No. 10/838,510.
USPTO; Notice of Allowance dated Jul. 12, 2005 in U.S. Appl. No. 10/838,510.
USPTO; Non-Final Office Action dated Oct. 17, 2006 in U.S. Appl. No. 10/932,633.
USPTO; Non-Final Office Action dated Apr. 19, 2007 in U.S. Appl. No. 10/932,633.
USPTO; Notice of Allowance dated Sep. 10, 2007 in U.S. Appl. No. 10/932,633.
USPTO; Office Action dated Feb. 15, 2011 in U.S. Appl. No. 12/118,596.
USPTO; Notice of Allowance dated Aug. 4, 2011 in U.S. Appl. No. 12/118,596.
USPTO; Non-Final Office Action dated Apr. 28, 2010 in U.S. Appl. No. 12/121,085.
USPTO; Notice of Allowance dated Jul. 26, 2010 in U.S. Appl. No. 12/121,085.
USPTO; Notice of Allowance dated Oct. 4, 2010 in U.S. Appl. No. 12/121,085.
USPTO; Non-Final Office Action dated Sep. 13, 2010 in U.S. Appl. No. 12/140,809.
USPTO; Final Office Action dated Dec. 28, 2010 in U.S. Appl. No. 12/140,809.
USPTO; Notice of Allowance dated Mar. 17, 2011 in U.S. Appl. No. 12/140,809.
USPTO; Non-Final Office Action dated Mar. 15, 2011 in U.S. Appl. No. 12/193,924.
USPTO; Foma; Office Action dated Sep. 30, 2011 in U.S. Appl. No. 12/193,924.
USPTO; Non-Final Office Action dated Oct. 24, 2012 in U.S. Appl. No. 12/193,924.
USPTO; Final Office Action dated Apr. 17, 2013 in U.S. Appl. No. 12/193,924.
USPTO; Advisory Action dated Jul. 9, 2013 in U.S. Appl. No. 12/193,924.
USPTO; Non-Final Office Action dated Jul. 28, 2011 in U.S. Appl. No. 12/330,096.
USPTO; Final Office Action dated Jan. 13, 2012 in U.S. Appl. No. 12/330,096.
USPTO; Notice of Allowance dated Mar. 6, 2012 in U.S. Appl. No. 12/330,096.
USPTO; Non-Final Office Action dated Mar. 20, 2012 in U.S. Appl. No. 12/330,096.
USPTO; Notice of Allowance dated Jun. 7, 2012 in U.S. Appl. No. 12/330,096.
USPTO; Non-Final Office Action dated Apr. 1, 2010 in U.S. Appl. No. 12/357,174.
USPTO; Final Office Action dated Sep. 1, 2010 in U.S. Appl. No. 12/357,174.
USPTO; Notice of Allowance dated Dec. 13, 2010 in U.S. Appl. No. 12/357,174.
USPTO; Non-Final Office Action dated Dec. 29, 2010 in U.S. Appl. No. 12/362,023.
USPTO; Non-Final Office Action dated Jul. 26, 2011 in U.S. Appl. No. 12/416,809.
USPTO; Final Office Action dated Dec. 6, 2011 in U.S. Appl. No. 12/416,809.
USPTO; Notice of Allowance dated Apr. 2, 2012 in U.S. Appl. No. 12/416,809.
USPTO; Advisory Action dated Feb. 3, 2012 in U.S. Appl. No. 12/416,809.
USPTO; Notice of Allowance dated Jun. 16, 2011 in U.S. Appl. No. 12/430,751.
USPTO; Notice of Allowance dated Jul. 27, 2011 in U.S. Appl. No. 12/430,751.
USPTO; Non-Final Office Action dated Aug. 3, 2011 in U.S. Appl. No. 12/436,300.
USPTO; Final Office Action dated Jan. 23, 2012 in U.S. Appl. No. 12/436,300.
USPTO; Advisory Action dated Mar. 6, 2012 in U.S. Appl. No. 12/436,300.
USPTO; Non-Final Office Action dated May 22, 2012 in U.S. Appl. No. 12/436,300.
USPTO; Notice of Allowance dated Nov. 28, 2012 in U.S. Appl. No. 12/436,300.
USPTO; Non-Final Office Action dated Apr. 11, 2012 in U.S. Appl. No. 12/436,306.
USPTO; Final Office Action dated Sep. 26, 2012 in U.S. Appl. No. 12/436,306.
USPTO; Non-Final Office Action dated May 31, 2013 in U.S. Appl. No. 12/436,306.
USPTO; Final Office Action dated Oct. 17, 2013 in U.S. Appl. No. 12/436,306.
USPTO; Non-Final Office Action dated Feb. 4, 2014 in U.S. Appl. No. 12/436,306.
USPTO; Final Office Action dated Jun. 23, 2014 in U.S. Appl. No. 12/436,306.
USPTO; Advisory Action dated Oct. 1, 2014 in U.S. Appl. No. 12/436,306.
USPTO; Non-Final Office Action dated Feb. 3, 2015 in U.S. Appl. No. 12/436,306.
USPTO; Final Office Action dated May 13, 2015 in U.S. Appl. No. 12/436,306.
USPTO; Non-Final Office Action dated Oct. 14, 2015 in U.S. Appl. No. 12/436,306.
USPTO; Final Office Action dated Dec. 31, 2015 in U.S. Appl. No. 12/436,306.
USPTO; Notice of Allowance dated Feb. 3, 2016 in U.S. Appl. No. 12/436,306.
USPTO; Non-Final Office Action dated Aug. 3, 2011 in U.S. Appl. No. 12/436,315.

(56) References Cited

OTHER PUBLICATIONS

USPTO; Notice of Allowance dated Nov. 17, 2011 in U.S. Appl. No. 12/436,315.
USPTO; Notice of Allowance dated Oct. 1, 2010 in U.S. Appl. No. 12/467,017.
USPTO; Non-Final Office Action dated Mar. 18, 2010 in U.S. Appl. No. 12/489,252.
USPTO; Notice of Allowance dated Sep. 2, 2010 in U.S. Appl. No. 12/489,252.
USPTO; Non-Final Office Action dated Dec. 15, 2010 in U.S. Appl. No. 12/553,759.
USPTO; Final Office Action dated May 4, 2011 in U.S. Appl. No. 12/553,759.
USPTO; Advisory Action dated Jul. 13, 2011 in U.S. Appl. No. 12/553,759.
USPTO; Non-Final Office Action dated Sep. 6, 2011 in U.S. Appl. No. 12/553,759.
USPTO; Notice of Allowance dated Jan. 27, 2012 in U.S. Appl. No. 12/553,759.
USPTO; Non-Final Office Action dated Oct. 19, 2012 in U.S. Appl. No. 12/618,355.
USPTO; Final Office Action dated May 8, 2013 in U.S. Appl. No. 12/618,355.
USPTO; Advisory Action dated Jul. 23, 2013 in U.S. Appl. No. 12/618,355.
USPTO; Non-Final Office Action dated Apr. 8, 2015 in U.S. Appl. No. 12/618,355.
USPTO; Final Office Action dated Oct. 22, 2015 in U.S. Appl. No. 12/618,355.
USPTO; Advisory Action dated Mar. 4, 2016 in U.S. Appl. No. 12/618,355.
USPTO; Non-Final Office Action dated Jun. 30, 2016 in U.S. Appl. No. 12/618,355.
USPTO; Final Office Action dated Feb. 10, 2017 in U.S. Appl. No. 12/618,355.
USPTO; Advisory Action dated May 16, 2017 in U.S. Appl. No. 12/618,355.
USPTO; Non-Final Office Action dated Nov. 29, 2017 in U.S. Appl. No. 12/618,355.
USPTO; Final Office Action dated Aug. 10, 2018 in U.S. Appl. No. 12/618,355.
USPTO; Notice of Allowance dated Apr. 4, 2019 in U.S. Appl. No. 12/618,355.
USPTO; Non-Final Office Action dated Feb. 16, 2012 in U.S. Appl. No. 12/618,419.
USPTO; Final Office Action dated Jun. 22, 2012 in U.S. Appl. No. 12/618,419.
USPTO; Non-Final Office Action dated Nov. 27, 2012 in U.S. Appl. No. 12/618,419.
USPTO; Advisory Action dated Aug. 9, 2012 in U.S. Appl. No. 12/618,419.
USPTO; Notice of Allowance dated Apr. 12, 2013 in U.S. Appl. No. 12/618,419.
USPTO; Non-Final Office Action dated Jun. 12, 2013 in U.S. Appl. No. 12/618,419.
USPTO; Notice of Allowance dated Oct. 9, 2013 in U.S. Appl. No. 12/618,419.
USPTO; Non-Final Office Action dated Dec. 6, 2011 in U.S. Appl. No. 12/718,731.
USPTO; Notice of Allowance dated Mar. 16, 2012 in U.S. Appl. No. 12/718,731.
USPTO; Office Action dated Feb. 26, 2013 in U.S. Appl. No. 12/754,223.
USPTO; Final Office Action dated Jun. 28, 2013 in U.S. Appl. No. 12/754,223.
USPTO; Office Action dated Feb. 25, 2014 in U.S. Appl. No. 12/754,223.
USPTO; Final Office Action dated Jul. 14, 2014 in U.S. Appl. No. 12/754,223.
USPTO; Non-Final Office Action dated Mar. 25, 2015 in U.S. Appl. No. 12/754,223.
USPTO; Final Office Action dated Aug. 12, 2015 in U.S. Appl. No. 12/754,223.
USPTO; Notice of Allowance dated May 23, 2016 in U.S. Appl. No. 12/754,223.
USPTO; Office Action dated Apr. 23, 2013 in U.S. Appl. No. 12/763,037.
USPTO; Final Office Action dated Oct. 21, 2013 in U.S. Appl. No. 12/763,037.
USPTO; Office Action dated Oct. 8, 2014 in U.S. Appl. No. 12/763,037.
USPTO; Notice of Allowance dated Jan. 27, 2015 in U.S. Appl. No. 12/763,037.
USPTO; Non-Final Office Action dated Jan. 24, 2011 in U.S. Appl. No. 12/778,808.
USPTO; Notice of Allowance dated May 9, 2011 in U.S. Appl. No. 12/778,808.
USPTO; Notice of Allowance dated Oct. 12, 2012 in U.S. Appl. No. 12/832,739.
USPTO; Non-Final Office Action dated Oct. 16, 2012 in U.S. Appl. No. 12/847,848.
USPTO; Final Office Action dated Apr. 22, 2013 in U.S. Appl. No. 12/847,848.
USPTO; Advisory Action dated Jul. 1, 2013 in U.S. Appl. No. 12/847,848.
USPTO; Notice of Allowance dated Jan. 16, 2014 in U.S. Appl. No. 12/847,848.
USPTO; Office Action dated Dec. 6, 2012 in U.S. Appl. No. 12/854,818.
USPTO; Final Office Action dated Mar. 13, 2013 in U.S. Appl. No. 12/854,818.
USPTO; Office Action dated Aug. 30, 2013 in U.S. Appl. No. 12/854,818.
USPTO; Final Office Action dated Mar. 26, 2014 in U.S. Appl. No. 12/854,818.
USPTO; Office Action dated Jun. 3, 2014 in U.S. Appl. No. 12/854,818.
USPTO; Non-Final Office Action dated Jul. 11, 2012 in U.S. Appl. No. 12/875,889.
USPTO; Notice of Allowance dated Jan. 4, 2013 in U.S. Appl. No. 12/875,889.
USPTO; Notice of Allowance dated Jan. 9, 2012 in U.S. Appl. No. 12/901,323.
USPTO; Non-Final Office Action dated Nov. 20, 2013 in U.S. Appl. No. 12/910,607.
USPTO; Final Office Action dated Apr. 28, 2014 in U.S. Appl. No. 12/910,607.
USPTO; Advisory Action dated Jul. 9, 2014 in U.S. Appl. No. 12/910,607.
USPTO; Notice of Allowance dated Aug. 15, 2014 in U.S. Appl. No. 12/910,607.
USPTO; Non-Final Office Action dated Oct. 24, 2012 in U.S. Appl. No. 12/940,906.
USPTO; Final Office Action dated Feb. 13, 2013 in U.S. Appl. No. 12/940,906.
USPTO; Notice of Allowance dated Apr. 23, 2013 in U.S. Appl. No. 12/940,906.
USPTO; Non-Final Office Action dated Dec. 7, 2012 in U.S. Appl. No. 12/953,870.
USPTO; Final Office Action dated Apr. 22, 2013 in U.S. Appl. No. 12/953,870.
USPTO; Advisory Action dated Jul. 8, 2013 in U.S. Appl. No. 12/953,870.
USPTO; Non-Final Office Action dated Aug. 28, 2013 in U.S. Appl. No. 12/953,870.
USPTO; Final Office Action dated Apr. 17, 2014 in U.S. Appl. No. 12/953,870.
USPTO; Non-Final Office Action dated Sep. 19, 2012 in U.S. Appl. No. 13/016,735.
USPTO; Final Office Action dated Feb. 11, 2013 in U.S. Appl. No. 13/016,735.

(56) References Cited

OTHER PUBLICATIONS

USPTO; Notice of Allowance dated Apr. 24, 2013 in U.S. Appl. No. 13/016,735.
USPTO; Non-Final Office Action dated Apr. 4, 2012 in U.S. Appl. No. 13/030,438.
USPTO; Final Office Action dated Aug. 22, 2012 in U.S. Appl. No. 13/030,438.
USPTO; Notice of Allowance dated Oct. 24, 2012 in U.S. Appl. No. 13/030,438.
USPTO; Non-Final Office Action dated Dec. 3, 2012 in U.S. Appl. No. 13/040,013.
USPTO; Notice of Allowance dated May 3, 2013 in U.S. Appl. No. 13/040,013.
USPTO; Non-Final Office Action dated Feb. 15, 2012 in U.S. Appl. No. 13/085,531.
USPTO; Notice of Allowance dated Jul. 12, 2012 in U.S. Appl. No. 13/085,531.
USPTO; Notice of Allowance dated Sep. 13, 2012 in U.S. Appl. No. 13/085,698.
USPTO; Non-Final Office Action dated Mar. 29, 2013 in U.S. Appl. No. 13/094,402.
USPTO; Final Office Action dated Jul. 17, 2013 in U.S. Appl. No. 13/094,402.
USPTO; Notice of Allowance dated Sep. 30, 2013 in U.S. Appl. No. 13/094,402.
USPTO; Office Action dated Oct. 7, 2013 in U.S. Appl. No. 13/102,980.
USPTO; Final Office Action dated Mar. 25, 2014 in U.S. Appl. No. 13/102,980.
USPTO; Advisory Action dated Jun. 12, 2014 in U.S. Appl. No. 13/102,980.
USPTO; Notice of Allowance dated Jul. 3, 2014 in U.S. Appl. No. 13/102,980.
USPTO; Notice of Allowance dated Sep. 17, 2014 in U.S. Appl. No. 13/102,980.
USPTO; Non-Final Office Action dated Jul. 17, 2014 in U.S. Appl. No. 13/154,271.
USPTO; Final Office Action dated Jan. 2, 2015 in U.S. Appl. No. 13/154,271.
USPTO; Non-Final Office Action dated May 27, 2015 in U.S. Appl. No. 13/154,271.
USPTO; Final Office Action dated Nov. 23, 2015 in U.S. Appl. No. 13/154,271.
USPTO; Notice of Allowance dated Feb. 10, 2016 in U.S. Appl. No. 13/154,271.
USPTO; Non-Final Office Action dated Jun. 27, 2016 in U.S. Appl. No. 13/166,367.
USPTO; Final Office Action dated Dec. 30, 2016 in U.S. Appl. No. 13/166,367.
USPTO; Advisory Action dated Apr. 21, 2017 in U.S. Appl. No. 13/166,367.
USPTO; Notice of Allowance dated Jun. 28, 2017 in U.S. Appl. No. 13/166,367.
USPTO; Non-Final Office Action dated Oct. 27, 2014 in U.S. Appl. No. 13/169,951.
USPTO; Final Office Action dated May 26, 2015 in U.S. Appl. No. 13/169,951.
USPTO; Non-Final Office Action dated Sep. 1, 2015 in U.S. Appl. No. 13/169,951.
USPTO; Final Office Action dated Mar. 3, 2016 in U.S. Appl. No. 13/169,951.
USPTO; Non-Final Office Action dated Jun. 9, 2016 in U.S. Appl. No. 13/169,951.
USPTO; Final Office Action dated Dec. 9, 2016 in U.S. Appl. No. 13/169,951.
USPTO; Advisory Action dated May 13, 2016 in U.S. Appl. No. 13/169,951.
USPTO; Advisory Action dated Feb. 15, 2017 in U.S. Appl. No. 13/169,951.
USPTO; Non-Final Office Action dated Apr. 26, 2017 in U.S. Appl. No. 13/169,951.
USPTO; Final Office Action dated Nov. 2, 2017 in U.S. Appl. No. 13/169,951.
USPTO; Advisory Action dated Feb. 8, 2018 in U.S. Appl. No. 13/169,951.
USPTO; Non-Final Office Action dated Apr. 6, 2018 in U.S. Appl. No. 13/169,951.
USPTO; Final Office Action dated Nov. 2, 2018 in U.S. Appl. No. 13/169,951.
USPTO; Advisory Action dated Feb. 4, 2019 in U.S. Appl. No. 13/169,951.
USPTO; Notice of Allowance dated Apr. 4, 2019 in U.S. Appl. No. 13/169,951.
USPTO; Non-Final Office Action dated Jun. 24, 2014 in U.S. Appl. No. 13/181,407.
USPTO; Final Office Action dated Sep. 24, 2014 in U.S. Appl. No. 13/181,407.
USPTO; Advisory Action dated Dec. 17, 2014 in U.S. Appl. No. 13/181,407.
USPTO; Non-Final Office Action dated Jan. 2, 2015 in U.S. Appl. No. 13/181,407.
USPTO; Final Office Action dated Apr. 8, 2015 in U.S. Appl. No. 13/181,407.
USPTO; Non-Final Office Action dated Jan. 23, 2013 in U.S. Appl. No. 13/184,351.
USPTO; Final Office Action dated Jul. 29, 2013 in U.S. Appl. No. 13/184,351.
USPTO; Advisory Action dated Nov. 7, 2013 in U.S. Appl. No. 13/184,351.
USPTO; Non-Final Office Action dated Jul. 16, 2014 in U.S. Appl. No. 13/184,351.
USPTO; Final Office Action dated Feb. 17, 2015 in U.S. Appl. No. 13/184,351.
USPTO; Advisory Action dated May 18, 2015 in U.S. Appl. No. 13/184,351.
USPTO; Non-Final Office Action dated Aug. 10, 2015 in U.S. Appl. No. 13/184,351.
USPTO; Final Office Action dated Feb. 12, 2016 in U.S. Appl. No. 13/184,351.
USPTO; Non-Final Office Action dated Dec. 15, 2016 in U.S. Appl. No. 13/184,351.
USPTO; Final Office Action dated Jun. 15, 2017 in U.S. Appl. No. 13/184,351.
USPTO; Advisory Action dated Oct. 4, 2017 in U.S. Appl. No. 13/184,351.
USPTO; Non-Final Office Action dated Jul. 26, 2018 in U.S. Appl. No. 13/184,351.
USPTO; Final Office Action dated Dec. 28, 2018 in U.S. Appl. No. 13/184,351.
USPTO; Non-Final Office Action dated Aug. 19, 2019 in U.S. Appl. No. 13/184,351.
USPTO; Notice of Allowance dated Jul. 6, 2020 in U.S. Appl. No. 13/184,351.
USPTO; Non-Final Office Action dated Sep. 17, 2014 in U.S. Appl. No. 13/187,300.
USPTO; Final Office Action dated Apr. 15, 2015 in U.S. Appl. No. 13/187,300.
USPTO; Non-Final Office Action dated Apr. 7, 2016 in U.S. Appl. No. 13/187,300.
USPTO; Final Office Acton dated Sep. 23, 2016 in U.S. Appl. No. 13/187,300.
USPTO; Non-Final Office Action dated Jan. 30, 2017 in U.S. Appl. No. 13/187,300.
USPTO; Final Office Action dated Aug. 9, 2017 in U.S. Appl. No. 13/187,300.
USPTO; Examiner's Answer to Appeal Brief dated Apr. 20, 2018 in U.S. Appl. No. 13/187,300.
USPTO; Patent Board Decision dated Sep. 23, 2019 in U.S. Appl. No. 13/187,300.
USPTO; Non-Final Office Action dated Oct. 1, 2012 in U.S. Appl. No. 13/191,762.

(56) References Cited

OTHER PUBLICATIONS

USPTO; Final Office Action dated Apr. 10, 2013 in U.S. Appl. No. 13/191,762.
USPTO; Notice of Allowance dated Aug. 15, 2013 in U.S. Appl. No. 13/191,762.
USPTO; Non-Final Office Action dated Oct. 22, 2012 in U.S. Appl. No. 13/238,960.
USPTO; Final Office Action dated May 3, 2013 in U.S. Appl. No. 13/238,960.
USPTO; Non-Final Office Action dated Apr. 26, 2013 in U.S. Appl. No. 13/250,721.
USPTO; Notice of Allowance dated Sep. 11, 2013 in U.S. Appl. No. 13/250,721.
USPTO; Non-Final Office Action dated Jul. 2, 2014 in U.S. Appl. No. 13/283,408.
USPTO; Final Office Action dated Jan. 29, 2015 in U.S. Appl. No. 13/283,408.
USPTO; Non-Final Office Action dated Jun. 17, 2015 in U.S. Appl. No. 13/283,408.
USPTO; Final Office Action dated Dec. 18, 2015 in U.S. Appl. No. 13/283,408.
USPTO; Advisory Action dated Mar. 28, 2016 in U.S. Appl. No. 13/283,408.
USPTO; Notice of Allowance dated Mar. 28, 2016 in U.S. Appl. No. 13/283,408.
USPTO; Non-Final Office Action dated Jul. 30, 2014 in U.S. Appl. No. 13/284,642.
USPTO; Notice of Allowance dated Feb. 11, 2015 in U.S. Appl. No. 13/284,642.
USPTO; Non-Final Office Action dated Jan. 28, 2014 in U.S. Appl. No. 13/312,591.
USPTO; Final Office Action dated May 14, 2014 in U.S. Appl. No. 13/312,591.
USPTO; Advisory Action dated Aug. 26, 2014 in U.S. Appl. No. 13/312,591.
USPTO; Non-Final Office Action dated Nov. 26, 2014 in U.S. Appl. No. 13/312,591.
USPTO; Final Office Action dated Mar. 20, 2015 in U.S. Appl. No. 13/312,591.
USPTO; Notice of Allowance dated May 14, 2015 in U.S. Appl. No. 13/312,591.
USPTO; Notice of Allowance dated Jun. 11, 2015 in U.S. Appl. No. 13/312,591.
USPTO; Non-Final Office Action dated Apr. 9, 2014 in U.S. Appl. No. 13/333,420.
USPTO; Notice of Allowance dated Sep. 15, 2014 in U.S. Appl. No. 13/333,420.
USPTO; Office Action dated Feb. 11, 2013 in U.S. Appl. No. 13/339,609.
USPTO; Final Office Action dated May 17, 2013 in U.S. Appl. No. 13/339,609.
USPTO; Office Action dated Aug. 29, 2013 in U.S. Appl. No. 13/339,609.
USPTO; Final Office Action dated Dec. 18, 2013 in U.S. Appl. No. 13/339,609.
USPTO; Notice of Allowance dated Apr. 7, 2014 in U.S. Appl. No. 13/339,609.
USPTO; Non-Final Office Action dated Oct. 10, 2012 in U.S. Appl. No. 13/406,791.
USPTO; Final Office Action dated Jan. 31, 2013 in U.S. Appl. No. 13/406,791.
USPTO; Advisory Action dated Mar. 27, 2013 in U.S. Appl. No. 13/406,791.
USPTO; Non-Final Office Action dated Apr. 25, 2013 in U.S. Appl. No. 13/406,791.
USPTO; Final Office Action dated Aug. 23, 2013 in U.S. Appl. No. 13/406,791.
USPTO; Advisory Action dated Oct. 29, 2013 in U.S. Appl. No. 13/406,791.
USPTO; Non-Final Office Action dated Dec. 4, 2013 in U.S. Appl. No. 13/406,791.
USPTO; Final Office Action dated Apr. 21, 2014 in U.S. Appl. No. 13/406,791.
USPTO; Non-Final Office Action dated Jan. 14, 2013 in U.S. Appl. No. 13/410,970.
USPTO; Notice of Allowance dated Feb. 14, 2013 in U.S. Appl. No. 13/410,970.
USPTO; Non-Final Office Action dated Feb. 13, 2014 in U.S. Appl. No. 13/411,271.
USPTO; Non-Final Office Action dated Jul. 31, 2014 in U.S. Appl. No. 13/411,271.
USPTO; Advisory Action dated Apr. 22, 2015 in U.S. Appl. No. 13/411,271.
USPTO; Final Office Action dated Jan. 16, 2015 in U.S. Appl. No. 13/411,271.
USPTO; Notice of Allowance dated Oct. 6, 2015 in U.S. Appl. No. 13/411,271.
USPTO; Office Action dated Feb. 4, 2014 in U.S. Appl. No. 13/439,528.
USPTO; Final Office Action dated Jul. 8, 2014 in U.S. Appl. No. 13/439,528.
UPPTO; Notice of Allowance dated Oct. 21, 2014 in U.S. Appl. No. 13/439,528.
USPTO; Non-Final Office Action dated Apr. 11, 2013 in U.S. Appl. No. 13/450,368.
USPTO; Notice of Allowance dated Jul. 17, 2013 in U.S. Appl. No. 13/450,368.
USPTO; Non-Final Office Action dated May 23, 2013 in U.S. Appl. No. 13/465,340.
USPTO; Final Office Action dated Oct. 30, 2013 in U.S. Appl. No. 13/465,340.
USPTO; Notice of Allowance dated Feb. 12, 2014 in U.S. Appl. No. 13/465,340.
USPTO; Non-Final Office Action dated Oct. 17, 2013 in U.S. Appl. No. 13/493,897.
USPTO; Notice of Allowance dated Mar. 20, 2014 in U.S. Appl. No. 13/493,897.
USPTO; Non-Final Office Action dated Dec. 20, 2013 in U.S. Appl. No. 13/535,214.
USPTO; Final Office Action dated Jun. 18, 2014 in U.S. Appl. No. 13/535,214.
USPTO; Notice of Allowance dated Oct. 23, 2014 in U.S. Appl. No. 13/535,214.
USPTO; Non-Final Office Action dated Sep. 11, 2013 in U.S. Appl. No. 13/550,419.
USPTO; Final Office Action dated Jan. 27, 2014 in U.S. Appl. No. 13/550,419.
USPTO; Advisory Action dated Mar. 31, 2014 in U.S. Appl. No. 13/550,419.
USPTO; Notice of Allowance dated May 29, 2014 in U.S. Appl. No. 13/550,419.
USPTO; Non-Final Office Action dated Aug. 8, 2014 in U.S. Appl. No. 13/563,066.
USPTO; Final Office Action dated Feb. 12, 2015 in U.S. Appl. No. 13/563,066.
USPTO; Advisory Action dated Apr. 16, 2015 in U.S. Appl. No. 13/563,066.
USPTO; Notice of Allowance dated Jun. 12, 2015 in U.S. Appl. No. 13/563,066.
USPTO; Notice of Allowance dated Jul. 16, 2015 in U.S. Appl. No. 13/563,066.
USPTO; Non-Final Office Action dated May 28, 2013 in U.S. Appl. No. 13/563,274.
USPTO; Notice of Allowance dated Sep. 27, 2013 in U.S. Appl. No. 13/563,274.
USPTO; Non-Final Office Action dated Nov. 7, 2013 in U.S. Appl. No. 13/565,564.
USPTO; Final Office Action dated Feb. 28, 2014 in U.S. Appl. No. 13/565,564.
USPTO; Advisory Action dated May 5, 2014 in U.S. Appl. No. 13/565,564.

(56) References Cited

OTHER PUBLICATIONS

USPTO; Non-Final Office Action dated Jul. 2, 2014 in U.S. Appl. No. 13/565,564.
USPTO; Notice of Allowance dated Nov. 3, 2014 in U.S. Appl. No. 13/565,564.
USPTO; Notice of Allowance dated Sep. 13, 2013 in U.S. Appl. No. 13/566,069.
USPTO; Non-Final Office Action dated Aug. 30, 2013 in U.S. Appl. No. 13/570,067.
USPTO; Notice of Allowance dated Jan. 6, 2014 in U.S. Appl. No. 13/570,067.
USPTO; Non-Final Office Action dated Oct. 15, 2014 in U.S. Appl. No. 13/597,043.
USPTO; Final Office Action dated Mar. 13, 2015 in U.S. Appl. No. 13/597,043.
USPTO; Notice of Allowance dated Aug. 28, 2015 in U.S. Appl. No. 13/597,043.
USPTO; Non-Final Office Action dated Feb. 12, 2015 in U.S. Appl. No. 13/597,108.
USPTO; Final Office Action dated Jun. 1, 2015 in U.S. Appl. No. 13/597,108.
USPTO; Advisory Action dated Sep. 2, 2015 in U.S. Appl. No. 13/597,108.
USPTO; Non-Final Office Action dated Dec. 8, 2015 in U.S. Appl. No. 13/597,108.
USPTO; Final Office Action dated Jun. 2, 2016 in U.S. Appl. No. 13/597,108.
USPTO; Non-Final Office Action dated Sep. 15, 2016 in U.S. Appl. No. 13/597,108.
USPTO; Notice of Allowance dated Mar. 7, 2017 in U.S. Appl. No. 13/597,108.
USPTO; Notice of Allowance dated Mar. 27, 2014 in U.S. Appl. No. 13/604,498.
USPTO; Non-Final Office Action dated Nov. 15, 2013 in U.S. Appl. No. 13/612,538.
USPTO; Non-Final Office Action dated Jul. 10, 2014 in U.S. Appl. No. 13/612,538.
USPTO; Notice of Allowance dated Feb. 25, 2015 in U.S. Appl. No. 13/612,538.
USPTO; Non-Final Office Action dated Apr. 15, 2015 in U.S. Appl. No. 13/646,403.
USPTO; Final Office Action dated Oct. 15, 2015 in U.S. Appl. No. 13/646,403.
USPTO; Notice of Allowance dated Feb. 2, 2016 in U.S. Appl. No. 13/646,403.
USPTO; Non-Final Office Action dated May 15, 2014 in U.S. Appl. No. 13/646,471.
USPTO; Final Office Action dated Aug. 18, 2014 in U.S. Appl. No. 13/646,471.
USPTO; Advisory Action dated Nov. 14, 2014 in U.S. Appl. No. 13/646,471.
USPTO; Non-Final Office Action dated Dec. 16, 2014 in U.S. Appl. No. 13/646,471.
USPTO; Final Office Action dated Apr. 21, 2015 in U.S. Appl. No. 13/646,471.
USPTO; Non-Final Office Action dated Aug. 19, 2015 in U.S. Appl. No. 13/646,471.
USPTO; Final Office Action dated Jan. 22, 2016 in U.S. Appl. No. 13/646,471.
USPTO; Advisory Action dated Apr. 15, 2016 in U.S. Appl. No. 13/646,471.
USPTO; Non-Final Office Action dated Jun. 2, 2016 in U.S. Appl. No. 13/646,471.
USPTO; Final Office Action dated Oct. 20, 2016 in U.S. Appl. No. 13/646,471.
USPTO; Non-Final Office Action dated May 28, 2015 in U.S. Appl. No. 13/651,144.
USPTO; Final Office Action dated Dec. 14, 2017 in U.S. Appl. No. 13/651,144.
USPTO; Final Office Action dated Nov. 19, 2015 in U.S. Appl. No. 13/651,144.
USPTO; Advisory Action dated Feb. 12, 2016 in U.S. Appl. No. 13/651,144.
USPTO; Non-Final Office Action dated May 10, 2016 in U.S. Appl. No. 13/651,144.
USPTO; Final Office Action dated Sep. 20, 2016 in U.S. Appl. No. 13/651,144.
USPTO; Advisory Action dated Dec. 29, 2016 in U.S. Appl. No. 13/651,144.
USPTO; Non-Final Office Action dated May 17, 2017 in U.S. Appl. No. 13/651,144.
USPTO; Non-Final Office Action dated Dec. 14, 2017 in U.S. Appl. No. 13/651,144.
USPTO; Advisory Action dated Apr. 19, 2018 in U.S. Appl. No. 13/651,144.
USPTO; Non-Final Office Action dated Sep. 20, 2018 in U.S. Appl. No. 13/651,144.
USPTO; Final Office Action dated Mar. 15, 2019 in U.S. Appl. No. 13/651,144.
USPTO; Non-Final Office Action dated Sep. 18, 2019 in U.S. Appl. No. 13/651,144.
USPTO; Notice of Allowance dated Feb. 10, 2020 in U.S. Appl. No. 13/651,144.
USPTO; Advisory Action dated Jun. 26, 2015 in U.S. Appl. No. 13/791,246.
USPTO; Non-Final Office Action dated Jun. 18, 2015 in U.S. Appl. No. 13/665,366.
USPTO; Final Office Action dated Mar. 1, 2016 in U.S. Appl. No. 13/665,366.
USPTO; Advisory Action dated May 13, 2016 in U.S. Appl. No. 13/665,366.
USPTO; Non-Final Office Action dated Jun. 17, 2016 in U.S. Appl. No. 13/665,366.
USPTO; Final Office Action dated May 3, 2017 in U.S. Appl. No. 13/665,366.
USPTO; Non-Final Office Action dated Apr. 3, 2015 in U.S. Appl. No. 13/677,133.
USPTO; Notice of Allowance dated Aug. 4, 2015 in U.S. Appl. No. 13/677,133.
USPTO; Notice of Allowance dated Aug. 24, 2015 in U.S. Appl. No. 13/677,133.
USPTO; Office Action dated Jun. 2, 2014 in U.S. Appl. No. 13/677,151.
USPTO; Final Office Action dated Nov. 14, 2014 in U.S. Appl. No. 13/677,151.
USPTO; Notice of Allowance dated Feb. 26, 2015 in U.S. Appl. No. 13/677,151.
USPTO; Notice of Allowance dated Mar. 17, 2015 in U.S. Appl. No. 13/677,151.
USPTO; Non-Final Office Action dated Aug. 20, 2013 in U.S. Appl. No. 13/679,502.
USPTO; Final Office Action dated Feb. 25, 2014 in U.S. Appl. No. 13/679,502.
USPTO; Notice of Allowance dated May 2, 2014 in U.S. Appl. No. 13/679,502.
USPTO; Non-Final Office Action dated Jul. 21, 2015 in U.S. Appl. No. 13/727,324.
USPTO; Final Office Action dated Jan. 22, 2016 in U.S. Appl. No. 13/727,324.
USPTO; Advisory Action dated Apr. 6, 2016 in U.S. Appl. No. 13/727,324.
USPTO; Non-Final Office Action dated May 25, 2016 in U.S. Appl. No. 13/727,324.
USPTO; Final Office Action dated Dec. 1, 2016 in U.S. Appl. No. 13/727,324.
USPTO; Notice of Allowance dated Mar. 1, 2017 in U.S. Appl. No. 13/727,324.
USPTO; Non-Final Office Action dated Oct. 24, 2013 in U.S. Appl. No. 13/749,878.
USPTO; Non-Final Office Action dated Jun. 18, 2014 in U.S. Appl. No. 13/749,878.

(56) References Cited

OTHER PUBLICATIONS

USPTO; Final Office Action dated Dec. 10, 2014 in U.S. Appl. No. 13/749,878.
USPTO; Notice of Allowance Mar. 13, 2015 dated in U.S. Appl. No. 13/749,878.
USPTO; Non-Final Office Action dated Sep. 16, 2013 in U.S. Appl. No. 13/760,160.
USPTO; Final Office Action dated Dec. 27, 2013 in U.S. Appl. No. 13/760,160.
USPTO; Non-Final Office Action dated Jun. 4, 2014 in U.S. Appl. No. 13/760,160.
USPTO; Final Office Action dated Sep. 25, 2014 in U.S. Appl. No. 13/760,160.
USPTO; Final Office Action dated Jan. 28, 2015 in U.S. Appl. No. 13/760,160.
USPTO; Final Office Action dated May 12, 2015 in U.S. Appl. No. 13/760,160.
USPTO; Notice of Allowance dated Oct. 21, 2015 in U.S. Appl. No. 13/760,160.
USPTO; Notice of Allowance dated Jan. 20, 2016 in U.S. Appl. No. 13/760,160.
USPTO; Office Action dated Apr. 23, 2014 in U.S. Appl. No. 13/784,362.
USPTO; Notice of Allowance dated Aug. 13, 2014 in U.S. Appl. No. 13/784,362.
USPTO; Non-Final Office Action dated Dec. 19, 2013 in U.S. Appl. No. 13/784,388.
USPTO; Notice of Allowance dated Jun. 4, 2014 in U.S. Appl. No. 13/784,388.
USPTO; Non-Final Office Action dated Sep. 19, 2014 in U.S. Appl. No. 13/791,246.
USPTO; Final Office Action dated Mar. 25, 2015 in U.S. Appl. No. 13/791,246.
USPTO; Non-Final Office Action dated Oct. 26, 2015 in U.S. Appl. No. 13/791,246.
USPTO; Final Office Action dated Apr. 20, 2016 in U.S. Appl. No. 13/791,246.
USPTO; Advisory Action dated Jul. 13, 2016 in U.S. Appl. No. 13/791,246.
USPTO; Non-Final Office Action dated Aug. 11, 2016 in U.S. Appl. No. 13/791,246.
USPTO; Notice of Allowance dated Oct. 19, 2016 in U.S. Appl. No. 13/791,246.
USPTO; Notice of Allowance dated Nov. 25, 2016 in U.S. Appl. No. 13/791,246.
USPTO; Non-Final Office Action dated Nov. 6, 2015 in U.S. Appl. No. 13/791,339.
USPTO; Final Office Action dated Apr. 12, 2016 in U.S. Appl. No. 13/791,339.
USPTO; Advisory Action dated Jul. 14, 2016 in U.S. Appl. No. 13/791,339.
USPTO; Notice of Allowance dated Aug. 24, 2016 in U.S. Appl. No. 13/791,339.
USPTO; Non-Final Office Action dated Mar. 21, 2014 in U.S. Appl. No. 13/799,708.
USPTO; Notice of Allowance dated Oct. 31, 2014 in U.S. Appl. No. 13/799,708.
USPTO; Non-Final Office Action dated Oct. 9, 2014 in U.S. Appl. No. 13/874,708.
USPTO; Notice of Allowance dated Mar. 10, 2015 in U.S. Appl. No. 13/874,708.
USPTO; Notice of Allowance dated Apr. 10, 2014 in U.S. Appl. No. 13/901,341.
USPTO; Notice of Allowance dated Jun. 6, 2014 in U.S. Appl. No. 13/901,341.
USPTO; Non-Final Office Action dated Jan. 2, 2015 in U.S. Appl. No. 13/901,372.
USPTO; Final Office Action dated Apr. 16, 2015 in U.S. Appl. No. 13/901,372.
USPTO; Notice of Allowance dated Aug. 5, 2015 in U.S. Appl. No. 13/901,372.
USPTO; Advisory Action dated Jun. 29, 2015 in U.S. Appl. No. 13/901,372.
USPTO; Non-Final Office Action dated Jul. 8, 2015 in U.S. Appl. No. 13/901,400.
USPTO; Final Office Action dated Jan. 14, 2016 in U.S. Appl. No. 13/901,400.
USPTO; Notice of Allowance dated Apr. 12, 2016 in U.S. Appl. No. 13/901,400.
USPTO; Non-Final Office Action dated Apr. 24, 2014 in U.S. Appl. No. 13/912,666.
USPTO; Final Office Action dated Sep. 25, 2014 in U.S. Appl. No. 13/912,666.
USPTO; Advisory Action dated Dec. 11, 2014 in U.S. Appl. No. 13/912,666.
USPTO; Non-Final Office Action dated Jan. 26, 2015 in U.S. Appl. No. 13/912,666.
USPTO; Notice of Allowance dated Jun. 25, 2015 in U.S. Appl. No. 13/912,666.
USPTO; Non-Final Office Action dated Dec. 16, 2014 in U.S. Appl. No. 13/915,732.
USPTO; Final Office Action dated Apr. 10, 2015 in U.S. Appl. No. 13/915,732.
USPTO; Notice of Allowance dated Jun. 19, 2015 in U.S. Appl. No. 13/915,732.
USPTO; Notice of Allowance dated Mar. 17, 2015 in U.S. Appl. No. 13/923,197.
USPTO; Non-Final Office Action dated Sep. 12, 2014 in U.S. Appl. No. 13/941,134.
USPTO; Notice of Allowance dated Jan. 20, 2015 in U.S. Appl. No. 13/941,134.
USPTO; Non-Final Office Action dated Jul. 30, 2015 in U.S. Appl. No. 13/941,216.
USPTO; Final Office Action dated Mar. 1, 2016 in U.S. Appl. No. 13/941,216.
USPTO; Non-Final Office Action dated Jun. 15, 2016 in U.S. Appl. No. 13/941,216.
USPTO; Notice of Allowance dated Sep. 13, 2016 in U.S. Appl. No. 13/941,216.
USPTO; Notice of Allowance dated Nov. 14, 2016 in U.S. Appl. No. 13/941,216.
USPTO; Non-Final Office Action dated Jan. 14, 2014 in U.S. Appl. No. 13/941,226.
USPTO; Non-Final Office Action dated Jul. 8, 2014 in U.S. Appl. No. 13/941,226.
USPTO; Non-Final Office Action dated Feb. 3, 2015 in U.S. Appl. No. 13/941,226.
USPTO; Final Office Action dated Feb. 12, 2016 in U.S. Appl. No. 13/941,226.
USPTO; Advisory Action dated Jul. 29, 2016 in U.S. Appl. No. 13/941,226.
USPTO; Non-Final Office Action dated Aug. 8, 2017 in U.S. Appl. No. 13/941,226.
USPTO; Notice of Allowance dated Aug. 13, 2018 in U.S. Appl. No. 13/941,226.
USPTO; Notice of Allowance dated Oct. 3, 2018 in U.S. Appl. No. 13/941,226.
USPTO; Non-Final Office Action dated Oct. 30, 2014 in U.S. Appl. No. 13/948,055.
USPTO; Notice of Allowance dated Feb. 27, 2015 in U.S. Appl. No. 13/948,055.
USPTO; Notice of Allowance dated Mar. 31, 2015 in U.S. Appl. No. 13/948,055.
USPTO; Non-Final Office Action dated Jun. 29, 2015 in U.S. Appl. No. 13/966,782.
USPTO; Final Office Action dated Jan. 4, 2016 in U.S. Appl. No. 13/966,782.
USPTO; Notice of Allowance dated Mar. 21, 2016 in U.S. Appl. No. 13/966,782.
USPTO; Notice of Allowance dated Oct. 7, 2015 in U.S. Appl. No. 13/973,777.

(56) References Cited

OTHER PUBLICATIONS

USPTO; Non-Final Office Action dated Feb. 20, 2015 in U.S. Appl. No. 14/018,231.
USPTO; Notice of Allowance dated Jul. 20, 2015 in U.S. Appl. No. 14/018,231.
USPTO; Non-Final Office Action dated Apr. 7, 2015 in U.S. Appl. No. 14/018,345.
USPTO; Final Office Action dated Sep. 14, 2015 in U.S. Appl. No. 14/018,345.
USPTO; Notice of Allowance dated Jan. 14, 2016 in U.S. Appl. No. 14/018,345.
USPTO; Notice of Allowance dated Mar. 17, 2016 in U.S. Appl. No. 14/018,345.
USPTO; Non-Final Office Action dated Mar. 26, 2015 in U.S. Appl. No. 14/031,982.
USPTO; Final Office Action dated Aug. 28, 2015 in U.S. Appl. No. 14/031,982.
USPTO; Notice of Allowance dated Nov. 17, 2015 in U.S. Appl. No. 14/031,982.
USPTO; Non-Final Office Action dated Jan. 2, 2015 in U.S. Appl. No. 14/040,196.
USPTO; Non-Final Office Action dated Apr. 28, 2015 in U.S. Appl. No. 14/040,196.
USPTO; Notice of Allowance dated Sep. 11, 2015 in U.S. Appl. No. 14/040,196.
USPTO; Non-Final Action dated Dec. 3, 2015 in U.S. Appl. No. 14/050,150.
USPTO; Final Office Action dated Jun. 15, 2016 in U.S. Appl. No. 14/050,150.
USPTO; Final Office Action dated Jul. 8, 2016 in U.S. Appl. No. 14/050,150.
USPTO; Notice of Allowance dated Oct. 20, 2016 in U.S. Appl. No. 14/050,150.
USPTO; Non-Final Office Action dated Dec. 15, 2014 in U.S. Appl. No. 14/065,114.
USPTO; Final Office Action dated Jun. 19, 2015 in U.S. Appl. No. 14/065,114.
USPTO; Advisory Action dated Aug. 24, 2015 in U.S. Appl. No. 14/065,114.
USPTO; Non-Final Office Action dated Oct. 7, 2015 in U.S. Appl. No. 14/065,114.
USPTO; Notice of Allowance dated Feb. 22, 2016 in U.S. Appl. No. 14/065,114.
USPTO; Non-Final Office Action dated Nov. 14, 2014 in U.S. Appl. No. 14/069,244.
USPTO; Notice of Allowance dated Mar. 25, 2015 in U.S. Appl. No. 14/069,244.
USPTO; Non-Final Office Action dated Mar. 19, 2015 in U.S. Appl. No. 14/079,302.
USPTO; Final Office Action dated Sep. 1, 2015 in U.S. Appl. No. 14/079,302.
USPTO; Non-Final Office Action dated Dec. 23, 2015 in U.S. Appl. No. 14/079,302.
USPTO; Non-Final Office Action dated Apr. 27, 2016 in U.S. Appl. No. 14/079,302.
USPTO; Final Office Action dated Aug. 22, 2016 in U.S. Appl. No. 14/079,302.
USPTO; Notice of Allowance dated Dec. 14, 2016 in U.S. Appl. No. 14/079,302.
USPTO; Advisory Action dated Nov. 10, 2015 in U.S. Appl. No. 14/079,302.
USPTO; Non-Final Office Action dated Sep. 9, 2015 in U.S. Appl. No. 14/090,750.
USPTO; Final Office Action dated Feb. 11, 2016 in U.S. Appl. No. 14/090,750.
USPTO; Advisory Action dated May 5, 2016 in U.S. Appl. No. 14/090,750.
USPTO; Non-Final Office Action dated Jun. 14, 2016 in U.S. Appl. No. 14/090,750.
USPTO; Advisory Action dated Dec. 21, 2016 in U.S. Appl. No. 14/090,750.
USPTO; Advisory Action dated Jan. 30, 2018 in U.S. Appl. No. 14/090,750.
USPTO; Final Office Action dated Sep. 28, 2016 in U.S. Appl. No. 14/090,750.
USPTO; Non-Final Office Action dated Jun. 23, 2017 in U.S. Appl. No. 14/090,750.
USPTO; Final Office Action dated Nov. 17, 2017 in U.S. Appl. No. 14/090,750.
USPTO; Non-Final Office Action dated Mar. 12, 2018 in U.S. Appl. No. 14/090,750.
USPTO; Notice of Allowance dated Aug. 29, 2018 in U.S. Appl. No. 14/090,750.
USPTO; Non-Final Office Action dated Mar. 19, 2015 in U.S. Appl. No. 14/166,462.
USPTO; Notice of Allowance dated Sep. 3, 2015 in U.S. Appl. No. 14/166,462.
USPTO; Non-Final Office Action dated Nov. 17, 2015 in U.S. Appl. No. 14/172,220.
USPTO; Notice of Allowance dated Apr. 22, 2016 in U.S. Appl. No. 14/172,220.
USPTO; Office Action dated May 29, 2014 in U.S. Appl. No. 14/183,187.
USPTO; Final Office Action dated Nov. 7, 2014 in U.S. Appl. No. 14/183,187.
USPTO; Advisory Action dated Feb. 20, 2015 in U.S. Appl. No. 14/183,187.
USPTO; Non-Final Office Action dated Mar. 16, 2015 in U.S. Appl. No. 14/183,187.
USPTO; Final Office Action dated Jul. 10, 2015 in U.S. Appl. No. 14/183,187.
USPTO; Notice of Allowance dated Aug. 31, 2015 in U.S. Appl. No. 14/183,187.
USPTO; Non-Final Office Action dated Jan. 11, 2016 in U.S. Appl. No. 14/188,760.
USPTO; Final Office Action dated Aug. 25, 2016 in U.S. Appl. No. 14/188,760.
USPTO; Advisory Action dated Jan. 12, 2017 in U.S. Appl. No. 14/188,760.
USPTO; Non-Final Office Action dated Mar. 23, 2017 in U.S. Appl. No. 14/188,760.
USPTO; Final Office Action dated Oct. 5, 2017 in U.S. Appl. No. 14/188,760.
USPTO; Advisory Action dated Jan. 3, 2018 in U.S. Appl. No. 14/188,760.
USPTO; Non-Final Office Action dated Apr. 18, 2018 in U.S. Appl. No. 14/188,760.
USPTO; Final Office Action dated Jan. 25, 2019 in U.S. Appl. No. 14/188,760.
USPTO; Non-Final Office Action dated Aug. 8, 2019 in U.S. Appl. No. 14/188,760.
USPTO; Notice of Allowance dated Feb. 10, 2020 in U.S. Appl. No. 14/188,760.
USPTO; Non-Final Office Action dated Oct. 8, 2015 in U.S. Appl. No. 14/218,374.
USPTO; Final Office Action dated Feb. 23, 2016 in U.S. Appl. No. 14/218,374.
USPTO; Advisory Action dated Apr. 29, 2016 in U.S. Appl. No. 14/218,374.
USPTO; Notice of Allowance dated Aug. 5, 2016 in U.S. Appl. No. 14/218,374.
USPTO; Non-Final Office Action dated Jul. 15, 2016 in U.S. Appl. No. 14/218,690.
USPTO; Final Office Action dated Nov. 14, 2016 in U.S. Appl. No. 14/218,690.
USPTO; Non-Final Office Action dated Apr. 6, 2017 in U.S. Appl. No. 14/218,690.
USPTO; Final Office Action dated Jul. 20, 2017 in U.S. Appl. No. 14/218,690.
USPTO; Non-Final Office Action dated Jan. 11, 2018 in U.S. Appl. No. 14/218,690.

(56) References Cited

OTHER PUBLICATIONS

USPTO; Final Office Action dated May 24, 2018 in U.S. Appl. No. 14/218,690.
USPTO; Notice of Allowance dated Sep. 24, 2018 in U.S. Appl. No. 14/218,690.
USPTO; Non-Final Office Action dated Sep. 22, 2015 in U.S. Appl. No. 14/219,839.
USPTO; Final Office Action dated Mar. 25, 2016 in U.S. Appl. No. 14/219,839.
USPTO; Non-Final Office Action dated Dec. 22, 2016 in U.S. Appl. No. 14/219,839.
USPTO; Advisory Action dated Jun. 30, 2016 in U.S. Appl. No. 14/219,839.
USPTO; Final Office Action dated Jul. 6, 2017 in U.S. Appl. No. 14/219,839.
USPTO; Non-Final Office Action dated Mar. 27, 2018 in U.S. Appl. No. 14/219,839.
USPTO; Final Office Action dated Nov. 1, 2018 in U.S. Appl. No. 14/219,839.
USPTO; Advisory Action dated Jan. 22, 2019 in U.S. Appl. No. 14/219,839.
USPTO; Non-Final Office Action dated Jul. 15, 2019 in U.S. Appl. No. 14/219,839.
USPTO; Final Office Action dated Jan. 27, 2020 in U.S. Appl. No. 14/219,839.
USPTO; Advisory Action dated Apr. 24, 2020 in U.S. Appl. No. 14/219,839.
USPTO; Advisory Action dated Apr. 24, 2020 in U.S. Appl. No. 14/219,879.
USPTO; Non-Final Office Action dated Nov. 25, 2015 in U.S. Appl. No. 14/219,879.
USPTO; Final Office action dated May 19, 2016 in U.S. Appl. No. 14/219,879.
USPTO; Advisory Action dated Aug. 22, 2016 in U.S. Appl. No. 14/219,879.
USPTO; Non-Final Office Action dated Dec. 23, 2016 in U.S. Appl. No. 14/219,879.
USPTO; Final Office action dated Jul. 6, 2017 in U.S. Appl. No. 14/219,879.
USPTO; Advisory Action dated Oct. 5, 2017 in U.S. Appl. No. 14/219,879.
USPTO; Non-Final Office Action dated Apr. 6, 2018 in U.S. Appl. No. 14/219,879.
USPTO; Final Office Action dated Nov. 2, 2018 in U.S. Appl. No. 14/219,879.
USPTO; Advisory Action dated Jan. 22, 2019 in U.S. Appl. No. 14/219,879.
USPTO; Non-Final Office Action dated Jun. 24, 2019 in U.S. Appl. No. 14/219,879.
USPTO; Final Office Action dated Jan. 13, 2020 in U.S. Appl. No. 14/219,879.
USPTO; Non-Final Office Action dated Sep. 18, 2015 in U.S. Appl. No. 14/244,689.
USPTO; Notice of Allowance dated Feb. 11, 2016 in U.S. Appl. No. 14/244,689.
USPTO; Non-Final Office Action dated Oct. 7, 2015 in U.S. Appl. No. 14/246,969.
USPTO; Final Office Action dated May 4, 2016 in U.S. Appl. No. 14/246,969.
USPTO; Advisory Action dated Aug. 2, 2016 in U.S. Appl. No. 14/246,969.
USPTO; Non-Final Office Action dated Aug. 12, 2016 in U.S. Appl. No. 14/246,969.
USPTO; Notice of Allowance dated Feb. 27, 2017 in U.S. Appl. No. 14/246,969.
USPTO; Non-Final Office Action dated Nov. 20, 2015 in U.S. Appl. No. 14/260,701.
USPTO; Notice of Allowance dated Jun. 2, 2016 in U.S. Appl. No. 14/260,701.
USPTO; Notice of Allowance dated Feb. 23, 2016 in U.S. Appl. No. 14/327,134.
USPTO; Non-Final Office Action dated Aug. 19, 2015 in U.S. Appl. No. 14/268,348.
USPTO; Non-Final Office Action dated Jan. 6, 2016 in U.S. Appl. No. 14/268,348.
USPTO; Final Office Action dated Apr. 29, 2016 in U.S. Appl. No. 14/268,348.
USPTO; Notice of Allowance dated Aug. 19, 2016 in U.S. Appl. No. 14/268,348.
USPTO; Notice of Allowance dated Aug. 30, 2016 in U.S. Appl. No. 14/268,348.
USPTO; Non-Final Office Action dated Oct. 20, 2015 in U.S. Appl. No. 14/281,477.
USPTO; Notice of Allowance dated Mar. 28, 2016 in U.S. Appl. No. 14/281,477.
USPTO; Non-Final Office Action dated Jan. 13, 2017 in U.S. Appl. No. 14/444,744.
USPTO; Final Office Action dated Jul. 10, 2017 in U.S. Appl. No. 14/444,744.
USPTO; Non-Final Office Action dated Nov. 29, 2017 in U.S. Appl. No. 14/444,744.
USPTO; Final Office Action dated Mar. 28, 2018 in U.S. Appl. No. 14/444,744.
USPTO; Non-Final Office Action dated Jul. 27, 2018 in U.S. Appl. No. 14/444,744.
USPTO; Final Office Action dated Feb. 7, 2019 in U.S. Appl. No. 14/444,744.
USPTO; Non-Final Office Action dated Aug. 8, 2019 in U.S. Appl. No. 14/444,744.
USPTO; Final Office Action dated Feb. 20, 2020 in U.S. Appl. No. 14/444,744.
USPTO; Non-Final Office Action dated Apr. 28, 2020 in U.S. Appl. No. 14/444,744.
USPTO; Notice of Allowance dated Sep. 3, 2020 in U.S. Appl. No. 14/444,744.
USPTO; Non-Final Office Action dated May 18, 2016 in U.S. Appl. No. 14/449,838.
USPTO; Notice of Allowance dated Nov. 28, 2016 in U.S. Appl. No. 14/449,838.
USPTO; Non-Final Office Action dated Feb. 12, 2015 in U.S. Appl. No. 14/457,058.
USPTO; Final Office Action dated Jul. 14, 2015 in U.S. Appl. No. 14/457,058.
USPTO; Non-Final Office Action dated Nov. 6, 2015 in U.S. Appl. No. 14/457,058.
USPTO; Advisory Action dated Nov. 6, 2015 in U.S. Appl. No. 14/457,058.
USPTO; Final Office Acton dated Jun. 17, 2016 in U.S. Appl. No. 14/457,058.
USPTO; Advisory Action dated Sep. 21, 2016 in U.S. Appl. No. 14/457,058.
USPTO; Non-Final Office Action dated Oct. 6, 2016 in U.S. Appl. No. 14/457,058.
USPTO; Final Office Acton dated May 4, 2017 in U.S. Appl. No. 14/457,058.
USPTO; Non-Final Office Action dated Oct. 19, 2017 in U.S. Appl. No. 14/457,058.
USPTO; Final Office Action dated Jun. 14, 2018 in U.S. Appl. No. 14/457,058.
USPTO; Non-Final Office Action dated Jan. 11, 2019 in U.S. Appl. No. 14/457,058.
USPTO; Final Office Action dated Jun. 25, 2019 in U.S. Appl. No. 14/457,058.
USPTO; Non-Final Office Action dated Oct. 31, 2019 in U.S. Appl. No. 14/457,058.
USPTO; Final Office Action dated May 15, 2020 in U.S. Appl. No. 14/457,058.
USPTO; Notice of Allowance dated Aug. 6, 2020 in U.S. Appl. No. 14/457,058.
USPTO; Non-Final Office Action dated Sep. 16, 2016 in U.S. Appl. No. 14/465,252.

(56) References Cited

OTHER PUBLICATIONS

USPTO; Final Office Action dated Nov. 1, 2016 in U.S. Appl. No. 14/465,252.
USPTO; Non-Final Office Action dated Mar. 6, 2017 in U.S. Appl. No. 14/465,252.
USPTO; Final Office Action dated Jun. 9, 2017 in U.S. Appl. No. 14/465,252.
USPTO; Notice of Allowance dated Oct. 3, 2017 in U.S. Appl. No. 14/465,252.
USPTO; Non-Final Office Action dated Nov. 24, 2015 in U.S. Appl. No. 14/498,036.
USPTO; Final Office Action dated Apr. 5, 2016 in U.S. Appl. No. 14/498,036.
USPTO; Advisory Action dated Jun. 16, 2016 in U.S. Appl. No. 14/498,036.
USPTO; Notice of Allowance dated Aug. 17, 2016 in U.S. Appl. No. 14/498,036.
USPTO; Non-Final Office Action dated Apr. 10, 2015 in U.S. Appl. No. 14/505,290.
USPTO; Notice of Allowance dated Aug. 21, 2015 in U.S. Appl. No. 14/505,290.
USPTO; Non-Final Office Action dated Dec. 17, 2015 in U.S. Appl. No. 14/508,296.
USPTO; Final Office Action dated May 26, 2016 in U.S. Appl. No. 14/508,296.
USPTO; Advisory Action dated Aug. 17, 2016 in U.S. Appl. No. 14/508,296.
USPTO; Non-Final Office Action dated Sep. 8, 2016 in U.S. Appl. No. 14/508,296.
USPTO; Final Office Action dated Dec. 7, 2016 in U.S. Appl. No. 14/508,296.
USPTO; Notice of Allowance dated Jan. 27, 2017 in U.S. Appl. No. 14/508,296.
USPTO; Non-Final Office Action dated Apr. 6, 2017 in U.S. Appl. No. 14/508,489.
USPTO; Final Office Action dated Oct. 4, 2017 in U.S. Appl. No. 14/508,489.
USPTO; Non-Final Office Action dated May 15, 2018 in U.S. Appl. No. 14/508,489.
USPTO; Final Office Action dated Nov. 28, 2018 in U.S. Appl. No. 14/508,489.
USPTO; Non-Final Office Action dated Apr. 4, 2019 in U.S. Appl. No. 14/508,489.
USPTO; Final Office Action dated Aug. 20, 2019 in U.S. Appl. No. 14/508,489.
USPTO; Advisory Action dated Oct. 28, 2019 in U.S. Appl. No. 14/508,489.
USPTO; Non-Final Office Action dated Mar. 5, 2020 in U.S. Appl. No. 14/508,489.
USPTO; Final Office Action dated Aug. 20, 2020 in U.S. Appl. No. 14/508,489.
USPTO; Notice of Allowance dated Nov. 3, 2020 in U.S. Appl. No. 14/508,489.
USPTO; Non-Final Office Action dated Jan. 16, 2015 in U.S. Appl. No. 14/563,044.
USPTO; Final Office Action dated Jul. 16, 2015 in U.S. Appl. No. 14/563,044.
USPTO; Notice of Allowance dated Oct. 15, 2015 in U.S. Appl. No. 14/563,044.
USPTO; Notice of Allowance dated Dec. 2, 2015 in U.S. Appl. No. 14/563,044.
USPTO; Non-Final Office Action dated May 4, 2016 in U.S. Appl. No. 14/568,647.
USPTO; Final Office Action dated Sep. 29, 2016 in U.S. Appl. No. 14/568,647.
USPTO; Advisory Action dated Dec. 21, 2016 in U.S. Appl. No. 14/568,647.
USPTO; Non-Final Office Action dated Feb. 2, 2017 in U.S. Appl. No. 14/568,647.
USPTO; Final Office Action dated May 19, 2017 in U.S. Appl. No. 14/568,647.
USPTO; Non-Final Office Action dated Sep. 14, 2017 in U.S. Appl. No. 14/568,647.
USPTO; Final Office Action dated Jan. 23, 2018 in U.S. Appl. No. 14/568,647.
USPTO; Advisory Action dated Apr. 12, 2018 in U.S. Appl. No. 14/568,647.
USPTO; Non-Final Office Action dated May 25, 2018 in U.S. Appl. No. 14/568,647.
USPTO; Non-Final Office Action dated Oct. 1, 2015 in U.S. Appl. No. 14/571,126.
USPTO; Final Office Action dated Feb. 22, 2016 in U.S. Appl. No. 14/571,126.
USPTO; Notice of Allowance dated May 18, 2016 in U.S. Appl. No. 14/571,126.
USPTO; Notice of Allowance dated Jun. 2, 2016 in U.S. Appl. No. 14/571,126.
USPTO; Non-Final Office Action dated Nov. 25, 2015 in U.S. Appl. No. 14/598,532.
USPTO; Notice of Allowance dated May 16, 2016 in U.S. Appl. No. 14/598,532.
USPTO; Non-Final Office Action dated Jan. 15, 2016 in U.S. Appl. No. 14/606,364.
USPTO; Final Office Action dated Jun. 14, 2016 in U.S. Appl. No. 14/606,364.
USPTO; Advisory Action dated Aug. 25, 2016 in U.S. Appl. No. 14/606,364.
USPTO; Final Office Action dated Jan. 12, 2017 in U.S. Appl. No. 14/606,364.
USPTO; Non-Final Office Action dated May 10, 2017 in U.S. Appl. No. 14/606,364.
USPTO; Notice of Allowance dated Aug. 16, 2017 in U.S. Appl. No. 14/606,364.
USPTO; Non-Final Office Action dated Mar. 3, 2016 in U.S. Appl. No. 14/622,603.
USPTO; Notice of Allowance dated Aug. 2, 2016 in U.S. Appl. No. 14/622,603.
USPTO; Notice of Allowance dated Feb. 16, 2016 in U.S. Appl. No. 14/634,342.
USPTO; Non-Final Office Action dated Oct. 19, 2017 in U.S. Appl. No. 14/645,234.
USPTO; Non-Final Office Action dated May 16, 2018 in U.S. Appl. No. 14/645,234.
USPTO; Final Office Action dated Aug. 10, 2018 in U.S. Appl. No. 14/645,234.
USPTO; Notice of Allowance dated Aug. 15, 2019 in U.S. Appl. No. 14/645,234.
USPTO; Non-Final Office Action dated Jun. 7, 2017 in U.S. Appl. No. 14/656,588.
USPTO; Final Office Action dated Dec. 26, 2017 in U.S. Appl. No. 14/656,588.
USPTO; Non-Final Office Action dated Apr. 6, 2018 in U.S. Appl. No. 14/656,588.
USPTO; Notice of Allowance dated Nov. 19, 2018 in U.S. Appl. No. 14/656,588.
USPTO; Non-Final Office Action dated Mar. 21, 2016 in U.S. Appl. No. 14/659,152.
USPTO; Final Office Action dated Jul. 29, 2016 in U.S. Appl. No. 14/659,152.
USPTO; Notice of Allowance dated Nov. 22, 2016 in U.S. Appl. No. 14/659,152.
USPTO; Non-Final Office Action dated Nov. 19, 2015 in U.S. Appl. No. 14/659,437.
USPTO; Final Office Action dated Mar. 17, 2016 in U.S. Appl. No. 14/659,437.
USPTO; Notice of Allowance dated May 31, 2016 in U.S. Appl. No. 14/659,437.
USPTO; Non-Final Office Action dated Sep. 7, 2017 in U.S. Appl. No. 14/660,755.
USPTO; Notice of Allowance dated Oct. 2, 2017 in U.S. Appl. No. 14/660,755.

(56) References Cited

OTHER PUBLICATIONS

USPTO; Notice of Allowance dated Mar. 25, 2016 in U.S. Appl. No. 14/693,138.
USPTO; Non-Final Office Action dated Aug. 3, 2017 in U.S. Appl. No. 14/752,712.
USPTO; Final Office Action dated Nov. 29, 2017 in U.S. Appl. No. 14/752,712.
USPTO; Advisory Action dated Feb. 15, 2018 in U.S. Appl. No. 14/752,712.
USPTO; Non-Final Office Action dated Mar. 21, 2018 in U.S. Appl. No. 14/752,712.
USPTO; Final Office Action dated Sep. 5, 2018 in U.S. Appl. No. 14/752,712.
USPTO; Non-Final Office Action dated Dec. 28, 2018 in U.S. Appl. No. 14/752,712.
USPTO; Notice of Allowance dated Jun. 11, 2019 in U.S. Appl. No. 14/752,712.
USPTO; Non-Final Office Action dated Nov. 29, 2017 in U.S. Appl. No. 14/793,323.
USPTO; Final Office Action dated Mar. 29, 2018 in U.S. Appl. No. 14/793,323.
USPTO; Non-Final Office Action dated Aug. 10, 2018 in U.S. Appl. No. 14/793,323.
USPTO; Final Office Action dated Feb. 25, 2019 in U.S. Appl. No. 14/793,323.
UPSTO; Non-Final Office Action dated Jun. 27, 2019 in U.S. Appl. No. 14/793,323.
USPTO; Notice of Allowance dated Nov. 14, 2019 in U.S. Appl. No. 14/793,323.
USPTO; Non-Final Office Action dated Jun. 16, 2017 in U.S. Appl. No. 14/798,136.
USPTO; Notice of Allowance dated Oct. 5, 2017 in U.S. Appl. No. 14/798,136.
USPTO; Non-Final Office Action dated Mar. 30, 2016 in U.S. Appl. No. 14/808,979.
USPTO; Final Office Acton dated Sep. 30, 2016 in U.S. Appl. No. 14/808,979.
USPTO; Non-Final Office Action dated Dec. 20, 2016 in U.S. Appl. No. 14/808,979.
USPTO; Final Office Action dated Jun. 8, 2017 in U.S. Appl. No. 14/808,979.
USPTO; Non-Final Office Action dated Sep. 21, 2017 in U.S. Appl. No. 14/808,979.
USPTO; Final Office Action dated Mar. 14, 2018 in U.S. Appl. No. 14/808,979.
USPTO; Notice of Allowance dated Jun. 27, 2018 in U.S. Appl. No. 14/808,979.
USPTO; Non-Final Office Action dated Feb. 23, 2018 in U.S. Appl. No. 14/817,953.
USPTO; Notice of Allowance dated Jul. 11, 2018 in U.S. Appl. No. 14/817,953.
USPTO; Non-Final Office Action dated Sep. 1, 2016 in U.S. Appl. No. 14/827,177.
USPTO; Notice of Allowance dated Jan. 27, 2017 in U.S. Appl. No. 14/827,177.
USPTO; Non-Final Office Action dated Sep. 9, 2016 in U.S. Appl. No. 14/829,565.
USPTO; Final Office Action dated Feb. 9, 2017 in U.S. Appl. No. 14/829,565.
USPTO; Advisory Action dated Apr. 20, 2017 in U.S. Appl. No. 14/829,565.
USPTO; Non-Final Office Action dated Sep. 19, 2017 in U.S. Appl. No. 14/829,565.
USPTO; Final Office Action dated Mar. 5, 2018 in U.S. Appl. No. 14/829,565.
USPTO; Advisory Action dated Aug. 10, 2018 in U.S. Appl. No. 14/829,565.
USPTO; Non-Final Office Action dated Sep. 6, 2018 in U.S. Appl. No. 14/829,565.
USPTO; Final Office Action dated Apr. 18, 2019 in U.S. Appl. No. 14/829,565.
USPTO; Advisory Action dated Jul. 22, 2019 in U.S. Appl. No. 14/829,565.
USPTO; Non-Final Office Action dated Sep. 19, 2019 in U.S. Appl. No. 14/829,565.
USPTO; Final Office Action dated Mar. 3, 2020 in U.S. Appl. No. 14/829,565.
USPTO; Advisory Action dated Jun. 22, 2020 in U.S. Appl. No. 14/829,565.
USPTO; Non-Final Office Action dated Aug. 3, 2020 in U.S. Appl. No. 14/829,565.
USPTO; Non-Final Office Action dated Apr. 29, 2016 in U.S. Appl. No. 14/835,637.
USPTO; Final Office Action dated Nov. 25, 2016 in U.S. Appl. No. 14/835,637.
USPTO; Advisory Action dated Feb. 14, 2017 in U.S. Appl. No. 14/835,637.
USPTO; Notice of Allowance dated Apr. 25, 2017 in U.S. Appl. No. 14/835,637.
USPTO; Non-Final Office Action dated Jul. 29, 2016 in U.S. Appl. No. 14/884,695.
USPTO; Final Office Action dated Feb. 9, 2017 in U.S. Appl. No. 14/884,695.
USPTO; Advisory Action dated Apr. 20, 2017 in U.S. Appl. No. 14/884,695.
USPTO; Non-Final Office Action dated May 18, 2017 in U.S. Appl. No. 14/884,695.
USPTO; Notice of Allowance dated Oct. 20, 2017 in U.S. Appl. No. 14/884,695.
USPTO; Non-Final Office Action dated May 18, 2017 in U.S. Appl. No. 14/886,571.
USPTO; Final Office Action dated Sep. 21, 2017 in U.S. Appl. No. 14/886,571.
USPTO; Notice of Allowance dated Dec. 6, 2017 in U.S. Appl. No. 14/886,571.
USPTO; Non-Final Office Action dated Dec. 1, 2016 in U.S. Appl. No. 14/919,536.
USPTO; Final Office Action dated Mar. 28, 2017 in U.S. Appl. No. 14/919,536.
USPTO; Non-Final Office Action dated Aug. 29, 2017 in U.S. Appl. No. 14/919,536.
USPTO; Final Office Action dated May 11, 2018 in U.S. Appl. No. 14/919,536.
USPTO; Notice of Allowance dated Oct. 4, 2018 in U.S. Appl. No. 14/919,536.
USPTO; Notice of Allowance dated Nov. 19, 2018 in U.S. Appl. No. 14/919,536.
USPTO; Non-Final Office Action dated May 3, 2016 in U.S. Appl. No. 14/937,053.
USPTO; Notice of Allowance dated Jul. 26, 2016 in U.S. Appl. No. 14/937,053.
USPTO; Non-Final Office Action dated Dec. 15, 2016 in U.S. Appl. No. 14/938,180.
USPTO; Notice of Allowance dated Nov. 9, 2017 in U.S. Appl. No. 14/938,180.
USPTO; Non-Final Office Action dated Apr. 14, 2017 in U.S. Appl. No. 14/956,115.
USPTO; Final Office Action dated Jul. 21, 2017 in U.S. Appl. No. 14/956,115.
USPTO; Notice of Allowance dated Dec. 14, 2017 in U.S. Appl. No. 14/956,115.
USPTO; Notice of Allowance dated Feb. 3, 2017 in U.S. Appl. No. 14/977,291.
USPTO; Non-Final Office Action dated Aug. 12, 2016 in U.S. Appl. No. 14/981,434.
USPTO; Notice of Allowance dated Nov. 21, 2016 in U.S. Appl. No. 14/981,434.
USPTO; Non-Final Office Action dated Jan. 12, 2017 in U.S. Appl. No. 14/981,468.
USPTO; Notice of Allowance dated Jun. 7, 2017 in U.S. Appl. No. 14/981,468.

(56) References Cited

OTHER PUBLICATIONS

USPTO; Non-Final Office Action dated Mar. 22, 2016 in U.S. Appl. No. 14/987,420.
USPTO; Final Office Action dated Jun. 10, 2016 in U.S. Appl. No. 14/987,420.
USPTO; Non-Final Office Action dated Dec. 14, 2016 in U.S. Appl. No. 14/997,683.
USPTO; Final Office Action dated Apr. 14, 2017 in U.S. Appl. No. 14/997,683.
USPTO; Non-Final Office Action dated Sep. 1, 2017 in U.S. Appl. No. 14/997,683.
USPTO; Final Office Action dated Feb. 6, 2018 in U.S. Appl. No. 14/997,683.
USPTO; Advisory Action dated May 2, 2018 in U.S. Appl. No. 14/997,683.
USPTO; Non-Final Office Action dated Jun. 20, 2018 in U.S. Appl. No. 14/997,683.
USPTO; Final Office Action dated Dec. 10, 2018 in U.S. Appl. No. 14/997,683.
USPTO; Notice of Allowance dated Mar. 25, 2019 in U.S. Appl. No. 14/997,683.
USPTO; Non-Final Office Action dated Sep. 23, 2016 in U.S. Appl. No. 15/048,422.
USPTO; Notice of Allowance dated May 4, 2017 in U.S. Appl. No. 15/048,422.
USPTO; Non-Final Office Action dated Aug. 4, 2017 in U.S. Appl. No. 15/050,159.
USPTO; Notice of Allowance dated Feb. 7, 2018 in U.S. Appl. No. 15/050,159.
USPTO; Non-Final Office Action dated Apr. 22, 2016 in U.S. Appl. No. 15/055,122.
USPTO; Notice of Allowance dated Sep. 15, 2016 in U.S. Appl. No. 15/055,122.
USPTO; Non-Final Office Action dated Feb. 20, 2018 in U.S. Appl. No. 15/060,412.
USPTO; Final Office Action dated Oct. 19, 2018 in U.S. Appl. No. 15/060,412.
USPTO; Non-Final Office Action dated Jun. 3, 2019 in U.S. Appl. No. 15/060,412.
USPTO; Final Office Action dated Dec. 26, 2019 in U.S. Appl. No. 15/060,412.
USPTO; Notice of Allowance dated Mar. 5, 2020 in U.S. Appl. No. 15/060,412.
USPTO; Non-Final Office Action dated Aug. 27, 2018 in U.S. Appl. No. 15/067,028.
USPTO; Notice of Allowance dated Dec. 21, 2018 in U.S. Appl. No. 15/067,028.
USPTO; Non-Final Office Action dated Sep. 26, 2018 in U.S. Appl. No. 15/074,813.
USPTO; Notice of Allowance dated Feb. 25, 2019 in U.S. Appl. No. 15/074,813.
USPTO; Non-Final Office Action dated Jan. 9, 2018 in U.S. Appl. No. 15/135,224.
USPTO; Notice of Allowance dated Jun. 29, 2018 in U.S. Appl. No. 15/135,224.
USPTO; Non-Final Office Action dated Jan. 9, 2018 in U.S. Appl. No. 15/135,258.
USPTO; Final Office Action dated Jul. 6, 2018 in U.S. Appl. No. 15/135,258.
USPTO; Non-Final Office Action dated Nov. 23, 2018 in U.S. Appl. No. 15/135,258.
USPTO; Final Office Action dated Mar. 14, 2019 in U.S. Appl. No. 15/135,258.
USPTO; Non-Final Office Action dated Jul. 19, 2019 in U.S. Appl. No. 15/135,258.
USPTO; Final Office Action dated Oct. 24, 2019 in U.S. Appl. No. 15/135,258.
USPTO; Advisory Action dated Jan. 3, 2020 in U.S. Appl. No. 15/135,258.
USPTO; Non-Final Office Action dated Feb. 13, 2020 in U.S. Appl. No. 15/135,258.
USPTO; Final Office Action dated Jun. 1, 2020 in U.S. Appl. No. 15/135,258.
USPTO; Non-Final Office Action dated Jan. 9, 2018 in U.S. Appl. No. 15/135,333.
USPTO; Notice of Allowance dated Aug. 18, 2020 in U.S. Appl. No. 15/135,258.
USPTO; Notice of Allowance dated Sep. 14, 2018 in U.S. Appl. No. 15/135,333.
USPTO; Non-Final Office Action dated Nov. 21, 2016 in U.S. Appl. No. 15/144,481.
USPTO; Final Office Action dated May 26, 2017 in U.S. Appl. No. 15/144,481.
USPTO; Non-Final Office Action dated Sep. 21, 2017 in U.S. Appl. No. 15/144,481.
USPTO; Notice of Allowance dated Mar. 26, 2018 in U.S. Appl. No. 15/144,481.
USPTO; Notice of Allowance dated Apr. 11, 2018 in U.S. Appl. No. 15/144,481.
USPTO; Non-Final Office Action dated Apr. 13, 2017 in U.S. Appl. No. 15/144,506.
USPTO; Final Office Action dated Oct. 10, 2017 in U.S. Appl. No. 15/144,506.
USPTO; Final Office Action dated Jul. 26, 2018 in U.S. Appl. No. 15/144,506.
USPTO; Notice of Allowance dated Mar. 13, 2019 in U.S. Appl. No. 15/144,506.
USPTO; Non-Final Office Action dated Oct. 9, 2018 in U.S. Appl. No. 15/182,504.
USPTO; Final Office Action dated Mar. 28, 2019 in U.S. Appl. No. 15/182,504.
USPTO; Notice of Allowance dated Jul. 17, 2019 in U.S. Appl. No. 15/182,504.
USPTO; Non-Final Office Action dated Nov. 28, 2016 in U.S. Appl. No. 15/203,632.
USPTO; Final Office Action dated Jun. 7, 2017 in U.S. Appl. No. 15/203,632.
USPTO; Advisory Action dated Aug. 23, 2017 in U.S. Appl. No. 15/203,632.
USPTO; Notice of Allowance dated Sep. 20, 2017 in U.S. Appl. No. 15/203,632.
USPTO; Non-Final Office Action dated Nov. 29, 2016 in U.S. Appl. No. 15/203,642.
USPTO; Final Office Action dated Apr. 13, 2017 in U.S. Appl. No. 15/203,642.
USPTO; Advisory Action dated Jun. 22, 2017 in U.S. Appl. No. 15/203,642.
USPTO; Notice of Allowance dated Aug. 7, 2017 in U.S. Appl. No. 15/203,642.
USPTO; Non-Final Office Action dated Jun. 1, 2017 in U.S. Appl. No. 15/205,827.
USPTO; Final Office Action dated Oct. 16, 2017 in U.S. Appl. No. 15/205,827.
USPTO; Non-Final Office Action dated May 14, 2018 in U.S. Appl. No. 15/205,827.
USPTO; Final Office Action dated Oct. 9, 2018 in U.S. Appl. No. 15/205,827.
USPTO; Non-Final Office Action dated Mar. 28, 2019 in U.S. Appl. No. 15/205,827.
USPTO; Final Office Action dated Aug. 9, 2019 in U.S. Appl. No. 15/205,827.
USPTO; Advisory Action dated Oct. 22, 2019 in U.S. Appl. No. 15/205,827.
USPTO; Notice of Allowance dated Dec. 3, 2019 in U.S. Appl. No. 15/205,827.
USPTO; Non-Final Office Action dated Mar. 31, 2017 in U.S. Appl. No. 15/205,890.
USPTO; Notice of Allowance dated Oct. 16, 2017 in U.S. Appl. No. 15/205,890.
USPTO; Non-Final Office Action dated Jan. 20, 2017 in U.S. Appl. No. 15/210,256.

(56) References Cited

OTHER PUBLICATIONS

USPTO; Notice of Allowance dated May 18, 2017 in U.S. Appl. No. 15/210,256.
USPTO; Notice of Allowance dated Jul. 24, 2017 in U.S. Appl. No. 15/210,256.
USPTO; Non Final Office Action dated Apr. 21, 2017 in U.S. Appl. No. 15/222,715.
USPTO; Notice of Allowance dated Jul. 14, 2017 in U.S. Appl. No. 15/222,715.
USPTO; Notice of Allowance dated Sep. 27, 2017 in U.S. Appl. No. 15/222,715.
USPTO; Non-Final Office Action dated Feb. 3, 2017 in U.S. Appl. No. 15/222,738.
USPTO; Notice of Allowance dated May 22, 2017 in U.S. Appl. No. 15/222,738.
USPTO; Notice of Allowance dated Aug. 23, 2017 in U.S. Appl. No. 15/222,738.
USPTO; Non-Final Office Action dated Jan. 17, 2017 in U.S. Appl. No. 15/222,749.
USPTO; Final Office Action dated May 5, 2017 in U.S. Appl. No. 15/222,749.
USPTO; Non-Final Office Action dated Sep. 7, 2017 in U.S. Appl. No. 15/222,749.
USPTO: Final Office Action dated Jun. 4, 2018 in U.S. Appl. No. 15/222,749.
USPTO; Notice of Allowance dated Aug. 30, 2018 in U.S. Appl. No. 15/222,749.
USPTO; Non-Final Office Action dated Jan. 3, 2017 in U.S. Appl. No. 15/222,780.
USPTO; Final Office Action dated May 5, 2017 in U.S. Appl. No. 15/222,780.
USPTO; Non-Final Office Action dated Sep. 7, 2017 in U.S. Appl. No. 15/222,780.
USPTO; Final Office Action dated May 17, 2018 in U.S. Appl. No. 15/222,780.
USPTO; Non-Final Office Action dated Oct. 1, 2018 in U.S. Appl. No. 15/222,780.
USPTO; Notice of Allowance dated Apr. 19, 2019 in U.S. Appl. No. 15/222,780.
USPTO; Notice of Allowance dated Jul. 12, 2018 in U.S. Appl. No. 15/254,605.
USPTO; Non-Final Office Action dated Aug. 28, 2017 in U.S. Appl. No. 15/254,724.
USPTO; Notice of Allowance dated Jan. 17, 2018 in U.S. Appl. No. 15/254,724.
USPTO; Notice of Allowance dated Apr. 2, 2018 in U.S. Appl. No. 15/254,724.
USPTO; Non-Final Office Action dated May 22, 2018 in U.S. Appl. No. 15/262,990.
USPTO; Non-Final Office Action dated Sep. 13, 2018 in U.S. Appl. No. 15/262,990.
USPTO; Non-Final Office Action dated Jan. 30, 2019 in U.S. Appl. No. 15/262,990.
USPTO; Final Office Action dated May 13, 2019 in U.S. Appl. No. 15/262,990.
USPTO; Advisory Action dated Jul. 22, 2019 in U.S. Appl. No. 15/262,990.
USPTO; Non-Final Office Action dated Aug. 5, 2019 in U.S. Appl. No. 15/262,990.
USPTO; Final Office Action dated Nov. 19, 2019 in U.S. Appl. No. 15/262,990.
USPTO; Advisory Action dated Jan. 30, 2020 in U.S. Appl. No. 15/262,990.
USPTO; Non-Final Office Action dated Oct. 6, 2020 in U.S. Appl. No. 15/262,990.
USPTO; Non-Final Office Action dated Aug. 3, 2018 in U.S. Appl. No. 15/273,488.
USPTO; Final Office Action dated Jan. 11, 2019 in U.S. Appl. No. 15/273,488.
USPTO; Notice of Allowance dated Apr. 19, 2019 in U.S. Appl. No. 15/273,488.
USTPO; Non-Final Office Action dated Jul. 2, 2018 in U.S. Appl. No. 15/286,503.
USPTO; Final Office Action dated Feb. 7, 2019 in U.S. Appl. No. 15/286,503.
USPTO; Non-Final Office Action dated Jun. 27, 2019 in U.S. Appl. No. 15/286,503.
USPTO; Final Office Action dated Jan. 6, 2020 in U.S. Appl. No. 15/286,503.
USPTO; Advisory Action dated Mar. 31, 2020 in U.S. Appl. No. 15/286,503.
USPTO; Non-Final Office Action dated Apr. 16, 2020 in U.S. Appl. No. 15/286,503.
USPTO; Final Office Action dated Oct. 2, 2020 in U.S. Appl. No. 15/286,503.
USPTO; Non-Final Office Action dated Dec. 14, 2018 in U.S. Appl. No. 15/340,512.
USPTO; Notice of Allowance dated May 24, 2019 in U.S. Appl. No. 15/340,512.
USPTO; Non-Final Office Action dated Oct. 23, 2017 in U.S. Appl. No. 15/377,439.
USPTO; Final Office Action dated Apr. 16, 2018 in U.S. Appl. No. 15/377,439.
USPTO; Advisory Action dated Aug. 8, 2018 in U.S. Appl. No. 15/377,439.
USPTO; Non-Final Office Action dated Nov. 14, 2018 in U.S. Appl. No. 15/377,439.
USPTO; Final Office Action dated Jun. 25, 2019 in U.S. Appl. No. 15/377,439.
USPTO; Non-Final Office Action dated Nov. 7, 2019 in U.S. Appl. No. 15/377,439.
USPTO; Final Office Action dated May 13, 2020 in U.S. Appl. No. 15/377,439.
USPTO; Non-Final Office Action dated Sep. 2, 2020 in U.S. Appl. No. 15/377,439.
USPTO; Notice of Allowance dated Aug. 8, 2017 in U.S. Appl. No. 15/380,895.
USPTO; Notice of Allowance dated Oct. 11, 2017 in U.S. Appl. No. 15/380,895.
USPTO; Non-Final Office Action dated May 31, 2019 in U.S. Appl. No. 15/380,909.
USPTO; Final Office Action dated Dec. 12, 2019 in U.S. Appl. No. 15/380,909.
USPTO; Non-Final Office Action dated Jul. 1, 2020 in U.S. Appl. No. 15/380,909.
USPTO; Non-Final Office Action dated Jan. 4, 2018 in U.S. Appl. No. 15/380,921.
USPTO; Final Office Action dated Jun. 28, 2018 in U.S. Appl. No. 15/380,921.
USPTO; Non-Final Office Action dated Feb. 25, 2019 in U.S. Appl. No. 15/380,921.
USPTO; Final Office Action dated Sep. 18, 2019 in U.S. Appl. No. 15/380,921.
USPTO; Non-Final Office Action dated Jan. 15, 2020 in U.S. Appl. No. 15/380,921.
USPTO; Final Office Action dated Jul. 23, 2020 in U.S. Appl. No. 15/380,921.
USPTO; Non-Final Office Action dated Oct. 3, 2017 in U.S. Appl. No. 15/388,410.
USPTO; Final Office Action dated May 15, 2018 in U.S. Appl. No. 15/388,410.
USPTO; Notice of Allowance dated Nov. 14, 2018 in U.S. Appl. No. 15/388,410.
USPTO; Notice of Allowance dated Dec. 28, 2018 in U.S. Appl. No. 15/388,410.
USPTO; Non-Final Office Action dated Aug. 11, 2017 in U.S. Appl. No. 15/397,237.
USPTO; Notice of Allowance dated Dec. 22, 2017 in U.S. Appl. No. 15/397,237.
USPTO; Non-Final Office Action dated Apr. 12, 2017 in U.S. Appl. No. 15/397,319.

(56) References Cited

OTHER PUBLICATIONS

USPTO; Final Office Action dated Jul. 12, 2017 in U.S. Appl. No. 15/397,319.
USPTO; Notice of Allowance dated Dec. 15, 2017 in U.S. Appl. No. 15/397,319.
USPTO; Non-Final Office Action dated Feb. 5, 2019 in U.S. Appl. No. 15/402,993.
USPTO; Final Office Action dated May 21, 2019 in U.S. Appl. No. 15/402,993.
USPTO; Advisory Action dated Jul. 29, 2019 in U.S. Appl. No. 15/402,993.
USPTO; Non-Final Office Action dated Oct. 24, 2019 in U.S. Appl. No. 15/402,993.
USPTO; Final Office Action dated Feb. 19, 2020 in U.S. Appl. No. 15/402,993.
USPTO; Advisory Action dated Apr. 2, 2020 in U.S. Appl. No. 15/402,993.
USPTO; Non-Final Office Action dated May 27, 2020 in U.S. Appl. No. 15/402,993.
USPTO; Final Office Action dated Sep. 8, 2020 in U.S. Appl. No. 15/402,993.
USPTO; Advisory Action dated Nov. 9, 2020 in U.S. Appl. No. 15/402,993.
USPTO; Non-Final Office Action dated Sep. 20, 2018 in U.S. Appl. No. 15/410,503.
USPTO; Final Office Action dated Feb. 4, 2019 in U.S. Appl. No. 15/410,503.
USPTO; Non-Final Office Action dated Apr. 25, 2019 in U.S. Appl. No. 15/410,503.
USPTO; Notice of Allowance dated Aug. 14, 2019 in U.S. Appl. No. 15/410,503.
USPTO; Non-Final Office Action dated Aug. 7, 2018 in U.S. Appl. No. 15/428,808.
USPTO; Final Office Action dated Jan. 11, 2019 in U.S. Appl. No. 15/428,808.
USPTO; Notice of Allowance dated Apr. 25, 2019 in U.S. Appl. No. 15/428,808.
USPTO; Non-Final Office Action dated Apr. 6, 2018 in U.S. Appl. No. 15/434,051.
USPTO; Final Office Action dated Aug. 29, 2018 in U.S. Appl. No. 15/434,051.
USPTO; Advisory Action dated Dec. 4, 2018 in U.S. Appl. No. 15/434,051.
USPTO; Non-Final Office Action dated Jan. 25, 2019 in U.S. Appl. No. 15/434,051.
USPTO; Notice of Allowance dated Jun. 3, 2019 in U.S. Appl. No. 15/434,051.
USPTO; Notice of Allowance dated Oct. 6, 2017 in U.S. Appl. No. 15/450,199.
USPTO; Non-Final Office Action dated Dec. 15, 2017 in U.S. Appl. No. 15/466,149.
USPTO; Notice of Allowance dated Apr. 20, 2018 in U.S. Appl. No. 15/466,149.
USPTO; Non-Final Office Action dated Apr. 6, 2018 in U.S. Appl. No. 15/472,750.
USPTO; Notice of Allowance dated Nov. 30, 2018 in U.S. Appl. No. 15/472,750.
USPTO; Non-Final Office Action dated Dec. 6, 2017 in U.S. Appl. No. 15/476,035.
USPTO; Notice of Allowance dated Mar. 21, 2018 in U.S. Appl. No. 15/476,035.
USPTO; Notice of Allowance dated Aug. 14, 2018 in U.S. Appl. No. 15/476,035.
USPTO; Non-Final Office Action dated Oct. 4, 2017 in U.S. Appl. No. 15/489,453.
USPTO; Final Office Action dated Apr. 19, 2018 in U.S. Appl. No. 15/489,453.
USPTO; Non-Final Office Action dated Sep. 10, 2018 in U.S. Appl. No. 15/489,453.
USPTO; Final Office Action dated Feb. 27, 2019 in U.S. Appl. No. 15/489,453.
USPTO; Non-Final Office Action dated Jun. 5, 2019 in U.S. Appl. No. 15/489,453.
USPTO; Notice of Allowance dated Oct. 7, 2019 in U.S. Appl. No. 15/489,453.
USPTO; Notice of Allowance dated Dec. 19, 2017 in U.S. Appl. No. 15/489,660.
USPTO; Final Office Action dated May 1, 2019 in U.S. Appl. No. 15/491,726.
USPTO; Non-Final Office Action dated May 31, 2018 in U.S. Appl. No. 15/491,726.
USPTO; Non-Final Office Action dated Oct. 3, 2019 in U.S. Appl. No. 15/491,726.
USPTO; Final Office Action dated Apr. 17, 2020 in U.S. Appl. No. 15/491,726.
USPTO; Non-Final Office Action dated Sep. 30, 2020 in U.S. Appl. No. 15/491,726.
USPTO; Non-Final Office Action dated Jan. 16, 2018 in U.S. Appl. No. 15/499,647.
USPTO; Notice of Allowance dated May 23, 2018 in U.S. Appl. No. 15/499,647.
USPTO; Non-Final Office Action dated Jun. 21, 2018 in U.S. Appl. No. 15/499,647.
USPTO; Notice of Allowance dated Nov. 1, 2018 in U.S. Appl. No. 15/499,647.
USPTO; Notice of Allowance dated Nov. 15, 2018 in U.S. Appl. No. 15/499,647.
USPTO; Office Action dated Aug. 30, 2018 in U.S. Appl. No. 15/589,849.
USPTO; Final Office Action dated Mar. 6, 2019 in U.S. Appl. No. 15/589,849.
USPTO; Non-Final Office Action dated Jun. 28, 2019 in U.S. Appl. No. 15/589,849.
USPTO; Final Office Action dated Jan. 8, 2020 in U.S. Appl. No. 15/589,849.
USPTO; Notice of Allowance dated Feb. 28, 2020 in U.S. Appl. No. 15/589,849.
USPTO; Office Action dated May 3, 2018 in U.S. Appl. No. 15/589,861.
USPTO; Non-Final Office Action dated Dec. 21, 2018 in U.S. Appl. No. 15/589,861.
USPTO; Final Office Action dated Jun. 26, 2019 in U.S. Appl. No. 15/589,861.
USPTO; Advisory Action dated Sep. 20, 2019 in U.S. Appl. No. 15/589,861.
USPTO; Non-Final Office Action dated Jan. 13, 2020 in U.S. Appl. No. 15/589,861.
USPTO; Final Office Action dated Jul. 8, 2020 in U.S. Appl. No. 15/589,861.
USPTO; Notice of Allowance dated Oct. 16, 2020 in U.S. Appl. No. 15/589,861.
USPTO; Non-Final Office Action dated Apr. 4, 2018 in U.S. Appl. No. 15/592,730.
USPTO; Final Office Action dated Nov. 16, 2018 in U.S. Appl. No. 15/592,730.
USPTO; Advisory Action dated Mar. 15, 2019 in U.S. Appl. No. 15/592,730.
USPTO; Notice of Allowance dated Aug. 21, 2019 in U.S. Appl. No. 15/592,730.
USPTO; Non-Final Office Action dated Mar. 7, 2019 in U.S. Appl. No. 15/598,169.
USPTO; Final Office Action dated Jun. 25, 2019 in U.S. Appl. No. 15/598,169.
USPTO; Notice of Allowance dated Sep. 11, 2019 in U.S. Appl. No. 15/598,169.
USPTO; Non-Final Office Action dated Mar. 10, 2020 in U.S. Appl. No. 15/611,707.
USPTO; Final Office Action dated Sep. 16, 2020 in U.S. Appl. No. 15/611,707.
USPTO; Advisory Action dated Nov. 20, 2020 in U.S. Appl. No. 15/611,707.

(56) References Cited

OTHER PUBLICATIONS

USPTO; Ex Parte Quayle Action dated Mar. 21, 2019 in U.S. Appl. No. 15/615,489.
USPTO; Non-Final Office Action dated Sep. 4, 2019 in U.S. Appl. No. 15/615,489.
USPTO; Notice of Allowance dated Feb. 28, 2020 in U.S. Appl. No. 15/615,489.
USPTO; Non-Final Office Action dated Feb. 1, 2019 in U.S. Appl. No. 15/627,189.
USPTO; Notice of Allowance dated May 21, 2019 in U.S. Appl. No. 15/627,189.
USPTO; Non-Final Office Action dated Nov. 9, 2018 in U.S. Appl. No. 15/636,307.
USPTO; Final Office Action dated Mar. 6, 2019 in U.S. Appl. No. 15/636,307.
USPTO; Non-Final Office Action dated Jul. 16, 2019 in U.S. Appl. No. 15/636,307.
USPTO; Final Office Action dated Nov. 12, 2019 in U.S. Appl. No. 15/636,307.
USPTO; Advisory Action dated Jan. 17, 2020 in U.S. Appl. No. 15/636,307.
USPTO; Non-Final Office Action dated Mar. 11, 2020 in U.S. Appl. No. 15/636,307.
USPTO; Final Office Action dated Jun. 16, 2020 in U.S. Appl. No. 15/636,307.
USPTO; Non-Final Office Action dated Sep. 3, 2020 in U.S. Appl. No. 15/636,307.
USPTO; Notice of Allowance dated Jul. 18, 2018 in U.S. Appl. No. 15/640,239.
USPTO; Notice of Allowance dated Aug. 30, 2018 in U.S. Appl. No. 15/640,239.
USPTO; Non-Final Office Action dated Jun. 5, 2018 in U.S. Appl. No. 15/650,686.
USPTO; Final Office Action dated Nov. 20, 2018 in U.S. Appl. No. 15/650,686.
USPTO; Notice of Allowance dated Jun. 24, 2019 in U.S. Appl. No. 15/650,686.
USPTO; Non-Final Office Action dated Sep. 21, 2018 in U.S. Appl. No. 15/659,631.
USPTO; Notice of Allowance dated Feb. 21, 2019 in U.S. Appl. No. 15/659,631.
USPTO; Non-Final Office Action dated Jul. 29, 2019 in U.S. Appl. No. 15/660,797.
USPTO; Notice of Allowance dated Nov. 7, 2019 in U.S. Appl. No. 15/660,797.
USPTO; Non-Final Office Action dated Aug. 9, 2018 in U.S. Appl. No. 15/660,805.
USPTO; Non-Final Office Action dated Mar. 1, 2019 in U.S. Appl. No. 15/660,805.
USPTO; Notice of Allowance dated Aug. 22, 2019 in U.S. Appl. No. 15/660,805.
USPTO; Non-Final Office Action dated Aug. 27, 2018 in U.S. Appl. No. 15/662,107.
USPTO; Notice of Allowance dated Feb. 21, 2019 in U.S. Appl. No. 15/662,107.
USPTO; Non-Final Office Action dated Dec. 4, 2018 in U.S. Appl. No. 15/672,063.
USPTO; Notice of Allowance dated Mar. 20, 2019 in U.S. Appl. No. 15/672,063.
USPTO; Non-Final Office Action dated Oct. 10, 2019 in U.S. Appl. No. 15/672,096.
USPTO; Final Office Action dated Mar. 27, 2020 in U.S. Appl. No. 15/672,096.
USPTO; Notice of Allowance dated May 20, 2020 in U.S. Appl. No. 15/672,096.
USPTO; Notice of Allowance dated Jul. 2, 2020 in U.S. Appl. No. 15/672,096.
USPTO; Non-Final Office Action dated Feb. 8, 2019 in U.S. Appl. No. 15/672,119.
USPTO; Final Office Action dated Jul. 16, 2019 in U.S. Appl. No. 15/672,119.
USPTO; Advisory Action dated Sep. 23, 2019 in U.S. Appl. No. 15/672,119.
USPTO; Notice of Allowance dated Feb. 7, 2020 in U.S. Appl. No. 15/672,119.
USPTO; Non-Final Office Action dated Jul. 27, 2018 in U.S. Appl. No. 15/673,110.
USPTO; Notice of Allowance dated Jan. 9, 2019 in U.S. Appl. No. 15/673,110.
USPTO; Non-Final Office Action dated Apr. 25, 2018 in U.S. Appl. No. 15/673,278.
USPTO; Notice of Allowance dated May 6, 2019 in U.S. Appl. No. 15/673,278.
USPTO; Non-Final Office Action dated Jan. 18, 2018 in U.S. Appl. No. 15/683,701.
USPTO; Notice of Allowance dated Jan. 9, 2019 in U.S. Appl. No. 15/683,701.
USPTO; Final Office Action dated Aug. 24, 2018 in U.S. Appl. No. 15/683,701.
USPTO; Advisory Action dated Nov. 26, 2018 in U.S. Appl. No. 15/683,701.
USPTO; Non-Final Office Action dated Dec. 18, 2018 in U.S. Appl. No. 15/690,017.
USPTO; Final Office Action dated Jul. 26, 2019 in U.S. Appl. No. 15/690,017.
USPTO; Non-Final Office Action dated Nov. 20, 2019 in U.S. Appl. No. 15/690,017.
USPTO; Final Office Action dated May 27, 2020 in U.S. Appl. No. 15/690,017.
USPTO; Advisory Action dated Aug. 6, 2020 in U.S. Appl. No. 15/690,017.
USPTO; Non-Final Office Action dated Aug. 24, 2020 in U.S. Appl. No. 15/690,017.
USPTO; Non-Final Office Action dated Aug. 9, 2018 in U.S. Appl. No. 15/691,241.
USPTO; Final Office Action dated Jan. 11, 2019 in U.S. Appl. No. 15/691,241.
USPTO; Non-Final Office Action dated Mar. 19, 2019 in U.S. Appl. No. 15/691,241.
USPTO; Final Office Action dated Jan. 24, 2020 in U.S. Appl. No. 15/691,241.
USPTO; Advisory Action dated Jun. 19, 2020 in U.S. Appl. No. 15/691,241.
USPTO; Non-Final Office Action dated Oct. 6, 2020 in U.S. Appl. No. 15/691,241.
USPTO; Non-Final Office Action dated Dec. 6, 2018 in U.S. Appl. No. 15/705,955.
USPTO; Notice of Allowance dated Apr. 16, 2019 in U.S. Appl. No. 15/705,955.
USPTO; Non-Final Office Action dated Feb. 11, 2019 in U.S. Appl. No. 15/707,786.
USPTO; Final Office Action dated Aug. 12, 2019 in U.S. Appl. No. 15/707,786.
USPTO; Notice of Allowance dated Nov. 7, 2019 in U.S. Appl. No. 15/707,786.
USPTO; Non-Final Office Action dated Jun. 14, 2018 in U.S. Appl. No. 15/711,989.
USPTO; Notice of Allowance dated Dec. 6, 2018 in U.S. Appl. No. 15/711,989.
USPTO; Non-Final Office Action dated May 29, 2018 in U.S. Appl. No. 15/719,208.
USPTO; Final Office Action dated Dec. 13, 2018 in U.S. Appl. No. 15/719,208.
USPTO; Non-Final Office Action dated Jun. 25, 2019 in U.S. Appl. No. 15/719,208.
USPTO; Notice of Allowance dated Jan. 29, 2020 in U.S. Appl. No. 15/719,208.
USPTO; Non-Final Office Action dated Oct. 4, 2018 in U.S. Appl. No. 15/726,222.
USPTO; Notice of Allowance dated Apr. 19, 2019 in U.S. Appl. No. 15/726,222.

(56) References Cited

OTHER PUBLICATIONS

USPTO; Non-Final Office Action dated Apr. 19, 2018 in U.S. Appl. No. 15/726,959.
USPTO; Final Office Action dated Nov. 14, 2018 in U.S. Appl. No. 15/726,959.
USPTO; Non-Final Office Action dated Jul. 8, 2019 in U.S. Appl. No. 15/726,959.
USPTO; Final Office Action dated Jan. 7, 2020 in U.S. Appl. No. 15/726,959.
USPTO; Advisory Action dated Mar. 16, 2020 in U.S. Appl. No. 15/726,959.
USPTO; Non-Final Office Action dated Apr. 3, 2020 in U.S. Appl. No. 15/726,959.
USPTO; Final Office Action dated Sep. 24, 2020 in U.S. Appl. No. 15/726,959.
USPTO; Non-Final Office Action dated Sep. 26, 2019 in U.S. Appl. No. 15/727,432.
USPTO; Notice of Allowance dated Jan. 6, 2020 in U.S. Appl. No. 15/727,432.
USPTO; Non-Final Office Action dated May 17, 2018 in U.S. Appl. No. 15/729,485.
USPTO; Notice of Allowance dated Jan. 23, 2019 in U.S. Appl. No. 15/729,485.
USPTO; Non-Final Office Action dated Nov. 28, 2018 in U.S. Appl. No. 15/795,056.
USPTO; Final Office Action dated Apr. 19, 2019 in U.S. Appl. No. 15/795,056.
USPTO; Final Office Action dated Jul. 31, 2019 in U.S. Appl. No. 15/795,056.
USPTO; Non-Final Office Action dated Nov. 20, 2019 in U.S. Appl. No. 15/795,056.
USPTO; Notice of Allowance dated Mar. 12, 2020 in U.S. Appl. No. 15/795,056.
USPTO; Non-Final Office Action dated Jun. 26, 2018 in U.S. Appl. No. 15/796,593.
USPTO; Final Office Action dated Feb. 21, 2019 in U.S. Appl. No. 15/796,593.
USPTO; Non-Final Office Action dated Jun. 14, 2019 in U.S. Appl. No. 15/796,593.
USPTO; Notice of Allowance dated Dec. 31, 2019 in U.S. Appl. No. 15/796,593.
USPTO; Non-Final Office Action dated Dec. 26, 2017 in U.S. Appl. No. 15/798,120.
USPTO; Notice of Allowance dated Jun. 13, 2018 in U.S. Appl. No. 15/798,120.
USPTO; Non-Final Office Action dated Dec. 21, 2018 in U.S. Appl. No. 15/798,150.
USPTO; Notice of Allowance dated May 14, 2019 in U.S. Appl. No. 15/798,150.
USPTO; Non-Final Office Action dated Aug. 9, 2018 in U.S. Appl. No. 15/798,201.
USPTO; Final Office Action dated Dec. 14, 2018 in U.S. Appl. No. 15/798,201.
UPSTO; Non-Final Office Action dated Oct. 2, 2019 in U.S. Appl. No. 15/798,201.
USPTO; Final Office Action dated Mar. 19, 2020 in U.S. Appl. No. 15/798,201.
USPTO; Advisory Action dated May 26, 2020 in U.S. Appl. No. 15/798,201.
USPTO; Non-Final Office Action dated Jul. 10, 2020 in U.S. Appl. No. 15/798,201.
USPTO; Notice of Allowance dated Oct. 21, 2020 in U.S. Appl. No. 15/798,201.
USPTO; Non-Final Office Action dated Nov. 15, 2019 in U.S. Appl. No. 15/802,154.
USPTO; Final Office Action dated Mar. 11, 2020 in U.S. Appl. No. 15/802,154.
USPTO; Advisory Action dated May 19, 2020 in U.S. Appl. No. 15/802,154.
USPTO; Non-Final Office Action dated Jul. 2, 2020 in U.S. Appl. No. 15/802,154.
USPTO; Notice of Allowance dated Oct. 26, 2020 in U.S. Appl. No. 15/802,154.
USPTO; Non-Final Office Action dated Jul. 2, 2018 in U.S. Appl. No. 15/815,483.
USPTO; Final Office Action dated Mar. 7, 2019 in U.S. Appl. No. 15/815,483.
USPTO; Non-Final Office Action dated Aug. 20, 2019 in U.S. Appl. No. 15/815,483.
USPTO; Final Office Action dated Jan. 13, 2020 in U.S. Appl. No. 15/815,483.
USPTO; Advisory Action dated Mar. 25, 2020 in U.S. Appl. No. 15/815,483.
USPTO; Non-Final Office Action dated Apr. 24, 2020 in U.S. Appl. No. 15/815,483.
USPTO; Notice of Allowance dated Sep. 30, 2020 in U.S. Appl. No. 15/815,483.
USPTO; Non-Final Office Action dated Sep. 26, 2018 in U.S. Appl. No. 15/832,188.
USPTO; Notice of Allowance dated Dec. 5, 2017 in U.S. Appl. No. 15/832,188.
USPTO; Non-Final Office Action dated Mar. 17, 2020 in U.S. Appl. No. 15/835,328.
USPTO; Final Office Action dated Sep. 17, 2020 in U.S. Appl. No. 15/835,328.
USPTO; Non-Final Office Action dated Feb. 20, 2020 in U.S. Appl. No. 15/835,352.
USPTO; Final Office Action dated Aug. 6, 2020 in U.S. Appl. No. 15/835,352.
USPTO; Non-Final Office Action dated Sep. 10, 2018 in U.S. Appl. No. 15/836,547.
USPTO; Non-Final Office Action dated Mar. 13, 2019 in U.S. Appl. No. 15/836,547.
USPTO; Notice of Allowance dated Aug. 16, 2019 in U.S. Appl. No. 15/836,547.
USPTO; Notice of Allowance dated Aug. 17, 2020 in U.S. Appl. No. 15/843,899.
USPTO; Non-Final Office Action dated Jul. 31, 2019 in U.S. Appl. No. 15/860,564.
USPTO; Final Office Action dated Nov. 13, 2019 in U.S. Appl. No. 15/860,564.
USPTO; Advisory Action dated Jan. 21, 2020 in U.S. Appl. No. 15/860,564.
USPTO; Non-Final Office Action dated Mar. 30, 2020 in U.S. Appl. No. 15/860,564.
USPTO; Notice of Allowance dated Jun. 30, 2020 in U.S. Appl. No. 15/860,564.
USPTO; Non-Final Office Action dated Mar. 20, 2020 in U.S. Appl. No. 15/861,418.
USPTO; Final Office Action dated Jun. 11, 2020 in U.S. Appl. No. 15/861,418.
USPTO; Notice of Allowance dated Aug. 19, 2020 in U.S. Appl. No. 15/861,418.
USPTO; Non-Final Office Action dated Jul. 23, 2018 in U.S. Appl. No. 15/863,340.
USPTO; Notice of Allowance dated Dec. 10, 2018 in U.S. Appl. No. 15/863,340.
USPTO; Non-Final Office Action dated Jan. 11, 2019 in U.S. Appl. No. 15/879,209.
USPTO; Non-Final Office Action dated Jan. 22, 2019 in U.S. Appl. No. 15/879,209.
USPTO; Final Office Action dated Aug. 21, 2019 in U.S. Appl. No. 15/879,209.
USPTO; Advisory Action dated Nov. 5, 2019 in U.S. Appl. No. 15/879,209.
USPTO; Notice of Allowance dated Jan. 16, 2020 in U.S. Appl. No. 15/879,209.
USPTO; Non-Final Office Action dated Apr. 17, 2019 in U.S. Appl. No. 15/886,225.
USPTO; Notice of Allowance dated Sep. 23, 2019 in U.S. Appl. No. 15/886,225.

(56) References Cited

OTHER PUBLICATIONS

USPTO; Non-Final Office Action dated Nov. 15, 2018 in U.S. Appl. No. 15/890,037.
USPTO; Final Office Action dated May 2, 2019 in U.S. Appl. No. 15/890,037.
USPTO; Non-Final Office Action dated Oct. 24, 2019 in U.S. Appl. No. 15/890,037.
USPTO; Final Office Action dated Feb. 26, 2020 in U.S. Appl. No. 15/890,037.
USPTO; Advisory Action dated Jun. 5, 2020 in U.S. Appl. No. 15/890,037.
USPTO; Non-Final Office Action dated Sep. 2, 2020 in U.S. Appl. No. 15/890,037.
USPTO; Notice of Allowance dated Feb. 8, 2019 in U.S. Appl. No. 15/892,756.
USPTO; Non-Final Office Action dated Apr. 24, 2019 in U.S. Appl. No. 15/896,986.
USPTO; Final Office Action dated Nov. 19, 2019 in U.S. Appl. No. 15/896,986.
USPTO; Advisory Action dated Feb. 7, 2020 in U.S. Appl. No. 15/896,986.
USPTO; Non-Final Office Action dated Mar. 24, 2020 in U.S. Appl. No. 15/896,986.
USPTO; Final Office Action dated Jun. 15, 2020 in U.S. Appl. No. 15/896,986.
USPTO; Notice of Allowance dated Aug. 26, 2020 in U.S. Appl. No. 15/896,986.
USPTO; Non-Final Office Action dated Sep. 19, 2019 in U.S. Appl. No. 15/897,578.
USPTO; Notice of Allowance dated Mar. 27, 2020 in U.S. Appl. No. 15/897,578.
USPTO; Non-Final Office Action dated May 30, 2019 in U.S. Appl. No. 15/900,425.
USPTO; Notice of Allowance dated Dec. 17, 2019 in U.S. Appl. No. 15/900,425.
USPTO; Non-Final Office Action dated Sep. 9, 2020 in U.S. Appl. No. 15/909,705.
USPTO; Non-Final Office Action dated Mar. 8, 2019 in U.S. Appl. No. 15/917,224.
USPTO; Final Office Action dated Aug. 28, 2019 in U.S. Appl. No. 15/917,224.
USPTO; Advisory Action dated Nov. 27, 2019 in U.S. Appl. No. 15/917,224.
USPTO; Non-Final Office Action dated May 1, 2020 in U.S. Appl. No. 15/917,224.
USPTO; Final Office Action dated Sep. 24, 2020 in U.S. Appl. No. 15/917,224.
USPTO; Non-Final Office Action dated Feb. 8, 2019 in U.S. Appl. No. 15/917,262.
USPTO; Final Office Action dated Jun. 14, 2019 in U.S. Appl. No. 15/917,262.
USPTO; Notice of Allowance dated Aug. 30, 2019 in U.S. Appl. No. 15/917,262.
USPTO; Non-Final Office Action dated Dec. 23, 2019 in U.S. Appl. No. 15/923,834.
USPTO; Final Office Action dated Mar. 12, 2020 in U.S. Appl. No. 15/923,834.
USPTO; Advisory Action dated May 15, 2020 in U.S. Appl. No. 15/923,834.
USPTO; Non-Final Office Action dated Jul. 6, 2020 in U.S. Appl. No. 15/923,834.
USPTO; Final Office Action dated Oct. 19, 2020 in U.S. Appl. No. 15/923,834.
USPTO; Non-Final Office Action dated May 8, 2019 in U.S. Appl. No. 15/925,532.
USPTO; Final Office Action dated Nov. 27, 2019 in U.S. Appl. No. 15/925,532.
USPTO; Non-Final Office Action dated May 1, 2020 in U.S. Appl. No. 15/925,532.
USPTO; Final Office Action dated Oct. 15, 2020 in U.S. Appl. No. 15/925,532.
USPTO; Non-Final Office Action dated Oct. 6, 2020 in U.S. Appl. No. 15/940,729.
USPTO; Non-Final Office Action dated Jul. 22, 2019 in U.S. Appl. No. 15/940,759.
USPTO; Final Office Action dated Feb. 19, 2020 in U.S. Appl. No. 15/940,759.
USPTO; Advisory Action dated Apr. 23, 2020 in U.S. Appl. No. 15/940,759.
USPTO; Non-Final Office Action dated Aug. 3, 2020 in U.S. Appl. No. 15/940,759.
USPTO; Non-Final Office Action dated Mar. 29, 2019 in U.S. Appl. No. 15/940,801.
USPTO; Notice of Allowance dated Aug. 26, 2019 in U.S. Appl. No. 15/940,801.
USPTO; Non-Final Rejection dated Nov. 29, 2019 in U.S. Appl. No. 15/949,990.
USPTO; Notice of Allowance dated Mar. 12, 2020 in U.S. Appl. No. 15/949,990.
USPTO; Notice of Allowance dated May 31, 2019 in U.S. Appl. No. 15/957,565.
USPTO; Non-Final Office Action dated Jan. 31, 2020 in U.S. Appl. No. 15/962,980.
USPTO; Final Office Action dated Apr. 30, 2020 in U.S. Appl. No. 15/962,980.
USPTO; Advisory Action dated Jul. 2, 2020 in U.S. Appl. No. 15/962,980.
USPTO; Non-Final Office Action dated Sep. 14, 2020 in U.S. Appl. No. 15/962,980.
USPTO; Non-Final Office Action dated Oct. 6, 2020 in U.S. Appl. No. 15/967,146.
USPTO; Non-Final Office Action dated Apr. 2, 2020 in U.S. Appl. No. 15/974,948.
USPTO; Final Office Action dated Sep. 3, 2020 in U.S. Appl. No. 15/974,948.
USPTO; Non-Final Office Action dated May 15, 2020 in U.S. Appl. No. 15/974,988.
USPTO; Notice of Allowance dated Oct. 14, 2020 in U.S. Appl. No. 15/974,988.
USPTO; Non-Final Office Action dated Jan. 16, 2020 in U.S. Appl. No. 15/985,261.
USPTO; Notice of Allowance dated Apr. 3, 2020 in U.S. Appl. No. 15/985,261.
USPTO; Non-Final Office Action dated Apr. 19, 2019 in U.S. Appl. No. 15/985,298.
USPTO; Notice of Allowance dated Aug. 22, 2019 in U.S. Appl. No. 15/985,298.
USPTO; Non-Final Office Action dated Jun. 12, 2020 in U.S. Appl. No. 15/985,539.
USPTO; Final Office Action dated Nov. 25, 2020 in U.S. Appl. No. 15/985,539.
USPTO; Non-Final Office Action dated Feb. 21, 2019 in U.S. Appl. No. 15/987,755.
USPTO; Notice of Allowance dated Jul. 31, 2019 in U.S. Appl. No. 15/987,755.
USPTO; Non-Final Office Action dated Feb. 20, 2020 in U.S. Appl. No. 15/996,286.
USPTO; Final Office Action dated Jul. 24, 2020 in U.S. Appl. No. 15/996,286.
USPTO; Advisory Action dated Oct. 7, 2020 in U.S. Appl. No. 15/996,286.
USPTO; Non-Final Office Action dated Apr. 1, 2020 in U.S. Appl. No. 15/997,445.
USPTO; Final Office Action dated Oct. 2, 2020 in U.S. Appl. No. 15/997,445.
USPTO; Notice of Allowance dated Jul. 10, 2020 in U.S. Appl. No. 15/998,775.
USPTO; Non-Final Office Action dated Mar. 3, 2020 in U.S. Appl. No. 16/000,109.
USPTO; Final Office Action dated Sep. 14, 2020 in U.S. Appl. No. 16/000,109.

(56) References Cited

OTHER PUBLICATIONS

USPTO; Non-Final Office Action dated Jul. 29, 2019 in U.S. Appl. No. 16/000,125.
USPTO; Final Office Action dated Jan. 13, 2020 in U.S. Appl. No. 16/000,125.
USPTO; Advisory Action dated Apr. 3, 2020 in U.S. Appl. No. 16/000,125.
USPTO; Non-Final Office Action dated Jun. 5, 2020 in U.S. Appl. No. 16/000,125.
USPTO; Final Office Action dated Oct. 6, 2020 in U.S. Appl. No. 16/000,125.
USPTO; Non-Final Office Action dated Apr. 22, 2020 in U.S. Appl. No. 16/000,156.
USPTO; Final Office Action dated Oct. 22, 2020 in U.S. Appl. No. 16/000,156.
USPTO; Non-Final Office Action dated May 7, 2020 in U.S. Appl. No. 16/004,041.
USPTO; Final Office Action dated Oct. 15, 2020 in U.S. Appl. No. 16/004,041.
USPTO; Non-Final Office Action dated Jul. 16, 2019 in U.S. Appl. No. 16/014,981.
USPTO; Non-Final Office Action dated Jan. 16, 2020 in U.S. Appl. No. 16/014,981.
USPTO; Notice of Allowance dated Jun. 24, 2020 in U.S. Appl. No. 16/014,981.
USPTO; Non-Final Office Action dated Jan. 24, 2019 in U.S. Appl. No. 16/018,692.
USPTO; Final Office Action dated Aug. 23, 2019 in U.S. Appl. No. 16/018,692.
USPTO; Non-Final Office Action dated Dec. 11, 2019 in U.S. Appl. No. 16/018,692.
USPTO; Notice of Allowance dated Jan. 30, 2020 in U.S. Appl. No. 16/018,692.
USPTO; Non-Final Office Action dated Aug. 7, 2019 in U.S. Appl. No. 16/024,390.
USPTO; Notice of Allowance dated Nov. 26, 2019 in U.S. Appl. No. 16/024,390.
USPTO; Notice of Allowance dated Apr. 9, 2019 in U.S. Appl. No. 16/026,711.
USPTO; Non-Final Office Action dated Mar. 4, 2020 in U.S. Appl. No. 16/036,692.
USPTO; Notice of Allowance dated May 26, 2020 in U.S. Appl. No. 16/036,692.
USPTO; Non-Final Office Action dated Apr. 25, 2019 in U.S. Appl. No. 16/038,024.
USPTO; Final Office Action dated Nov. 29, 2019 in U.S. Appl. No. 16/038,024.
USPTO; Advisory Action dated Feb. 28, 2020 in U.S. Appl. No. 16/038,024.
USPTO; Notice of Allowance dated Mar. 23, 2020 in U.S. Appl. No. 16/038,024.
USPTO; Non-Final Office Action dated Sep. 8, 2020 in U.S. Appl. No. 16/039,817.
USPTO; Non-Final Office Action dated Jul. 25, 2019 in U.S. Appl. No. 16/039,867.
USPTO; Final Office Action dated Jan. 28, 2020 in U.S. Appl. No. 16/039,867.
USPTO; Notice of Allowance dated Apr. 3, 2020 in U.S. Appl. No. 16/039,867.
USPTO; Non-Final Office Action dated Nov. 24, 2020 in U.S. Appl. No. 16/039,938.
USPTO; Non-Final Office Action dated Aug. 4, 2020 in U.S. Appl. No. 16/042,791.
USPTO; Notice of Allowance dated Jul. 10, 2019 in U.S. Appl. No. 16/046,218.
USPTO; Non-Final Office Action dated Apr. 30, 2020 in U.S. Appl. No. 16/055,532.
USPTO; Final Office Action dated Jul. 30, 2020 in U.S. Appl. No. 16/055,532.
USPTO; Final Office Action dated Nov. 3, 2020 in U.S. Appl. No. 16/055,532.
USPTO; Non-Final Office Action dated May 27, 2020 in U.S. Appl. No. 16/100,012.
USPTO; Notice of Allowance dated Sep. 14, 2020 in U.S. Appl. No. 16/100,012.
USPTO; Non-Final Office Action dated Feb. 20, 2020 in U.S. Appl. No. 16/105,745.
USPTO; Final Office Action dated Jun. 23, 2020 in U.S. Appl. No. 16/105,745.
USPTO; Advisory Action dated Aug. 25, 2020 in U.S. Appl. No. 16/105,745.
USPTO; Non-Final Office Action dated Nov. 25, 2020 in U.S. Appl. No. 16/105,745.
USPTO; Non-Final Office Action dated Feb. 24, 2020 in U.S. Appl. No. 16/105,761.
USPTO; Final Office Action dated Apr. 21, 2020 in U.S. Appl. No. 16/105,761.
USPTO; Advisory Action dated Jul. 8, 2020 in U.S. Appl. No. 16/105,761.
USPTO; Non-Final Office Action dated Nov. 25, 2020 in U.S. Appl. No. 16/105,761.
USPTO; Non-Final Office Action dated Mar. 19, 2020 in U.S. Appl. No. 16/105,802.
USPTO; Final Office Action dated Jun. 26, 2020 in U.S. Appl. No. 16/105,802.
USPTO; Final Office Action dated Nov. 17, 2020 in U.S. Appl. No. 16/105,802.
USPTO; Non-Final Office Action dated Sep. 8, 2020 in U.S. Appl. No. 16/108,950.
USPTO; Non-Final Office Action dated Mar. 16, 2020 in U.S. Appl. No. 16/116,708.
USPTO; Final Office Action dated Sep. 2, 2020 in U.S. Appl. No. 16/116,708.
USPTO; Advisory Action dated Nov. 17, 2020 in U.S. Appl. No. 16/116,708.
USPTO; Non-Final Office Action dated Feb. 6, 2020 in U.S. Appl. No. 16/117,530.
USPTO; Non-Final Office Action dated Jun. 22, 2020 in U.S. Appl. No. 16/128,282.
USPTO; Final Office Action dated Nov. 19, 2020 in U.S. Appl. No. 16/128,282.
USPTO; Non-Final Office Action dated Apr. 21, 2020 in U.S. Appl. No. 16/130,798.
USPTO; Notice of Allowance dated Aug. 5, 2020 in U.S. Appl. No. 16/130,798.
USPTO; Non-Final Office Action dated Jan. 6, 2020 in U.S. Appl. No. 16/132,142.
USPTO; Final Office Action dated Jun. 5, 2020 in U.S. Appl. No. 16/132,142.
USPTO; Advisory Action dated Aug. 24, 2020 in U.S. Appl. No. 16/132,142.
USPTO; Non-Final Office Action dated Oct. 16, 2020 in U.S. Appl. No. 16/132,142.
USPTO; Non-Final Office Action dated Feb. 28, 2020 in U.S. Appl. No. 16/137,974.
USPTO; Final Office Action dated Aug. 20, 2020 in U.S. Appl. No. 16/137,974.
USPTO; Notice of Allowance dated Nov. 3, 2020 in U.S. Appl. No. 16/137,974.
USPTO; Non-Final Office Action dated Apr. 2, 2019 in U.S. Appl. No. 16/147,047.
USPTO; Final Office Action dated Sep. 25, 2019 in U.S. Appl. No. 16/147,047.
USPTO; Notice of Allowance dated Jan. 3, 2020 in U.S. Appl. No. 16/147,047.
USPTO; Non-Final Office Action dated Jul. 30, 2020 in U.S. Appl. No. 16/151,074.
USPTO; Non-Final Office Action dated Nov. 5, 2019 in U.S. Appl. No. 16/152,260.
USPTO; Advisory Action dated Sep. 16, 2020 in U.S. Appl. No. 16/152,260.

(56) References Cited

OTHER PUBLICATIONS

USPTO; Final Office Action dated Jul. 15, 2020 in U.S. Appl. No. 16/152,260.
USPTO; Non-Final Office Action dated Nov. 9, 2020 in U.S. Appl. No. 16/152,260.
USPTO; Non-Final Office Action dated Aug. 6, 2019 in U.S. Appl. No. 16/158,077.
USPTO; Final Office Action dated Mar. 2, 2020 in U.S. Appl. No. 16/158,077.
USPTO; Advisory Action dated Jun. 9, 2020 in U.S. Appl. No. 16/158,077.
USPTO; Notice of Allowance dated Jul. 24, 2020 in U.S. Appl. No. 16/158,077.
USPTO; Non-Final Office Action dated Aug. 29, 2019 in U.S. Appl. No. 16/161,744.
USPTO; Final Office Action dated Mar. 17, 2020 in U.S. Appl. No. 16/161,744.
USPTO; Notice of Allowance dated Jun. 19, 2020 in U.S. Appl. No. 16/161,744.
USPTO; Non-Final Office Action dated Jul. 23, 2020 in U.S. Appl. No. 16/167,164.
USPTO; Non-Final Office Action dated Aug. 16, 2019 in U.S. Appl. No. 16/167,225.
USPTO; Final Office Action dated Dec. 16, 2019 in U.S. Appl. No. 16/167,225.
USPTO; Notice of Allowance dated Mar. 5, 2020 in U.S. Appl. No. 16/167,225.
USPTO; Notice of Allowance dated Apr. 17, 2019 in U.S. Appl. No. 16/171,098.
USPTO; Notice of Allowance dated May 1, 2019 in U.S. Appl. No. 16/171,098.
USPTO; Non-Final Office Action dated Aug. 7, 2020 in U.S. Appl. No. 16/172,535.
USPTO; Final Office Action dated Oct. 16, 2020 in U.S. Appl. No. 16/172,535.
USPTO; Non-Final Office Action dated Nov. 4, 2020 in U.S. Appl. No. 16/176,517.
USPTO; Non-Final Office Action dated Oct. 29, 2020 in U.S. Appl. No. 16/183,258.
USPTO; Non-Final Office Action dated Apr. 2, 2019 in U.S. Appl. No. 16/188,690.
USPTO; Final Office Action dated Sep. 26, 2019 in U.S. Appl. No. 16/188,690.
USPTO; Notice of Allowance dated Dec. 16, 2019 in U.S. Appl. No. 16/188,690.
USPTO; Notice of Allowance dated Jul. 28, 2020 in U.S. Appl. No. 16/193,789.
USPTO; Notice of Allowance dated Jul. 7, 2020 in U.S. Appl. No. 16/194,041.
USPTO; Notice of Allowance dated Oct. 3, 2019 in U.S. Appl. No. 16/200,100.
USPTO; Non-Final Office Action dated May 29, 2020 in U.S. Appl. No. 16/205,899.
USPTO; Final Office Action dated Nov. 27, 2020 in U.S. Appl. No. 16/205,899.
USPTO; Non-Final Office Action dated Aug. 19, 2019 in U.S. Appl. No. 16/208,062.
USPTO; Notice of Allowance dated Jan. 28, 2020 in U.S. Appl. No. 16/208,062.
USPTO; Non-Final Office Action dated Jul. 15, 2020 in U.S. Appl. No. 16/210,922.
USPTO; Non-Final Office Action dated Sep. 16, 2019 in U.S. Appl. No. 16/213,702.
USPTO; Notice of Allowance dated Dec. 9, 2019 in U.S. Appl. No. 16/213,702.
USPTO; Non-Final Office Action dated Jan. 8, 2020 in U.S. Appl. No. 16/219,555.
USPTO; Final Office Action dated Jun. 19, 2020 in U.S. Appl. No. 16/219,555.
USPTO; Advisory Action dated Sep. 11, 2020 in U.S. Appl. No. 16/219,555.
USPTO; Non-Final Office Action dated Sep. 30, 2020 in U.S. Appl. No. 16/219,555.
USPTO; Non-Final Office Action dated Feb. 19, 2020 in U.S. Appl. No. 16/242,829.
USPTO; Final Office Action dated Jun. 15, 2020 in U.S. Appl. No. 16/242,829.
USPTO; Advisory Action dated Aug. 11, 2020 in U.S. Appl. No. 16/242,829.
USPTO; Notice of Allowance dated Sep. 23, 2020 in U.S. Appl. No. 16/242,829.
USPTO; Non-Final Office Action dated Sep. 3, 2020 in U.S. Appl. No. 16/242,852.
USPTO; Non-Final Office Action dated Jan. 30, 2020 in U.S. Appl. No. 16/245,006.
USPTO; Notice of Allowance dated May 29, 2020 in U.S. Appl. No. 16/245,006.
USPTO; Non-Final Office Action dated Sep. 24, 2019 in U.S. Appl. No. 16/251,534.
USPTO; Final Office Action dated Jan. 10, 2020 in U.S. Appl. No. 16/251,534.
USPTO; Advisory Action dated Apr. 3, 2020 in U.S. Appl. No. 16/251,534.
USPTO; Non-Final Office Action dated Apr. 24, 2020 in U.S. Appl. No. 16/251,534.
USPTO; Final Office Action dated Oct. 14, 2020 in U.S. Appl. No. 16/251,534.
USPTO; Non-Final Office Action dated May 27, 2020 in U.S. Appl. No. 16/252,567.
USPTO; Final Office Action dated Nov. 18, 2020 in U.S. Appl. No. 16/252,567.
USPTO; Non-Final Office Action dated Apr. 16, 2020 in U.S. Appl. No. 16/255,639.
USPTO; Notice of Allowance dated Aug. 6, 2020 in U.S. Appl. No. 16/255,639.
USPTO; Non-Final Office Action dated Jun. 30, 2020 in U.S. Appl. No. 16/258,187.
USPTO; Notice of Allowance dated Aug. 5, 2020 in U.S. Appl. No. 16/258,187.
USPTO; Non-Final Office Action dated Dec. 18, 2019 in U.S. Appl. No. 16/280,964.
USPTO; Notice of Allowance dated May 21, 2020 in U.S. Appl. No. 16/280,964.
USPTO; Non-Final Office Action dated Jan. 9, 2020 in U.S. Appl. No. 16/317,774.
USPTO; Notice of Allowance dated Apr. 15, 2020 in U.S. Appl. No. 16/317,774.
USPTO; Non-Final Office Action dated Mar. 2, 2020 in U.S. Appl. No. 16/356,394.
USPTO; Final Office Action dated Jun. 30, 2020 in U.S. Appl. No. 16/356,394.
USPTO; Notice of Allowance dated Aug. 31, 2020 in U.S. Appl. No. 16/356,394.
USPTO; Notice of Allowance dated Jun. 13, 2019 in U.S. Appl. No. 16/396,475.
USPTO; Non-Final Office Action dated Aug. 5, 2020 in U.S. Appl. No. 16/397,045.
USPTO; Non-Final Office Action dated Aug. 19, 2020 in U.S. Appl. No. 16/400,814.
USPTO; Non-Final Office Action dated Dec. 26, 2019 in U.S. Appl. No. 16/417,938.
USPTO; Notice of Allowance dated Mar. 30, 2020 in U.S. Appl. No. 16/417,938.
USPTO; Non-Final Office Action dated Dec. 31, 2019 in U.S. Appl. No. 16/427,288.
USPTO; Notice of Allowance dated Apr. 16, 2020 in U.S. Appl. No. 16/427,288.
USPTO; Non-Final Office Action dated May 12, 2020 in U.S. Appl. No. 16/454,063.
USPTO; Notice of Allowance dated Sep. 18, 2020 in U.S. Appl. No. 16/454,063.

(56) References Cited

OTHER PUBLICATIONS

USPTO; Non-Final Office Action dated Dec. 31, 2019 in U.S. Appl. No. 16/455,406.
USPTO; Notice of Allowance dated Apr. 17, 2020 in U.S. Appl. No. 16/455,406.
USPTO; Non-Final Office Action dated Nov. 27, 2020 in U.S. Appl. No. 16/468,258.
USPTO; Non-Final Office Action dated Nov. 5, 2020 in U.S. Appl. No. 16/546,543.
USPTO; Non-Final Office Action dated Jun. 11, 2020 in U.S. Appl. No. 16/598,768.
USPTO; Notice of Allowance dated Sep. 16, 2020 in U.S. Appl. No. 16/598,768.
USPTO; Final Office Action dated Jan. 10, 2020 in U.S. Appl. No. 16/674,894.
USPTO; Notice of Allowance dated Apr. 21, 2020 in U.S. Appl. No. 16/674,894.
USPTO; Non-Final Office Action dated Oct. 16, 2020 in U.S. Appl. No. 16/679,885.
USPTO; Non-Final Office Action dated Nov. 16, 2020 in U.S. Appl. No. 16/713,311.
USPTO; Non-Final Office Action dated Apr. 13, 2020 in U.S. Appl. No. 16/833,279.
USPTO; Final Office Action dated Oct. 2, 2020 in U.S. Appl. No. 16/833,279.
USPTO; Non-Final Office Action dated Jul. 9, 2020 in U.S. Appl. No. 16/897,158.
USPTO; Notice of Allowance dated Nov. 12, 2020 in U.S. Appl. No. 16/897,158.
USPTO; Non-Final Office Action dated Aug. 4, 2020 in U.S. Appl. No. 16/926,192.
USPTO; Notice of Allowance dated May 14, 2012 in U.S. Appl. No. 29/411,637.
USPTO; Notice of Allowance dated Oct. 2, 2013 in U.S. Appl. No. 29/412,887.
USPTO; Non-Final Office Action dated Mar. 16, 2015 in U.S. Appl. No. 29/447,298.
USPTO; Notice of Allowance dated Jul. 6, 2015 in U.S. Appl. No. 29/447,298.
USPTO; Notice of Allowance dated Dec. 19, 2013 in U.S. Appl. No. 29/448,094.
USPTO; Notice of Allowance dated Nov. 26, 2014 in U.S. Appl. No. 29/481,301.
USPTO; Notice of Allowance dated Feb. 17, 2015 in U.S. Appl. No. 29/481,308.
USPTO; Notice of Allowance dated Jan. 12, 2015 in U.S. Appl. No. 29/481,312.
USPTO; Notice of Allowance dated Apr. 30, 2015 in U.S. Appl. No. 29/481,315.
USPTO; Notice of Allowance dated May 11, 2015 in U.S. Appl. No. 29/511,011.
USPTO; Notice of Allowance dated May 11, 2015 in U.S. Appl. No. 29/514,153.
USPTO; Notice of Allowance dated Dec. 14, 2015 in U.S. Appl. No. 29/514,264.
USPTO; Notice of Allowance dated Jun. 16, 2017 in U.S. Appl. No. 29/570,711.
USPTO; Non-Final Office Action dated Apr. 16, 2019 in U.S. Appl. No. 29/604,101.
USPTO; Notice of Allowance dated Oct. 30, 2019 in U.S. Appl. No. 29/604,101.
USPTO; Notice of Allowance dated Jun. 26, 2018 in U.S. Appl. No. 29/604,288.
USPTO; Ex Parte Quayle Action dated Dec. 17, 2019 in U.S. Appl. No. 29/615,000.
USPTO; Notice of Allowance dated Jun. 10, 2020 in U.S. Appl. No. 29/615,000.
USPTO; Non-Final Office Action dated Aug. 21, 2019 in U.S. Appl. No. 29/634,768.
USPTO; Notice of Allowance dated Jan. 23, 2020 in U.S. Appl. No. 29/634,768.
USPTO; Non-Final Office Action dated Feb. 20, 2019 in U.S. Appl. No. 29/646,377.
USPTO; Final Office Action dated Jul. 15, 2019 in U.S. Appl. No. 29/646,377.
USPTO; Notice of Allowance dated Nov. 14, 2019 in U.S. Appl. No. 29/646,377.
USPTO; Non-Final Office Action dated Apr. 24, 2020 in U.S. Appl. No. 29/726,623.
USPTO; Final Office Action dated Sep. 9, 2020 in U.S. Appl. No. 29/726,623.
USPTO; Notice of Allowance dated Nov. 23, 2020 in U.S. Appl. No. 29/726,623.
WIPO; International Search Report dated Oct. 13, 1998 in Application No. PCT/FI1998/000571.
WIPO; International Search Report and Written Opinion dated Nov. 16, 2017 in Application No. PCT/IB2017/001015.
WIPO; International Search Report and Written Opinion dated Nov. 13, 2017 in Application No. PCT/IB2017/001050.
WIPO; International Search Report and Written Opinion dated Nov. 30, 2017 in Application No. PCT/IB2017/001070.
WIPO; International Search Report and Written Opinion dated Jan. 25, 2018 in Application No. PCT/IB2017/001262.
WIPO; International Search Report and Written Opinion dated Sep. 14, 2018 in Application No. PCT/IB2017/001640.
WIPO: International Search Report and Written Opinion dated Jun. 1, 2018 in Application No. PCT/IB2017/001644.
WIPO; International Search Report and Written Opinion dated Nov. 6, 2018 in Application No. PCT/IB2017/001652.
WIPO: International Search Report and Written Opinion dated Jun. 1, 2018 in Application No. PCT/IB2017/001656.
WIPO; International Search Report and Written Opinion dated Jan. 25, 2019 in Application No. PCT/IB2018/000192.
WIPO; International Search Report and Written Opinion dated Jul. 9, 2018 in Application No. PCT/IB2018/000419.
WIPO; International Search Report and Written Opinion dated Jan. 4, 2019 in Application No. PCT/IB2018/000936.
WIPO; International Search Report and Written Opinion dated Dec. 20, 2018 in Application No. PCT/IB2018/001003.
WIPO; International Search Report and Written Opinion dated Dec. 20, 2018 in Application No. PCT/IB2018/001022.
WIPO; International Search Report and Written Opinion dated Jun. 28, 2019 in Application No. PCT/IB2019/000084.
WIPO; International Search Report and Written Opinion dated Nov. 19, 2019 in Application No. PCT/IB2019/000127.
WIPO; International Search Report and Written Opinion dated Jan. 10, 2020 in Application No. PCT/IB2019/000729.
WIPO; International Search Report and Written Opinion dated Dec. 20, 2019 in Application No. PCT/IB2019/000805.
WIPO; International Search Report and Written Opinion dated Dec. 20, 2019 in Application No. PCT/IB2019/000817.
WIPO; International Search Report and Written Opinion dated May 23, 2019 in Application No. PCT/IB2019/050974.
WIPO; International Search Report dated Jul. 13, 1990 in Application No. PCT/NL1990/000027.
WIPO; International Search Report dated Jan. 11, 1990 in Application No. PCT/NL1990/000042.
WIPO; International Search Report dated Feb. 26, 1991 in Application No. PCT/NL1990/000166.
WIPO; International Search Report dated Oct. 25, 1991 in Application No. PCT/NL1991/000108.
WIPO; International Search Report dated Oct. 17, 1997 in Application No. PCT/NL1997/000398.
WIPO; International Preliminary Examination Report dated Oct. 2, 1998 in Application No. PCT/NL1997/000398.
WIPO; International Search Report dated Apr. 24, 1998 in Application No. PCT/NL1998/000055.
WIPO; International Preliminary Examination Report dated Feb. 24, 1999 in Application No. PCT/NL1998/000055.
WIPO; International Search Report dated May 27, 1998 in Application No. PCT/NL1998/000105.

(56) References Cited

OTHER PUBLICATIONS

WIPO; International Search Report dated May 8, 1998 in Application No. PCT/NL1998/000151.
WIPO; International Preliminary Examination Report dated Mar. 23, 1999 in Application No. PCT/NL1998/000151.
WIPO; International Search Report dated May 27, 1998 in Application No. PCT/NL1998/000167.
WIPO; International Preliminary Examination Report dated Jul. 13, 1999 in Application No. PCT/NL1998/000167.
WIPO; International Search Report dated Jul. 8, 1998 in Application No. PCT/NL1998/000204.
WIPO; International Search Report dated Aug. 21, 1998 in Application No. PCT/NL1998/000246.
WIPO; International Search Report dated Oct. 16, 1998 in Application No. PCT/NL1998/000383.
WIPO; International Preliminary Examination Report dated Sep. 16, 1999 in Application No. PCT/NL1998/000383.
WIPO; International Search Report dated Apr. 15, 1999 in Application No. PCT/NL1999/000047.
WIPO; International Search Report dated Oct. 12, 1999 in Application No. PCT/NL1999/000487.
WIPO; International Search Report dated Dec. 16, 1999 in Application No. PCT/NL1999/000583.
WIPO; Written Opinion dated Jul. 24, 2000 in Application No. PCT/NL1999/000583.
WIPO; International Preliminary Examination Report dated Jan. 22, 2001 in Application No. PCT/NL1999/000583.
WIPO; International Search Report dated Apr. 19, 2000 in Application No. PCT/NL2000/000020.
WIPO; Written Opinion dated Oct. 17, 2000 in Application No. PCT/NL2000/000020.
WIPO; International Search Report and Written Opinion dated Apr. 17, 2019 in Application No. PCT/NL2018/050787.
WIPO; International Search Report and Written Opinion dated Apr. 29, 2019 in Application No. PCT/NL2018/050791.
WIPO; International Search Report dated Dec. 16, 1999 in Application No. PCT/RU1999/000328.
WIPO; International Preliminary Examination Report dated Jun. 29, 2001 in Application No. PCT/RU1999/000328.
WIPO; International Preliminary Report on Patentability dated Nov. 24, 2009 and International Search Report dated Jul. 31, 2008 in Application No. PCT/US2008/063919.
WIPO; International Preliminary Report on Patentability dated Feb. 24, 2010 in Application No. PCT/US2008/074063.
WIPO; International Preliminary Report on Patentability dated Nov. 26, 2009 in Application No. PCT/US2009/043454.
WIPO; International Preliminary Report on Patentability dated Jun. 14, 2011 in Application No. PCT/US2009/066377.
WIPO; International Search report and Written Opinion dated Nov. 12, 2010 in Application No. PCT/US2010/030126.
WIPO; International Preliminary Report on Patentability dated Oct. 11, 2011 Application No. PCT/US2010/030126.
WIPO; International Preliminary Report on Patentability dated Nov. 9, 2011 in Application No. PCT/US2010/033244.
WIPO; International Preliminary Report on Patentability dated Nov. 9, 2011 in Application No. PCT/US2010/033248.
WIPO; International Preliminary Report on Patentability dated Nov. 9, 2011 in Application No. PCT/US2010/033252.
WIPO; International Search report and Written Opinion dated Jan. 20, 2011 in Application No. PCT/US2010/045368.
WIPO; International Search report and Written Opinion dated Feb. 6, 2013 in Application No. PCT/US2012/065343.
WIPO; International Search report and Written Opinion dated Feb. 13, 2013 in Application No. PCT/US2012/065347.
Akiyama et al. "Macro- and micro-scale simulation of growth rate and composition in MOCVD of yttria-stabilized zirconia" J. Crystal Growth 241, pp. 352-362 (2002).
Alen, "Atomic layer deposition of TaN, NbN and MoN films for Cu Metallizations," University of Helsinki Finland, 72 pages, (2005).
Altiere et al. "Review Article: Plasma-surface interactions at the atomic scale for patterning metals" J. Vac. Sci. Technol. A 35, 05C203, 13 pages (2017).
Ande et al. "Role of Surface Termination in Atomic Layer Deposition of Silicon Nitride" J. Phys. Chem. Lett., 6(18), 16 pages (2015).
Arita et al. "Electrical and optical properties of germanium-doped zinc oxide thin films" Materials Transactions, vol. 45, No. 11, pp. 3180-3183 (2004).
Arnold et al., "Novel single-layer vanadium sulphide phases" 2D Materials, 5, 045009, 11 pages (2018).
Athavale et al., "Realization of Atomic Layer Etching of Silicon", Journal of Vacuum Science and Technology B, vol. 14, pp. 3702-3705 (1996).
Atta et al. "The Catalytic Activity of Ruthenates ARuO3 (A=Ca, Sr or Ba) for the Hydrogen Evolution Reaction in Acidic Medium" Int. J. Electrochem. Sci. 7, pp. 725-746 (2012).
Ballal "Mass Transfer in Porous Solids under Pulsating Pressure Conditions" SLJ International, vol. 35, Nov. 4, pp. 446-448 (1995).
Bark et al. "Large-area niobium disulfide thin films as transparent electrodes for devices based on two-dimensional materials," Nanoscale, published online, 7 pages (2012).
Barreca et al. "Cobalt oxide nanomaterials by vapor phase synthesis for fast and reversible lithium storage" J Phys Chem C,114, 10054-10060 (2010).
Basuvalingam et al. "NS-WeA6—Low Temperature ALD for Phase-controlled Synthesis of 2D Transition Metal (M=Ti, Nb) di-(MX2) and Tri-(MX3) Sulfides," AVS 19th International Conference on Atomic Layer Deposition (ALD 2019)), Jul. 22, 2019, Abstract, 1 page (2019).
Bearzotti, et al., "Fast Humidity Response of a Metal Halide-Doped Novel Polymer," Sensors and Actuators B, 7, pp. 451-454, (1992).
Becker et al., "Atomic Layer Deposition of Insulating Hafnium and Zirconium Nitrides," Chem. Mater., 16, 3497-3501 (2004).
Beynet et al. "Low temperature plasma-enhanced ALD enables cost-effective spacer defined double patterning," Proceedings of SPIE, 7520, (2009).
Bhatnagar et al., "Copper Interconnect Advances to Meet Moore's Law Milestones," Solid State Technology, 52, 10 (2009).
Boscher et al., "Atmosphere Pressure Chemical Vapour Deposition of NbSe2 Thin Films on Glass" Eur. J. Inorg. Chem., pp. 1255-1259 (2006).
Brewin et al. "UPS to deploy Bluetooth, wireless LAN network" Internet, pp. 1-5 (2001).
Bulletin Plasma Source—Dec. 2002: Type AX7610—Downstream Plasma Source. Source location: MKS Instruments, Inc. http://www.mksinst.com/. Accessed: Aug. 6, 2015. pp. 1-4 (2002).
Bulletin ASTRONe—Apr. 2002: Type AX7680—Reactive Gas Generator. Source location: MKS Instruments, Inc. http://www.mksinst.com/. Accessed: Aug. 6, 2015. pp. 1-2 (2002).
Bulletin ASTRONex—Jul. 2009: Type AX7685—Reactive Gas Generator. Source location: MKS Instruments, Inc. http://www.mksinst.com/. Accessed: Aug. 6, 2015. pp. 1-2 (2002).
Bulletin ASTRON hf-s—Mar. 2005: Type AX7645—Reactive Gas Generator. Source location: MKS Instruments, Inc. http://www.mksinst.com/. Accessed: Aug. 6, 2015. pp. 1-2 (2005).
Bulletin ENG-Xstream-340-09 OM Aug. 2006: Xstream with Active Matching Network Remote Plasma Source. Advanced Energy Industries, Inc. http://www.advanced-energy.net.cn/upload/File/Sources/ENG-Xstream-340-09.pdf. Accessed: Jul. 19, 2016. pp. 1-4 (2006).
Bulletin R*evolution—Sep. 2006: Type AX7690—Remote Plasma Source. Source location: MKS Instruments, Inc. http://www.mksinst.com/. Accessed: Aug. 6, 2015. pp. 1-2 (2006).
Buriak, "Organometallic Chemistry on Silicon and Germanium Surfaces," Chemical Reviews, 102, 5 (2002).
Cahiez et al. "Cobalt-Catalyzed cross coupling reaction between functionalized primary and secondary alkyl halides and aliphatic grignard reagents" Adv. Synth. Catal, 350, 1484-1488 (2008).
Callaghan et al. "Magnetic Interactions in Ternary Ruthenium Oxides" Inorganic Chemistry, vol. 5, No. 9, pp. 1572-1576 (1966).
Cant et al., "Chemisorption Sites on Porous Silica Glass and on Mixed-Oxide Catalysis," Can. J. Chem. 46, 1373 (1968).

(56) References Cited

OTHER PUBLICATIONS

Carmalt et al., "Chemical Vapor Deposition of Niobium Disulfide Thin Films" Eur. J. Inorg. Chem., pp. 4470-4476 (2004).

Casey et al. "Chemical Vapor Deposition of Mo onto Si" J. Electrochem. Soc.: Solid State Science, 114 (2), pp. 201-204 (1967).

Chang et al. "Small-Subthreshold-Swing and Low-Voltage Flexible Organic Thin-Film Transistors Which Use HfLaO as the Gate Dielectric," IEEE Electron Device Letters, Feb. 2009, pp. 133-135; vol. 30, No. 2; IEEE Electron Device Society.

Chatterjee et al. "Chemical Vapor Deposition of Boron Nitride Nanosheets on Metallic Substrates via Decaborane/Ammonia Reactions", Chem. Mater. 23, pp. 4414-4416 (2011).

Chatterjee et al., "Sub-100nm Gate Length Metal Gate NMOS Transistors Fabricated by a Replacement by a Replacement Gate Process," IEEE Semiconductor Process and Device Center, 821-824 (1997).

Chen et al., "A Self-Aligned Airgap Interconnect Scheme," IEEE International Interconnect Technology Conference, vol. 1-3, 146-148 (2009).

Chen et al., "Develop Gap-fill Process of Shallow Trench Isolation in 450mm Wafer by Advanced Flowable CVD Technology for Sub-20nm Node," 2016 27th Annual Semi Advanced Semiconductor.

Cheng et al., "Effect of carrier gas on the structure and electric properties of low dielectric constant SiCOH film using trimethylsilane prepared by plasma enhanced chemical vapor deposition," Thin Solid Films vol. 469-470, pp. 178-183 (2004).

Choi et al., "Improvement of Silicon Direct Bonding using Surfaces Activated by Hydrogen Plasma Treatment," Journal of the Korean Physical Society, 37, 6, 878-881 (2000).

Choi et al., "Low Temperature Formation of Silicon Oxide Thin Films by Atomic Layer Deposition Using NH3/O2 Plasma," ECS Solid State Letters, 2(12) P114-P116 (2013).

Choi et al. "UV irradiation effects on the bonding structure and electrical properties of ultra low-k SiOC(-H) thin films for 45 nm technology node" Current Applied Physics, 11, S109-S113 (2011).

Closser et al., "Molecular Layer Deposition Of A Highly Stable Silicon Oxycarbide Thin Film Using An Organic Chlorosilane And Water," ACS Applied Materials & Interfaces 10, pp. 24266-24274 (2018).

Coates, "Process Analytical Technology: Spectroscopic Tools and Implementation Strategies for the Chemical and Pharmaceutical Industries." Blackwell Publishing Ltd, 91-132, (2005).

Conroy et al., "The Preparation and Properties of Single Crystals of the 1S and 2S Polymorphs of Tantalum Disulfide" J. Solid State Chemistry, 4, pp. 345-350 (1972).

Crowell, "Chemical methods of thin film deposition: Chemical vapor deposition, atomic layer deposition, and related technologies," Journal of Vacuum Science & Technology A 21.5, (2003): S88-S95.

Cui et al., "Impact of Reductive N2/H2 Plasma on Porous Low-Dielectric Constant SiCOH Thin Films," Journal of Applied Physics 97, 113302, 1-8 (2005).

Crystal IS "Application Note: Using UV Reflective Materials to Maximize Disinfection"; AN011; Jun. 16, 2016, found at https://www.klaran.com/using-uv-reflective-materials-to-maximize-disinfection.

De Silva et al., "Inorganic Hardmask Development For Extreme Ultraviolet Patterning," Journal of Micro/Nanolithography, MEMS, and MOEMS 18(1) (2018).

Dingemans et al., "Comparison Between Aluminum Oxide Surface Passivation Films Deposited with Thermal Aid," Plasma Aid and Pecvd, 35th IEEE PVCS, Jun. 2010.

Drummond et al., "Hydrophobic Radiofrequency Plasma-Deposited Polymer Films: Dielectric Properties and Surface Forces," Colloids and Surfaces A, 129-130, 117-129 (2006).

Duffey et al., "Raman Scattering from 1T-TaS2" Solid State Communications 20, pp. 617-621 (1976).

Dufond et al. "Quantifying the Extent of Ligand Incorporation and the Effect on Properties of TiO 2 Thin Films Grown by Atomic Layer Deposition Using an Alkoxide or an Alkylamide" Chemistry of Material, American Chemical Society 32(4), pp. 1393-1407 (2020).

Dultsev et al. "Effect of UV radiation on the reactivity of porous methyl-doped SiO2 layers" Phys. Status Solidi C, 8, No. 6, pp. 1946-1949 (2011).

Easley et al., "Thermal Isolation of Microchip Reaction Chambers for Rapid Non-Contact DNA Amplification," J. Micromech. Microeng. 17, 1758-1766 (2007).

Elam et al., "New Insights into Sequential Infiltration Synthesis", ECS Transactions, vol. 69, pp. 147-157 (2015).

Elers et al. "Film Uniformity in Atomic Layer Deposition," Chemical Vapor Deposition, 12, pp. 13-24 (2006).

Ellis et al. "Nitrous Oxide (N2O) Processing for Silicon Oxynitride Gate Dielectrics." IBM Journal of Research and Development. 1999. 43[3]. pp. 287-300. (1999).

Esposito et al. "Preparation and characterization of lead ruthenate based composite cathodes for SOFC applications" Mater. Res. Soc. Symp. Proc., vol. 835, 6 pages (2005).

Fallica et al., "Dynamic Absorption Coefficients Of Chemically Amplified Resists And Nonchemically Amplified Resists At Extreme Ultraviolet", J. Micro/Nanolith. MEMS MOEMS 15(3), pp. 033506-1-033506-7 (2016).

"Fiji F200 200mm Thermal/Plasma ALD Systems: Installation and Use Manual." CAW-02635 Rev. 0.6 (Mar. 13, 2012). Cambridge NanoTech Inc. pp. 1-164 (2012).

Fray et al. "Aspects of the Application of Electrochemistry to the Extraction of Titanium and Its Applications" Materials Transactions, vol. 58, No. 3, pp. 306-312 (2017).

Freund et al. "Single crystal growth from separated educts and its application to lithium transition-metal oxides" Sci. Rep. 6, 35362, pp. 1-5 (2016).

Frequestly Asked Question, "What is a load lock chamber?", Kurt J. Lesker Company, www.lesker.com, p. 1 (2020).

Fu et al., "Controlled Synthesis of Atomically Thin 1T-TaS2 for Tunable Charge Density Wave Phase Transitions" Chem. Mater. 28, pp. 7613-7618 (2016).

Ge et al., "Carbon Nanotube-Based Synthetic Gecko Tapes," Department of Polymer Science, PNAS, 10792-10795 (2007).

Ge et al. "Large-scale synthesis of NbS2 nanosheets with controlled orientation on graphene by ambient pressure CVD," Nanoscale, vol. 5, 5773-5778 (2013).

George et al., "Atomic Layer Deposition: An Overview," Chem. Rev. 110, 111-131 (2010).

Gesheva et al. "Composition and Microstructure of Black Molybdenum Photothermal Converter Layers Deposited by the Pyrolytic Hydrogen Reduction of $MoO_2Cl_2$" Thin Solid Films, 79, pp. 39-49 (1981).

Glass et al. "The Chemical Vapor Deposition of Metal Boride Thin Films from Polyhedral Cluster Species", Winter and Hoffman, Inorganic Materials Synthesis. ACS Symposium Series; American Cemical Society: Washington DC, Chapter 10, pp. 130-143 (1999).

Gole et al. "Preparation of Nickel Sulfide Thin Films and Nanocrystallites Using Nickel Furfuraldehyde Thiosemicarbazone as Single-source Precursor," Advanced Materials Research, vols. 383-390, pp. 3828-3834 (2012).

Gordon et al. "A Kinetic Model for Step Coverage by Atomic Layer Deposition in Narrow Holes or Trenches." Chemical Vapor Deposition. 9 [2]. pp. 73-78 (2003).

Grill et al., "The Effect of Plasma Chemistry on the Damage Induced Porous SiCOH Dielectrics," IBM Research Division, RC23683 (W0508-008), Materials Science, 1-19 (2005).

Guan et al., "Voltage gated ion and molecule transport in engineered nanochannels: theory, fabrication and applications," Nanotechnology 25 (2014) 122001.

Gupta et al., "Charge carrier transport and electroluminescence in atomic layer deposited poly-GaN/c—Si heterojunction diodes," Journal of Applied Physics, 124, 084503 (2018).

Gupta et al., "Conversion of Metal Carbides to Carbide Derived Carbon by Reactive Ion Etching in Halogen Gas," Proceedings of SPIE—The International Society for Optical Engineering and Nanotechnologies for Space Applications, ISSN: 0277-786X (2006).

(56) References Cited

OTHER PUBLICATIONS

Habib et al. "Atmospheric oxygen plasma activation of silicon (100) surfaces," American Vacuum Society, 28(3), pp. 476-485 (2010).
Hamalainen et al., "Atomic Layer Deposition of Rhenium Disulfide," Adv. Mater. 30.24, 6 pages (2018).
Han et al., "van der Waals Metallic Transition Metal Dichalcogenides" Chem. Rev. 118, pp. 6297-6336 (2018).
Hansen. "A Primer on Vacuum Pressure Measurement." Vacuum Technology & Coating. Jun. 2009. pp. 36-42 (2009).
Hansen. "Speed, Pressure and Throughput: Part 1 System Diagnostics." Vacuum Technology & Coating. Sep. 2011. pp. 14-17 (2011).
Hansen. "Speed, Pressure and Throughput: Part 2 Managing Gas Flow in High Vacuum Systems." Vacuum Technology & Coating. Oct. 2011. pp. 19-22 (2011).
Hansen. "Speed, Pressure and Throughput: Part 3 Automating the Pressure Control Process." Vacuum Technology & Coating. Nov. 2011. pp. 22-25 (2011).
Hansen. "Speed, Pressure and Throughput: Part 4 Outgassing and Base Pressure." Vacuum Technology & Coating. Dec. 2011. pp. 22-25 (2011).
Hansen. "Speed, Pressure and Throughput: Part 5 Leaks and Gas Flow in Leak Detection." Vacuum Technology & Coating. Jan. 2012. pp. 18-21 (2011).
Hargreaves et al., "New Fluorides and Oxyfluorides of Rhenium," J. Chem. Soc., pp. 1099-1103 (1960).
Harrison et al., "Poly-gate Replacement Through Contact Hole (PRETCH): A New Method for High-K/ Metal Gate and Multi-Oxide Implementation on Chip," IEEE (2004).
Hayashi et al. "Spectroscopic properties of nitrogen doped hydrogenated amorphous carbon films grown by radio frequency plasma-enhanced chemical vapor deposition," Journal of Applied Physics. vol. 89, No. 12, pp. 7924-7931 (2001).
Heo et al., "Structural Characterization of Nanoporous Low-Dielectric Constant SiCOH Films Using Organosilane Precursors," NSTI-Nanotech, vol. 4, 122-123 (2007).
Henke et al.., "X-Ray Interactions: Photo absorption, Scattering, Transmission, and Reflection at E=50-30,000 eV, Z=1-92," Atomic Data and Nuclear Data Tables, 54, 181-342 (1993).
Heyne et al., "The conversion mechanism of amorphous silicon to stoichiometric WS2" J. Materials Chemistry C, 6, pp. 4122-4130 (2018).
Hong et al. "Ultralow-dielectric-constant amoprhous boron nitride" Nature, vol. 582, 16 pages (2020).
Hossain et al., "Recent Advances in Two-Dimensional Materials with Charge Density Waves: Synthesis, Characterization and Applications" Crystals 7, 298, 19 pages (2017).
Hubert et al., "A Stacked SONOS Technology, up to 4 Levels and 6nm Crystalline Nanowires, With Gate-All-Around or Independent Gates (-Flash), Suitable for Full 3D Integration," Minatec, IEDM09-637-640 (2009).
Hudis, "Surface Crosslinking of Polyethylene Using a Hydrogen Glow Discharge," J. Appl. Polym. Sci., 16 (1972) 2397.
Ivanova et al. "ALD of Sc2O3 using Sc(Cp)3 and a Novel Heteroleptic Precursors" Presented on the AVS 19th International Conference on Atomic Layer Deposition, Jul. 23, 2019, Abstract, 1 page (2019).
Jensen et al. "Titanium, Zirconium, and Hafnium Tetrahydroborates as "Tailored" CVD Precursors for Metal Diboride Thin Films", J. Am. Chem. Soc. 110, pp. 1643-1644 (1988).
Johansson et al. "Towards absolute asymmetric synthesis. Synthesis and crystal structure of stereochemically labile MC12 (M=Co, Ni, Cu, Zn) complexes with diamine ligands," Inorganica Chimica Acta 358, pp. 3293-3302 (2005).
Johnson et al. "A brief review of atomic layer deposition: from fundamentals to applications" Materials Today, vol. 17, Issue 5, pp. 236-246 (2014).
Jones et al., "Growth of Aluminum Films by Low Pressure Chemical Vapour Deposition Using Tritertiarybutylaluminium," Journal of Crystal Growth 135, pp. 285-289, Elsevier Science B.V. (1994).
Jones et al., "Recent Developments in Metalorganic Precursors for Metalorganic Chemical Vapour Deposition," Journal of Crystal Growth 146, pp. 503-510, Elsevier Science B.V. (1995).
Jung et al., "Double Patterning of Contact Array with Carbon Polymer," Proc. Of SPIE, 6924, 69240C, 1-10 (2008).
Jung et al. "New Mechanisms for Ozone-Based ALO Growth of High-k Dielectrics via Nitrogen-Oxygen Species" ECS Transactions, 33(2), pp. 91-99 (2010).
Juppo et al. "Deposition of molybdenum thin films by an alternate supply of MoC1 5 and Zn" J of Vacuumn Science & Technology A, 16, pp. 2845-2850 (1998).
Katamreddy et al., "ALD and Characterization of Aluminum Oxide Deposited on Si(100) using Tris(diethylamino) Aluminum and Water Vapor," Journal of The Electrochemical Society, 153 (10) C701-C706 (2006).
Kern et al., "Chemically Vapor-Deposited Borophosphosilicate Glasses for Silicon Device Applications" RCE Review, 43, 3, pp. 423-457 (1982).
Kerrigan et al. "Low Temperature, Selective Atomic Layer Deposition of Cobalt Metal Films Using Bis(1,4-di-tert-butyl-1,3-diazadienyl)cobalt and Alkylamine Precursors," Chem. Materials, 29, pp. 7458-7466 (2017).
Khandelwal et al. "Low-temperature Ar/N2 remote plasma nitridation of SiO2 thin films," J. Vacuum Science & Technology A, 20(6), pp. 1989-1996 (2002).
Kim et al., "Passivation Effect on Low-k S/OC Dielectrics by H2 Plasma Treatment," Journal of the Korean Physical Society, 40, 1, 94-98 (2002).
Kim et al., "Characteristics of Low Temperature High Quality Silicon Oxide by Plasma Enhanced Atomic Layer Deposition with In-Situ Plasma Densification Process," The Electrochemical Society, ECS Transactions, College of Information and Communication Engineering, Sungkyunkwan University, 53(1), 321-329 (2013).
Kim et al., "Novel Flowable CVD Process Technology for sub-20nm Interlayer Dielectrics," IEEE International Interconnect Technology Conference (IITC 2012), San Jose, California, USA, Jun. 4-6, 2012, pp. 1-3 (2012).
Kim et al. "Thermal Decomposition of Tetrakis(ethylmethylamido) Titanium for Chemical Vapor Deposition of Titanium Nitride" Bull. Korean Chem. Soc., vol. 27, No. 2, 5 pages (2006).
King, Plasma Enhanced Atomic Layer Deposition of SiNx: H and SiO2, J. Vac. Sci. Technol., A29(4) (2011).
Kirsch et al. "Dipole model explaining high-k/metal gate field effect transistor threshold voltage tuning" Applied Physics Letters 92, 092901, 3 pages (2008).
Kjesbu, Abb Corporate Research, Internet, pp. 1-37 (2002).
Kliem et al. "Silyl Group Migrations Between Oxygen and Nitrogen in Aminosiloxanes"; Organosilicon Chemistry VI: from Molecules to Materials; pp. 216-221 (2005).
Klug et al., "Atomic Layer Deposition of Amorphous Niobium Carbide-Based Thin Film Superconductors," The Journal of Physical Chemistry C, vol. 115, pp. 25063-25071, (2011).
Kobayshi, et al., "Temperature Dependence of SiO2 Film Growth with Plasma-Enhanced Atomic Layer Deposition, " regarding Thin Solid Films, published by Elsevier in the International Journal on the Science and Technology of Condensed Matter, in vol. 520, No. 11, 3994-3998 (2012).
Kofuji et al. "Line-edge roughness increase due to wiggling enhanced by initial pattern waviness" Jpn. J. Appl. Phys. 53, 03DE01, pp. 1-7 (2014).
Kofuji et al. "Mechanism of wiggling enhancement due to HBr gas addition during amorphous carbon etching" Jpn. J. Appl. Phys. 54, 06FH04, pp. 107 (2015).
Kogelschatz et al. "Ozone Generation from Oxygen and Air: Discharge Physics And Reaction Mechanisms" Ozone Science & Engineering, 10, pp. 367-378 (1998).
Koo et al., "Characteristics of Al2O3 Thin Films Deposited Using Dimethylaluminum Isopropoxide and Trimethylaluminum Precursors by the Plasma-Enhanced Atomic-Layer Deposition Method," Journal of Physical Society, 48, 1, 131-136 (2006).
Koutsokeras et al. "Texture and Microstructure Evolution in Single-Phase TixTa1-xN Alloys of Rocksalt Structure," Journal of Applied Physics, 110, pp. 043535-1-043535-6, (2011).

(56) References Cited

OTHER PUBLICATIONS

Kovalgin et al. "Hot-Wire Assisted ALD: A Study Powered by In Situ Spectroscopic Ellipsometry" Adv. Mater. Interfaces 4, 1700058, 11 pages (2017).
Knoops et al., "Atomic Layer Deposition of Silicon Nitride from Bis(tert-butyloamino) silane and N2 Plasma," Applied Materials & Interfaces, American Chemical Society, A-E (2015).
Krenek et al. "IR Laser CVD of Nanodisperse Ge—Si—Sn Alloys Obtained by Dielectric Breakdown of GeH4/SiH4/SnH4 Mixtures", NanoCon 2014, Nov. 5-7, Brno, Czech Republic, EU.
Krumdieck et al. "Experimental Characterization and Modeling of Pulsed MOCVD with Ultrasonic Atomization of Liquid Precusor" Chem. Vap. Deposition, 7 (2), pp. 85-90 (2001).
Krumdieck "Kinetic Model of Low Pressure Film Deposition from Single Precursor Vapor in a Well-Mixed, Cold-Wall Reactor" Acta mater., 49, pp. 583-588 (2001).
Kucheyev et al. "Mechanisms of Atomic Layer Deposition on Substrates with Ultrahigh Aspect Ratios." Langmuir. 24 [3]. pp. 943-948 (2008).
Kuchumov et al. "Pulsed MO CVD Processes of MgO Layer Deposition from Mg(thd)2" ECS Trans. 25, pp. 927-934 (2009).
Kukli et al. "Atomic Layer Deposition and Chemical Vapor Deposition of Tantalum Oxide by Successive and Simultaneous Pulsing of Tantalum Ethoxide and Tantalum Chloride" Chem. Mater. 12, pp. 1914-1920 (2000).
Kukli et al. "Atomic Layer Epitaxy Growth of Tantalum Oxide Thin Films from Ta(OC2H5)5 and H20" The Electrochemical Society, vol. 142, No. 5, pp. 1670-1674 (1995).
Kukli et al., "Influence of atomic layer deposition parameters on the phase content of Ta2O5 films" J. Crystal Growth, 212, pp. 459-468 (2000).
Kukli et al., "Properties of hafnium oxide films grown by atomic layer deposition from hafnium tetraiodide and oxygen". Journal of Applied Physics, vol. 92, No. 10, Nov. 15, 2002, pp. 5698-5703 (2002).
Kukli et al., "Properties of tantalum oxide thin films grown by atomic layer deposition" Thin Solid Films, 260, pp. 135-142 (1995).
Kumar et al. "Bringing the benefits of Java to Bluetooth" http://www.allembedded.com/story/OEG20020519S001, pp. 1-3 (2002).
Kurosawa et al., "Synthesis and Characterization of Plasma-Polymerized Hexamethyldisiloxane Films," Thin Solid Films, 506-507, 176-179 (2006).
Kwon et al., "Substrate Selectivity of (tBu-Allyl)Co(CO)3 during Thermal Atomic Layer Deposition of Cobalt," Chem. Materials, 24, pp. 1025-1030 (2012).
Lanford et al., "The Hydrogen Content of Plasmadeposited Silicon Nitride," J. Appl. Phys., 49, 2473 (1978).
Lee et al., "Characteristics Of Low-K Sioc Films Deposited Via Atomic Layer Deposition," Thin Solid Films 645, pp. 334-339 (2018).
Lee et al., Layer Selection by Multi-Level Permutation in 3-D Stacked NAND Flash Memory, IEEE Electron Device Letters, vol. 37, No. 7, 866-869 (2016).
Levy et al., "Reflow Mechanisms of Contact Vias in VLSI Processing" J. Electrochem. Soc.: Solid-State Science and Technology, 133, 7, pp. 1417-1424 (1986).
Lewis et al. "Hawley's Condensed Chemical Dictionary" 12th Edition; excerpt pp. 1027-1038 (2005).
Li et al., "Metallic Transition-Metal Dichalcogenide Nanocatalysts for Energy Conversion" Chem. 4, pp. 1510-1537 (2018).
Liang et al. "Conversion of Metal Carbides to Carbide Derived Carbon by Reactive Ion Etching in Halogen Gas" Micro (MEMS) and Nanotechnologies for Space Applications, Thomas George et al. vol. 6223, 2006 p. 62230J-I to 62230J-11 lines 3-14 in the "Abstract" section and lines 7-9 in the "Introduction" section of p. 1, lines 3-4 in the "Introduction" section and lines 3-4 in the "Experimental Procedure" section of p. 2 (2006).
Lieberman, et al., "Principles of Plasma Discharges and Materials Processing," Second Edition, 368-381 (2005).
Lim et al., "Low-Temperature Growth of SiO2 Films by Plasma-Enhanced Atomic Layer Deposition," ETRI Journal, 27 (1), 118-121 (2005).
Lim et al. "Synthesis and Characterization of Volatile, Thermally Stable, Reactive Transistion Metal Amidinates," Inorg. Chem., 42, pp. 7951-7958 (2003).
Liu et al., "Research, Design, and Experiment of End Effector for Wafer Transfer Robot," Industrial Robot: An International Journal, 79-91 (2012).
Liu et al., "Van der Waals metal-semiconductor junction: Weak Fermi level pinning enables effective tuning of Schottky barrier" Sci. Adv. 2: e1600069, 7 pages (2016).
Londergan et al. "Engineered Low Resistivity Titanium-Tantalum Nitride Films by Atomic Layer Deposition," Mat. Res. Soc. Symp. Proc., vol. 714E, pp. L5.3.1-L5.3.6 (2001).
Longrie et al., "Plasma-Enhanced ALD of Platinum with O2, N2 and NH3 Plasmas", ECS Journal of Solid State Science and Technology, vol. 1, pp. Q123-Q129 (2012).
MacKenzie et al. "Stress Control of Si-Based PEVCD Dielectrics," Proc. Symp. Silicon Nitrode and Silicon Dioxide Thin Insulating Films & Other Emerging Dielectrics VIII, 148-159 (2005).
Mackus et al., "Optical Emission Spectroscopy as a Tool for Studying Optimizing and Monitoring Plasma-Assisted Atomic Layer Deposition Processes," Journal of Vacuum Science and Technology, 77-87 (2010).
Maeng et al. Electrical properties of atomic layer disposition Hf02 and Hf0xNy on Si substrates with various crystal orientations, Journal of the Electrochemical Society, Apr. 2008, p. H267-H271, vol. 155, No. 4, Department of Materials Science and Engineering, Pohang University of Science and Technology, Pohang, Korea (2008).
Maeno, "Gecko Tape Using Carbon Nanotubes," Nitto Denko Gihou, 47, 48-51 (2009).
Makela et al. "Thermal Atomic Layer Deposition of Continuous and Highly Conducting Gold Thin Films," Chem. Materials, 29, pp. 6130-6136 (2017).
Mameli et al. "Area-Selective Atomic Layer Deposition of SiO2 Using Acetylacetone as a Chemoselective Inhibitor in an ABC-Type Cycle" ACS Nano 11, pp. 9303-9311 (2017).
Mameli et al. "Isotropic Atomic Layer Etching of ZnO Using Acetylacetone and O2 Plama" ACS Appl. Mater. Interfaces 10, pp. 38588-38595 (2018).
Marsik et al., "Effect of Ultraviolet Curing Wavelength on Low-k Dielectric Material Properties and Plasma Damage Resistance," Sciencedirect.com, 519, 11, 3619-3626 (2011).
Mason et al., "Hydrolysis of Tri-tert-butylaluminum: The First Structural Characterization of Alkylalumoxanes [(R2A1)2O]n and (RAIO)n," J. American Chemical Society, vol. 115, No. 12, pp. 4971-4984 (1993).
Massachusetts Institute of Technology Lincoln Laboratory, "Solid State Research," Quarterly Technical Report (1995).
Mattinen et al., "Crystalline tungsten sulfide thin films by atomic layer deposition and mild annealing" J. Vac. Sci. Tech. 37, 020921, 35 pages (2019).
Maydannik et al., "Spatial atomic layer deposition: Performance of low temperature H2O and O3oxidant chemistry for flexible electronics encapsulation", Journal of Vacuum Science and Technology: Part A AVS/ AIP, vol. 33 (1901).
Meng et al., "Atomic Layer of Deposition of Silicon Nitride Thin Films: A Review of Recent Progress, Challenges, and Outlooks," Materials, 9, 1007 (2016).
Miller et al. "Carbon nitrides: synthesis and characterization of a new class of functional materials," Phys.Chem.Chem.Phys., 19, pp. 15613-15638 (2017).
Mix et al., "Characterization of plasma-polymerized allyl alcohol polymers and copolymers with styrene," Adhes. Sci. Technol., 21 (2007), S. 487-507.
Moeen, "Design, Modelling and Characterization of Si/SiGe Structures for IR Bolometer Applications," KTH Royal Institute of Technology. Information and Communication Technology, Department of Integrated Devices and Circuits, Stockholm Sweden (2015).

(56) References Cited

OTHER PUBLICATIONS

Morishige et al., "Thermal Desorption and Infrared Studies of Ammonia Amines and Pyridines Chemisorbed on Chromic Oxide," J. Chem. Soc., Faraday Trans. 1, 78, 2947-2957 (1982).
Mosleh et al., "Enhancement of Material Quality of (Si)GeSn Films Grown by SnC14 Precursor," ECS Transactions, 69 (5), 279-285 (2015).
Mukai et al., "A Study of CD Budget in Spacer Patterning Technology," Proc. Of SPIE, 6924, 1-8 (2008).
Naito et al. "Electrical Transport Properties in 2H-NbS2, -NbSe2, -TaS2 and -TaSe2," J. of Physical Society of Japan, vol. 51, No. 1, 219-227 (1982).
Nakano et al., "Layer-by-Layer Epitaxial Growth of Scalable WSe2 on Sapphire by Molecular Beam Epitaxy" Nano. Lett. 17, pp. 5595-5599 (2017).
Naslain et al. "Synthesis of highly tailored ceramic matrix composites by pressure-pulsed CVI" Solid State Ionics, 141-142, pp. 541-548 (2001).
Ngo et al. "Atomic layer deposition of photoactive CoO/SrTiO3 and CoO/TiO2 on Si(001) for visible light driven photoelectrochemical water oxidation," J. Applied Physics, 114, 9 pages (2013).
Niinisto et al. "Advanced electronic and optoelectronic materials by Atomic Layer Deposition: An overview with special emphasis on recent progress in processing of high-k dielectrics and other oxide materials" Pus. Stat. Sol. (a) 201, No. 7, pp. 1443-1452 (2004).
Nogueira et al., "Production of Highly Hydrophobic Films Using Low Frequency and High Density Plasma," Revista Brasileira de Aplicacoes de Vacuo, 25(1), 45-53 (2006).
Novaro et al. Theoretical Study on a Reaction Pathway of Ziegler-Natta-Type Catalysis, J. Chem. Phys. 68(5), Mar. 1, 1978 p. 2337-2351.
Ohchi et al. "Reducing damage to Si substrates during gate etching processes." Japanese Journal of Applied Physics 47.7R 5324 (2008).
Ohtsu et al. "Influences of Gap Distance on Plasma Characteristics in Narrow Gap Capacitatively Coupled Radio-Frequency Discharge," vol. 43, No. 2, pp. 795-799 (2004).
Ohzawa et al. "Preparation of fibrous SiC shape using pressure-pulsed chemical vapour infiltration and its properties as a high-temperature filter" J. of Materials Processing Technology, 96, pp. 151-156 (1999).
Okamoto et al., "Luminescent Properties of Pr3+-sensitized LaPO4: Gd3+ Ultraviolet-B Phosphor Under Vacuum-Ultraviolet Light Excitation," J. App. Phys. 106, 013522 (2009).
O'Malley et al. "Structure and properties of ordered Li2IrO3 and Li2PtO3" Journal of Solid State Chemistry 181, pp. 1803-1809 (2008).
Park et al. "Atomic layer deposition of Y2O3 films using hetroleptic liquid (iPrCp)2Y(iPr-amd) precursor" J. Mater. Chem. C, 2, 9 pages (2014).
Park, "Substituted Aluminum Metal Gate on High-K Dielectric for Low Work-Function and Fermi-Level Pinning Free," 4 pages, IEEE 0-7803-8684-1/04 (2004).
Peters et al., "Aerosol-Assisted Chemical Vapor Deposition of NbS2 and TaS2 Thin Films from Pentakis(dimethylamido)metal Complexes and 2-Methylpropanethiol" Eur. J. Inorg. Chem., pp. 4179-4185 (2005).
Pichler. "Intrinsic Point Defects, Impurities and Their Diffusion in Silicon," Springer-Verlag Wien, p. 367 (2004).
Portet et al., "Impact of Synthesis Conditions on Surface Chemistry and Structure of Carbide-Derived Carbons," Thermochimica Acta, 497, 137-142 (2010).
Posseme et al. "Alternative process for thin layer etching: Application to nitride spacer etching stopping on silicon germanium" Apply. Phys. Lett. 105, 051604, pp. 1-4 (2014).
Potts et al., "Low Temperature Plasma-Enhanced Atomic Layer Deposition of metal Oxide Thin Films," Journal of the Electrochemical Society, 157, 66-74 (2010).
Potts et al., "Room-Temperature ALD of Metal Oxide Thin Films by Energy-Enhanced ALD", Chemical Vapor Deposition, vol. 19, pp. 125-133 (2013).
Presser, et al., "Effect of Pore Size on Carbon Dioxide Sorption by Carbide Derived Carbon," Energy & Environmental Science 4.8, 3059-3066 (2011).
Provine et al. "Atomic Layer Deposition: Introduction to the Theory and Cambridge Nanotech Savannah & Fiji" NNIN ALD Roadshow Presentation, 49 pages (2012).
Provine et al., "Correlation of Film Density and Wet Etch Rate in Hydrofluoric Acid of Plasma Enhanced Atomic Layer Deposited Silicon Nitride," AIP Advances, 6 (2016).
Qin et al., "Chemical Vapor Deposition Growth of Degenerate p-Type Mo-Doped ReS2 Films and Their Homojunction," ACS Appl. Mater. Interfaces, 9(18), pp. 15583-15591 (2007).
Radamson et al. "Growth of Sn-alloyed Group IV Materials for Photonic and Electronic Applications" Chapter 5 pp. 129-144, Manufacturing Nano Structures (2014).
Roddy, "Transport Reactions and Vaporization Studies of Some Vanadium Halides", Iowa State university of Science and Technology dissertation, 207 pages (1962).
Rosemount 1199 Diaphragm Seal Systems, Product Data Sheet, 92 pages (2008).
Rossing et al. "Acoustics of Eastern and Western bells, Old and New" J of Acoustical Society of Japan; 10(5); pp. 241-252 (1989).
Ryu et al., "Persistent Charge-Density-Wave Order in Single-Layer TaSe2" Nano. Lett. 18, pp. 689-694 (2018).
Saeki et al. "Reaction Process of Vanadium Tetrachloride with Ammonia in the Vapor Phase and Properties of the Vanadium Nitride Formed" Bull. Chem. Soc. Jpn., 55, pp. 3446-3449 (1982).
Sakuma et al., "Highly Scalable Horizontal Channel 3-D NAND Memory Excellent in Compatibility with Conventional Fabrication Technology," IEEE Electron Device Letters, vol. 34, No. 9, 1142-1144 (2013).
Salim, "In-situ Fourier Transform Infrared Spectroscopy of Chemistry and Growth in Chemical Vapor Deposition," Massachusetts Institute of Technology, 187 pages (1995).
Salim et al., "In Situ Concentration Monitoring in a Vertical OMVPE Reactor by Fiber-Optics-Based Fourier Transform Infrared Spectroscopy," Journal of Crystal Growth 169, pp. 443-449, Elsevier Science B.V. (1996).
Samal et al., "Low-Temperature (<200° C.) Plasma Enhanced Atomic Deposition of Dense Titanium Nitride Thin Films" (2012).
Sanders et al., "Crystalline and electronic structure of single-layer TaS$_2$," Phys. Rev. B. 94, 081404, 6 pages (2016).
Schindler, Dissertation, Next Generation High-k Dielectrics for DRAM Produced by Atomic Layer Deposition Studied by Transmission Electron Microscopy (2015).
Schmatz et al., "Unusual Isomerization Reactions in 1.3-Diaza-2-Silcyclopentanes," Organometallics, 23, 1180-1182 (2004).
Sellers, Making Your Own Timber Dogs, Paul Sellers blog, Published on Nov. 18, 2014, [online], [site visted Jun. 10, 2017]. Available from Internet, <URL: https://paulsellers.com/2014/11/making-your-own-timber-dogs/>.
Selvaraj et al., "Selective Atomic Layer Deposition of Zirconia on Copper Patterned Silicon Substrates Using Ethanol as Oxygen Source as Well as Copper Reductant," J. Vac. Sci. Technol. A32(1), (2014).
Selvaraj et al., "Surface Selective Atomic Layer Deposition of Hafnium Oxide for Copper Diffusion Barrier Application Using Tetrakis (diethylamino) Hafnium and Ethanol," 225th ECS Meeting, Meeting Abstract, (May 12, 2014).
Senateur et al. "Pulsed Injection MOCVD of Functional Electronic Oxides" Adv. Mater. Opt. Electron, 10, pp. 155-161 (2000).
Seshadri et al., "Ultrathin Extreme Ultraviolet Patterning Stack Using Polymer Brush As An Adhesion Promotion Layer," Journal of Micro/Nanolithography, MEMS, and MOEMS 16(3) (2017).
Shamma et al., "PDL Oxide Enabled Doubling," Proc. Of SPIE, 6924, 69240D, 1-10 (2008).
Shevtsov et al. "An Apparatus for Pulse Chemical Vapor Deposition of Layers" Instruments and Experimental Techniques, vol. 56, No. 3, pp. 353-357 (2013).
Shevtsov et al. "Effect of Spatial Image Transfer in a Pulse MOCVD Process" Physics Procedia 46, pp. 27-32 (2013).

(56) References Cited

OTHER PUBLICATIONS

Simchi et al., "Sulfidation of 2D transition metals (Mo, W, Re, Nb, Ta): thermodynamics, processing, and characterization" J. Materials Science 52: 17, 9 pages (2017).
Spear et al., "Chemical Transport Reactions in the Vanadium-Silicon-Oxygen System and the Ternary Phase Diagram", Journal of the Less-Common Metals, 14, pp. 69-75 (1968).
Stanley et al. "Feedgas for Modern High-Performance Ozone Generators" Ozonia Ltd., Duebendorf, Switzerland. 7 pages. Available Jul. 14, 2017 online at: http://www.degremont-technologies.com/cms_medias/pdf/tech_ozonia_feedgas.pdf (1999).
Stannowski et al. "Growth process and properties of silicon nitride deposited by hot-wire chemical vapor deposition" J Applied Physics, vol. 93 No. 5, 9 pages (2013).
Su et al. "A Polymer Precursor Route to Metal Borides", Chem. Mater., 5, pp. 1659-1668 (1993).
Svetin et al., "Three-dimensional resistivity and switching between correlated electronic states in 1T-TaS$_2$" Nature, Scientific Reports Apr. 12, 2017, 7:46048, 10 pages (2017).
Tatehaba et al., "Adhesion Energy of Polystyrene and Substrate in Function Water," 5th International Symposium of Cleaning Technology in Semiconductor Device Manufacturing, pp. 560-565 (1998).
Tidman et al. "Resistivity of thin TaS2 crystals," Can. J. Phys., vol. 54, 2306-2309 (1976).
Todi et al., "Characterization of Pt—Ru Binary Alloy Thin Films for Work Function Tuning," IEEE Electron Device Letters, vol. 27, No. 7, pp. 542-545 (2006).
Tomozeiu et al. "Effects of UV photon irradiation on SiOx (0<x<2) structural properties" Applied Surface Science 253, pp. 376-380 (2006).
Trumbore et al. "Solid solubilities of aluminum and gallium in germanium," J. of Physics and Chemistry of Solids, vol. 11, Issues 3-4, 239-240 (1959).
Tseng et al., "Etch Properties of Resists Modified by Sequential Infiltration Synthesis," American Vacuum Society (2011).
Tseng et al., "Enhanced Block Copolymer Lithography Using Sequntial Infiltration Synthesis," Journal of Physical Chemistry, vol. 5, 17725-17729 (2011).
Ueda et al. "Enhanced Sidewall Grown (ESG) process: towards PEALD with conformality above 100%," Extended Abstracts of the 2011 International Conference on Solid State Devices and Materials, Nagoya, pp. 34-35 (2011).
U.S. Appl. No. 60/394,086, filed Jul. 3, 2002 in the name of Jacques Schmitt, and entitled "ALD on a Rotary Susceptor" pp. 1-23 (2002).
U.S. Appl. No. 62/293,897 filed Feb. 11, 2016 in the names of Bernardo Donoso et al., and entitled "Vapor Based Site-Isolated Processing Systems and Methods" pp. 1-51 (2016).
Vallat et al. "Area selective deposition of TiO2 by intercalation of plasma etching cycles in PEALD process: A bottom up approach for the simplification of 3D integration scheme" Journal of Vacuum Science & Technology A 37(2), 12 pages (2019).
Vallat et al. "Selective deposition of Ta2O5 by adding plasma etching super-cycles in plasma enhanced atomic layer deposition steps" Journal of Vacuum Science & Technology A 35(1), 7 pages (2016).
Varma, et al., "Effect of Metal Halides on Thermal, Mechanical, and Electrical Properties of Polypyromelitimide Films," Journal of Applied Polymer Science, vol. 32, pp. 3987-4000, (1986).
Vasilev, "Borophosphosilicate Glass Films in Silicon Microelectronics, Part 1: Chemical Vapor Deposition, Composition, and Properties" Russian Microelectronics, vol. 33, No. 5, pp. 271-284 (2004).
Venkatesan et al. "A rugged lead-ruthenate pyrochlore membrane catalyst for highly seelctive oxidation of alcohols" J. Molecular Catalysis A: Chemical 250, pp. 87-93 (2006).
Voltaix, "Meterial Safety Data Sheet for: Trisilylamine", pp. 1-8, (2014).
Wang et al., "Tritertiarybutylaluminum as an Organometallic Source for Epitaxial Growth of AlGaSb," Appl. Phys. Lett. 67 (10), Sep. 4, pp. 1384-1386, American Institute of Physics (1995).

Wirths, et al., "SiGeSn Growth tudies Using Reduced Pressure Chemical Vapor Deposition Towards Optoeleconic Applications, " This Soid Films, 557, 183-187 (2014).
Xiao "Introduction to Semiconductor Manufacturing Technology" SPIE Press, ISBN 978-0-08194-9092-6, pp. 237-245 (2012).
Xing et al., "Ising Superconductivity and Quantum Phase Transition in Macro-Size Monolayer NbSe2" Nano. Lett. 17, pp. 6802-6807 (2017).
Xu et al., "14NM Metal Gate Film Stack Development and Challenges," SMIC et al. (2016).
Xu et al., "Contacts between Two- and Three-Dimensional Materials: Ochmic, Schottky, and p-n Heterojunctions" ACS Nano 10, pp. 4895-4919 (2016).
Yoshida, et al., Threshold Voltage Tuning for 10NM and Beyond CMOS Integration, Solid State Technology, 57(7): 23-25 (2014).
Yu et al., "Modulation of the Ni FUSI Workfunction by Yb Doping: from Midgap to N-Type Band-Edge," 4 pages, IEEE 0-7803-9269-8/05 (2005).
Yuan et al. "A Bifunctional Air Electrode Catalyzed by Lead Ruthenate for Li-Air Batteries" ECS Transactions 69(19), pp. 23-32 (2015).
Yuan et al., "Facile Synthesis of Single Crystal Vanadium Disulfide Nanosheets by Chemical Vapor Deposition for Efficient Hydrogen Evolution Reaction" Adv. Mater. 27, pp. 5605-5609 (2015).
Yun et al., "Behavior of Various Organosilicon Molecules in PECVD Processes for Hydrocarbon-Doped Silicon Oxide Films," Solid State Phenomena, vol. 124-126, 347-350 (2007).
Yun et al., "Comparison of Atomic Scale Etching of Poly-Si in Inductively Coupled Ar and He Plasmas", Korean Journal of Chemical Engineering, vol. 24, 670-673 (2007).
Yun et al., "Single-Crystalline Si Stacked Array (STAR) NAND Flash Memory," IEEE Transactions on Electron Devices, vol. 58, No. 4, 1006-1014 (2011).
Yun et al., "Effect of Plasma on Characteristics of Zirconium Oxide Films Deposited by Plasma-Enhanced Atomic Layer Deposition," Electrochemical and Solid State Letters, 8(11) F47-F50 (2005).
Yushin et al., "Carbon-Derived Carbon," Department of Materials Science and Engineering, Taylor & Francis Group, LLC (2006).
Zhao et al. "Surface Chemistry of Thermal Dry Etching of Cobalt Thin Films Using Hexafluoroacetylacetone (hfacH)" Appl Surf Sci. 455, pp. 438-445 (2018).
Zhao et al. "Thermal and Plasma-Enhanced Atomic Layer Deposition of Yttrium Oxide Films and the Properties of Water Wettability" Appl. Mater. Interfac. 12(2), 9 pages (2019).
Zhou et al., "A library of atomically thin metal chalcogenides" Nature 556, pp. 355-361 (2018).
Chemistry Stack Exchange, "Why is CF4 Non-Polar and CHF Polar," https://chemistry.stackexchange.com/questions/31604/why-is-cf4-non-polar-and-chf3-polar, (2015).
Crystal IS "Application Note: Using UV Reflective Materials to Maximize Disinfection"; AN011; Jun. 16, 2016.
IPS Water Heater Pan Adapter Kit, Nov. 1, 2015, [online], [site visited Dec. 4, 2019]; URL: http://es.ipscorp.com/watertite/protectivesystem/whpanadapter (2015).
"Polyurethane_HF"; webpage; no date. Cited in Notice of References dated May 18, 2017 in U.S. Appl. No. 14/884,695.
Rhenium trioxide; https://en.wikipedia.org/wiki/Rhenium_trioxide [online]; last edited on Feb. 18, 2017.
Scientific and Technical Information Center EIC 2800 Search Report dated Feb. 16, 2012.
CNIPA; Notice of Allowance dated Dec. 21, 2020 in Application No. 201610982040.X.
CNIPA; Office Action dated Nov. 20, 2020 in Application No. 201710762817.6.
CNIPA; Notice of Allowance dated Dec. 28, 2020 in Application No. 201930704935.1.
CNIPA; Notice of Allowance dated Dec. 10, 2020 in Application No. 202030352604.9.
CNIPA; Office Action dated Jan. 25, 2021 in Application No. 202030579755.8.
JPO; Notice of Allowance dated Nov. 27, 2020 in Application No. 2016-206625.

(56) References Cited

OTHER PUBLICATIONS

JPO; Office Action dated Jan. 26, 2021 in Application No. 2017-139817.
JPO; Notice of Allowance dated Nov. 26, 2020 in Application No. 2020-502653.
KIPO; Office Action dated Jan. 25, 2021 in Application No. 10-2014-0011765.
KIPO; Notice of Allowance dated Jan. 4, 2021 in Application No. 10-2014-0060120.
KIPO; Notice of Allowance dated Jan. 4, 2021 in Application No. 10-2014-0071653.
KIPO; Office Action dated Nov. 29, 2020 in Application No. 10-2014-0105478.
KIPO; Office Action dated Feb. 17, 2021 in Application No. 10-2014-0122903.
KIPO; Office Action dated Jan. 25, 2021 in Application No. 10-2014-0145220.
KIPO; Office Action dated Jan. 6, 2021 in Application No. 10-2015-0025314.
KIPO; Office Action dated Dec. 23, 2020 in Application No. 10-2019-0044213.
KIPO; Office Action dated Nov. 14, 2020 in Application No. 10-2020-0101096.
KIPO; Notice of Allowance dated Oct. 20, 2020 in Application No. 30-2019-0054642.
KIPO; Notice of Allowance dated Oct. 22, 2020 in Application No. 30-2019-0058566 (M001).
KIPO; Notice of Allowance dated Oct. 22, 2020 in Application No. 30-2019-0058566 (M002).
KIPO; Notice of Allowance dated Dec. 1, 2020 in Application No. 30-2019-0061607.
KIPO; Office Action dated Jan. 26, 2021 in Application No. 30-2020-0005953 (M001).
KIPO; Office Action dated Jan. 26, 2021 in Application No. 30-2020-0005953 (M002).
KIPO; Notice of Allowance dated Dec. 23, 2020 in Application No. 30-2020-0006059.
KIPO; Notice of Allownace dated Dec. 25, 2020 in Application No. 30-2020-0006223.
KIPO; Notice of Allowance dated Feb. 1, 2021 in Application No. 30-2020-0006385.
KIPO; Notice of Allowance dated Feb. 1, 2021 in Application No. 30-2020-0006391.
TIPO; Office Action dated Dec. 2, 2020 in Application No. 105131896.
TIPO; Notice of Allowance dated Jan. 29, 2021 in Application No. 105142668.
TIPO; Notice of Allowance dated Dec. 10, 2020 in Application No. 106108152.
TIPO; Notice of Allowance dated Jan. 25, 2021 in Application No. 106111548.
TIPO; Office Action dated Jan. 6, 2021 in Application No. 106115126.
TIPO; Office Action dated Dec. 21, 2020 in Application No. 106122231.
TIPO; Office Action dated Dec. 29, 2020 in Application No. 106124126.
TIPO; Office Action dated Dec. 9, 2020 in Application No. 106124128.
TIPO; Office Action dated Jan. 25, 2021 in Application No. 106124129.
TIPO; Office Action dated Dec. 9, 2020 in Application No. 106124130.
TIPO; Office Action dated Jan. 20, 2021 in Application No. 106129491.
TIPO; Office Action dated Feb. 8, 2021 in Application No. 106133152.
TIPO; Notice of Allowance dated Nov. 24, 2020 in Application No. 108307599.
TIPO; Notice of Allowance dated Jan. 11, 2021 in Application No. 108307599D01.
TIPO; Notice of Allowance dated Jan. 11, 2021 in Application No. 109300591.
TIPO; Notice of Allowance dated Jan. 11, 2021 in Application No. 109300593.
TIPO; Office Action dated Jan. 11, 2021 in Application No. 109300594.
USPTO; Non-Final Office Action dated Dec. 1, 2020 in U.S. Appl. No. 14/219,879.
USPTO; Final Office Action dated Feb. 1, 2021 in U.S. Appl. No. 14/829,565.
USPTO; Non-Final Office Action dated Dec. 24, 2020 in U.S. Appl. No. 15/286,503.
USPTO; Final Office Action dated Feb. 12, 2021 in U.S. Appl. No. 15/377,439.
USPTO Non-Final Office Action dated Dec. 10, 2020 in U.S. Appl. No. 15/380,921.
USPTO; Non-Final Office Action dated Feb. 3, 2021 in U.S. Appl. No. No. 15/611,707.
USPTO; Final Office Action dated Jan. 19, 2021 in U.S. Appl. No. 15/636,307.
USPTO; Non-Final Office Action dated Jan. 6, 2021 in U.S. Appl. No. 15/726,959.
USPTO; Advisory Action dated Dec. 15, 2020 in U.S. Appl. No. 15/835,328.
USPTO; Notice of Allowance dated Jan. 14, 2021 in U.S. Appl. No. 15/835,352.
USPTO; Final Office Action dated Jan. 11, 2021 in U.S. Appl. No. 15/890,037.
USPTO; Advisory Action dated Jan. 8, 2021 in U.S. Appl. No. 15/923,834.
USPTO; Advisory Action dated Dec. 24, 2020 in U.S. Appl. No. 15/925,532.
USPTO; Non-Final Office Action dated Jan. 25, 2021 in U.S. Appl. No. 15/925,532.
USPTO; Final Office Action dated Feb. 18, 2021 in U.S. Appl. No. 15/940,729.
USPTO; Final Office Action dated Jan. 12, 2021 in U.S. Appl. No. 15/940,759.
USPTO; Final Office Action dated Dec. 15, 2020 in U.S. Appl. No. 15/962,980.
USPTO; Advisory Action dated Oct. 27, 2020 in U.S. Appl. No. 15/974,948.
USPTO; Advisory Action dated Dec. 10, 2020 in U.S. Appl. No. 16/000,109.
USPTO; Advisory Action dated Dec. 15, 2020 in U.S. Appl. No. 16/000,125.
USPTO; Advisory Action dated Dec. 14, 2020 in U.S. Appl. No. 16/000,156.
USPTO; Advisory Action dated Dec. 22, 2020 in U.S. Appl. No. 16/004,041.
USPTO; Advisory Action dated Jan. 14, 2021 in U.S. Appl. No. 16/055,532.
USPTO; Final Office Action dated Dec. 15, 2020 in U.S. Appl. No. 16/108,950.
USPTO; Final Office Action dated Jan. 6, 2021 in U.S. Appl. No. 16/117,530.
USPTO; Notice of Allowance dated Feb. 12, 2021 in U.S. Appl. No. 16/128,282.
USPTO; Notice of Allowance dated Feb. 8, 2021 in U.S. Appl. No. 16/132,142.
USPTO; Final Office Action dated Dec. 14, 2020 in U.S. Appl. No. 16/151,074.
USPTO; Advisory Action dated Feb. 16, 2021 in U.S. Appl. No. 16/151,074.
USPTO; Final Office Action dated Dec. 18, 2020 in U.S. Appl. No. 16/167,164.
USPTO; Advisory Action dated Dec. 21, 2020 in U.S. Appl. No. 16/172,535.
USPTO; Final Office Action dated Jan. 29, 2021 in U.S. Appl. No. 16/176,517.
USPTO; Non-Final Office Action dated Dec. 11, 2021 in U.S. Appl. No. 16/202,941.
USPTO; Final Office Action dated Dec. 9, 2020 in U.S. Appl. No. 16/210,922.
USPTO; Notice of Allowance dated Dec. 15, 2020 in U.S. Appl. No. 16/242,852.
USPTO; Advisory Action dated Jan. 22, 2021 in U.S. Appl. No. 16/252,567.

(56) References Cited

OTHER PUBLICATIONS

USPTO; Final Office Action dated Dec. 8, 2020 in U.S. Appl. No. 16/397,045.
USPTO; Advisory Action dated Jan. 27, 2021 in U.S. Appl. No. 16/397,045.
USPTO; Final Office Action dated Dec. 14, 2020 in U.S. Appl. No. 16/400,814.
USPTO; Non-Final Office Action dated Jan. 12, 2021 in U.S. Appl. No. 16/453,249.
USPTO; Non-Final Office Action dated Dec. 28, 2020 in U.S. Appl. No. 16/517,122.
USPTO; Non-Final Office Action dated Feb. 11, 2021 in U.S. Appl. No. 16/565,460.
USPTO; Notice of Allowance dated Jan. 25, 2021 in U.S. Appl. No. 16/679,885.
USPTO; Non-Final Office Action dated Feb. 8, 2021 in U.S. Appl. No. 16/685,787.
USPTO; Non-Final Office Action dated Jan. 8, 2021 in U.S. Appl. No. 16/752,514.
USPTO; Notice of Allowance dated Dec. 28, 2020 in U.S. Appl. No. 16/833,279.
Aoyagi et al. "Laser-assisted atomic layer epitaxy" Materials Science and Engineering, pp. 121-132 (1991).
Galesic et al. "Formation of vanadium nitride by rapid thermal processing" Thin Solid Films 349(1), 7 pages (1999).
Kim et al. "High Growth Rate in Atomic Layer Deposition of TiO2 Thin Films by UV Irradiation" Electrochemical and Solid-State Letters, 14(4), pp. H146-H148 (2011).
Lee et al. "Enahancement of Iodine Adsorption on Ruthenium Glue Layer for Seedless CECVD of Cu" Electrochemical and Solid-State Letters, 8(2) C39-C42 (2005).
Lee et al. "Growth without Postannealing of Monoclinic VO2 Thin Film by Atomic Layer Deposition Using VC14 as Precursor" Coatings, 8, 431, pp. 1-11 (2018).
Lee et al. "Photo-Induced Atomic Layer Deposition of Tantalum Oxide Thin Films from Ta(OC2H5)5 and O2" J of the Electrochemical Society. 151(1) pp. C52-C55 (2004).
Merdrignac-Conanec et al. "Nitridation under ammonia of high surface area vanadium aerogels" Journal of Solid State Chemistry 178(1), 8 pages (2005).
Nikolic et al. "The dependence of the work function of rare earth metals on their electron structure" Microelectronics Journal 27, 93-96 (1996).
Putkonen et al. "Low-Temperature ALE Deposition of Y2O3 Thin Films from β-Diketonate Precursors" Chemical Vapor Deposition 7(1) pp. 44-50 (2001).
U.S. Appl. No. 62/274,238, filed Jan. 1, 2016 in the names of Alexander S. Polyak et al., and entitled "Non-Metallic Thermal CVD/ALD Gas Injector and Purge System" pp. 1-63 (2016).
Vayrynen et al. "Photo-Assisted Atomic Layer Deposition and Chemical Vapor Deposition of Metal and Metal Oxide Thin Films" Thesis, Oct. 2015, 146 pages (2005).
CNIPA; Office Action dated Mar. 30, 2021 in Application No. 201610131743.1.
CNIPA; Office Action dated Mar. 1, 2021 in Application No. 201710131319.1.
CNIPA; Notice of Allowance dated Mar. 30, 2021 in Application No. 201710762817.6.
CNIPA; Office Action dated Jan. 28, 2021 in Application No. 201711057557.9.
CNIPA; Office Action dated Jan. 26, 2021 in Application No. 201711057929.8.
CNIPA; Office Action dated Apr. 19, 2021 in Application No. 201711328250.8.
CNIPA; Notice of Allowance dated Apr. 7, 2021 in Application No. 201780044761.9.
CNIPA; Office Action dated Jan. 29, 2021 in Application No. 201780076230.8.
CNIPA; Office Action dated Jan. 27, 2021 in Application No. 201780076321.1.
CNIPA; Office Action dated Mar. 24, 2021 in Application No. 201880048547.5.
CNIPA; Office Action dated Dec. 22, 2020 in Application No. 201910378791.4.
CNIPA; Notice of Allowance dated Apr. 7, 2021 in Application No. 202030579755.8.
EPO; Extended European Search Report dated Apr. 6, 2021 in Application No. 21150514.4.
JPO; Notice of Allowance dated Apr. 6, 2021 in Application No. 2017-139817.
JPO; Office Action dated Mar. 31, 2021 in Application No. 2018-024655.
JPO; Notice of Allowance dated Mar. 17, 2021 in Application No. 2020-010953.
KIPO; Office Action dated Mar. 23, 2021 in Application No. 10-2014-0011765.
KIPO; Office Action dated Apr. 27, 2021 in Application No. 10-2014-0027217.
KIPO; Notice of Allowance dated Apr. 15, 2021 in Application No. 10-2014-0103853.
KIPO; Notice of Allowance dated Mar. 25, 2021 in Application No. 10-2014-0128626.
KIPO; Office Action dated Apr. 20, 2021 in Application No. 10-2014-0136089.
KIPO; Office Action dated Mar. 19, 2021 in Application No. 10-2014-0156196.
KIPO; Office Action dated Mar. 29, 2021 in Application No. 10-2014-0165685.
KIPO; Office Action dated Apr. 5, 2021 in Application No. 10-2015-0031720.
KIPO; Office Action dated Apr. 19, 2021 in Application No. 10-2015-0035094.
KIPO; Office Action dated Mar. 8, 2021 in Application No. 10-2017-0054647.
KIPO; Office Action dated Mar. 10, 2021 in Application No. 10-2017-0055703.
KIPO; Notice of Allowance dated May 24, 2021 in Application No. 10-2020-0101096.
KIPO; Notice of Allowance dated Apr. 1, 2021 in Application No. 30-2020-0030139 (M001).
KIPO; Notice of Allowance dated Apr. 1, 2021 in Application No. 30-2020-0030139 (M002).
TIPO; Notice of Allowance dated May 13, 2021 in Application No. 105122394.
TIPO; Notice of Allowance dated Mar. 5, 2021 in Application No. 105131284.
TIPO; Office Action dated Feb. 25, 2021 in Application No. 105134275.
TIPO; Notice of Allowance dated Mar. 4, 2021 in Application No. 106100823.
TIPO; Notice of Allowance dated May 6, 2021 in Application No. 106108522.
TIPO; Notice of Allowance dated Mar. 4, 2021 in Application No. 106111693.
TIPO; Office Action dated Feb. 25, 2021 in Application No. 106121797.
TIPO; Office Action dated Apr. 26, 2021 in Application No. 106122231.
TIPO; Office Action dated Apr. 22, 2021 in Application No. 106124126.
TIPO; Office Action dated Apr. 22, 2021 in Application No. 106124128.
TIPO; Notice of Allowance dated Mar. 25, 2021 in Application No. 106124130.
TIPO; Office Action dated Mar. 4, 2021 in Application No. 106127948.
TIPO; Office Action dated Mar. 15, 2021 in Application No. 106129971.
TIPO; Office Action dated Apr. 7, 2021 in Application No. 106135925.
TIPO; Office Action dated Apr. 7, 2021 in Application No. 106136905.
TIPO; Office Action dated Mar. 29, 2021 in Application No. 106143559.
TIPO; Office Action dated Mar. 31, 2021 in Application No. 106143570.

(56) References Cited

OTHER PUBLICATIONS

TIPO; Office Action dated Jan. 15, 2021 in Application No. 108142842.
TIPO; Office Action dated Jan. 25, 21 in Application No. 108143562.
TIPO; Notice of Allowance dated May 18, 2021 in Application No. 109300595.
TIPO; Notice of Allowance dated Mar. 30, 2021 in Application No. 109305460.
USPTO; Notice of Allowance dated Feb. 10, 2021 in U.S. Appl. No. 14/219,839.
USPTO; Advisory Action dated Apr. 13, 2021 in U.S. Appl. No. 14/829,565.
USPTO; Non-Final Office Action dated May 12, 2021 in U.S. Appl. No. 14/829,565.
USPTO; Final Office Action dated Feb. 24, 2021 in U.S. Appl. No. 15/262,990.
USPTO; Advisory Action dated Apr. 28, 2021 in U.S. Appl. No. 15/262,990.
USPTO; Final Office Action dated Mar. 25, 2021 in U.S. Appl. No. 15/286,503.
USPTO; Advisory Action dated Apr. 30, 2021 in U.S. Appl. No. 15/377,439.
USPTO; Final Office Action dated Jan. 7, 2021 in U.S. Appl. No. 15/380,909.
USPTO; Non-Final Office Action dated Feb. 9, 2021 in U.S. Appl. No. 15/402,993.
USPTO; Final Office Action dated May 21, 2021 in U.S. Appl. No. 15/402,993.
USPTO; Final Office Action dated Jun. 2, 2021 in U.S. Appl. No. 15/611,707.
USPTO; Advisory Action dated Mar. 25, 2021 in U.S. Appl. No. 15/636,307.
USPTO; Non-Final Office Action dated Apr. 21, 2021 in U.S. Appl. No. 15/636,307.
USPTO; Final Office Action dated Mar. 10, 2021 in U.S. Appl. No. 15/690,017.
USPTO; Notice of Allowance dated Apr. 16, 2021 in U.S. Appl. No. 15/691,241.
USPTO; Non-Final Office Action dated Mar. 18, 2021 in U.S. Appl. No. 15/835,328.
USPTO; Notice of Allowance dated Mar. 19, 2021 in U.S. Appl. No. 15/890,037.
USPTO; Final Office Action dated Apr. 19, 2021 in U.S. Appl. No. 15/909,705.
USPTO; Non-Final Office Action dated May 20, 2021 in U.S. Appl. No. 15/917,224.
USPTO; Non-Final Office Action dated Feb. 18, 2021 in U.S. Appl. No. 15/923,834.
USPTO; Advisory Action dated Apr. 28, 2021 in U.S. Appl. No. 15/940,729.
USPTO; Notice of Allowance dated Apr. 7, 2021 in U.S. Appl. No. 15/940,759.
USPTO; Advisory Action dated Feb. 22, 2021 in U.S. Appl. No. 15/962,980.
USPTO; Final Office Action dated Apr. 13, 2021 in U.S. Appl. No. 15/967,146.
USPTO; Advisory Action dated Jun. 2, 2021 in U.S. Appl. No. 15/967,146.
USPTO; Non-Final Office Action dated Feb. 19, 2021 in U.S. Appl. No. 15/974,948.
USPTO; Non-Final Office Action dated May 25, 2021 in U.S. Appl. No. 15/985,539.
USPTO; Non-Final Office Action dated Apr. 5, 2021 in U.S. Appl. No. 15/996,286.
USPTO; Non-Final Office Action dated Feb. 4, 2021 in U.S. Appl. No. 16/000,109.
USPTO; Non-Final Office Action dated May 19, 2021 in U.S. Appl. No. 16/000,125.
USPTO; Notice of Allowance dated Feb. 5, 2021 in U.S. Appl. No. 16/000,156.
USPTO; Non-Final Office Action dated Mar. 19, 2021 in U.S. Appl. No. 16/004,041.
USPTO; Final Office Action dated Mar. 23, 2021 in U.S. Appl. No. 16/039,817.
USPTO; Advisory Action dated May 28, 2021 in U.S. Appl. No. 16/039,817.
USPTO; Final Office Action dated Mar. 8, 2021 in U.S. Appl. No. 16/042,791.
USPTO; Advisory Action dated May 14, 2021 in U.S. Appl. No. 16/042,791.
USPTO; Notice of Allowance dated Mar. 10, 2021 in U.S. Appl. No. 16/055,532.
USPTO; Final Office Action dated Mar. 23, 2021 in U.S. Appl. No. 16/105,745.
USPTO; Final Office Action dated Mar. 24, 2021 in U.S. Appl. No. 16/105,761.
USPTO; Advisory Action dated May 20, 2021 in U.S. Appl. No. 16/105,761.
USPTO; Final Office Action dated Mar. 18, 2021 in U.S. Appl. No. 16/105,802.
USPTO; Advisory Action dated May 27, 2021 in U.S. Appl. No. 16/105,802.
USPTO; Advisory Action dated Feb. 17, 2021 in U.S. Appl. No. 16/108,950.
USPTO; Non-Final Office Action dated Apr. 13, 2021 in U.S. Appl. No. 16/108,950.
USPTO; Notice of Allowance dated Mar. 23, 2021 in U.S. Appl. No. 16/116,708.
USPTO; Advisory Action dated Mar. 10, 2021 in U.S. Appl. No. 16/117,530.
USPTO; Non-Final Office Action dated Mar. 23, 2021 in U.S. Appl. No. 16/151,074.
USPTO; Final Office Action dated May 6, 2021 in U.S. Appl. No. 16/152,260.
USPTO; Notice of Allowance dated Feb. 24, 2021 in U.S. Appl. No. 16/167,164.
USPTO; Non-Final Office Action dated Feb. 19, 2021 in U.S. Appl. No. 16/172,535.
USPTO; Final Office Action dated May 27, 2021 in U.S. Appl. No. 16/172,535.
USPTO; Advisory Action dated Apr. 5, 2021 in U.S. Appl. No. 16/176,517.
USPTO; Notice of Allowance dated May 13, 2021 in U.S. Appl. No. 16/176,517.
USPTO; Notice of Allowance dated Feb. 19, 2021 in U.S. Appl. No. 16/183,258.
USPTO; Notice of Allowance dated Feb. 10, 2021 in U.S. Appl. No. 16/205,899.
USPTO; Non-Final Office Action dated Mar. 29, 2021 in U.S. Appl. No. 16/206,589.
USPTO; Advisory Action dated Feb. 25, 2021 in U.S. Appl. No. 16/210,922.
USPTO; Final Office Action dated Mar. 29, 2021 in U.S. Appl. No. 16/219,555.
USPTO; Non-Final Office Action dated May 2, 2021 in U.S. Appl. No. 16/240,392.
USPTO; Advisory Action dated Jan. 26, 2021 in U.S. Appl. No. 16/251,534.
USPTO; Non-Final Office Action dated Feb. 23, 2021 in U.S. Appl. No. 16/251,534.
USPTO; Non-Final Office Action dated Mar. 30, 2021 in U.S. Appl. No. 16/252,567.
USPTO; Non-Final Office Action dated Mar. 4, 2021 in U.S. Appl. No. 16/252,569.
USPTO; Non-Final Office Action dated Apr. 20, 2021 in U.S. Appl. No. 16/397,045.
USPTO; Notice of Allowance dated Mar. 10, 2021 in U.S. Appl. No. 16/400,814.
USPTO; Non-Final Office Action dated May 7, 2021 in U.S. Appl. No. 16/423,824.
USPTO; Notice of Allowance dated Apr. 28, 2021 in U.S. Appl. No. 16/453,249.

(56) References Cited

OTHER PUBLICATIONS

USPTO; Final Office Action dated May 20, 2021 in U.S. Appl. No. 16/468,258.
USPTO; Notice of Allowance dated Apr. 26, 2021 in U.S. Appl. No. 16/517,122.
USPTO; Final Office Action dated May 12, 2021 in U.S. Appl. No. 16/546,543.
USPTO; Non-Final Office Action dated Feb. 1, 2021 in U.S. Appl. No. 16/563,473.
USPTO; Non-Final Office Action dated May 10, 2021 in U.S. Appl. No. 16/601,593.
USPTO; Non-Final Office Action dated Feb. 24, 2021 in U.S. Appl. No. 16/637,134.
USPTO; Notice of Allowance dated Jun. 2, 2021 in U.S. Appl. No. 16/637,134.
USPTO; Notice of Allowance dated Apr. 30, 2021 in U.S. Appl. No. 16/685,787.
USPTO; Non-Final Office Action dated Apr. 5, 2021 in U.S. Appl. No. 16/704,835.
USPTO; Final Office Action dated Feb. 22, 2021 in U.S. Appl. No. 16/713,311.
USPTO; Notice of Allowance dated May 20, 2021 in U.S. Appl. No. 16/752,514.
USPTO; Notice of Allowance dated May 24, 2021 in U.S. Appl. No. 16/765,125.
USPTO; Non-Final Office Action dated Apr. 15, 2021 in U.S. Appl. No. 16/789,138.
USPTO; Notice of Allowance dated May 12, 2021 in U.S. Appl. No. 16/800,114.
USPTO; Non-Final Office Action dated Apr. 5, 2021 in U.S. Appl. No. 16/816,078.
USPTO; Non-Final Office Action dated May 19, 2021 in U.S. Appl. No. 16/828,753.
USPTO; Non-Final Office Action dated May 4, 2021 in U.S. Appl. No. 16/872,045.
USPTO; Non-Final Office Action dated May 3, 2021 in U.S. Appl. No. 16/878,443.
USPTO; Non-Final Office Action dated Dec. 31, 2020 in U.S. Appl. No. 16/924,595.
USPTO; Non-Final Office Action dated May 25, 2021 in U.S. Appl. No. 16/935,280.
USPTO; Non-Final Office Action dated Apr. 14, 2021 in U.S. Appl. No. 17/009,093.
USPTO; Ex Parte Quayle Action dated Apr. 13, 2021 in U.S. Appl. No. 29/679,620.
USPTO; Notice of Allowance dated May 19, 2021 in U.S. Appl. No. 29/702,881.
Aubin et al. "Very low temperature (450° C.) selective epitaxial growth of heavily in situ boron-doped SiGe layers" Semiconductor Science and Technology, 30, 10 pages (2015).
Barnscheidt et al. "Highly boron-doped germanium layers on Si(001) grown by carbon-mediated epitaxy" Semiconductor Science and Technology, 33, 9 pages (2018).
Belyansky et al. "Low Temperature Borophosphosilicate Glass (BPSG) Process for High Aspect Ratio Gap Fill" www.electrochem.org/dl/ma/201/pdfs/0705.pdf, downloaded May 15, 2021, 1 page.
Cheremisin et al. "UV-laser modification and selective ion-beam etching of amorphous vanadium pentoxide thin films" Phys. Status Solidi A, Applications and materials science, 206 (7), pp. 1484-1487 (2009).
Dingemans et al. "Plasma-Assisted ALD for the Conformal Deposition of SiO2: Process, Material and Electronic Properties" J of the Electrochemical Society, 159(3), H277-H285 (2012).
G02-1152 "Atomic Layer Deposition of Al2O3 with Alcohol Oxidants for Impeding Substrate Oxidation" Abstract. Oct. 16, 2019 (2019).
Imamura et al. "Cyclic C4F8 and O2 plasma etching of TiO2 for high-aspect-ratio three-dimensional devices" Template for JJAP Regular Papers, Jan. 2014, pp. 29 (2014).
Kim et al. "A process for topographically selective deposition on 3D nanostructures by ion implantation" ACS Nano, 10, 4, 4451-4458 (2016).
Lee et al. "Ultraviolet light enhancement of Ta2O5 dry etch rates" J. of Vacuum Science & Technology B: Microelectronics and Nanometer Structures Processing, Measurement, and Phenomena, 18, pp. 293-295 (2000).
Musschoot et al. "Atomic layer deposition of titanium nitride from TDMAT precursor" Microelectronic Engineering, 86, pp. 72-77 (2009).
Noircler et al. "Transmission electron microscopy characterization of low temperature boron doped silicon epitaxial films" CrystEngComm, 22(33), pp. 5464-5472 (2020).
Oyama et al. "Topotactic synthesis of vanadium nitride solid foams" Journal of Materials Research vol. 8. No. 6, pp. 1450-1454 (1993).
Rimoldi et al. "Atomic Layer Deposition of Rhenium-Aluminum Oxide Thin Films and ReOx Incorporation in a Metal-Organic Framework" Applied Materials & Interfaces, 9, pp. 35067-35074 (2017).
Standard Motor Products LX249 Ignition Pick Up, Nov. 11, 2005, Amazon.com, May 10, 2021. URL: https://www.amazon.com/Standard-Motor-Products-LX249-Ignition/dp/B000C7ZTS4/ (2005).
Tao et al. "Improved performance of GeON as charge storage layer in flash memory by optimal annealing" Microelectronics Reliability, vol. 52, pp. 2597-2601 (2012).
Wirths et al. "Low temperature RPCVD epitaxial growth of SilxGex using Si2H6 and Ge2H6" Solid-State Electronics, 88, pp. 2-9 (2013).
Yanguas-Gil et al. "Modulation of the Growth Per Cycle in Atomic Layer Deposition Using Reversible Surface Functionalization" Chemistry of Materials, 25, pp. 4849-4860 (2013).
CNIPA; Office Action dated Jul. 21, 2021 in Application No. 201610131743.1.
CNIPA; Office Action dated Jul. 23, 2021 in Application No. 201710131319.1.
CNIPA; Notice of Allowance dated Jun. 3, 2021 in Application No. 201711057929.8.
CNIPA; Office Action dated Sep. 13, 2021 in Application No. 201780076230.8.
CNIPA; Office Action dated Sep. 13, 2021 in Application No. 201780076321.1.
CNIPA; Office Action dated Apr. 30, 2021 in Application No. 201810018936.5.
CNIPA; Office Action dated Apr. 16, 2021 in Application No. 201810116717.0.
CNIPA; Notice of Allowance dated Sep. 15, 2021 in Application No. 201810116717.0.
CNIPA; Office Action dated May 26, 2021 in Application No. 201810215131.X.
CNIPA; Office Action dated Jun. 16, 2021 in Application No. 201810344382.8.
CNIPA; Notice of Allowance dated Oct. 11, 2021 in Application No. 201810344382.8.
CNIPA; Office Action dated Jul. 5, 2021 in Application No. 201810530514.6.
CNIPA; Office Action dated Jun. 30, 2021 in Application No. 201810755771.X.
CNIPA; Office Action dated Sep. 23, 2021 in Application No. 201880048547.5.
CNIPA; Office Action dated May 19, 2021 in Application No. 201880072606.2.
CNIPA; Office Action dated May 31, 2021 in Application No. 201910857144.1.
CNIPA; Office Action dated Jun. 2, 2021 in Application No. 201910920881.1.
CNIPA; Office Action dated Jul. 5, 2021 in Application No. 201911042495.3.
CNIPA; Office Action dated Apr. 27, 2021 in Application No. 201911250100.9.
CNIPA; Office Action dated Jul. 7, 2021 in Application No. 201980011788.7.
CNIPA; Notice of Allowance dated Jun. 16, 2021 in Application No. 202130111248.6.

(56) References Cited

OTHER PUBLICATIONS

EPO; Extended European Search Report dated Aug. 11, 2021 in Application No. 21169226.4.
JPO; Notice of Allowance dated Aug. 11, 2021 in Application No. 2018-024655.
JPO; Office Action dated Aug. 2, 2021 in Application No. 2019-504674.
JPO; Office Action dated Sep. 10, 2021 in Application No. 2019-531445.
JPO; Notice of Allowance dated Jun. 30, 2021 in Application No. 2021-004208.
KIPO; Office Action dated Jun. 28, 2021 in Application No. 10-2014-0027217.
KIPO; Notice of Allowance dated May 27, 2021 in Application No. 10-2014-0105478.
KIPO; Notice of Allowance dated Aug. 17, 2021 in Application No. 10-2014-0122903.
KIPO; Notice of Allowance dated Sep. 8, 2021 in Application No. 10-2014-0136089.
KIPO; Notice of Allowance dated Jul. 6, 2021 in Application No. 10-2014-0145220.
KIPO; Notice of Allowance dated Sep. 23, 2021 in Application No. 2014-0156196.
KIPO; Notice of Allowance dated Jul. 21, 2021 in Application No. 10-2015-0025314.
KIPO; Office Action dated May 19, 2021 in Application No. 10-2015-0036819.
KIPO; Office Action dated Jun. 23, 2021 in Application No. 10-2015-0037658.
KIPO; Office Action dated Sep. 6, 2021 in Application No. 10-2015-0046393.
KIPO; Office Action dated Jun. 10, 2021 in Application No. 2015-61391.
KIPO; Office Action dated Sep. 3, 2021 in Application No. 2017-37847.
KIPO; Office Action dated Aug. 2, 2021 in Application No. 2017-43865.
KIPO; Office Action dated Oct. 1, 2021 in Application No. 2017-43919.
KIPO; Office Action dated Sep. 28, 2021 in Application No. 2017-49172.
KIPO; Notice of Allowance dated Sep. 28, 2021 in Application No. 2017-54647.
KIPO; Office Action dated in Aug. 30, 2021 in Application No. 2017-81515.
KIPO; Office Action dated Sep. 10, 2021 in Application No. 2017-86083.
KIPO; Office Action dated Jun. 29, 2021 in Application No. 10-2017-0066979.
KIPO; Notice of Allowance dated Jun. 24, 2021 in Application No. 10-2019-0044213.
KIPO; Office Action dated Jun. 17, 2021 in Application No. 10-2021-0051860.
KIPO; Office Action dated Aug. 18, 2021 in Application No. 10-2021-0090283.
KIPO; Notice of Allowance dated Sep. 2, 2021 in Application No. 30-2020-0047043.
TIPO; Office Action dated Jun. 22, 2021 in Application No. 104108277.
TIPO; Notice of Allowance dated Sep. 22, 2021 in Application No. 104108277.
TIPO; Office Action dated Jun. 2, 2021 in Application No. 105129977.
TIPO; Notice of Allowance dated Sep. 9, 2021 in Application No. 105129977.
TIPO; Notice of Allowance dated Jun. 4, 2021 in Application No. 105131896.
TIPO; Notice of Allowance dated Jul. 30, 2021 in Application No. 105134275.
TIPO; Notice of Allowance dated Feb. 24, 2021 in Application No. 106113604.
TIPO; Notice of Allowance dated Sep. 3, 2021 in Application No. 106115126.
TIPO; Office Action dated Jun. 21, 2021 in Application No. 106120902.
TIPO; Notice of Allowance dated Jun. 30, 2021 in Application No. 106121797.
TIPO; Notice of Allowance dated Sep. 1, 2021 in Application No. 106122231.
TIPO; Notice of Allowance dated Jun. 3, 2021 in Application No. 106123203.
TIPO; Notice of Allowance dated Aug. 24, 2021 in Application No. 106124129.
TIPO; Notice of Allowance dated Jul. 28, 2021 in Application No. 106129491.
TIPO; Notice of Allowance dated Aug. 10, 2021 in Application No. 106129971.
TIPO; Office Action dated Jun. 15, 2021 in Application No. 106133152.
TIPO; Notice of Allowance dated Oct. 12, 2021 in Application No. 106135925.
TIPO; Office Action dated Jul. 13, 2021 in Application No. 106138996.
TIPO; Notice of Allowance dated Sep. 24, 2021 in Application No. 106143559.
TIPO; Office Action dated Aug. 5, 2021 in Application No. 106143566.
TIPO; Office Action dated May 26, 2021 in Application No. 106143568.
TIPO; Notice of Allowance dated Jul. 30, 2021 in Application No. 106143570.
TIPO; Office Action dated Jun. 7, 2021 in Application No. 107103230.
TIPO; Office Action dated Aug. 10, 2021 in Application No. 107103230.
TIPO; Office Action dated Sep. 8, 2021 in Application No. 107105788.
TIPO; Office Action dated Aug. 3, 2021 in Application No. 107105982.
TIPO; Office Action dated Aug. 16, 2021 in Application No. 107114888.
TIPO; Office Action dated Sep. 28, 2021 in Application No. 109112983.
TIPO; Office Action dated Sep. 13, 2021 in Application No. 109119438.
TIPO; Office Action dated Oct. 18, 2021 in Application No. 109300594.
TIPO; Notice of Allowance dated Jun. 9, 2021 in Application No. 109303437.
TIPO; Notice of Allowance dated Oct. 1, 2021 in Application No. 110118827.
TIPO; Notice of Allowance dated Jun. 30, 2021 in Application No. 110301018.
TIPO; Notice of Allowance dated Jul. 29, 2021 in Application No. 110301101.
TIPO; Notice of Allowance dated Jul. 27, 2021 in Application No. 110302670.
USPTO; Final Office Action dated Aug. 4, 2021 in U.S. Appl. No. 14/219,879.
USPTO; Non-Final Office Action dated Jun. 10, 2021 in U.S. Appl. No. 15/262,990.
USPTO; Final Office Action dated Oct. 1, 2021 in U.S. Appl. No. 15/262,990.
USPTO; Non-Final Office Action dated Jul. 9, 2021 in U.S. Appl. No. 15/286,503.
USPTO; Notice of Allowance dated Jun. 29, 2021 in U.S. Appl. No. 15/377,439.
USPTO; Non-Final Office Action dated Jun. 25, 2021 in U.S. Appl. No. 15/380,909.
USPTO; Final Office Action dated Jun. 21, 2021 in U.S. Appl. No. 15/380,921.
USPTO; Advisory Action dated Aug. 30, 2021 in U.S. Appl. No. 15/380,921.
USPTO; Non-Final Office Action dated Oct. 6, 2021 in U.S. Appl. No. 15/380,921.
USPTO; Advisory Action dated Jul. 27, 2021 in U.S. Appl. No. 15/402,993.
USPTO; Final Office Action dated Jun. 9, 2021 in U.S. Appl. No. 15/491,726.
USPTO; Advisory Action dated Aug. 24, 2021 in U.S. Appl. No. 15/491,726.

(56) References Cited

OTHER PUBLICATIONS

USPTO; Non-Final Office Action dated Sep. 28, 2021 in U.S. Appl. No. 15/491,726.
USPTO; Notice of Allowance dated Aug. 25, 2021 in U.S. Appl. No. 15/611,707.
USPTO; Non-Final Office Action dated Sep. 16, 2021 in U.S. Appl. No. 15/636,307.
USPTO; Advisory Action dated Jun. 11, 2021 in U.S. Appl. No. 15/690,017.
USPTO; Non-Final Office Action dated Jun. 17, 2021 in U.S. Appl. No. 15/690,017.
USPTO; Final Office Action dated Jul. 15, 2021 in U.S. Appl. No. 15/726,959.
USPTO; Advisory Action dated Sep. 21, 2021 in U.S. Appl. No. 15/726,959.
USPTO; Notice of Allowance dated Sep. 15, 2021 in U.S. Appl. No. 15/835,328.
USPTO; Advisory Action dated Jun. 11, 2021 in U.S. Appl. No. 15/909,705.
USPTO; Notice of Allowance dated Jun. 4, 2021 in U.S. Appl. No. 15/923,834.
USPTO; Final Office Action dated Jun. 28, 2021 in U.S. Appl. No. 15/925,532.
USPTO; Advisory Action dated Aug. 27, 2021 in U.S. Appl. No. 15/925,532.
USPTO; Non-Final Office Action dated Oct. 6, 2021 in U.S. Appl. No. 15/925,532.
USPTO; Non-Final Office Action dated Jun. 16, 2021 in U.S. Appl. No. 15/940,729.
USPTO; Notice of Allowance dated Sep. 28, 2021 in U.S. Appl. No. 15/940,729.
USPTO; Non-Final Office Action dated Aug. 2, 2021 in U.S. Appl. No. 15/962,980.
USPTO; Non-Final Office Action dated Oct. 4, 2021 in U.S. Appl. No. 15/967,146.
USPTO; Final Office Action dated Aug. 3, 2021 in U.S. Appl. No. 15/974,948.
USPTO; Advisory Action dated Oct. 21, 2021 in U.S. Appl. No. 15/974,948.
USPTO; Final Office Action dated Oct. 12, 2021 in U.S. Appl. No. 15/996,286.
USPTO; Non-Final Office Action dated Jul. 9, 2021 in U.S. Appl. No. 15/997,445.
USPTO; Final Office Action dated Aug. 5, 2021 in U.S. Appl. No. 16/000,109.
USPTO; Final Office Action dated Oct. 20, 2021 in U.S. Appl. No. 16/000,125.
USPTO; Final Office Action dated Sep. 3, 2021 in U.S. Appl. No. 16/004,041.
USPTO; Non-Final Office Action dated Oct. 22, 2021 in U.S. Appl. No. 16/042,791.
USPTO; Non-Final Office Action dated Sep. 28, 2021 in U.S. Appl. No. 16/105,745.
USPTO; Non-Final Office Action dated Sep. 29, 2021 in U.S. Appl. No. 16/105,761.
USPTO; Non-Final Office Action dated Jun. 25, 2021 in U.S. Appl. No. 16/105,802.
USPTO; Final Office Action dated Jul. 27, 2021 in U.S. Appl. No. 16/108,950.
USPTO; Advisory Action dated Oct. 1, 2021 in U.S. Appl. No. 16/108,950.
USPTO; Non-Final Office Action dated Jun. 18, 2021 in U.S. Appl. No. 16/117,530.
USPTO; Final Office Action dated Jul. 8, 2021 in U.S. Appl. No. 16/151,074.
USPTO; Notice of Allowance dated Sep. 17, 2021 in U.S. Appl. No. 16/151,074.
USPTO; Non-Final Office Action dated Sep. 16, 2021 in U.S. Appl. No. 16/152,260.
USPTO; Advisory Action dated Aug. 2, 2021 in U.S. Appl. No. 16/172,535.
USPTO; Non-Final Office Action dated Oct. 15, 2021 in U.S. Appl. No. 16/172,535.
USPTO; Final Office Action dated Jun. 14, 2021 in U.S. Appl. No. 16/202,941.
USPTO; Advisory Action dated Aug. 16, 2021 in U.S. Appl. No. 16/202,941.
USPTO; Non-Final Office Action dated Sep. 20, 2021 in U.S. Appl. No. 16/202,941.
USPTO; Final Office Action dated Jul. 26, 2021 in U.S. Appl. No. 16/206,589.
USPTO; Notice of Allowance dated Sep. 13, 2021 in U.S. Appl. No. 16/206,589.
USPTO; Non-Final Office Action dated Aug. 25, 2021 in U.S. Appl. No. 16/210,922.
USPTO; Final Office Action dated Sep. 1, 2021 in U.S. Appl. No. 16/240,392.
USPTO; Notice of Allowance dated Oct. 15, 2021 in U.S. Appl. No. 16/240,392.
USPTO; Final Office Action dated Sep. 7, 2021 in U.S. Appl. No. 16/251,534.
USPTO; Final Office Action dated Aug. 18, 2021 in U.S. Appl. No. 16/252,567.
USPTO; Final Office Action dated Jul. 21, 2021 in U.S. Appl. No. 16/252,569.
USPTO; Advisory Action dated Jul. 15, 2021 in U.S. Appl. No. 16/468,258.
USPTO; Non-Final Office Action dated Oct. 21, 2021 in U.S. Appl. No. 16/468,258.
USPTO; Advisory Action dated Jul. 8, 2021 in U.S. Appl. No. 16/546,543.
USPTO; Ex Parte Quayle Action dated Aug. 6, 2021 in U.S. Appl. No. 16/563,473.
USPTO; Notice of Allowance dated Sep. 30, 2021 in U.S. Appl. No. 16/563,473.
USPTO; Non-Final Office Action dated Oct. 5, 2021 in U.S. Appl. No. 16/588,807.
USPTO; Notice of Allowance dated Oct. 18, 2021 in U.S. Appl. No. 16/601,593.
USPTO; Non-Final Office Action dated Jun. 11, 2021 in U.S. Appl. No. 16/671,847.
USPTO; Non-Final Office Action dated Jun. 24, 2021 in U.S. Appl. No. 16/673,860.
USPTO; Non-Final Office Action dated Sep. 28, 2021 in U.S. Appl. No. 16/692,859.
USPTO; Notice of Allowance dated Jul. 20, 2021 in U.S. Appl. No. 16/704,835.
USPTO; Non-Final Office Action dated Aug. 31, 2021 in U.S. Appl. No. 16/712,707.
USPTO; Non-Final Office Action dated Sep. 21, 2021 in U.S. Appl. No. 16/736,336.
USPTO; Final Office Action dated Sep. 15, 2021 in U.S. Appl. No. 16/789,138.
USPTO; Non-Final Office Action dated Jun. 24, 2021 in U.S. Appl. No. 16/792,058.
USPTO; Notice of Allowance dated Oct. 19, 2021 in U.S. Appl. No. 16/792,058.
USPTO; Non-Final Office Action dated Oct. 6, 2021 in U.S. Appl. No. 16/792,544.
USPTO; Notice of Allowance dated Sep. 27, 2021 in U.S. Appl. No. 16/792,571.
USPTO; Non-Final Office Action dated Aug. 17, 2021 in U.S. Appl. No. 16/797,346.
USPTO; Notice of Allowance dated Jul. 21, 2021 in U.S. Appl. No. 16/816,078.
USPTO; Non-Final Office Action dated Jun. 23, 2021 in U.S. Appl. No. 16/827,012.
USPTO; Non-Final Office Action dated Feb. 23, 2021 in U.S. Appl. No. 16/827,506.
USPTO; Notice of Allowance dated May 27, 2021 in U.S. Appl. No. 16/827,506.

(56) References Cited

OTHER PUBLICATIONS

USPTO; Final Office Action dated Oct. 6, 2021 in U.S. Appl. No. 16/828,753.
USPTO; Non-Final Office Action dated Jul. 28, 2021 in U.S. Appl. No. 16/835,283.
USPTO; Non-Final Office Action dated Oct. 4, 2021 in U.S. Appl. No. 16/840,960.
USPTO; Non-Final Office Action dated Aug. 3, 2021 in U.S. Appl. No. 16/849,793.
USPTO; Non-Final Office Action dated Jun. 15, 2021 in U.S. Appl. No. 16/861,144.
USPTO; Final Office Action dated Sep. 17, 2021 in U.S. Appl. No. 16/861,144.
USPTO; Non-Final Office Action dated Sep. 1, 2021 in U.S. Appl. No. 16/867,385.
USPTO; Final Office Action dated Oct. 7, 2021 in U.S. Appl. No. 16/872,045.
USPTO; Final Office Action dated Oct. 14, 2021 in U.S. Appl. No. 16/878,443.
USPTO; Non-Final Office Action dated Oct. 4, 2021 in U.S. Appl. No. 16/886,405.
USPTO; Non-Final Office Action dated Jul. 28, 2021 in U.S. Appl. No. 16/888,423.
USPTO; Non-Final Office Action dated Oct. 13, 2021 in U.S. Appl. No. 16/893,206.
USPTO; Notice of Allowance dated Jun. 17, 2021 in U.S. Appl. No. 16/924,595.
USPTO; Non-Final Office Action dated Jul. 27, 2021 in U.S. Appl. No. 16/930,193.
USPTO; Non-Final Office Action dated Jun. 25, 2021 in U.S. Appl. No. 16/930,305.
USPTO; Non-Final Office Action dated Sep. 14, 2021 in U.S. Appl. No. 16/932,707.
USPTO; Non-Final Office Action dated Oct. 4, 2021 in U.S. Appl. No. 16/935,275.
USPTO; Notice of Allowance dated Sep. 22, 2021 in U.S. Appl. No. 16/935,280.
USPTO; Non-Final Office Action dated Aug. 23, 2021 in U.S. Appl. No. 16/938,868.
USPTO; Non-Final Office Action dated Oct. 12, 2021 in U.S. Appl. No. 16/944,763.
USPTO; Non-Final Office Action dated Aug. 19, 2021 in U.S. Appl. No. 16/992,806.
USPTO; Non-Final Office Action dated Jul. 7, 2021 in U.S. Appl. No. 16/999,065.
USPTO; Final Office Action dated Oct. 21, 2021 in U.S. Appl. No. 16/999,065.
USPTO; Final Office Action dated Jul. 23, 2021 in U.S. Appl. No. 17/009,093.
USPTO; Advisory Action dated Oct. 5, 2021 in U.S. Appl. No. 17/009,093.
USPTO; Non-Final Office Action dated Sep. 28, 2021 in U.S. Appl. No. 17/023,129.
USPTO; Notice of Allowance dated Oct. 14, 2021 in U.S. Appl. No. 17/024,092.
USPTO; Notice of Allowance dated Oct. 4, 2021 in U.S. Appl. No. 17/028,066.
USPTO; Non-Final Office Action dated Sep. 10, 2021 in U.S. Appl. No. 17/038,514.
USPTO; Non-Final Office Action dated Oct. 22, 2021 in U.S. Appl. No. 17/073,544.
USPTO; Non-Final Office Action dated Sep. 30, 2021 in U.S. Appl. No. 17/093,224.
USPTO; Non-Final Office Action dated Sep. 22, 2021 in U.S. Appl. No. 17/126,275.
USPTO; Non-Final Office Action dated Sep. 23, 2021 in U.S. Appl. No. 17/254,111.
USPTO; Non-Final Office Action dated Sep. 27, 2021 in U.S. Appl. No. 17/254,366.
USPTO; Notice of Allowance dated Jul. 1, 2021 in U.S. Appl. No. 29/679,620.
USPTO; Notice of Allowance dated Jul. 9, 2021 in U.S. Appl. No. 29/692,490.
USPTO; Non-Final Office Action dated Jul. 14, 2021 in U.S. Appl. No. 29/695,044.
USPTO; Notice of Allowance dated Jun. 8, 2021 in U.S. Appl. No. 29/696,472.
USPTO; Notice of Allowance dated Sep. 21, 2021 in U.S. Appl. No. 29/702,865.
Alen et al. "Atomic layer deposition of molybdenum nitride thin films for cu metallizations" J of The Electrochemical Society, 152(5) G361-G366 (2005).
Best et al. "Complex Halides of the Transition Metals. 24.1 Reactions of Dimeric Molybdenum (II) Halide Complexes Containing Strong Metal-Metal Bonds with Bidentate Tertiary Phosphines and Arsines" Inorganic Chemistry, vol. 17, No. 1, pp. 99-104 (1978).
Blakeney et al. "Atomic Layer Deposition of Aluminum Metal Films Using a Thermally Stable Aluminum Hydride Reducing Agent" Chem. Mater., 30, pp. 1844-1848 (2018).
Buitrago et al. "SnOx high-efficiency EUV interference lithography gratings towards the ultimate resolution in photolithography" Abstract, 1 page (2016).
Buitrago et al. "State-of-the-art EUV materials and processes for the 7 nm node and beyond" Proc of SPIE, vol. 10143, 8 pages (2017).
Cheng et al. "Improved High-Temperature Leakage in High-Density MIM Capcitors by Using a TiLaO Dielectric and an Ir Electrode" IEEE Electron Device Letters, vol. 28, No. 12, 3 pages (2007).
Firestop Support Plate, Type B, 6 In Apr. 4, 2012, Amazon. Com, May 10, 2021, https://www.amazon.com/AmeriVent-Firestop-Support-Plate-Type/dp/B007R7W951/ (2012).
Gertsch et al. "SF4 as the Fluorination Reactant for Al2O3 and VO2 Thermal Atomic Layer Etching" Chem. Mater., 31, pp. 3624-3635 (2019).
Han et al. "Synthesis and characterization of novel zinc precursors for ZnO thin film deposition by atomic layer deposition" Dalton Transactions 49.14 (2020): 4306-4314.
Hayashi et al. "2,2-Difluoro-1,3-dimethylimidazolidine (DFI). A new fluorinating agent" Chem. Commun. pp. 1618-1619 (2002).
Imai et al. "Energetic stability and magnetic moment of tri-, tetra-, and octa-ferromagnetic element nitrides predicted by first-principle calculations" J of Alloys and Compounds, vol. 611, 19 pages (2019).
Jacoby "Chemical deposition methods to the rescue" Cen. Acs. Org., pp. 29-32 (2018).
Jiang et al. "Sensitizer for EUV Chemically Amplified Resist: Metal versus Halogen" J of Photopolymer Science and Technology, vol. 32, No. 1, pp. 21-25 (2019).
Kang et al. "Optical Performance of Extreme Ultraviolet Lithography Mask with an Indium Tin Oxide Absorber" J of Nanoscience and Nanotechnology, vol. 12, pp. 3330-3333 (2012).
Kim et al. "Atomic layer deposition of transition metals for silicide contact formation: Growth characteristics and silicidation" Microelectronic Engineering, 106, pp. 69-75 (2013).
Lim et al. "Atomic layer deposition of transition metals" Nature Materials, vol. 2 pp. 749-754 (2003).
Maina et al. "Atomic layer deposition of transition metal films and nanostructures for electronic and catalytic applications" Critical Reviews in Solid State and Materials Sciences, Abstract, 2 pages (2020).
Miikkulainen et al. "Crystallinity of inorganic films grown by atomic layer deposition: Overview and general trends" Journal of Applied Physics, 112, 102 pages (2013).
Niskanen et al. "Radical-enhanced atomic layer deposition of metallic copper thin films" Journal of the Electrochemical Society 152(1) pp. G25-G28 (2004).
O'Hanlon "A User's Guide to Vacuum Technology" Third Edition, Chapter 19, pp. 359-378 (2003).
Ovanesyan et al. "Atomic Layer Deposition of SiCxNy Using Si2Cl6 and CH3NH2 Plasma" Chem. Mater. 2017, 29, pp. 6269-6278 (2017).

(56) References Cited

OTHER PUBLICATIONS

Park et al. "Superfilling CVD of copper using a catalytic surfactant" Proceedings of the IEEE 2001 International Interconnect Technology Conference, 3 pages (2001).

Petrov et al. "1,1,2,2-Tetrafluoroethyl-N,N-dimethylamine: a new selective fluorinating agent" J of Fluorine Chemistry, 109, pp. 25-31 (2001).

Popov et al. "Atomic Layer Deposition of PbI2 Thin Films" Chem. Mater. 31, pp. 1101-1109 (2019).

Popovici et al. "High-performance (EOT<0.4nm, Jg~10-7 A/cm2) ALD-deposited Ru\SrTiO3 stack for next generations DRAM pillar capacitor" 2018 IEEE International Electron Devices Meeting (IEDM), 4 pages (2018).

Puurunen "Surface Chemistry of Atomic Layer Depostion: A Case Study for the Trimethylaluminum/Water Process" Journal of Applied Physics, 97, 55 pages (2005).

Rahemi et al. "Variation in electron work function with temperature and its effect on the Young's modulus of metals" Scripta Materialia, 99, pp. 41-44 (2015).

SciFinder Search Results on hydrazido-based precursor for boron nitride films, search conducted Nov. 5, 2020, 5 pages (2020).

Shiba et al. "Stable yttrium oxyfluoride used in plasma process chamber" J. Vac. Sci. Technol. A, 35(2), 6 pages (2017).

Shigemoto et al. "Thermal cleaning of silicon nitride with fluorine and additive mixture" 1 page (2007).

Takaoka et al. "F-Propene-Dialkylamine Reaction Products as Fluorinating Agents" Bulletin of the Chemical Socity of Japan, vol. 52 (11), pp. 3377-3380 (1979).

Tsoutsou et al. "Atomic layer deposition of LaxZr1—xO2-d (x=0.25) high-k dielectrics for advanced gate stacks" Applied Physics Letters, 94, 3 pages (2009).

U.S. Appl. No. 60/545,181, filed Feb. 13, 2004 in the names of Matthew G. Goodman et al., and entitled "Forced Flow Susceptor with Exit Holes and Veins for Improvided Process" pp. 1-15 (2004).

U.S. Appl. No. 60/591,258, filed Jul. 26, 2004 in the names of Jeroen Stoutyesdijk et al., and entitled "Susceptor Support for Eliminating Backside Nodules" pp. 1-71 (2004).

U.S. Appl. No. 62/504,470, filed May 10, 2017 in the names of Jennifer Y. Sun et al., and entitled "Metal-Oxy-Fluoride Films for Chamber Components" pp. 1-82 (2017).

Van Asselt et al. "New Palladium Complexes of Cis-Fixed Bidentate Nitrogen Ligands as Catalysts for Carbon-Carbon Bond Formation" Organometallics, 11, pp. 1999-2001 (1992).

Van Asselt et al. "On the Mechanism of Formation of Homocoupled Products in the Carbon-Carbon Cross-Coupling Reaction Catalyzed by Palladium Complexes Containing Rigid Bidentate Nitrogen Ligands" Organometallics, 13, pp. 1972-1980 (1994).

Vayrynen et al. "Atomic Layer Deposition of Nickel Nitride Thin Films Using NiCL2 (TMPDA) and Tert-Butylhydrazine as Precursors" Phy. Status Solidi A, 216, 9 pages (2019).

Vesters et al. "Sensitizers in EUV Chemically Amplified Resist: Mechanism of sensitivity improvement" Proc. SPIE 10583 Extreme Ultraviolet (EUV) Lithography IX, 1058307, 11 pages (2018).

Wilklow-Marnell et al. "First-row transitional-metal oxalate resists for EUV" J. Micro/Nanolith. MEMS MOEMS 17(4) Oct.-Dec. 2018, 9 pages (2018).

Zhang et al. "Mechanical Stability of Air-gap Interconnects" Proc. Future Fab International, pp. 81-87 (2008).

Zientara et al. Journal of the European Ceramic Society, 27, Abstract, 1 page (2007).

\* cited by examiner

METHOD AND APPARATUS FOR TRANSMITTANCE MEASUREMENTS OF LARGE ARTICLES

CROSS-REFERENCE TO RELATED APPLICATIONS

This application is a non-provisional of, and claims priority to and the benefit of, U.S. Provisional Patent Application 62/970,057, filed Feb. 4, 2020 and entitled "METHOD AND APPARATUS FOR TRANSMITTANCE MEASUREMENTS OF LARGE ARTICLES," which is hereby incorporate by reference herein.

FIELD OF INVENTION

The present disclosure relates generally to methods and apparatus for measuring transmittance of light through an object. More particularly, the disclosure relates to methods and apparatus for verifying an object using light intensity and/or transmission measurements.

BACKGROUND OF THE DISCLOSURE

Quartz chambers can be used in a variety of applications. For example, quartz reaction chambers can be used in the manufacture of electronic devices, such as semiconductor devices, photoelectric devices, and the like.

Use of quartz chambers may be desirable for several reasons. For example, quartz material can be relatively inert with respect to precursors and/or reactants used in the manufacture of electronic devices. Further, quartz material exhibits high transparency to light over a wide range or wavelengths, including to light having a wavelength or wavelengths suitable for heating substrates within the quartz chamber during processing.

For several applications, such as vacuum process applications, it may be desirable to reinforce the quartz chamber using, for example, ribs of quartz material that can be welded to a surface of the quartz chamber. Such features (e.g., welds and/or ribs) may exhibit a different transparency to light of certain wavelengths, compared to a wall of the quartz chamber, particularly at an interface of the feature and the chamber wall. Further transparency of the features and/or the wall can vary across the reaction chamber. Such variation can result in a variation in an amount of heat or radiation supplied to a substrate.

Because of their relatively large size, it can be difficult to measure an intensity of light (or a transmittance of light) at multiple points of the reaction chamber wall and of the features, let alone to accurately measure the intensity and/or transmittance. Accordingly, improved methods and apparatus for measuring light intensity of transmittance of light through objects, particularly of large objects, are desired.

Any discussion, including discussion of problems and solutions, set forth in this section, has been included in this disclosure solely for the purpose of providing a context for the present disclosure, and should not be taken as an admission that any or all of the discussion was known at the time the invention was made or otherwise constitutes prior art.

SUMMARY OF THE DISCLOSURE

This summary is provided to introduce a selection of concepts in a simplified form. This summary is not intended to necessarily identify key features or essential features of the claimed subject matter, nor is it intended to be used to limit the scope of the claimed subject matter.

In some embodiments, methods of verifying an article having features thereon are provided. Exemplary methods include providing an apparatus, using the apparatus to measure a transmittance of light from the light source through a wall of the article, and determining a quality of the article based on measured transmittance values. The apparatus can include a first arm, a light source coupled to the first arm, a second arm, and a sensor coupled to the second arm. The article can be or include, for example, a reaction chamber. The methods can be used to determine a quality and/or a dimension (e.g., a width) of a feature, such as a feature (e.g., rib that is welded to a wall of the reaction chamber and/or a width of the weld). The light source can be outside or inside the reaction chamber. Similarly, the sensor can be inside or outside the chamber. The first and second arms can be moved together to measure multiple transmittance values—e.g., along a path (e.g., a line) of movement of the two arms. Other methods are also described below.

In accordance with additional embodiments of the disclosure, apparatus for verifying an article are provided. Exemplary apparatus can include a first arm, a light source coupled to the first arm, a second arm, and a sensor coupled to the second arm. The light source can emit light through the article and the sensor can receive light that is transmitted through the article. The article can include, for example, a (e.g., quartz) reaction chamber. The apparatus can further include a reflective surface coupled to the first or the second arm to direct light in a desired direction (e.g., from the light source toward the sensor). Exemplary apparatus can include a shield—e.g., coupled to the first or second arm. The apparatus can further comprise a member coupled to the first arm and the second arm. The apparatus can also include one or more motors to cause the first arm and the second arm to move in one or more (e.g., two) directions. Exemplary apparatus can include one or more data acquisition devices to receive information from the sensor. The apparatus can further include a database that stores information, such as measured intensity and/or transmittance values, coordinates associated with the measurements, and an identity associated with one or more articles. Other apparatus are also disclosed.

In accordance with further examples of the disclosure, a system can include an apparatus as described herein. The system may further include an article to be measured and/or a fixture for retaining the article.

These and other embodiments will become readily apparent to those skilled in the art from the following detailed description of certain embodiments having reference to the attached figures, the invention not being limited to any particular embodiment(s) disclosed.

BRIEF DESCRIPTION OF THE DRAWING FIGURES

While the specification concludes with claims particularly pointing out and distinctly claiming what are regarded as embodiments of the invention, the advantages of embodiments of the disclosure may be more readily ascertained from the description of certain examples of the embodiments of the disclosure when read in conjunction with the accompanying drawings.

It will be appreciated that elements in the figures are illustrated for simplicity and clarity and have not necessarily been drawn to scale. For example, the dimensions of some of the elements in the figures may be exaggerated relative to other elements to help improve understanding of illustrated embodiments of the present disclosure.

DETAILED DESCRIPTION OF EXEMPLARY EMBODIMENTS

Although certain embodiments and examples are disclosed below, it will be understood by those in the art that the invention extends beyond the specifically disclosed embodiments and/or uses of the invention and obvious modifications and equivalents thereof. Thus, it is intended that the scope of the invention disclosed should not be limited by the particular disclosed embodiments described below.

The illustrations presented herein are not necessarily meant to be actual views of any particular apparatus or data, but may merely be idealized representations that are used to describe embodiments of the disclosure.

Figure 1:
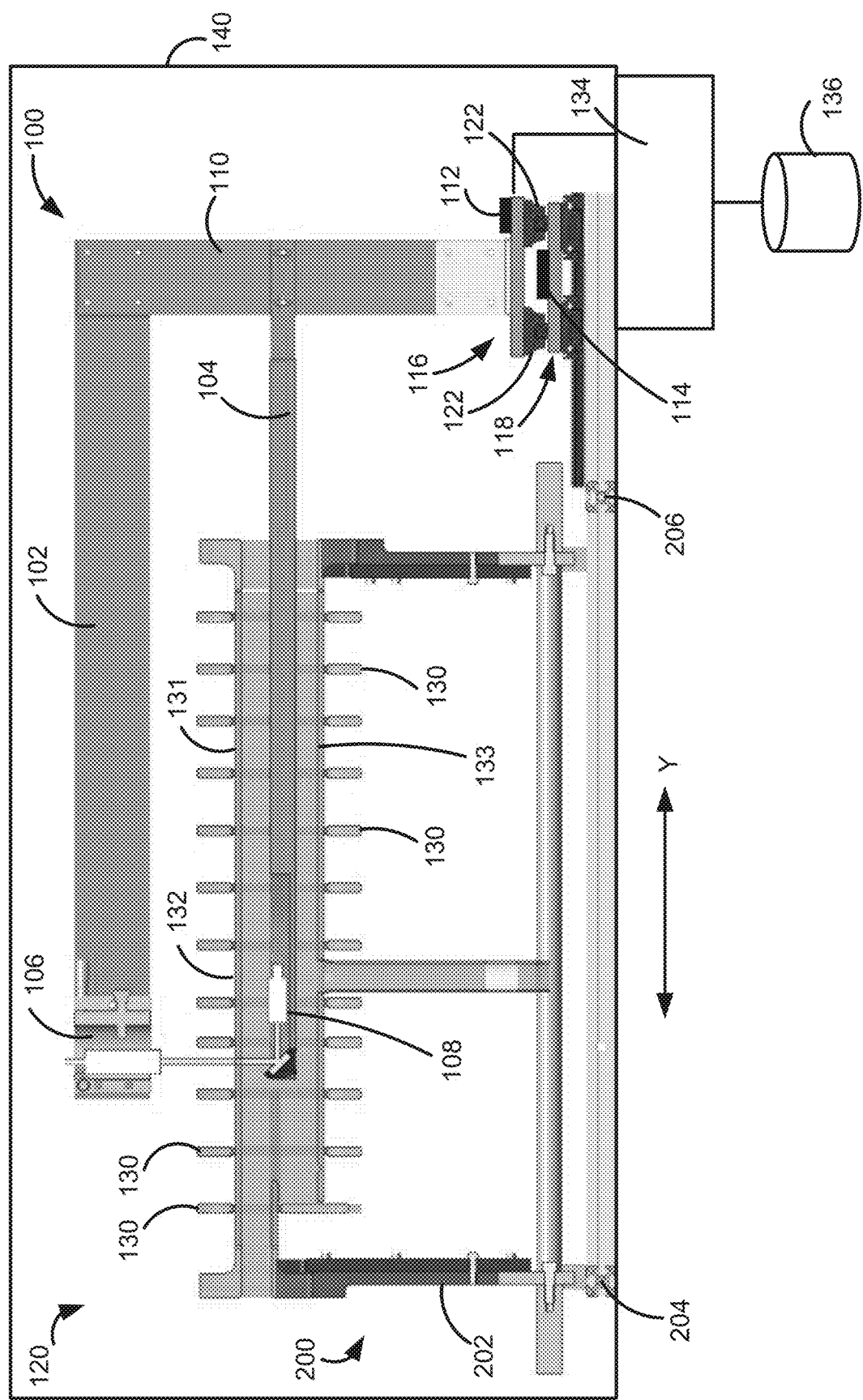
FIG. 1 illustrates a side view of an apparatus in accordance with examples of the disclosure.
Figure 2:
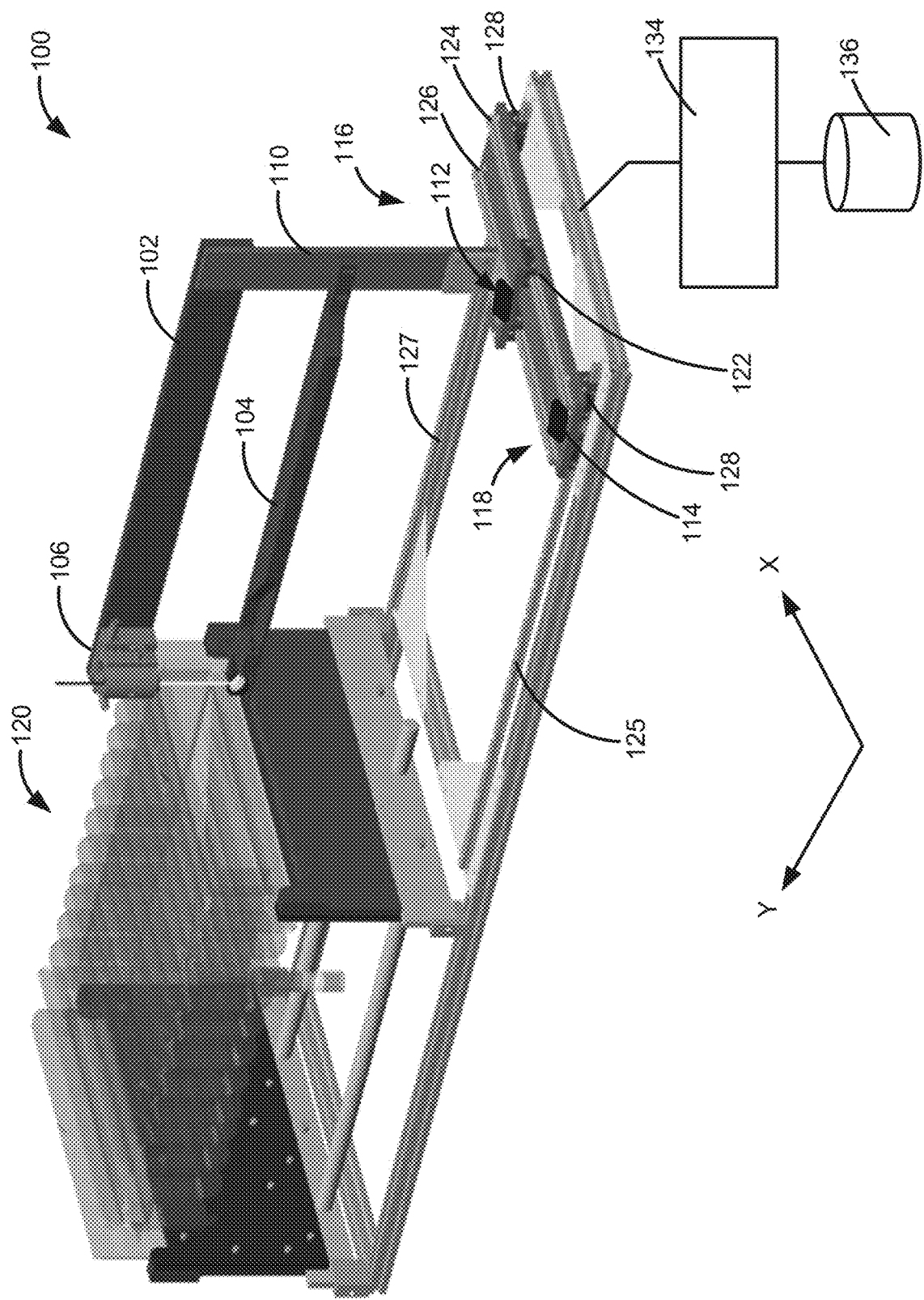
FIG. 2 illustrates a perspective view of the apparatus illustrated in FIG. 1.
Figure 3:
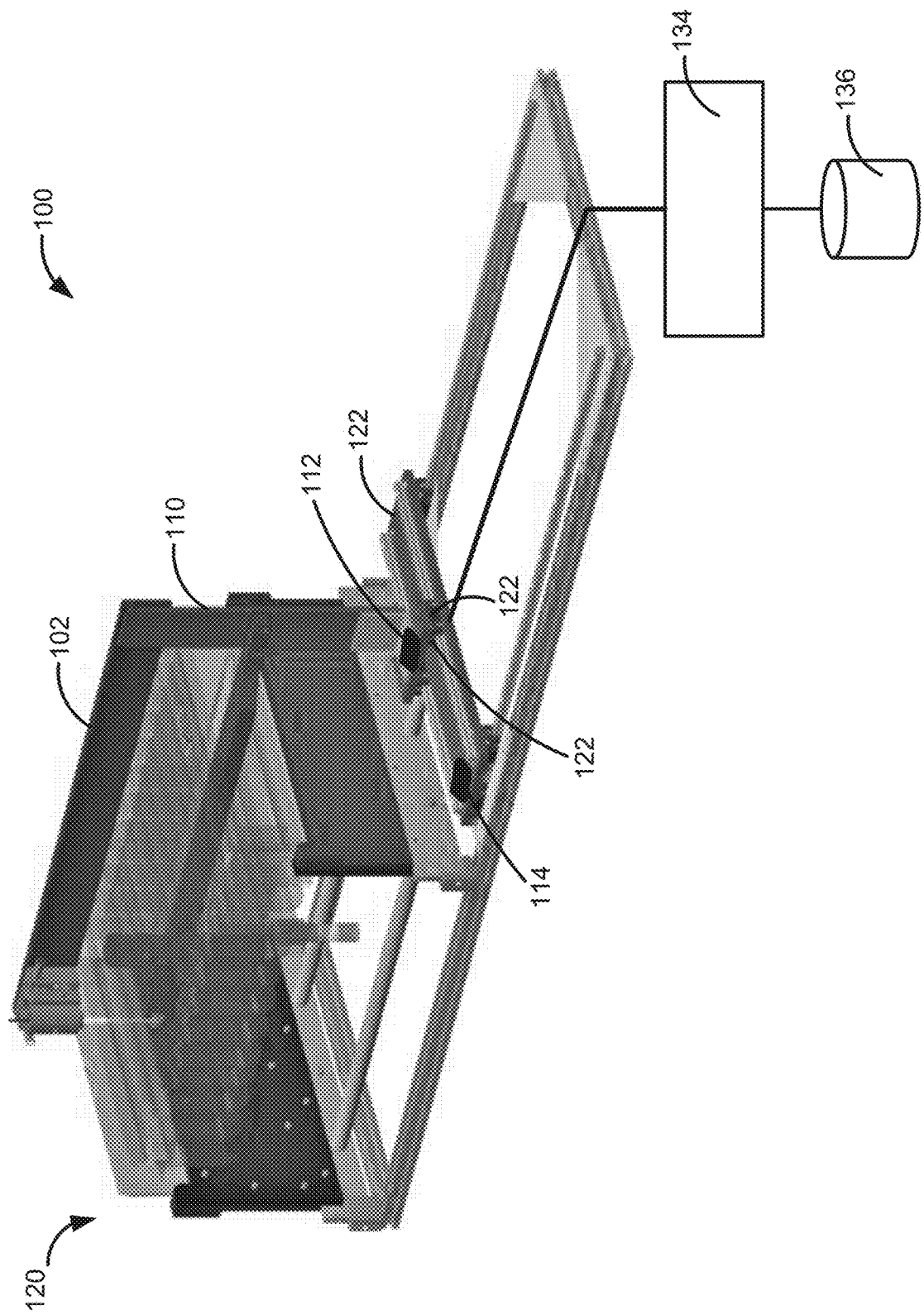
FIG. 3 illustrates another perspective view of the apparatus illustrated in FIG. 1.
Figure 4:
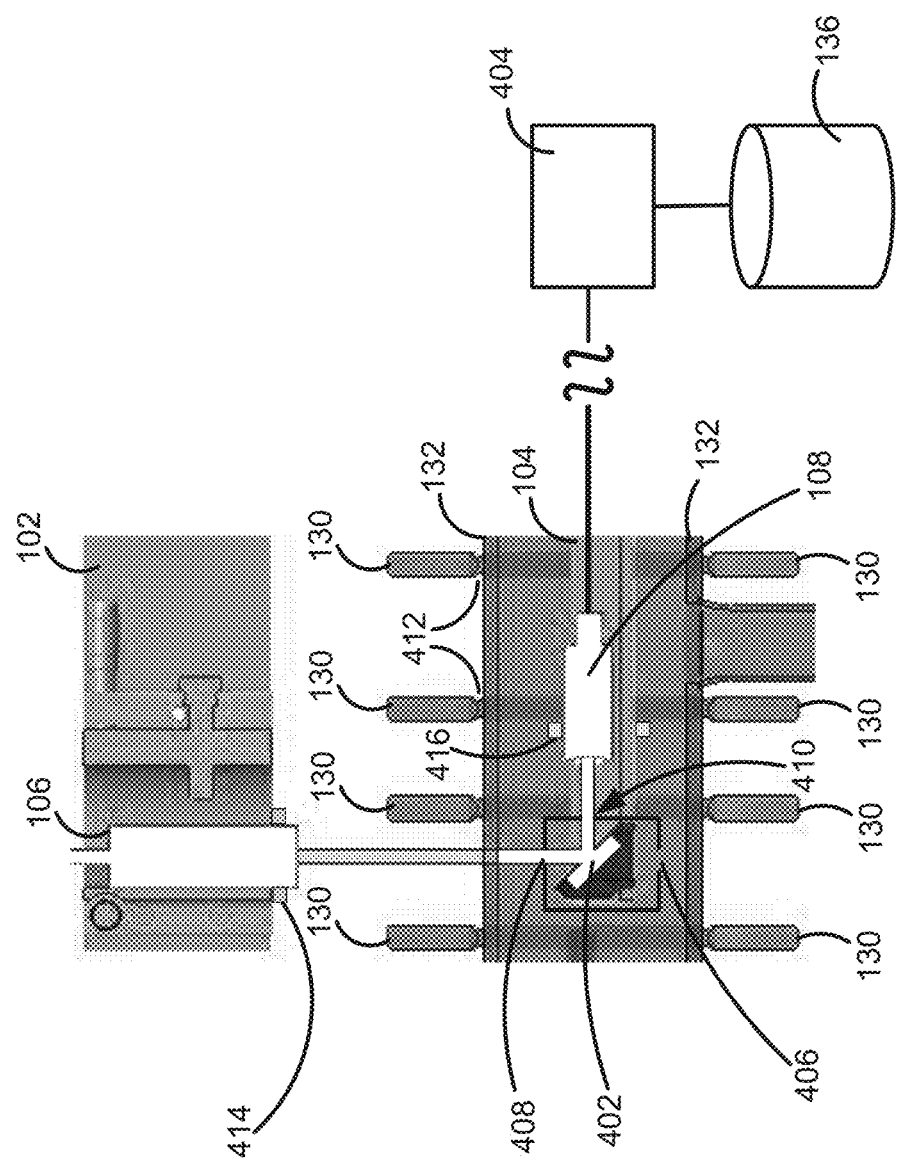
FIG. 4 illustrates an enlarged view of a light source and a sensor in accordance with examples of the disclosure.

Turning now to the drawing figures, FIG. 1 illustrates an apparatus 100 in accordance with exemplary embodiments of the disclosure. Apparatus 100 includes a first arm 102, a second arm 104, a light source 106 coupled to first arm 102, and a sensor 108 coupled to second arm 104. Apparatus 100 also includes a member 110, a first motor 112, a second motor 114, a first movement device 116, and a second movement device 118. FIG. 1 illustrates a side view of apparatus 100 with second arm 104 partially inserted into reaction chamber 120; FIG. 2 illustrates apparatus 100, with second arm 104 exterior to reaction chamber 120; FIG. 3 illustrates apparatus 100, with second arm 104 inserted within reaction chamber 120; FIG. 4 illustrates a close-up view of ends of first arm 102, second arm 104, light source 106, and sensor 108.

Various examples of the present disclosure provide methods and apparatus for measuring intensity of light transmitted through an article. The measured light intensity can be used to calculate a transmittance of the light through the article using the formula: transmittance=sample beam intensity/reference beam intensity. In other words, transmittance of light through the article can be calculated by comparing measured light intensity to a reference beam intensity. The reference beam intensity can be the intensity measured between light source 106 and sensor 108 when an article is not interposed between light source 106 and sensor 108—e.g., when nothing is between light source 106 and sensor 108. As set forth in more detail below, measured transmittance values can be used to verify an article (e.g., a go or no go for the article) based on, for example, comparison of measurements to values of known good articles and/or known bad articles.

During operation, a method of measuring light intensity, measuring transmittance, and/or of verifying an article can include providing an article, such as a reaction chamber 120, providing one of the first arm 102 and the second arm 104 on one side (e.g., within) of the article and the other of the first arm 102 and the second arm 104 on another side (e.g., outside) of the article to thereby measure one or more of light intensity and transmittance through the article or through a wall of the article. In the illustrated example, second arm 104 extends into reaction chamber 120 and first arm 102 is exterior to reaction chamber 120. In this case, light intensity and/or transmittance is measured through an upper section 131 of a wall 132 of reaction chamber 120. In accordance with other examples, first arm 102 can be placed within reaction chamber 120 and second arm 104 can be exterior to reaction chamber 120 to measure a lower section 133 of wall 132. In accordance with some examples, one or more (e.g., an array of) sensors 108 can be coupled to second arm 104 within an article (e.g., reaction chamber) an be and/or traverse along a plane that would include a substrate during processing. This allows measuring actual irradiance of IR on the substrate and characterize the irradiation variation from tool to tool. Such techniques can assist with calibrating the articles/reaction chambers.

First arm 102 can comprise any suitable material. For example, first arm 102 can be formed of thermoplastic, such as Ultem. A length of first arm 102 can be such that to measure reaction chamber 120 or other articles ranging from, for example, about 1 mm to about 1000 mm, or higher.

Similarly, second arm 104 can comprise any suitable material—e.g., a thermoplastic, such as Ultem. Member 110 can also be formed of any suitable material, such as a metal Apparatus 100 can be used to measure large articles, such as reaction chamber 120. In accordance with examples, of the disclosure, an article can be about 1 mm to about 1000 mm in length and/or about 1 to about 750 mm in width.

First arm 102 can be fixedly or removably attached to member 110. By way of examples, first arm 102 can be welded, adhered to (e.g., using an adhesive, such as glue), and/or attached using one or more couplers, such as bolts, screws, rivets, or the like. Similarly, second arm 104 can be fixedly or removably attached to member 110 using the same or similar techniques.

A length of first arm 102 and/or a length of second arm 104 can be adjustable to allow for measuring articles of various lengths. Similarly, a length of member 110 can be adjustable and/or a distance between first arm 102 and second arm 104 can be adjustable.

In the illustrated example, member 110 is attached to a first movement device 116. First movement device 116 can include a first motor 112 and rotatable objects (e.g., wheels) 122 coupled to first motor 112. First motor 112 can be mechanically coupled to rotatable objects 122 to cause member 110 and hence first arm 102 and second arm 104 to move in a first (e.g., X) direction—e.g., along rails 124, 126. Member 110 can be fixedly or removably attached to movement device 116—e.g., using techniques described above.

Second movement device 118 includes a second motor 114 and rotatable objects (e.g., wheels) 128. Second motor 114 can be mechanically coupled to rotatable objects 128 to cause member 110 and hence first arm 102 and second arm 104 to move in a second (e.g., Y) direction—e.g., along rails 125, 127. Rails 124-127 can be formed of any suitable material, such as metal—e.g., aluminum.

Additionally or alternatively, first and second arms 102, 104 can extend in or out in the Y direction (away from or toward member 110) using, for example, a screw motor, while member 110 does or does not move the same distance. Further, first and second movement devices 116, 118 may additionally or alternatively include other devices, such as linear screw mechanisms or the like.

Light source 106 can include a light source that emits light that includes light that is at least partially transmitted by at least a portion of an article, such as reaction chamber 120.

By way of examples, light source 106 can include a source that emits light having one or more wavelengths in the range of ultraviolet to infrared electromagnetic waves. In some cases, light source 106 can emit visible light. In some cases, light source 106 can emit infrared radiation. In some cases, light source 106 can emit ultraviolet radiation. In accordance with some examples, light emitted from light source 106 can have a single wavelength or multiple wavelengths in the range of ultraviolet to infrared electromagnetic waves. Light source 106 can be selected to emit the same, similar (e.g., within about +/−ten percent), or a subset of wavelength(s) of light emitted by one or more heaters used to heat a substrate within reaction chamber 120. In some cases, light source 106 includes one or more lasers. Light source 106 can also include one or more lenses and/or apertures to focus and/or columnate the emitted light. Although illustrated with one light source 106, apparatus in accordance with this disclosure can include one or more light sources 106 coupled to first arm 102. An alignment device 414 can be used to facilitate alignment of light source 106 with sensor 108. Further, light source 106 can be tilted at desired angles using alignment device 414 or another device.

In accordance with other examples of the disclosure, light source 106 can include one or more lamps (e.g., infrared lamps), which can be coupled to first arm 102 or to another fixture. In these cases, sensor 108 can be used to measure light intensity from the one or more lamps at various locations within reaction chamber 120. When the one or more light sources include a plurality of light sources, interaction of light emitted from the one or more light sources and/or shadow effects (e.g., from one or more structures) can be measured. In these cases, the apparatus can be used to determine variation associated with the one or more lamps—e.g., a distance between the lamps and the reaction chamber, an output of the lamps, an orientation of the lamps, or the like.

Sensor 108 includes a device to detect intensity of light transmitted through a portion of an article—e.g., a wall of reaction chamber 120. Sensor 108 can include, for example, a photodiode, a thermopile, or the like. Sensor 108 can be aligned on second arm 104 to receive light from light source 106—for example, a center point of light emitted from light source 106 can be aligned with a center point of sensor 108. In some cases, sensor 108 can include a filter, such that sensor 108 is configured to measure intensity of one or more predetermined wavelengths and/or to filter out one or more wavelengths of light that are not to be measured. Although illustrated with one sensor 108, apparatus in accordance with this disclosure can include one or more sensors 108 coupled to second arm 104.

In some cases, sensor 108 can be aligned within the light path of light source 106 to directly receive light from light source 106. In other cases, a reflective surface (e.g., a mirror) 402 can be used to direct light from light source 106 to sensor 108. An alignment device 416 can be used to facilitate alignment of sensor 108 with light source 106 and/or mirror 402. Further, sensor 108 can be tilted at desired angles using alignment device 416 or another device.

In addition, as illustrated in FIG. 4, apparatus 100 can include a shield 406 to mitigate scattering of light. Shield 406 can be formed of, for example, plastic or ceramic material to mitigate any metal contamination within reaction chamber 120. Shield 406 can include a first aperture 408. First aperture 408 can be smaller than a diameter of a beam of light from light source 206—e.g., to columnate the beam of light. Additionally or alternatively, shield 406 can include an aperture 410 between light source 106 or mirror 402 and sensor 108.

Reaction chamber 120 or other articles can be formed of, for example, quartz, or other material that is at least partially transparent to wavelength of the light emitted from light source 106. As illustrated in the figures, reaction chamber 120 can include support structures 130 (e.g., ribs) that provide support to reaction chamber 120 when, for example, a pressure within reaction chamber 120 is different (e.g., lower) than a pressure exterior to reaction chamber 120. Support structures 130 can be integrally formed on a wall 132 of reaction chamber 120. Alternatively, support structures 130 can be welded or otherwise attached to wall 132.

For measurement, reaction chamber 120 can be coupled to a fixture 200, which includes a frame 202. Frame 202 can be formed of any suitable material, such as, for example, plastic.

Fixture 200 and/or apparatus 100 can include vibration dampening devices 204, 206 to mitigate any vibration from the surrounding environment and/or that may arise during use of apparatus 100. In some cases, vibration dampening devices can include resilient material.

Apparatus 100 can also include a controller 134 to cause first movement device 116 and/or second movement device 118 to move to desired locations. In accordance with examples of the disclosure, controller 134 can include a processor and memory to cause first movement device 116 to move to a desired location and then cause second movement device 118 to move to a plurality of locations in the Y direction to obtain intensity and/or transmittance measurements in the Y direction as illustrated in, for example, FIGS. 1-3. In accordance with examples of the disclosure, controller 134 can cause first movement device 116 to move in increments. Additionally or alternatively, controller 134 can cause second movement device 118 to move in increments. Additionally or alternatively, controller 134 can cause first arm 102 and second arm 104 to extend and retract in the Y direction.

Apparatus 100 can also include a data acquisition device 404, illustrated in FIG. 4. Data acquisition device 404 can include a processor and memory to collect and store intensity and/or transmittance values received from sensor 108. In some cases, data acquisition device 404 can form part of controller 134. In other cases, data acquisition device 404 can be a standalone device.

Apparatus 100 can also include a database 136 to store intensity and/or transmittance values, which can be associated with a location of an article, such as reaction chamber 120. By way of examples, database 136 can include article identification information, transmittance information and location information (e.g., X and Y coordinates) for multiple intensity/transmittance measurements, known good values for intensity/transmittance measurements, and/or known bad values for intensity/transmittance measurements. Database 136 can be a standalone device, or can form part of another device, such as controller 134, or the like.

Controller 134 can be configured to cause apparatus 100 to measure one or more intensity/transmittance measurements at one site, such that database 136 receives one or more values associated with each site. In the case of multiple measurements per site, data acquisition device 404 and/or another device can average the values for each site, and the values, average values, and/or a deviation (e.g., a standard deviation) of the measured values for each site and/or average values for each site and for each article can be stored.

As illustrated in FIG. 1, apparatus 100 can also include a housing 140. Housing 140 can encase apparatus 100 and can mitigate any light from light source 106 escaping to a surrounding environment and/or can mitigate environmental effects on the measured values.

Figure 5:
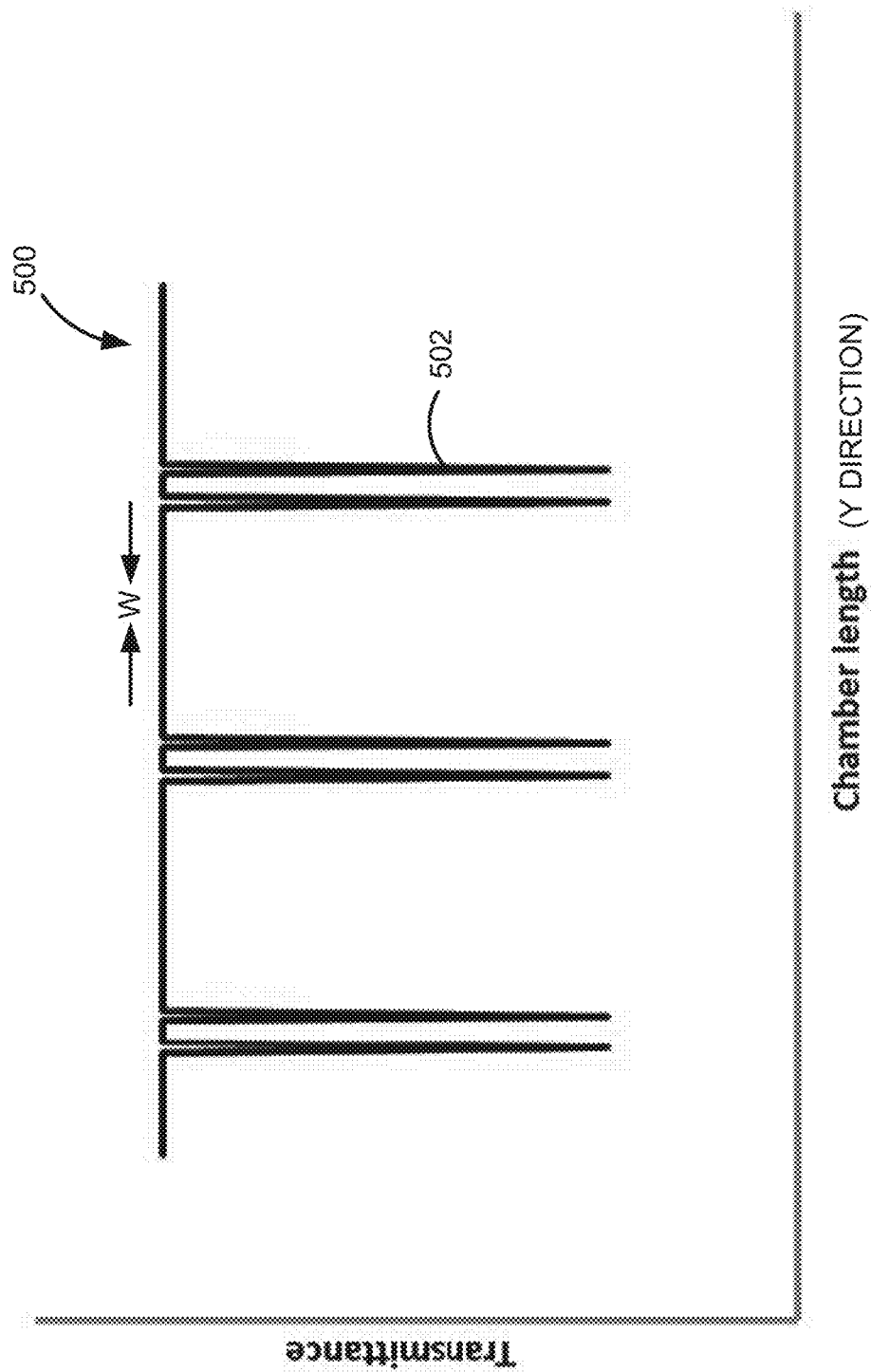
FIG. 5 illustrates transmittance values measured in accordance with examples of the disclosure.

FIG. 5 illustrates transmittance measurements 500 taken along a Y direction of reaction chamber 120. As illustrated, transmittance measurements 500 include perturbations 502, which can correspond to support structures or features 130 (e.g., an edge of a structure/feature) and/or welds 412 coupling support structures 130 to wall 132. A width, W, of one or more perturbations 502 can be analyzed to determine whether a weld 412 (e.g., a width of the weld) or other feature is within acceptable tolerances—e.g., by comparing measured intensity and/or transmittance values to known good or known bad values. Additionally or alternatively, other intensity or transmission measurements can be compared to values of known good articles (e.g., reaction chambers) to verify whether transmission of wavelength(s) of light is within an acceptable range.

The example embodiments of the disclosure described above do not limit the scope of the invention, since these embodiments are merely examples of the embodiments of the invention, which is defined by the appended claims and their legal equivalents. Any equivalent embodiments are intended to be within the scope of this invention. Indeed, various modifications of the disclosure, in addition to those shown and described herein, such as alternative useful combination of the elements described, may become apparent to those skilled in the art from the description. Such modifications and embodiments are also intended to fall within the scope of the appended claims.

What is claimed is:

1. A method of verifying an article having features thereon, the method comprising the steps of:
   providing an apparatus comprising:
      a first arm;
      a light source coupled to the first arm;
      a second arm;
      a first motor to cause the first arm and the second arm to move in a first direction;
      a second motor to cause the first arm and the second arm to move in a second direction; and
      a sensor coupled to the second arm,
      wherein the first direction and the second direction are linear directions;
   using the apparatus, measuring a transmittance of light from the light source through a wall of the article; and
   determining a quality of the article based on measured transmittance values,
   wherein the article comprises a reaction chamber, wherein the reaction chamber comprises at least one wall and a plurality of support structures that are integrally formed on or are attached to the at least one wall.

2. The method of claim 1, wherein the plurality of support structures are welded to the at least one wall, and wherein the step of determining comprises determining a quality of a weld of at least one of the plurality of support structures.

3. The method of claim 1, wherein, during the step of measuring, the light source is outside the article and the sensor is inside the article.

4. The method of claim 1, wherein, during the step of measuring, the light source is inside the article and the sensor is outside the article.

5. The method of claim 1, further comprising the steps of:
   moving the first arm and the second arm in the first direction;
   moving the first arm and the second arm in the second direction; and
   collecting a plurality of measurements along the first direction and the second direction.

6. The method of claim 1, wherein the step of determining a quality of the article based on measured transmittance values comprises determining a transmittance signal associated with an edge of a feature.

7. The method according to claim 6, further comprising a step of comparing the signal intensity associated with the edge of the feature with information in a database.

8. The method according to claim 1, wherein the article is coupled to a vibration dampening device.

9. The method of claim 1, wherein the reaction chamber is configured to hold a substrate, and wherein the second arm is configured to move in the reaction chamber along a plane of the substrate when the substrate is held in the reaction chamber.

* * * * *